United States Patent
Bell et al.

(10) Patent No.: US 10,385,024 B2
(45) Date of Patent: Aug. 20, 2019

(54) COMPOUNDS AND METHODS FOR INHIBITING NHE-MEDIATED ANTIPORT IN THE TREATMENT OF DISORDERS ASSOCIATED WITH FLUID RETENTION OR SALT OVERLOAD AND GASTROINTESTINAL TRACT DISORDERS

(71) Applicant: Ardelyx, Inc., Fremont, CA (US)

(72) Inventors: Noah Bell, Fremont, CA (US); Christopher Carreras, Fremont, CA (US); Dominique Charmot, Fremont, CA (US); Tao Chen, Fremont, CA (US); Michael Leadbetter, Fremont, CA (US); Jeffrey Jacobs, Fremont, CA (US); Jason Lewis, Fremont, CA (US)

(73) Assignee: ARDELYX, INC., Fremont, CA (US)

( * ) Notice: Subject to any disclaimer, the term of this patent is extended or adjusted under 35 U.S.C. 154(b) by 0 days.

(21) Appl. No.: 16/007,622

(22) Filed: Jun. 13, 2018

(65) Prior Publication Data

US 2019/0062279 A1    Feb. 28, 2019

Related U.S. Application Data

(63) Continuation of application No. 14/421,454, filed as application No. PCT/GB2013/052193 on Aug. 20, 2013, now abandoned.

(60) Provisional application No. 61/691,637, filed on Aug. 21, 2012.

(51) Int. Cl.

| | | |
|---|---|---|
| *C07D 217/18* | (2006.01) | |
| *C07D 401/14* | (2006.01) | |
| *C07D 217/14* | (2006.01) | |
| *A61K 31/4725* | (2006.01) | |
| *A61K 31/496* | (2006.01) | |
| *A61K 31/5377* | (2006.01) | |
| *A61K 45/06* | (2006.01) | |
| *A61K 47/32* | (2006.01) | |
| *A61K 47/36* | (2006.01) | |
| *A61K 47/38* | (2006.01) | |
| *A61K 47/60* | (2017.01) | |
| *A61K 47/55* | (2017.01) | |

(52) U.S. Cl.
CPC ........ *C07D 217/18* (2013.01); *A61K 31/4725* (2013.01); *A61K 31/496* (2013.01); *A61K 31/5377* (2013.01); *A61K 45/06* (2013.01); *A61K 47/32* (2013.01); *A61K 47/36* (2013.01); *A61K 47/38* (2013.01); *A61K 47/55* (2017.08); *A61K 47/60* (2017.08); *C07D 217/14* (2013.01); *C07D 401/14* (2013.01); *Y02A 50/414* (2018.01)

(58) Field of Classification Search
None
See application file for complete search history.

(56) References Cited

U.S. PATENT DOCUMENTS

| | | | |
|---|---|---|---|
| 6,451,781 B1 | 9/2002 | Kleemann et al. | |
| 8,541,448 B2 * | 9/2013 | Charmot | A61K 31/18 514/307 |
| 2001/0046958 A1 | 11/2001 | Treadway | |
| 2015/0299131 A1 | 10/2015 | Bell et al. | |

FOREIGN PATENT DOCUMENTS

| | | |
|---|---|---|
| CN | 102333759 A | 1/2012 |
| WO | 2010078449 A2 | 7/2010 |

OTHER PUBLICATIONS

Nekrasov, "Osnovi obshchei himii", Moskva, Himiya, p. 388 (1973).
Patent Cooperation Treaty, International Search Report and Written Opinion for PCT/GB2013/052193 dated Oct. 31, 2013.
Silva, et al., "Advances in prodrug design", Mini Rev Med Chem 5(10), 893-914 (2005).
Wang, "Factors of Gastric Retention Among Neurosurgery ICU Patients with Enteral Nutrition Support", Chinese Nursing Management 11(4), 63-66 (2011). (Abstract).

* cited by examiner

*Primary Examiner* — Heidi Reese
(74) *Attorney, Agent, or Firm* — Viksnins Harris Padys Malen LLP

(57) ABSTRACT

The present disclosure is directed to compounds and methods for the treatment of disorders associated with fluid retention or salt overload, such as heart failure (in particular, congestive heart failure), chronic kidney disease, end-stage renal disease, liver disease, and peroxisome proliferator-activated receptor (PPAR) gamma agonist-induced fluid retention. The present disclosure is also directed to compounds and methods for the treatment of hypertension. The present disclosure is also directed to compounds and methods for the treatment of gastrointestinal tract disorders, including the treatment or reduction of pain associated with gastrointestinal tract disorders.

36 Claims, No Drawings

COMPOUNDS AND METHODS FOR INHIBITING NHE-MEDIATED ANTIPORT IN THE TREATMENT OF DISORDERS ASSOCIATED WITH FLUID RETENTION OR SALT OVERLOAD AND GASTROINTESTINAL TRACT DISORDERS

RELATED APPLICATIONS

This application is a continuation of U.S. patent application Ser. No. 14/421,454, filed Nov. 12, 2015, which is a National Stage application under 35 U.S.C. § 371 of International Application No. PCT/GB2013/052193, filed Aug. 20, 2013, which claims the benefit of priority to U.S. Provisional Patent Application No. 61/691,637, filed Aug. 21, 2012. The contents of the foregoing applications are hereby incorporated by reference in their entirety.

BACKGROUND

Field

The present disclosure is directed to compounds that are substantially active in the gastrointestinal tract to inhibit NHE-mediated antiport of sodium ions and hydrogen ions, and the use of such compounds in the treatment of disorders associated with fluid retention or salt overload and in the treatment of gastrointestinal tract disorders, including the treatment or reduction of pain associated with a gastrointestinal tract disorder.

Description of the Related Art

Disorders Associated with Fluid Retention and Salt Overload

According to the American Heart Association, more than 5 million Americans have suffered from heart failure, and an estimated 550,000 cases of congestive heart failure (CHF) occur each year (Schocken, D. D. et al., *Prevention of heart failure: a scientific statement from the American Heart Association Councils on Epidemiology and Prevention, Clinical Cardiology, Cardiovascular Nursing, and High Blood Pressure Research*; Quality of Care and Outcomes Research Interdisciplinary Working Group; and Functional Genomics and Translational Biology Interdisciplinary Working Group: Circulation, v. 117, no. 19, p. 2544-2565 (2008)). The clinical syndrome of congestive heart failure occurs when cardiac dysfunction prevents adequate perfusion of peripheral tissues. The most common form of heart failure leading to CHF is systolic heart failure, caused by contractile failure of the myocardium. A main cause of CHF is due to ischemic coronary artery disease, with or without infarction. Long standing hypertension, particularly when it is poorly controlled, may lead to CHF.

In patients with CHF, neurohumoral compensatory mechanisms (i.e., the sympathetic nervous system and the renin-angiotensin system) are activated in an effort to maintain normal circulation. The renin-angiotensin system is activated in response to decreased cardiac output, causing increased levels of plasma renin, angiotensin II, and aldosterone. As blood volume increases in the heart, cardiac output increases proportionally, to a point where the heart is unable to dilate further. In the failing heart, contractility is reduced, so the heart operates at higher volumes and higher filling pressures to maintain output. Filling pressures may eventually increase to a level that causes transudation of fluid into the lungs and congestive symptoms (e.g., edema, shortness of breath). All of these symptoms are related to fluid volume and salt retention, and this chronic fluid and salt overload further contribute to disease progression.

Compliance with the medication regimen and with dietary sodium restrictions is a critical component of self-management for patients with heart failure and may lengthen life, reduce hospitalizations and improve quality of life. Physicians often recommend keeping salt intake below 2.3 g per day and no more than 2 g per day for people with heart failure. Most people eat considerably more than this, so it is likely that a person with congestive heart failure will need to find ways to reduce dietary salt.

A number of drug therapies currently exist for patients suffering from CHF. For example, diuretics may be used or administered to relieve congestion by decreasing volume and, consequently, filling pressures to below those that cause pulmonary edema. By counteracting the volume increase, diuretics reduce cardiac output; however, fatigue and dizziness may replace CHF symptoms. Among the classes or types of diuretics currently being used is thiazides. Thiazides inhibit NaCl transport in the kidney, thereby preventing reabsorption of Na in the cortical diluting segment at the ending portion of the loop of Henle and the proximal portion of the distal convoluted tubule. However, these drugs are not effective when the glomerular filtration rate (GFR) is less than 30 ml/min. Additionally, thiazides, as well as other diuretics, may cause hypokalemia. Also among the classes or types of diuretics currently being used is loop diuretics (e.g., furosemide). These are the most potent diuretics and are particularly effective in treating pulmonary edema. Loop diuretics inhibit the NaKCl transport system, thus preventing reabsorption of Na in the loop of Henle.

Patients that have persistent edema despite receiving high doses of diuretics may be or become diuretic-resistant. Diuretic resistance may be caused by poor availability of the drug. In patients with renal failure, which has a high occurrence in the CHF population, endogenous acids compete with loop diuretics such as furosemide for the organic acid secretory pathway in the tubular lumen of the nephron. Higher doses, or continuous infusion, are therefore needed to achieve entrance of an adequate amount of drug into the nephron. However, recent meta-analysis have raised awareness about the long-term risk of chronic use of diuretics in the treatment of CHF. For instance, in a recent study (Ahmed et al., *Int J Cardiol.* 2008 Apr. 10; 125(2): 246-253) it was shown that chronic diuretic use was associated with significantly increased mortality and hospitalization in ambulatory older adults with heart failure receiving angiotensin converting enzyme inhibitor and diuretics.

Angiotensin-converting enzyme ("ACE") inhibitors are an example of another drug therapy that may be used to treat congestive heart failure. ACE inhibitors cause vasodilatation by blocking the renin-angiotensin-aldosterone system. Abnormally low cardiac output may cause the renal system to respond by releasing renin, which then converts angiotensinogen into angiotensin I. ACE converts angiotensin I into angiotensin II. Angiotensin II stimulates the thirst centers in the hypothalamus and causes vasoconstriction, thus increasing blood pressure and venous return. Angiotensin II also causes aldosterone to be released, causing reabsorption of Na and concomitant passive reabsorption of fluid, which in turn causes the blood volume to increase. ACE inhibitors block this compensatory system and improve cardiac performance by decreasing systemic and pulmonary vascular resistance. ACE inhibitors have shown survival benefit and conventionally have been a treatment of choice for CHF. However, since ACE inhibitors lower aldosterone, the K-secreting hormone, one of the side-effects of their use is hyperkalemia. In addition, ACE inhibitors have been show to lead to acute renal failure in certain categories of CHF patients. (See, e.g., C. S. Cruz et al., "Incidence and Predictors of Development of Acute Renal Failure Related to the Treatment of Congestive Heart Failure with ACE Inhibitors, Nephron Clin. Pract., v. 105, no. 2, pp c77-c83 (2007)).

Patients with end stage renal disease ("ESRD"), i.e., stage 5 chronic kidney failure, must undergo hemodialysis three times per week. The quasi-absence of renal function and ability to eliminate salt and fluid results in large fluctuations in body weight as fluid and salt build up in the body (sodium/volume overload). The fluid overload is characterized as interdialytic weight gain. High fluid overload is also worsened by heart dysfunction, specifically CHF. Dialysis is used to remove uremic toxins and also adjust salt and fluid homeostasis. However, symptomatic intradialytic hypotension (SIH) may occur when patients are over-dialyzed. SIH is exhibited in about 15% to 25% of the ESRD population (Davenport, A., C. Cox, and R. Thuraisingham, *Blood pressure control and symptomatic intradialytic hypotension in diabetic haemodialysis patients: a cross-sectional survey*; Nephron Clin. Pract., v. 109, no. 2, p. c65-c71 (2008)). Like in hypertensive and CHF patients, dietary restrictions of salt and fluid are highly recommended but poorly followed because of the poor palatability of low-salt food The cause of primary or "essential" hypertension is elusive. However, several observations point to the kidney as a primary factor. The strongest data for excess salt intake and elevated blood pressure come from INTERSALT, a cross-sectional study of greater than 10,000 participants. For individuals, a significant, positive, independent linear relation between 24-hour sodium excretion and systolic blood pressure was found. Higher individual 24-hour urinary sodium excretions were found to be associated with higher systolic/diastolic blood pressure on average, by 6-3/3-0 mm Hg. Primary hypertension is a typical example of a complex, multifactorial, and polygenic trait. All these monogenic hypertensive syndromes are virtually confined to mutated genes involving gain of function of various components of the renin-angiotensin-aldosterone system, resulting in excessive renal sodium retention. In a broad sense, these syndromes are characterized by increased renal sodium reabsorption arising through either primary defects in sodium transport systems or stimulation of mineralocorticoid receptor activity (Altun, B., and M. Arici, 2006, *Salt and blood pressure: time to challenge*; Cardiology, v. 105, no. 1, p. 9-16 (2006)). A much larger number of controlled studies have been performed on hypertensive subjects during the last three decades to determine whether sodium reduction will reduce established high blood pressure. Meta-analyses of these studies have clearly shown a large decrease in blood pressure in hypertensive patients.

In end stage liver disease (ESLD), accumulation of fluid as ascites, edema or pleural effusion due to cirrhosis is common and results from a derangement in the extracellular fluid volume regulatory mechanisms. Fluid retention is the most frequent complication of ESLD and occurs in about 50% of patients within 10 years of the diagnosis of cirrhosis. This complication significantly impairs the quality of life of cirrhotic patients and is also associated with poor prognosis. The one-year and five-year survival rate is 85% and 56%, respectively (Kashani et al., *Fluid retention in cirrhosis: pathophysiology and management*; QJM, v. 101, no. 2, p. 71-85 (2008)). The most acceptable theories postulate that the initial event in ascites formation in the cirrhotic patient is sinusoidal hypertension. Portal hypertension due to an increase in sinusoidal pressure activates vasodilatory mechanisms. In advanced stages of cirrhosis, arteriolar vasodilation causes underfilling of systemic arterial vascular space. This event, through a decrease in effective blood volume, leads to a drop in arterial pressure. Consequently, baroreceptor-mediated activation of renin-angiotensin aldosterone system, sympathetic nervous system and nonosmotic release of antidiuretic hormone occur to restore the normal blood homeostasis. These events cause further retention of renal sodium and fluid. Splanchnic vasodilation increases splanchnic lymph production, exceeding the lymph transportation system capacity, and leads to lymph leakage into the peritoneal cavity. Persistent renal sodium and fluid retention, alongside increased splanchnic vascular permeability in addition to lymph leakage into the peritoneal cavity, play a major role in a sustained ascites formation.

Thiazolidinediones (TZD's), such as rosiglitazone, are peroxisome proliferator-activated receptor (PPAR) gamma agonist agents used for the treatment of type-2 diabetes and are widely prescribed. Unfortunately, fluid retention has emerged as the most common and serious side-effect of TZD's and has become the most frequent cause of discontinuation of therapy. The incidence of TZD-induced fluid retention ranges from 7% in monotherapy and to as high as 15% when combined with insulin (Yan, T., Soodvilai, S., *PPAR Research* volume 2008, article ID 943614). The mechanisms for such side-effects are not fully understood but may be related in Na and fluid re-absorption in the kidney. However TZD-induced fluid retention is resistant to loop diuretics or thiazide diuretics, and combination of peroxisome proliferator-activated receptor (PPAR) alpha with PPAR gamma agonists, which were proposed to reduce such fluid overload, are associated with major adverse cardiovascular events.

In view of the foregoing, it is recognized that salt and fluid accumulation contribute to the morbidity and mortality of many diseases, including heart failure (in particular, congestive heart failure), chronic kidney disease, end-stage renal disease, liver disease and the like. It is also accepted that salt and fluid accumulation are risk factors for hypertension. Accordingly, there is a clear need for a medicament that, when administered to a patient in need, would result in a reduction in sodium retention, fluid retention, or preferably both. Such a medicament would more preferably also not involve or otherwise impair renal mechanisms of fluid/Na homeostasis.

One option to consider for treating excessive fluid overload is to induce diarrhea. Diarrhea may be triggered by several agents including, for example, laxatives such as sorbitol, polyethyleneglycol, bisacodyl and phenolphthaleine. Sorbitol and polyethyleneglycol triggers osmotic diarrhea with low levels of secreted electrolytes; thus, their utility in removing sodium salt from the GI tract is limited. The mechanism of action of phenolphthalein is not clearly established, but is thought to be caused by inhibition of the Na/K ATPase and the Cl/$HCO_3$ anion exchanger and stimulation of electrogenic anion secretion (see, e.g., Eherer, A. J., C. A. Santa Ana, J. Porter, and J. S. Fordtran, 1993, Gastroenterology, v. 104, no. 4, p. 1007-1012). However, some laxatives, such as phenolphthalein, are not viable options for the chronic treatment of fluid overload, due to the potential risk of carcinogenicity in humans. Furthermore, laxatives may not be used chronically, as they have been shown to be an irritant and cause mucosal damage. Accordingly, it should also be recognized that the induction of chronic diarrhea as part of an effort to control salt and fluid overload would be an undesired treatment modality for most patients. Any medicament utilizing the GI tract for this purpose would therefore need to control diarrhea in order to be of practical benefit.

One approach for the treatment of mild diarrhea is the administration of a fluid-absorbing polymer, such as the natural plant fiber psyllium. Polymeric materials, and more specifically hydrogel polymers, may also be used for the removal of fluid from the gastrointestinal (GI) tract. The use of such polymers is described in, for example, U.S. Pat. No. 4,470,975 and U.S. Pat. No. 6,908,609, the entire contents of which are incorporated herein by reference for all relevant and consistent purposes. However, for such polymers to effectively remove significant quantities of fluid, they must desirably resist the static and osmotic pressure range existing in the GI tract. Many mammals, including humans, make a soft feces with a water content of about 70%, and do so by transporting fluid against the high hydraulic resistance imposed by the fecal mass. Several studies show that the pressure required to dehydrate feces from about 80% to about 60% is between about 500 kPa and about 1000 kPa (i.e., about 5 to about 10 atm). (See, e.g., McKie, A. T., W. Powrie, and R. J. Naftalin, 1990, Am J Physiol, v. 258, no. 3 Pt 1, p. G391-G394; Bleakman, D, and R. J. Naftalin, 1990, Am J Physiol, v. 258, no. 3 Pt 1, p. G377-G390; Zammit, P. S., M. Mendizabal, and R. J. Naftalin, 1994, J Physiol, v. 477 (Pt 3), p. 539-548.) However, the static pressure measured intraluminally is usually between about 6 kPa and about 15 kPa. The rather high pressure needed to dehydrate feces is essentially due to an osmotic process and not a mechanical process produced by muscular forces. The osmotic pressure arises from the active transport of salt across the colonic mucosa that ultimately produces a hypertonic fluid absorption. The osmotic gradient produced drives fluid from the lumen to the serosal side of the mucosa. Fluid-absorbing polymers, such as those described in for example U.S. Pat. Nos. 4,470,975 and 6,908,609, may not be able to sustain such pressure. Such polymers may collapse in a normal colon where the salt absorption process is intact, hence removing a modest quantity of fluid and thereby salt.

Synthetic polymers that bind sodium have also been described. For example, ion-exchange polymeric resins, such as Dowex-type cation exchange resins, have been known since about the 1950's. However, with the exception of Kayexalate™ (or Kionex™), which is a polystyrene sulfonate salt approved for the treatment of hyperkalemia, cation exchange resins have very limited use as drugs, due at least in part to their limited capacity and poor cation binding selectivity. Additionally, during the ion-exchange process, the resins may release a stochiometric amount of exogenous cations (e.g., H, K, Ca), which may in turn potentially cause acidosis (H), hyperkalemia (K) or contribute to vascular calcification (Ca). Such resins may also cause constipation.

Gastrointestinal Tract Disorders

Constipation is characterized by infrequent and difficult passage of stool and becomes chronic when a patient suffers specified symptoms for over 12 non-consecutive weeks within a 12-month period. Chronic constipation is idiopathic if it is not caused by other diseases or by use of medications. An evidence-based approach to the management of chronic constipation in North America (Brandt et al., 2005, Am. J. Gastroenterol. 100(Suppl.1):S5-S21) revealed that prevalence is approximately 15% of the general population. Constipation is reported more commonly in women, the elderly, non-whites, and individuals from lower socioeconomic groups.

Irritable bowel syndrome (IBS) is a common GI disorder associated with alterations in motility, secretion and visceral sensation. A range of clinical symptoms characterizes this disorder, including stool frequency and form, abdominal pain and bloating. The recognition of clinical symptoms of IBS are yet to be defined, but it is now common to refer to diarrhea-predominant IBS (D-IBS) and constipation-predominant IBS (C-IBS), wherein D-IBS is defined as continuous passage of loose or watery stools and C-IBS as a group of functional disorders which present as difficult, infrequent or seemingly incomplete defecation. The pathophysiology of IBS is not fully understood, and a number of mechanisms have been suggested. Visceral hypersensitivity is often considered to play a major etiologic role and has been proposed to be a biological marker even useful to discriminate IBS from other causes of abdominal pain. In a recent clinical study (Posserud, I. et al, *Gastroenterology*, 2007; 133:1113-1123) IBS patients were submitted to a visceral sensitivity test (Balloon distention) and compared with healthy subjects. It revealed that 61% of the IBS patients had an altered visceral perception as measured by pain and discomfort threshold. Other reviews have documented the role of visceral hypersensitivity in abdominal pain symptomatic of various gastrointestinal tract disorders (Akbar, A, et al, *Aliment. Pharmaco. Ther.*, 2009, 30, 423-435; Bueno et al., *Neurogastroenterol Motility* (2007) 19 (suppl.1), 89-119). Colonic and rectal distention have been widely used as a tool to assess visceral sensitivity in animal and human studies. The type of stress used to induce visceral sensitivity varies upon the models (see for instance Eutamen, H *Neurogastroenterol Motil.* 2009 Aug. 25. [Epub ahead of print]), however stress such as Partial restraint stress (PRS) is a relatively mild, non-ulcerogenic model that is considered more representative of the IBS setting.

Constipation is commonly found in the geriatric population, particularly patients with osteoporosis who have to take calcium supplements. Calcium supplements have shown to be beneficial in ostoporotic patients to restore bone density but compliance is poor because of calcium-induced constipation effects.

Opioid-induced constipation (OIC) (also referred to as opioid-induced bowel dysfunction or opioid bowel dysfuntion (OBD)) is a common adverse effect associated with opioid therapy. OIC is commonly described as constipation; however, it is a constellation of adverse gastrointestinal (GI) effects, which also includes abdominal cramping, bloating, and gastroesophageal reflux. Patients with cancer may have disease-related constipation, which is usually worsened by opioid therapy. However, OIC is not limited to cancer patients. A recent survey of patients taking opioid therapy for pain of non-cancer origin found that approximately 40% of patients experienced constipation related to opioid therapy (<3 complete bowel movements per week) compared with 7.6% in a control group. Of subjects who required laxative therapy, only 46% of opioid-treated patients (control subjects, 84%) reported achieving the desired treatment results >50% of the time (Pappagallo, 2001, Am. J. Surg. 182(5A Suppl.):11S-18S).

Some patients suffering from chronic idiopathic constipation can be successfully treated with lifestyle modification, dietary changes and increased fluid and fiber intake, and these treatments are generally tried first. For patients who fail to respond to these approaches, physicians typically recommend laxatives, most of which are available over-the-counter. Use of laxatives provided over-the-counter is judged inefficient by about half of the patients (Johanson and Kralstein, 2007, Aliment. Pharmacol. Ther. 25(5):599-608).

Other therapeutic options currently prescribed or in clinical development for the treatment of IBS and chronic constipation including OIC are described in, for example: Chang et al., 2006, Curr. Teat. Options Gastroenterol. 9(4):314-323; Gershon and Tack, 2007, Gastroenterology 132(1):397-414; and, Hammerle and Surawicz, 2008, World J. Gastroenterol. 14(17):2639-2649. Such treatments include but are not limited to serotonin receptor ligands, chloride channel activators, opioid receptor antagonists, guanylate-cyclase receptor agonists and nucleotide P2Y(2) receptor agonists. Many of these treatment options are inadequate, as they may be habit forming, ineffective in some patients, may cause long term adverse effects, or otherwise are less than optimal.

Na$^+$/H$^+$ Exchanger (NHE) Inhibitors

A major function of the GI tract is to maintain water/Na homeostasis by absorbing virtually all water and Na to which the GI tract is exposed. The epithelial layer covering the apical surface of the mammalian colon is a typical electrolyte-transporting epithelium, which is able to move large quantities of salt and water in both directions across the mucosa. For example, each day the GI tract processes about 9 liters of fluid and about 800 meq of Na. (See, e.g., Zachos et al., *Molecular physiology of intestinal Na+/H+ exchange*; Annu. Rev. Physiol., v. 67, p. 411-443 (2005).) Only about 1.5 liters of this fluid and about 150 meq of this sodium originates from ingestion; rather, the majority of the fluid (e.g., about 7.5 liters) and sodium (about 650 meq) is secreted via the GI organs as part of digestion. The GI tract therefore represents a viable target for modulating systemic sodium and fluid levels.

Many reviews have been published on the physiology and secretory and/or absorption mechanisms of the GI tract (see, e.g., Kunzelmann et al., *Electrolyte transport in the mammalian colon: mechanisms and implications for disease*; Physiol. Rev., v. 82, no. 1, p. 245-289 (2002); Geibel, J. P.; *Secretion and absorption by colonic crypts*; Annu. Rev. Physiol, v. 67, p. 471-490 (2005); Zachos et al., supra; Kiela, P. R. et al., *Apical Na+/H+ exchangers in the mammalian gastrointestinal tract*; J. Physiol. Pharmacol., v. 57 Suppl. 7, p. 51-79 (2006)). The two main mechanisms of Na absorption are electroneutral and electrogenic transport. Electroneutral transport is essentially due to the Na$^+$/H$^+$ antiport NHE (e.g., NHE-3) and is responsible for the bulk of Na absorption. Electrogenic transport is provided by the epithelium sodium channel ("ENaC"). Electroneutral transport is located primarily in the ileal segment and proximal colon and electrogenic transport is located in the distal colon.

Plasma membrane NHEs contribute to maintenance of intracellular pH and volume, transcellular absorption of NaCl and NaHCO$_3$, and fluid balance carried out by epithelial cells, especially in the kidney, intestine, gallbladder, and salivary glands, as well as regulation of systemic pH. There exists a body of literature devoted to the role and clinical intervention on systemic NHEs to treat disorders related to ischemia and reperfusion for cardioprotection or renal protection. Nine isoforms of NHEs have been identified (Kiela, P. R., et al.; *Apical NA+/H+ exchangers in the mammalian gastrointestinal tract*; J. Physiol. Pharmacol., v. 57 Suppl 7, p. 51-79 (2006)), of which NHE-2, NHE-3 and NHE-8 are expressed on the apical side of the GI tract, with NHE-3 providing a larger contribution to transport. Another, yet to be identified, Cl-dependant NHE has been identified in the crypt of rat cells. In addition, much research has been devoted to identifying inhibitors of NHEs. The primary targets of such research have been NHE-1 and NHE-3 Small molecule NHE inhibitors are, for example, described in: U.S. Pat. Nos. 5,866,610; 6,399,824; 6,911,453; 6,703,405; 6,005,010; 6,736,705; 6,887,870; 6,737,423; 7,326,705; 5,824,691 (WO 94/026709); U.S. Pat. No. 6,399,824 (WO 02/024637); U.S. Pat. Pub. Nos. 2004/0039001 (WO 02/020496); 2005/0020612 (WO 03/055490); 2004/0113396 (WO 03/051866); 2005/0020612; 2005/0054705; 2008/0194621; 2007/0225323; 2004/0039001; 2004/0224965; 2005/0113396; 2007/0135383; 2007/0135385; 2005/0244367; 2007/0270414; International Publication Nos. WO 01/072742; WO 01/021582 (CA2387529); WO 97/024113 (CA02241531) and European Pat. No. EP0744397 (CA2177007); all of which are incorporated herein by reference in their entirety for all relevant and consistent purposes.

However, such research failed to develop or recognize the value or importance of NHE inhibitors that are not absorbed (i.e., not systemic) and target the gastrointestinal tract, as disclosed recently in WO 2010/078449. Such inhibitors can be utilized in the treatment of disorders associated with fluid retention and salt overload and in the treatment of GI tract disorders, including the treatment or reduction of pain associated with a gastrointestinal tract disorder. Such inhibitors are particular advantageous because they can be delivered with reduced fear of systemic on-target or off-target effects (e.g., little or no risk of renal involvement or other systemic effects.

Accordingly, while progress has been made in the foregoing fields, there remains a need in the art for novel compounds for use in the disorders associated with fluid retention and salt overload and in the treatment of gastrointestinal tract disorders, including the treatment or reduction of pain associated with a gastrointestinal tract disorder. The present invention fulfills this need and provides further related advantages.

BRIEF SUMMARY

In brief, the present invention is directed to compounds that are substantially active in the gastrointestinal tract to inhibit NHE-mediated antiport of sodium ions and hydrogen ions, and the use of such compounds in the treatment of disorders associated with fluid retention and salt overload and in the treatment of gastrointestinal tract disorders, including the treatment or reduction of pain associated with a gastrointestinal tract disorder.

In one embodiment, a compound is provided having the structure of Formula (I):

or a stereoisomer, prodrug or pharmaceutically acceptable salt thereof, wherein:

(a) NHE is a NHE-inhibiting small molecule moiety having the following structure of Formula (A):

(c) L is a bond or linker connecting the Core moiety to the NHE-inhibiting small molecule moieties.

In more specific embodiments, the NHE-inhibiting small molecule moiety has the following structure:

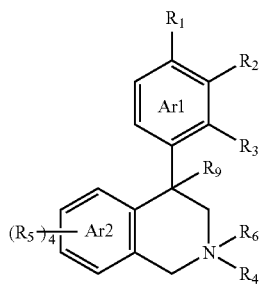

wherein:
each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$ alkyl-OH or a bond linking the NHE-inhibiting small molecule to L, provided at least one is a bond linking the NHE-inhibiting small molecule to L;

$R_4$ is selected from H, $C_1$-$C_7$ alkyl, or a bond linking the NHE-inhibiting small molecule to L;

$R_6$ is absent or selected from H and $C_1$-$C_7$ alkyl; and

Ar1 and Ar2 independently represent an aromatic ring or a heteroaromatic ring;

(b) Core is a Core moiety having the following structure of Formula (B):

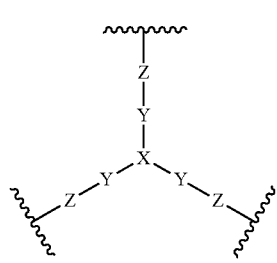

wherein:
X is selected from $C(X_1)$, N and $N(C_{1-6}$ alkyl);
$X_1$ is selected from hydrogen, optionally substituted alkyl, —$NX_aX_b$, —$NO_2$, —$NX_c$—$C(=O)$—$NX_c$—$X_a$, —$C(=O)NX_c$—$X_a$, —$NX_c$—$C(=O)$—$X_a$, —$NX_c$—$SO_2$—$X_a$, —$C(=O)$—$X_a$ and —$OX_a$,
each $X_a$ and $X_b$ are independently selected from hydrogen, optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroarylalkyl;
Y is $C_{1-6}$alkylene;
Z is selected from —$NZ_a$—$C(=O)$—$NZ_a$—, —$C(=O)NZ_a$—, —$NZ_a$—$C(=O)$— and heteroaryl when X is $CX_1$;
Z is selected from —$NZ_a$—$C(=O)$—$NZ_a$—, —$NZ_a$—$C(=O)$— and heteroaryl when X is N or $N(C_{1-6}$alkyl); and
each $X_c$ and $Z_a$ is independently selected from hydrogen and $C_{1-6}$alkyl; and wherein:
each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$ alkyl-OH or a bond linking the NHE-inhibiting small molecule to L, provided at least one is a bond linking the NHE-inhibiting small molecule to L.

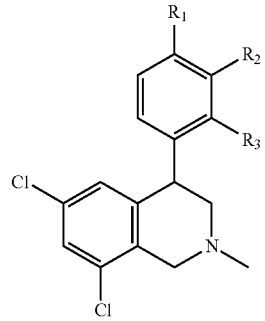

In further more specific embodiments, the NHE-inhibiting small molecule moiety has one of the following structures:

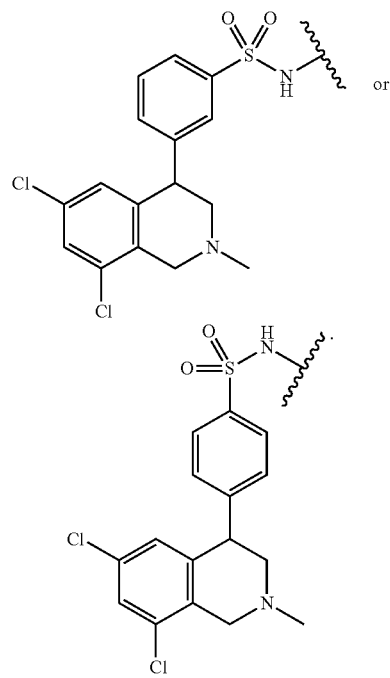

In other more specific embodiments, L is a polyalkylene glycol linker. For example, in certain embodiments, L is a polyethylene glycol linker.

In other more specific embodiments, X is $C(X_1)$. In further embodiments, each $X_c$ is hydrogen.

In other more specific embodiments, X is N.

In other more specific embodiments, each $Z_a$ is hydrogen.

In another embodiment, a compound is provided having the structure of Formula (II):

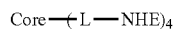

(II)

or a stereoisomer, prodrug or pharmaceutically acceptable salt thereof,
wherein:
(a) NHE is a NHE-inhibiting small molecule moiety having the structure of Formula (A):

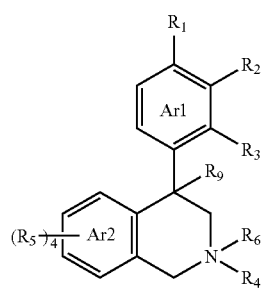

(A)

wherein:
each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-inhibiting small molecule to L, provided at least one is a bond linking the NHE-inhibiting small molecule to L;
is $R_4$ is selected from H, $C_1$-$C_7$ alkyl, or a bond linking the NHE-inhibiting small molecule to L;
$R_6$ is absent or selected from H and $C_1$-$C_7$ alkyl; and
Ar1 and Ar2 independently represent an aromatic ring or a heteroaromatic ring;
(b) Core is a Core moiety having the following structure of Formula (C):

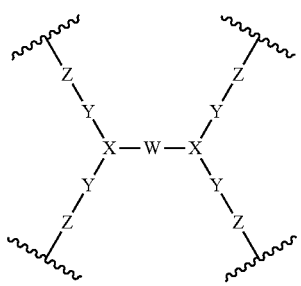

(C)

wherein:
W is selected from alkylene, polyalkylene glycol, —C(=O)—NH-(alkylene)-NH—C(=O)—, —C(=O)—NH-(polyalkylene glycol)-NH—C(=O)—, —C(=O)-(alkylene)-C(=O)—, —C(=O)-(polyalkylene glycol)-C(=O)— and cycloalkyl,
X is N;
Y is $C_{1-6}$alkylene;

Z is selected from —$NZ_a$—C(=O)—$NZ_a$—, —C(=O)$NZ_a$—, —$NZ_a$—C(=O)— and heteroaryl;
each $Z_a$ is independently selected from hydrogen and $C_{1-6}$alkyl; and
(c) L is a bond or linker connecting the Core moiety to the NHE-inhibiting small molecules.
In more specific embodiments, the NHE-inhibiting small molecule moiety has the following structure:

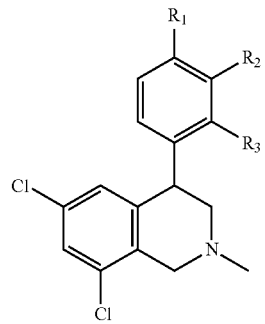

wherein:
each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H, $C_{1-6}$alkyl, —$C_{1-6}$alkyl-OH or a bond linking the NHE-inhibiting small molecule to L, provided at least one is a bond linking the NHE-inhibiting small molecule to L.
In further more specific embodiments, the NHE-inhibiting small molecule moiety has one of the following structures:

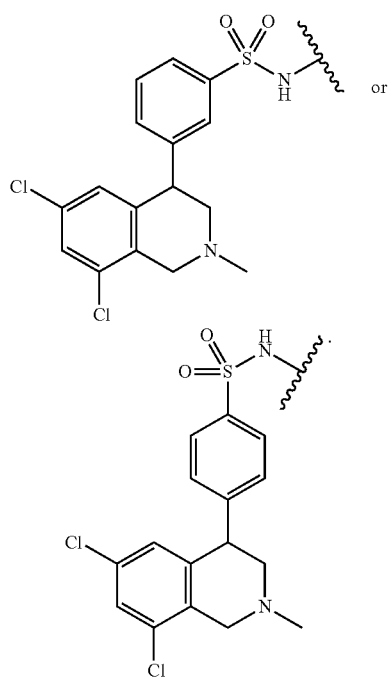

In other more specific embodiments, L is a polyalkylene glycol linker. For example, in certain embodiments, L is a polyethylene glycol linker.

In other more specific embodiments, X is C($X_1$). In further embodiments, each $X_c$ is hydrogen.

In other more specific embodiments, X is N.

In other more specific embodiments, each $Z_a$ is hydrogen.

In another embodiment, a pharmaceutical composition is provided comprising a compound as set forth above, or a stereoisomer, pharmaceutically acceptable salt or prodrug thereof, and a pharmaceutically acceptable carrier, diluent or excipient.

In further embodiments, the composition further comprises a fluid-absorbing polymer. In further embodiments, the fluid-absorbing polymer is delivered directly to the colon. In further embodiments, the fluid-absorbing polymer has a fluid absorbency of at least about 15 g of isotonic fluid per g of polymer under a static pressure of about 5 kPa. In further embodiments, the fluid-absorbing polymer has a fluid absorbency of at least about 15 g of isotonic fluid per g of polymer under a static pressure of about 10 kPa. In further embodiments, the fluid-absorbing polymer is characterized by a fluid absorbency of at least about 10 g/g. In further embodiments, the fluid-absorbing polymer is characterized by a fluid absorbency of at least about 15 g/g. In further embodiments, the fluid-absorbing polymer is superabsorbent. In further embodiments, the fluid-absorbing polymer is a crosslinked, partially neutralized polyelectrolyte hydrogel. In further embodiments, the fluid-absorbing polymer is a crosslinked polyacrylate. In further embodiments, the fluid-absorbing polymer is a polyelectrolyte. In further embodiments, the fluid-absorbing polymer is calcium Carbophil. In further embodiments, the fluid-absorbing polymer is prepared by a high internal phase emulsion process. In further embodiments, the fluid-absorbing polymer is a foam. In further embodiments, the fluid-absorbing polymer is prepared by a aqueous free radical polymerization of acrylamide or a derivative thereof, a crosslinker and a free radical initiator redox system in water. In further embodiments, the fluid-absorbing polymer is a hydrogel. In further embodiments, the fluid-absorbing polymer is an N-alkyl acrylamide. In further embodiments, the fluid-absorbing polymer is a superporous gel. In further embodiments, the fluid-absorbing polymer is naturally occurring. In further embodiments, the fluid-absorbing polymer is selected from the group consisting of xanthan, guar, wellan, hemicelluloses, alkyl-cellulose hydro-alkyl-cellulose, carboxy-alkyl-cellulose, carrageenan, dextran, hyaluronic acid and agarose. In further embodiments, the fluid-absorbing polymer is psyllium. In further embodiments, the fluid-absorbing polymer is a polysaccharide that includes xylose and arabinose. In further embodiments, the fluid-absorbing polymer is a polysaccharide that includes xylose and arabinose, wherein the ratio of xylose to arabinose is at least about 3:1, by weight.

In further embodiments, the composition further comprises another pharmaceutically active agent or compound. In further embodiments, the composition further comprises another pharmaceutically active agent or compound selected from the group consisting of a diuretic, cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent, lipid-lowering agent, and peroxisome proliferator-activated receptor (PPAR) gamma agonist agent. In further embodiments, the diuretic is selected from the group consisting of a high ceiling loop diuretic, a benzothiadiazide diuretic, a potassium sparing diuretic, and a osmotic diuretic. In further embodiments, the composition further comprises another pharmaceutically active agent or compound selected from the group consisting of an analgesic peptide or agent. In further embodiments, the composition further comprises another pharmaceutically active agent or compound selected from the group consisting of a laxative agent selected from a bulk-producing agent (e.g. psyllium husk (Metamucil)), methylcellulose (Citrucel), polycarbophil, dietary fiber, apples, stool softeners/surfactant (e.g., docusate, Colace, Diocto), a hydrating or osmotic agent (e.g., dibasic sodium phosphate, magnesium citrate, magnesium hydroxide (Milk of magnesia), magnesium sulfate (which is Epsom salt), monobasic sodium phosphate, sodium biphosphate), a hyperosmotic agent (e.g., glycerin suppositories, sorbitol, lactulose, and polyethylene glycol (PEG)).

In another embodiment, a method for inhibiting NHE-mediated antiport of sodium and hydrogen ions is provided, the method comprising administering to a mammal in need thereof a pharmaceutically effective amount of a compound or pharmaceutical composition as set forth above.

In another embodiment, a method for treating a disorder associated with fluid retention or salt overload is provided, the method comprising administering to a mammal in need thereof a pharmaceutically effective amount of a compound or pharmaceutical composition as set forth above.

In another embodiment, a method for treating a disorder selected from the group consisting of heart failure (such as congestive heart failure), chronic kidney disease, end-stage renal disease, liver disease, and peroxisome proliferator-activated receptor (PPAR) gamma agonist-induced fluid retention is provided, the method comprising administering to a mammal in need thereof a pharmaceutically effective amount of a compound or pharmaceutical composition as set forth above.

In another embodiment, a method for treating hypertension is provided, the method comprising administering to a mammal in need thereof a pharmaceutically effective amount of a compound or pharmaceutical composition as set forth above.

In further embodiments, the method comprises administering a pharmaceutically effective amount of the compound to the mammal in order to increase the mammal's daily fecal output of sodium and/or fluid. In further embodiments, the method comprises administering a pharmaceutically effective amount of the compound to the mammal in order to increase the mammal's daily fecal output of sodium by at least about 30 mmol, and/or fluid by at least about 200 ml. In further embodiments, the mammal's fecal output of sodium and/or fluid is increased without introducing another type of cation in a stoichiometric or near stoichiometric fashion via an ion exchange process. In further embodiments, the method further comprises administering to the mammal a fluid-absorbing polymer to absorb fecal fluid resulting from the use of the compound that is substantially active in the gastrointestinal tract to inhibit NHE-mediated antiport of sodium ions and hydrogen ions therein.

In further embodiments, the compound or composition is administered to treat hypertension. In further embodiments, the compound or composition is administered to treat hypertension associated with dietary salt intake. In further embodiments, administration of the compound or composition allows the mammal to intake a more palatable diet. In further embodiments, the compound or composition is administered to treat fluid overload. In further embodiments, the fluid overload is associated with congestive heart failure. In further embodiments, the fluid overload is associated with end stage renal disease. In further embodiments, the fluid overload is associated with peroxisome proliferator-activated receptor (PPAR) gamma agonist therapy. In further embodiments, the compound or composition is administered to treat sodium overload. In further embodiments, the compound or composition is administered to reduce interdialytic weight gain in ESRD patients. In further embodiments, the compound or composition is administered to treat edema. In further embodiments, the edema is caused by chemotherapy, pre-menstrual fluid overload or preeclampsia.

In further embodiments, the compound or composition is administered orally, by rectal suppository, or enema.

In further embodiments, the method comprises administering a pharmaceutically effective amount of the compound or composition in combination with one or more additional pharmaceutically active compounds or agents. In further embodiments, the one or more additional pharmaceutically active compounds or agents is selected from the group consisting of a diuretic, cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent, lipid-lowering agent, and peroxisome proliferator-activated receptor (PPAR) gamma agonist agent. In further embodiments, the diuretic is selected from the group consisting of a high ceiling loop diuretic, a benzothiadiazide diuretic, a potassium sparing diuretic, and a osmotic diuretic. In further embodiments, the pharmaceutically effective amount of the compound or composition, and the one or more additional pharmaceutically active compounds or agents, are administered as part of a single pharmaceutical preparation. In further embodiments, the pharmaceutically effective amount of the compound or composition, and the one or more additional pharmaceutically active compounds or agents, are administered as individual pharmaceutical preparations. In further embodiments, the individual pharmaceutical preparation are administered sequentially. In further embodiments, the individual pharmaceutical preparation are administered simultaneously.

In another embodiment, a method for treating a gastrointestinal tract disorder is provided, the method comprising administering to a mammal in need thereof a pharmaceutically effective amount of a compound or pharmaceutical composition as set forth above.

In further embodiments, the gastrointestinal tract disorder is a gastrointestinal motility disorder. In further embodiments, the gastrointestinal tract disorder is irritable bowel syndrome. In further embodiments, the gastrointestinal tract disorder is chronic constipation. In further embodiments, the gastrointestinal tract disorder is chronic idiopathic constipation. In further embodiments, the gastrointestinal tract disorder is chronic constipation occurring in cystic fibrosis patients. In further embodiments, the gastrointestinal tract disorder is opioid-induced constipation. In further embodiments, the gastrointestinal tract disorder is a functional gastrointestinal tract disorder. In further embodiments, the gastrointestinal tract disorder is selected from the group consisting of chronic intestinal pseudo-obstruction and colonic pseudo-obstruction. In further embodiments, the gastrointestinal tract disorder is Crohn's disease. In further embodiments, the gastrointestinal tract disorder is ulcerative colitis. In further embodiments, the gastrointestinal tract disorder is a disease referred to as inflammatory bowel disease. In further embodiments, the gastrointestinal tract disorder is associated with chronic kidney disease (stage 4 or 5). In further embodiments, the gastrointestinal tract disorder is constipation induced by calcium supplement. In further embodiments, the gastrointestinal tract disorder is constipation, and the constipation to be treated is associated with the use of a therapeutic agent. In further embodiments, the gastrointestinal tract disorder is constipation, and the constipation to be treated is associated with a neuropathic disorder. In further embodiments, the gastrointestinal tract disorder is constipation, and the constipation to be treated is post-surgical constipation (postoperative ileus). In further embodiments, the gastrointestinal tract disorder is constipation, and the constipation to be treated is idiopathic (functional constipation or slow transit constipation). In further embodiments, the gastrointestinal tract disorder is constipation, and the constipation to be treated is associated with neuropathic, metabolic or an endocrine disorder (e.g., diabetes mellitus, renal failure, hypothyroidism, hyperthyroidism, hypocalcaemia, Multiple Sclerosis, Parkinson's disease, spinal cord lesions, neurofibromatosis, autonomic neuropathy, Chagas disease, Hirschsprung's disease or cystic fibrosis, and the like). In further embodiments, the gastrointestinal tract disorder is constipation, and the constipation to be treated is due the use of drugs selected from analgesics (e.g., opioids), antihypertensives, anticonvulsants, antidepressants, antispasmodics and antipsychotics.

In another embodiment, a method for treating irritable bowel syndrome is provided, the method comprising administering to a mammal in need thereof a pharmaceutically effective amount of a compound or pharmaceutical composition as set forth above.

In further embodiments of the above embodiments, the compound or composition is administered to treat or reduce pain associated with a gastrointestinal tract disorder. In further embodiments, the compound or composition is administered to treat or reduce visceral hypersensitivity associated with a gastrointestinal tract disorder. In further embodiments, the compound or composition is administered to treat or reduce inflammation of the gastrointestinal tract. In further embodiments, the compound or composition is administered to reduce gastrointestinal transit time.

In further embodiments, the compound or composition is administered either orally or by rectal suppository.

In further embodiments, the method comprises administering a pharmaceutically effective amount of the compound or composition, in combination with one or more additional pharmaceutically active compounds or agents. In further embodiments, the one or more additional pharmaceutically active agents or compounds are an analgesic peptide or agent. In further embodiments, the one or more additional pharmaceutically active agents or compounds are selected from the group consisting of a laxative agent selected from a bulk-producing agent (e.g. psyllium husk (Metamucil)), methylcellulose (Citrucel), polycarbophil, dietary fiber, apples, stool softeners/surfactant (e.g., docusate, Colace, Diocto), a hydrating or osmotic agent (e.g., dibasic sodium phosphate, magnesium citrate, magnesium hydroxide (Milk of magnesia), magnesium sulfate (which is Epsom salt), monobasic sodium phosphate, sodium biphosphate), and a hyperosmotic agent (e.g., glycerin suppositories, sorbitol, lactulose, and polyethylene glycol (PEG)). In further embodiments, the pharmaceutically effective amount of the compound or composition, and the one or more additional pharmaceutically active compounds or agents, are administered as part of a single pharmaceutical preparation. In further embodiments, the pharmaceutically effective amount of the compound or composition, and the one or more additional pharmaceutically active compounds or agents, are administered as individual pharmaceutical preparations. In further embodiments, the individual pharmaceutical preparation are administered sequentially. In further embodiments, the individual pharmaceutical preparation are administered simultaneously.

These and other aspects of the invention will be apparent upon reference to the following detailed description.

DETAILED DESCRIPTION

In accordance with the present disclosure, and as further detailed herein below, it has been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of various disorders that may be associated with or caused by fluid retention and/or salt overload, and/or disorders such as heart failure (in particular, congestive heart failure), chronic kidney disease, end-stage renal disease, liver disease, and/or peroxisome proliferator-activated receptor (PPAR) gamma agonist-induced fluid retention. More specifically, it has been found that the inhibition of the NHE-mediated antiport of sodium ions and hydrogen ions in the GI tract increases the fecal excretion of sodium, effectively reducing systemic levels of sodium and fluid. This, in turn, improves the clinical status of a patient suffering from, for example, CHF, ESRD/CKD and/or liver disease. It has further been found that such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE-inhibiting compound.

Additionally, and also as further detailed herein below, it has further been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of hypertension, that may be associated with or caused by fluid retention and/or salt overload. More specifically, it has been found that the inhibition of the NHE-mediated antiport of sodium ions and hydrogen ions in the GI tract increases the fecal excretion of sodium, effectively reducing systemic levels of sodium and fluid. This, in turn, improves the clinical status of a patient suffering from hypertension. Such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE-inhibiting compound.

Additionally, and also as further detailed herein below, it has further been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of various gastrointestinal tract disorders, including the treatment or reduction of pain associated with gastrointestinal tract disorders, and more particularly to the restoration of appropriate fluid secretion in the gut and the improvement of pathological conditions encountered in constipation states. Applicants have further recognized that by blocking sodium ion re-absorption, the compounds of the present disclosure restore fluid homeostasis in the GI tract, particularly in situations wherein fluid secretion/absorption is altered in such a way that it results in a high degree of feces dehydration, low gut motility, and/or a slow transit-time producing constipation states and GI discomfort generally. It has further been found that such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE-inhibiting compound.

Due to the presence of NHEs in other organs or tissues in the body, the method of the present disclosure employs the use of compounds and compositions that are desirably highly selective or localized, thus acting substantially in the gastrointestinal tract without exposure to other tissues or organs. In this way, any systemic effects can be minimized (whether they are on-target or off-target). Accordingly, it is to be noted that, as used herein, and as further detailed elsewhere herein, "substantially active in the gastrointestinal tract" generally refers to compounds that are substantially systemically non-bioavailable and/or substantially impermeable to the layer of epithelial cells, and more specifically epithelium of the GI tract. It is to be further noted that, as used herein, and as further detailed elsewhere herein, "substantially impermeable" more particularly encompasses compounds that are impermeable to the layer of epithelial cells, and more specifically the gastrointestinal epithelium (or epithelial layer). "Gastrointestinal epithelium" refers to the membranous tissue covering the internal surface of the gastrointestinal tract. Accordingly, by being substantially impermeable, a compound has very limited ability to be transferred across the gastrointestinal epithelium, and thus contact other internal organs (e.g., the brain, heart, liver, etc.). The typical mechanism by which a compound can be transferred across the gastrointestinal epithelium is by either transcellular transit (a substance travels through the cell, mediated by either passive or active transport passing through both the apical and basolateral membranes) and/or by paracellular transit, where a substance travels between cells of an epithelium, usually through highly restrictive structures known as "tight junctions".

The compounds of the present disclosure may therefore not be absorbed, and are thus essentially not systemically bioavailable at all (e.g., impermeable to the gastrointestinal epithelium at all), or they show no detectable concentration of the compound in serum. Alternatively, the compounds may: (i) exhibit some detectable permeability to the layer of epithelial cells, and more particularly the epithelium of the GI tract, of less than about 20% of the administered compound (e.g., less than about 15%, about 10%, or even about 5%, and for example greater than about 0.5%, or 1%), but then are rapidly cleared in the liver (i.e., hepatic extraction) via first-pass metabolism; and/or (ii) exhibit some detectable permeability to the layer of epithelial cells, and more particularly the epithelium of the GI tract, of less than about 20% of the administered compound (e.g., less than about 15%, about 10%, or even about 5%, and for example greater than about 0.5%, or 1%), but then are rapidly cleared in the kidney (i.e., renal excretion).

Compounds may also be cleared from circulation unchanged into the bile by biliary excretion. The compounds of the present disclosure may therefore not exhibit detectable concentrations in the bile. Alternatively, the compounds may exhibit some detectable concentration in the bile and more particularly the epithelium of the biliary tract and gallbladder of 10 μM, less than 1 μM, less than 0.1 μM, less than 0.01 μM or less than about 0.001 μM.

In this regard it is to be still further noted that, as used herein, "substantially systemically non-bioavailable" generally refers to the inability to detect a compound in the systemic circulation of an animal or human following an oral dose of the compound. For a compound to be bioavailable, it must be transferred across the gastrointestinal epithelium (that is, substantially permeable as defined above), be transported via the portal circulation to the liver, avoid substantial metabolism in the liver, and then be transferred into systemic circulation.

Without being held to any particular theory, the NHE-inhibiting compounds (e.g., NHE-3, -2 and/or -8 inhibitors) of the present disclosure are believed to act via a distinct and unique mechanism, causing the retention of fluid and ions in the GI tract (and stimulating fecal excretion) rather than stimulating increased secretion of said fluid and ions. For example, lubiprostone (Amitiza® Sucampo/Takeda) is a bicyclic fatty acid prostaglandin E1 analog that activates the Type 2 Chloride Channel (ClC-2) and increases chloride-rich fluid secretion from the serosal to the mucosal side of the GI tract (see, e.g., Pharmacological Reviews for Amitiza®, NDA package). Linaclotide (MD-1100 acetate, Microbia/Forest Labs) is a 14 amino acid peptide analogue of an endogenous hormone, guanylin, and indirectly activates the Cystic Fibrosis Transmembrane Conductance Regulator (CFTR) thereby inducing fluid and electrolyte secretion into the GI (see, e.g., Li et al., J. Exp. Med., vol. 202 (2005), pp. 975-986). The substantially impermeable NHE-inhibiting compounds of the present disclosure act to inhibit the reuptake of salt and fluid rather than promote secretion. Since the GI tract processes about 9 liters of fluid and about 800 meq of Na each day, it is anticipated that NHE inhibition could permit the removal of substantial quantities of systemic fluid and sodium to resorb edema and resolve CHF symptoms.

I. Substantially Impermeable or Substantially Systemically Non-Bioavailable NHE-Inhibiting Compounds In one embodiment, a compound is provided having the structure of Formula (I):

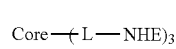
(I)

or a stereoisomer, prodrug or pharmaceutically acceptable salt thereof,
wherein:
(a) NHE is a NHE-inhibiting small molecule moiety having the following structure of Formula (A):

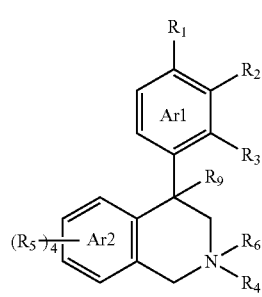
(A)

wherein:
each $R_1$, $R_2$, $R_3$, $R_5$ and $R_9$ are independently selected from H, halogen, $-NR_7(CO)R_8$, $-(CO)NR_7R_8$, $-SO_2-NR_7R_8$, $-NR_7SO_2R_8$, $-NR_7R_8$, $-OR_7$, $-O(CO)NR_7R_8$, $-NR_7(CO)OR_8$, and $-NR_7SO_2NR_8$, where $R_7$ and $R_8$ are independently selected from H, $C_{1-6}$ alkyl, $-C_{1-6}$ alkyl-OH or a bond linking the NHE-inhibiting small molecule to L, provided at least one is a bond linking the NHE-inhibiting small molecule to L;

$R_4$ is selected from H, $C_1$-$C_7$ alkyl, or a bond linking the NHE-inhibiting small molecule to L;

$R_6$ is absent or selected from H and $C_1$-$C_7$ alkyl; and

Ar1 and Ar2 independently represent an aromatic ring or a heteroaromatic ring;

(b) Core is a Core moiety having the following structure of Formula (B):

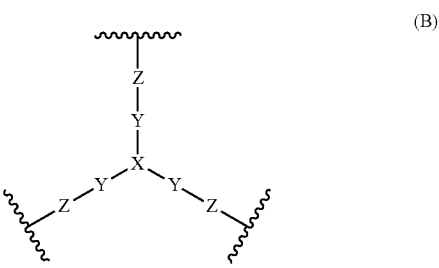
(B)

wherein:
is X is selected from $C(X_1)$, N and $N(C_{1-6}$ alkyl);
$X_1$ is selected from hydrogen, optionally substituted alkyl, $-NX_aX_b$, $-NO_2$, $-NX_c-C(=O)-NX_c-X_a$, $-C(=O)NX_c-X_a$, $-NX_c-C(=O)-X_a$, $-NX_c-SO_2-X_a$, $-C(=O)-X_a$ and $-OX_a$,
each $X_a$ and $X_b$ are independently selected from hydrogen, optionally substituted alkyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl and optionally substituted heteroarylalkyl;
Y is $C_{1-6}$alkylene;
Z is selected from $-NZ_a-C(=O)-NZ_a-$, $-C(=O)NZ_a-$, $-NZ_a-C(=O)-$ and heteroaryl when X is $CX_1$;
Z is selected from $-NZ_a-C(=O)-NZ_a-$, $-NZ_a-C(=O)-$ and heteroaryl when X is N or $N(C_{1-6}$ alkyl); and
each $X_c$ and $Z_a$ is independently selected from hydrogen and $C_{1-6}$ alkyl; and (c) L is a bond or linker connecting the Core moiety to the NHE-inhibiting small molecule moieties, the resulting NHE-inhibiting compound (i.e., a compound of Formula (I)) possessing overall physicochemical properties that render it substantially impermeable or substantially systemically non-bioavailable. The Core moiety may be bound to essentially any position on, or within, the NHE-inhibiting small molecule moiety, provided that the installation thereof does not significantly adversely impact NHE-inhibiting activity.

In another embodiment, a compound is provided having the structure of Formula (II):

(II)

or a stereoisomer, prodrug or pharmaceutically acceptable salt thereof, wherein:
(a) NHE is a NHE-inhibiting small molecule moiety having the structure of Formula (A):

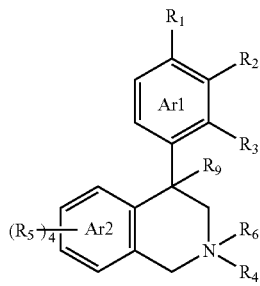

wherein:
each $R_1$, $R_2$, $R_3$, $R_5$ and $R_9$ are independently selected from H, halogen, $-NR_7(CO)R_8$, $-(CO)NR_7R_8$, $-SO_2-NR_7R_8$, $-NR_7SO_2R_8$, $-NR_7R_8$, $-OR_7$, $-SR_7$, $-O(CO)NR_7R_8$, $-NR_7(CO)OR_8$, and $-NR_7SO_2NR_8$, where $R_7$ and $R_8$ are independently selected from H, $C_{1-6}$ alkyl, $-C_{1-6}$ alkyl-OH or a bond linking the NHE-inhibiting small molecule to L, provided at least one is a bond linking the NHE-inhibiting small molecule to L;
$R_4$ is selected from H, $C_1$-$C_7$ alkyl, or a bond linking the NHE-inhibiting small molecule to L;
$R_6$ is absent or selected from H and $C_1$-$C_7$ alkyl; and
Ar1 and Ar2 independently represent an aromatic ring or a heteroaromatic ring;
(b) Core is a Core moiety having the following structure of Formula (C):

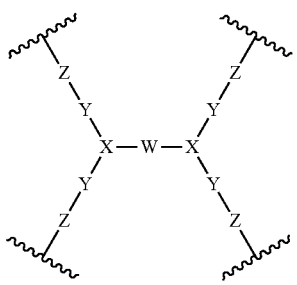

wherein:
W is selected from alkylene, polyalkylene glycol, —C(=O)—NH-(alkylene)-NH—C(=O)—, —C(=O)—NH-(polyalkylene glycol)-NH—C(=O)—, —C(=O)-(alkylene)-C(=O)—, —C(=O)-(polyalkylene glycol)-C(=O)— and cycloalkyl,
X is N;
Y is $C_{1-6}$ alkylene;
Z is selected from $-NZ_a-C(=O)-NZ_a-$, $-C(=O)NZ_a-$, $-NZ_a-C(=O)-$ and heteroaryl;
each $Z_a$ is independently selected from hydrogen and $C_{1-6}$ alkyl; and
(c) L is a bond or linker connecting the Core moiety to the NHE-inhibiting small molecules, the resulting NHE-inhibiting compound (i.e., a compound of Formula (II)) possessing overall physicochemical properties that render it substantially impermeable or substantially systemically non-bioavailable. The Core moiety may be bound to essentially any position on, or within, the NHE-inhibiting small molecule moiety, provided that the installation thereof does not significantly adversely impact NHE-inhibiting activity.

It is to be noted that, in the structures illustrated herein, all of the various linkages or bonds will not be shown in every instance. For example, in one or more of the structures illustrated above, a bond or connection between the NHE-inhibiting small molecule moiety and the Core moiety is not always shown. However, this should not be viewed in a limiting sense. Rather, it is to be understood that the NHE-inhibiting small molecule moiety is bound or connected in some way (e.g., by a bond or linker of some kind) to the Core moiety, such that the resulting NHE-inhibiting compound is suitable for use (i.e., substantially impermeable or substantially systemically non-bioavailable in the GI tract).

The above noted embodiments are further illustrated herein below. For example, the first representation below of an exemplary oligomer compound, wherein the various parts of the compound are identified, is intended to provide a broad context for the disclosure provided herein. It is to be noted that while each NHE-inhibiting small molecule moiety in the structure below is the same, it is within the scope of this disclosure that each is independently selected and may be the same or different. In the illustration below, the linker moiety is a polyethylene glycol (PEG) motif PEG derivatives are advantageous due in part to their aqueous solubility, which may help avoid hydrophobic collapse (the intramolecular interaction of hydrophobic motifs that can occur when a hydrophobic molecule is exposed to an aqueous environment (see, e.g., Wiley, R. A.; Rich, D. H. Medical Research Reviews 1993, 13(3), 327-384). The core moiety illustrated below is also advantageous because it provides some rigidity to the molecule, allowing an increase in distance between the NHE-inhibiting small molecule moieties while minimally increasing rotational degrees of freedom.

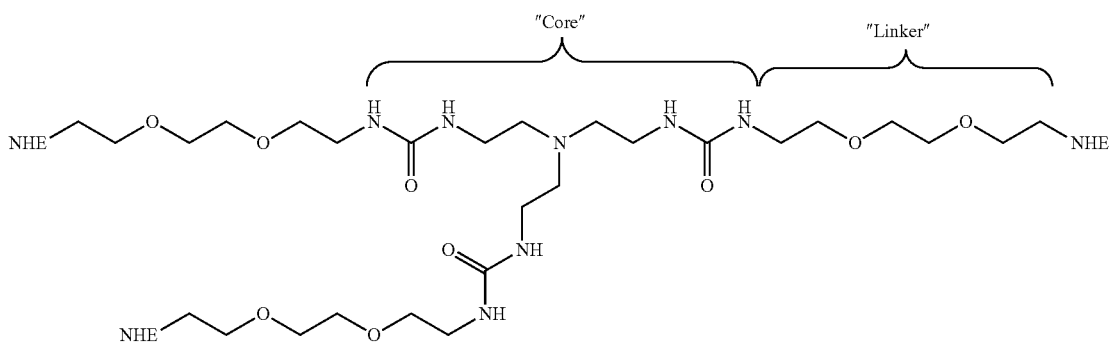

In designing and making the substantially impermeable or substantially systemically non-bioavailable NHE-inhibiting compounds that may be utilized for the treatments detailed in the instant disclosure, it may in some cases be advantageous to first determine a likely point of attachment on a NHE-inhibiting small molecule moiety, where a core or linker might be installed or attached before making a series of candidate multivalent or polyvalent compounds. This may be done by one skilled in the art via known methods by systematically installing functional groups, or functional groups displaying a fragment of the desired core or linker, onto various positions of the NHE-inhibiting small molecule moiety and then testing these adducts to determine whether the modified compound still retains desired biological properties (e.g., NHE-inhibiting activity). An understanding of the SAR of the compound also allows the design of cores and/or linkers that contribute positively to the activity of the resulting compounds.

Another aspect to be considered in the design of cores and linkers is the limiting or preventing of hydrophobic collapse. Compounds with extended hydrocarbon functionalities may collapse upon themselves in an intramolecular fashion, causing an increased enthalpic barrier for interaction with the desired biological target. Accordingly, when designing cores and linkers, these are preferably designed to be resistant to hydrophobic collapse. For example, conformational constraints such as rigid monocyclic, bicyclic or polycyclic rings can be installed in a core or linker to increase the rigidity of the structure. Unsaturated bonds, such as alkenes and alkynes, may also or alternatively be installed. Such modifications may ensure the NHE-inhibiting compound is accessible for productive binding with its target. Furthermore, the hydrophilicity of the linkers may be improved by adding hydrogen bond donor or acceptor motifs, or ionic motifs such as amines that are protonated in the GI, or acids that are deprotonated. Such modifications will increase the hydrophilicity of the core or linker and help prevent hydrophobic collapse. Furthermore, such modifications will also contribute to the impermeability of the resulting compounds by increasing tPSA.

It is understood that any embodiment of the compounds of the present invention, as set forth above, and any specific substituent set forth herein in such compounds, as set forth above, may be independently combined with other embodiments and/or substituents of such compounds to form embodiments of the inventions not specifically set forth above. In addition, in the event that a list of substituents is listed for any particular substituent in a particular embodiment and/or claim, it is understood that each individual substituent may be deleted from the particular embodiment and/or claim and that the remaining list of substituents will be considered to be within the scope of the invention. Furthermore, it is understood that in the present description, combinations of substituents and/or variables of the depicted formulae are permissible only if such contributions result in stable compounds.

II. Terminology, Physical and Performance Properties

A. Terminology

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.
"Cyano" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —$OR_a$ where $R_a$ is an alkyl radical as defined above containing one to twelve carbon atoms. Unless stated otherwise specifically in the specification, an alkoxy group may be optionally substituted.

"Alkylamino" refers to a radical of the formula —$NHR_a$ or —$NR_aR_a$ where each $R_a$ is, independently, an alkyl radical as defined above containing one to twelve carbon atoms. Unless stated otherwise specifically in the specification, an alkylamino group may be optionally substituted.

"Thioalkyl" refers to a radical of the formula —$SR_a$ where $R_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ here $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated to specifically in the specification, a cycloalkyl group may be optionally substituted.

"Cycloalkylalkyl" refers to a radical of the formula —$R_bR_d$ where $R_d$ is an alkylene chain as defined above and $R_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$, —$(CH_2CH_2O)_{2\text{-}10}R_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals "Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

In accordance with the present disclosure, the compounds described herein are designed to be substantially active or localized in the gastrointestinal lumen of a human or animal subject. The term "gastrointestinal lumen" is used interchangeably herein with the term "lumen," to refer to the space or cavity within a gastrointestinal tract (GI tract, which can also be referred to as the gut), delimited by the apical membrane of GI epithelial cells of the subject. In some embodiments, the compounds are not absorbed through the layer of epithelial cells of the GI tract (also known as the GI epithelium). "Gastrointestinal mucosa" refers to the layer(s) of cells separating the gastrointestinal lumen from the rest of the body and includes gastric and intestinal mucosa, such as the mucosa of the small intestine. A "gastrointestinal epithelial cell" or a "gut epithelial cell" as used herein refers to any epithelial cell on the surface of the gastrointestinal mucosa that faces the lumen of the gastrointestinal tract, including, for example, an epithelial cell of the stomach, an intestinal epithelial cell, a colonic epithelial cell, and the like.

"Substantially systemically non-bioavailable" and/or "substantially impermeable" as used herein (as well as variations thereof) generally refer to situations in which a statistically significant amount, and in some embodiments essentially all of the compound of the present disclosure (which includes the NHE-inhibitor small molecule), remains in the gastrointestinal lumen. For example, in accordance with one or more embodiments of the present disclosure, preferably at least about 70%, about 80%, about 90%, about 95%, about 98%, about 99%, or even about 99.5%, of the compound remains in the gastrointestinal lumen. In such cases, localization to the gastrointestinal lumen refers to reducing net movement across a gastrointestinal layer of epithelial cells, for example, by way of both transcellular and paracellular transport, as well as by active and/or passive transport. The compound in such embodiments is hindered from net permeation of a layer of gastrointestinal epithelial cells in transcellular transport, for example, through an apical membrane of an epithelial cell of the small intestine. The compound in these embodiments is also hindered from net permeation through the "tight junctions" in paracellular transport between gastrointestinal epithelial cells lining the lumen.

In this regard it is to be noted that, in one particular embodiment, the compound is essentially not absorbed at all by the GI tract or gastrointestinal lumen. As used herein, the terms "substantially impermeable" or "substantially systemically non-bioavailable" refers to embodiments wherein no detectable amount of absorption or permeation or systemic exposure of the compound is detected, using means generally known in the art.

In this regard it is to be further noted, however, that in alternative embodiments "substantially impermeable" or "substantially systemically non-bioavailable" provides or allows for some limited absorption in the GI tract, and more particularly the gut epithelium, to occur (e.g., some detectable amount of absorption, such as for example at least about 0.1%, 0.5%, 1% or more and less than about 30%, 20%, 10%, 5%, etc., the range of absorption being for example between about 1% and 30%, or 5% and 20%, etc.; stated another way, "substantially impermeable" or "substantially systemically non-bioavailable" refers to compounds that exhibit some detectable permeability to an epithelium layer of cells in the GI tract of less than about 20% of the administered compound (e.g., less than about 15%, about 10%, or even about 5%, and for example greater than about 0.5%, or 1%), but then are cleared by the liver (i.e., hepatic extraction) and/or the kidney (i.e., renal excretion).

B. Permeability

In this regard it is to be noted that, in various embodiments, the ability of a compound to be substantially systemically non-bioavailable is based on the compound charge, size, and/or other physicochemical parameters (e.g., polar surface area, number of hydrogen bond donors and/or acceptors therein, number of freely rotatable bonds, etc.). More specifically, it is to be noted that the absorption character of a compound can be selected by applying principles of pharmacodynamics, for example, by applying Lipinski's rule, also known as "the rule of five." Although not a rule, but rather a set of guidelines, Lipinski shows that small molecule drugs with (i) a molecular weight, (ii) a number of hydrogen bond donors, (iii) a number of hydrogen bond acceptors, and/or (iv) a water/octanol partition coefficient (Moriguchi Log P), greater than a certain threshold value, generally do not show significant systemic concentration (i.e., are generally not absorbed to any significant degree). (See, e.g., Lipinski et al., *Advanced Drug Delivery Reviews*, 46, 2001 3-26, incorporated herein by reference.) Accordingly, substantially systemically non-bioavailable compounds (e.g., substantially systemically non-bioavailable NHE-inhibiting compounds) can be designed to have molecular structures exceeding one or more of Lipinski's threshold values. (See also Lipinski et al., *Experimental and Computational Approaches to Estimate Solubility and Permeability in Drug Discovery and Development Settings*, Adv. Drug Delivery Reviews, 46:3-26 (2001); and Lipinski, *Drug-like Properties and the Causes of Poor Solubility and Poor Permeability*, J. Pharm. & Toxicol. Methods, 44:235-249 (2000), incorporated herein by reference.) In some embodiments, for example, a substantially impermeable or substantially systemically non-bioavailable NHE-inhibiting compound of the present disclosure can be constructed to feature one or more of the following characteristics: (i) a MW greater than about 500 Da, about 1000 Da, about 2500 Da, about 5000 Da, about 10,000 Da or more (in the non-salt form of the compound); (ii) a total number of NH and/or OH and/or other potential hydrogen bond donors greater than about 5, about 10, about 15 or more; (iii) a total number of O atoms and/or N atoms and/or other potential hydrogen bond acceptors greater than about 5, about 10, about 15 or more; and/or (iv) a Moriguchi partition coefficient greater than about $10^5$ (i.e., Log P greater than about 5, about 6, about 7, etc.), or alternatively less than about 10 (i.e., a Log P of less than 1, or even 0).

In addition to the parameters noted above, the molecular polar surface area (i.e., "PSA"), which may be characterized as the surface belonging to polar atoms, is a descriptor that has also been shown to correlate well with passive transport through membranes and, therefore, allows prediction of transport properties of drugs. It has been successfully applied for the prediction of intestinal absorption and Caco2 cell monolayer penetration. (For Caco2 cell monolayer penetration test details, see for example the description of the Caco2 Model provided in Example 31 of U.S. Pat. No. 6,737,423, the entire contents of which are incorporated herein by reference for all relevant and consistent purposes, and the text of Example 31 in particular, which may be applied for example to the evaluation or testing of the compounds of the present disclosure.) PSA is expressed in $Å^2$ (squared angstroms) and is computed from a three-dimensional molecular representation. A fast calculation method is now available (see, e.g., Ertl et al., *Journal of Medicinal Chemistry*, 2000, 43, 3714-3717, the entire contents of which are incorporated herein by reference for all relevant and consistent purposes) using a desktop computer and commercially available chemical graphic tools packages, such as ChemDraw. The term "topological PSA" (tPSA) has been coined for this fast-calculation method. tPSA is well correlated with human absorption data with common drugs (see, e.g., Table 1, below):

TABLE 1

| name | % FA[a] | TPSA[b] |
|---|---|---|
| metoprolol | 102 | 50.7 |
| nordiazepam | 99 | 41.5 |
| diazepam | 97 | 32.7 |
| oxprenolol | 97 | 50.7 |
| phenazone | 97 | 26.9 |
| oxazepam | 97 | 61.7 |
| alprenolol | 96 | 41.9 |
| practolol | 95 | 70.6 |
| pindolol | 92 | 57.3 |
| ciprofloxacin | 69 | 74.6 |
| metolazone | 64 | 92.5 |
| tranexamic acid | 55 | 63.3 |
| atenolol | 54 | 84.6 |
| sulpiride | 36 | 101.7 |
| mannitol | 26 | 121.4 |
| foscarnet | 17 | 94.8 |
| sulfasalazine | 12 | 141.3 |
| olsalazine | 2.3 | 139.8 |
| lactulose | 0.6 | 197.4 |
| raffinose | 0.3 | 268.7 |

(from Ertl et al., *J. Med. Chem.*, 2000, 43:3714-3717). Accordingly, in some preferred embodiments, the compounds of the present disclosure may be constructed to exhibit a tPSA value greater than about 100 $Å^2$, about 120 $Å^2$, about 130 $Å^2$, or about 140 $Å^2$, and in some instances about 150 $Å^2$, about 200 $Å^2$, about 250 $Å^2$, about 270 $Å^2$, about 300 $Å^2$, about 400 $Å^2$, or even about 500 $Å^2$, such that the compounds are substantially impermeable or substantially systemically non-bioavailable (as defined elsewhere herein).

Because there are exceptions to Lipinski's "rule," or the tPSA model, the permeability properties of the compounds of the present disclosure may be screened experimentally. The permeability coefficient can be determined by methods known to those of skill in the art, including for example by Caco-2 cell permeability assay and/or using an artificial membrane as a model of a gastrointestinal epithelial cell. (As previously noted above, see for example U.S. Pat. No. 6,737,423, Example 31 for a description of the Caco-2 Model, which is incorporated herein by reference). A synthetic membrane impregnated with, for example, lecithin and/or dodecane to mimic the net permeability characteristics of a gastrointestinal mucosa, may be utilized as a model of a gastrointestinal mucosa. The membrane can be used to separate a compartment containing the compound of the present disclosure from a compartment where the rate of permeation will be monitored. Also, parallel artificial membrane permeability assays (PAMPA) can be performed. Such in vitro measurements can reasonably indicate actual permeability in vivo. (See, for example, Wohnsland et al., *J. Med. Chem.*, 2001, 44:923-930; Schmidt et al., Millipore Corp. Application Note, 2002, no AN1725EN00, and no AN1728EN00, incorporated herein by reference.)

Accordingly, in some embodiments, the compounds utilized in the methods of the present disclosure may have a permeability coefficient, $P_{app}$, of less than about $100 \times 10^{-6}$ cm/s, or less than about $10 \times 10^{-6}$ cm/s, or less than about $1 \times 10^{-6}$ cm/s, or less than about $0.1 \times 10^{-6}$ cm/s, when measured using means known in the art (such as for example the permeability experiment described in Wohnsland et al., *J. Med. Chem.*, 2001, 44. 923-930, the contents of which is incorporated herein by reference).

As previously noted, in accordance with the present disclosure, a NHE-inhibiting small molecule moiety is modified as described above to hinder the net absorption through a layer of gut epithelial cells, rendering the resulting compound substantially systemically non-bioavailable. In various embodiments, the compounds of the present disclosure comprise an NHE-inhibiting small molecule moiety linked, coupled or otherwise attached to a moiety which renders the overall compound substantially impermeable or substantially systemically non-bioavailable. More specifically, the NHE-inhibiting small molecule moiety is coupled to a dimer, multimer or polymer moiety, such that the resulting compound is substantially impermeable or substantially systemically non-bioavailable. The dimer, multimer or polymer portion or moiety may be of a molecular weight greater than about 500 Daltons (Da), about 1000 Da, about 2500 Da, about 5000 Da, about 10,000 Da or more, and in particular may have a molecular weight in the range of about 1000 Daltons (Da) to about 500,000 Da, preferably in the range of about 5000 to about 200,000 Da, and more preferably may have a molecular weight that is sufficiently high to essentially preclude any net absorption through a layer of gut epithelial cells of the compound.

C. Persistent Inhibitory Effect

In other embodiments, the substantially impermeable or substantially systemically non-bioavailable NHE-inhibiting compounds utilized in the treatment methods of the present disclosure may additionally exhibit a persistent inhibitor effect. This effect manifests itself when the inhibitory action of a compound at a certain concentration in equilibrium with the epithelial cell (e.g., at or above its inhibitory concentration, IC) does not revert to baseline (i.e., sodium transport without inhibitor) after the compound is depleted by simple washing of the luminal content.

This effect can be interpreted as a result of the tight binding of the NHE-inhibiting compounds to the NHE protein at the intestinal apical side of the gut epithelial cell. The binding can be considered as quasi-irreversible to the extent that, after the compound has been contacted to with the gut epithelial cell and subsequently washed off said gut epithelial cell, the flux of sodium transport is still significantly lower than in the control without the compound. This persistent inhibitory effect has the clear advantage of maintaining drug activity within the GI tract even though the residence time of the active in the upper GI tract is short, and when no entero-biliary recycling process is effective to replenish the compound concentration near its site of action.

Such a persistent inhibitory effect has an obvious advantage in terms of patient compliance, but also in limiting drug exposure within the GI tract.

The persistence effect can be determined using in vitro methods; in one instance, cell lines expressing NHE transporters are split in different vials and treated with a NHE-inhibiting compound and sodium solution to measure the rate of sodium uptake. The cells in one set of vials are washed for different periods of time to remove the inhibitor, and sodium uptake measurement is repeated after the washing. Compounds that maintain their inhibitory effect after multiple/lengthy washing steps (compared to the inhibitory effect measured in the vials where washing does not occur) are persistent inhibitors. Persistence effect can also be characterized ex vivo by using the everted sac technique, whereby transport of Na is monitored using an excised segment of GI perfused with a solution containing the inhibitor and shortly after flushing the bathing solution with a buffer solution free from inhibitor. A persistence effect can also be characterized in vivo by observing the time needed for sodium balance to return to normal when the inhibitor treatment is discontinued. The limit of the method resides in the fact that apical cells (and therefore apical NHE transporters) are sloughed off after a period of 3 to 4 days, the typical turnover time of gut epithelial cells. A persistence effect can be achieved by increasing the residence time of the active compound at the apical surface of the gut epithelial cells; this can be obtained by designing NHE antiport inhibitors with several NHE-inhibiting small molecule moieties built-in the small molecule or oligomer (wherein "several" as used herein typically means at least about 2, about 4, about 6 or more). Examples of such structures in the context of analogs of the antibiotic vancomycin are given in Griffin, et al., *J. Am. Chem. Soc.*, 2003, 125, 6517-6531. Alternatively the compound comprises groups that contribute to increase the affinity towards the gut epithelial cell so as to increase the time of contact with the gut epithelial cell surface. Such groups are referred to as being "mucoadhesive." More specifically, the Core or L moiety can be substituted by such mucoadhesive groups, such as polyacrylates, partially deacetylated chitosan or polyalkylene glycol. (See also Patil, S. B. et al., *Curr. Drug. Deliv.*, 2008, October 5(4), pp. 312-8.)

D. GI Enzyme Resistance

Because the compounds utilized in the treatment methods of the present disclosure are preferably substantially systemically non-bioavailable, and/or preferably exhibit a persistent inhibitory effect, it is also desirable that, during their prolonged residence time in the gut, these compounds sustain the hydrolytic conditions prevailing in the upper GI tract. In such embodiments, compounds of the present disclosure are resistant to enzymatic metabolism. For example, administered compounds are preferably resistant to the activity of P450 enzymes, glucurosyl transferases, sulfotransferases, glutathione S-transferases, and the like, in the intestinal mucosa, as well as gastric (e.g., gastric lipase, and pepsine), pancreatic (e.g., trypsin, triglyceride pancreatic lipase, phospholipase A2, endonucleases, nucleotidases, and alpha-amylase), and brush-border enzymes (e.g., alkaline phosphatase, glycosidases, and proteases) generally known in the art.

The compounds that are utilized in methods of the present disclosure are also preferably resistant to metabolism by the bacterial flora of the gut; that is, the compounds are not substrates for enzymes produced by bacterial flora. In addition, the compounds administered in accordance with the methods of the present disclosure may be substantially inactive towards the gastrointestinal flora, and do not disrupt bacterial growth or survival. As a result, in various embodiments herein, the minimal inhibitory concentration (or "MIC") against GI flora is desirably greater than about 15 µg/ml, about 30 µg/ml, about 60 µg/ml, about 120 µg/ml, or even about 240 µg/ml, the MIC in various embodiments being for example between about 16 and about 32 µg/ml, or between about 64 and about 128 µg/ml, or greater than about 256 µg/ml.

To one skilled in the art of medicinal chemistry, metabolic stability can be achieved in a number of ways. Functionality susceptible to P450-mediated oxidation can be protected by, for example, blocking the point of metabolism with a halogen or other functional group. Alternatively, electron withdrawing groups can be added to a conjugated system to generally provide protection to oxidation by reducing the electrophilicity of the compound. Proteolytic stability can be achieved by avoiding secondary amide bonds, or by incorporating changes in stereochemistry or other modifications that prevent the drug from otherwise being recognized as a substrate by the metabolizing enzyme.

E. Sodium and/or Fluid Output

It is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof, may act to increase the patient's daily fecal output of sodium by at least about 20, about 30 mmol, about 40 mmol, about 50 mmol, about 60 mmol, about 70 mmol, about 80 mmol, about 90 mmol, about 100 mmol, about 125 mmol, about 150 mmol or more, the increase being for example within the range of from about 20 to about 150 mmol/day, or from about 25 to about 100 mmol/day, or from about 30 to about 60 mmol/day Additionally, or alternatively, it is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patent in need thereof, may act to increase the patient's daily fluid output by at least about 100 ml, about 200 ml, about 300 ml, about 400 ml, about 500 ml, about 600 ml, about 700 ml, about 800 ml, about 900 ml, about 1000 ml or more, the increase being for example within the range of from about 100 to about 1000 ml/day, or from about 150 to about 750 ml/day, or from about 200 to about 500 ml/day (assuming isotonic fluid).

F. $C_{max}$ and $IC_{50}$

It is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof at a dose resulting in at least a 10% increase in fecal water content, has a $C_{max}$ that is less than the $IC_{50}$ for NHE-3, more specifically, less than about 10× (10 times) the $IC_{50}$, and, more specifically still, less than about 100× (100 times) the $IC_{50}$.

Additionally, or alternatively, it is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof, may have a $C_{max}$ of less than about 10 ng/ml, about 7.5 ng/ml, about 5 ng/ml, about 2.5 ng/ml, about 1 ng/ml, or about 0.5 ng/ml, the $C_{max}$ being for example within the range of about 1 ng/ml to about 10 ng/ml, or about 2.5 ng/ml to about 7.5 ng/ml.

Additionally, or alternatively, it is also to be noted that, in various embodiments of the present disclosure, one or more of the NHE-inhibiting compounds detailed herein, when administered either alone or in combination with one or more additional pharmaceutically active compounds or agents (including, for example, a fluid-absorbing polymer) to a patient in need thereof, may have a $IC_{50}$ of less than about 10 µM, about 7.5 µM, about 5 µM, about 2.5 µM, about 1 µM, or about 0.5 µM, the $IC_{50}$ being for example within the range of about 1 µM to about 10 µM, or about 2.5 µM to about 7.5 µM.

Additionally, or alternatively, it is also to be noted that, in various embodiments of the present disclosure, one or more of the NHE-inhibiting compounds detailed herein, when administered to a patient in need thereof, may have a ratio of $IC_{50}:C_{max}$, wherein $IC_{50}$ and $C_{max}$ are expressed in terms of the same units, of at least about 10, about 50, about 100, about 250, about 500, about 750, or about 1000.

Additionally, or alternatively, it is also to be noted that, in various embodiments of the present disclosure, wherein one or more of the NHE-inhibiting compounds as detailed herein is orally administered to a patent in need thereof, within the therapeutic range or concentration, the maximum compound concentration detected in the serum, defined as $C_{max}$, is lower than the NHE inhibitory concentration $IC_{50}$ of said compound. As previously noted, as used herein, $IC_{50}$ is defined as the quantitative measure indicating the concentration of the compound required to inhibit 50% of the NHE-mediated Na/H antiport activity in a cell based assay.

III. Pharmaceutical Compositions and Methods of Treatment

A. Compositions and Methods

1. Fluid Retention and/or Salt Overload Disorders

A pharmaceutical composition or preparation that may be used in accordance with the present disclosure for the treatment of various disorders associated with fluid retention and/or salt overload in the gastrointestinal tract (e.g., hypertension, heart failure (in particular, congestive heart failure), chronic kidney disease, end-stage renal disease, liver disease and/or peroxisome proliferator-activated receptor (PPAR) gamma agonist-induced fluid retention) comprises, in general, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein). In some particular embodiments, the NHE-inhibiting compound, including any pharmaceutical composition comprising the compound, is administered with a fluid-absorbing polymer (as more fully described below).

A "subject" or "mammal" is preferably a human, but can also be an animal in need of treatment with a compound of the disclosure, e.g., companion animals (e.g., dogs, cats, and the like), farm animals (e.g., cows, pigs, horses and the like) and laboratory animals (e.g., rats, mice, guinea pigs and the like).

Subjects "in need of treatment" with a compound of the present disclosure, or subjects "in need of NHE inhibition" include subjects with diseases and/or conditions that can be treated with substantially impermeable or substantially systemically non-bioavailable NHE-inhibiting compounds, with or without a fluid-absorbing polymer, to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment may be suffering from hypertension; from salt-sensitive hypertension which may result from dietary salt intake; from a risk of a cardiovascular disorder (e.g., myocardial infarction, congestive heart failure and the like) resulting from hypertension; from heart failure (e.g., congestive heart failure) resulting in fluid or salt overload; from chronic kidney disease resulting in fluid or salt overload, from end stage renal disease resulting in fluid or salt overload; from liver disease resulting in fluid or salt overload; from peroxisome proliferator-activated receptor (PPAR) gamma agonist-induced fluid retention; or from edema resulting from congestive heart failure or end stage renal disease. In various embodiments, a subject in need of treatment typically shows signs of hypervolemia resulting from salt and fluid retention that are common features of congestive heart failure, renal failure or liver cirrhosis. Fluid retention and salt retention manifest themselves by the occurrence of shortness of breath, edema, ascites or interdialytic weight gain. Other examples of subjects that would benefit from the treatment are those suffering from congestive heart failure and hypertensive patients and, particularly, those who are resistant to treatment with diuretics, i.e., patients for whom very few therapeutic options are available. A subject "in need of treatment" also includes a subject with hypertension, salt-sensitive blood pressure and subjects with systolic/diastolic blood pressure greater than about 130-139/85-89 mm Hg.

Administration of NHE-inhibiting compounds, with or without administration of fluid-absorbing polymers, may be beneficial for patients put on "non-added salt" dietary regimen (i.e., 60-100 mmol of Na per day), to liberalize their diet while keeping a neutral or slightly negative sodium balance (i.e., the overall uptake of salt would be equal of less than the secreted salt). In that context, "liberalize their diet" means that patients treated may add salt to their meals to make the meals more palatable, or/and diversify their diet with salt-containing foods, thus maintaining a good nutritional status while improving their quality of life.

The treatment methods described herein may also help patients with edema associated with chemotherapy, premenstrual fluid overload and preeclampsia (pregnancy-induced hypertension).

Accordingly, it is to be noted that the present disclosure is further directed to methods of treatment involving the administration of the compound of the present disclosure, or a pharmaceutical composition comprising such a compound. Such methods may include, for example, a method for treating hypertension, the method comprising administering to the patient a substantially impermeable or substantially systemically non-bioavailable NHE-inhibiting compound, or a pharmaceutical composition comprising it. The method may be for reducing fluid overload associated with heart failure (in particular, congestive heart failure), the method comprising administering to the patient a substantially impermeable or substantially systemically non-bioavailable NHE-inhibiting compound or pharmaceutical composition comprising it. The method may be for reducing fluid overload associated with end stage renal disease, the method comprising administering to the patient a substantially impermeable or substantially systemically non-bioavailable NHE-inhibiting compound or composition comprising it. The method may be for reducing fluid overload associated with peroxisome proliferator-activated receptor (PPAR) gamma agonist therapy, the method comprising administering to the patient a substantially impermeable or substantially systemically non-bioavailable NHE-inhibiting compound or composition comprising it. Additionally, or alternatively, the method may be for decreasing the activity of an intestinal NHE transporter in a patient, the method comprising: administering to the patient a substantially impermeable or substantially systemically non-bioavailable NHE-inhibiting compound, or a composition comprising it.

2. Gastrointestinal Tract Disorders

A pharmaceutical composition or preparation that may be used in accordance with the present disclosure for the treatment of various gastrointestinal tract disorders, including the treatment or reduction of pain associated with gastrointestinal tract disorders, comprises, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein). In some particular embodiments, the NHE-inhibiting compound, including any pharmaceutical composition comprising the compound, is administered with a fluid-absorbing polymer (as more fully described below).

A "subject" is preferably a human, but can also be an animal in need of treatment with a compound of the disclosure, e.g., companion animals (e.g., dogs, cats, and the like), farm animals (e.g., cows, pigs, horses and the like) and laboratory animals (e.g., rats, mice, guinea pigs and the like).

Subjects "in need of treatment" with a compound of the present disclosure, or subjects "in need of NHE inhibition" include subjects with diseases and/or conditions that can be treated with substantially impermeable or substantially systemically non-bioavailable NHE-inhibiting compounds, with or without a fluid-absorbing polymer, to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment is suffering from a gastrointestinal tract disorder; the patient is suffering from a disorder selected from the group consisting of: a gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, and the like.

In various preferred embodiments, the constipation to be treated is: associated with the use of a therapeutic agent; associated with a neuropathic disorder; post-surgical constipation (postoperative ileus); associated with a gastrointestinal tract disorder; idiopathic (functional constipation or slow transit constipation); associated with neuropathic, metabolic or endocrine disorder (e.g., diabetes mellitus, renal failure, hypothyroidism, hyperthyroidism, hypocalcaemia, Multiple Sclerosis, Parkinson's disease, spinal cord lesions, neurofibromatosis, autonomic neuropathy, Chagas disease, Hirschsprung's disease or cystic fibrosis, and the like). Constipation may also be the result of surgery (postoperative ileus) or due the use of drugs such as analgesics (e.g., opioids), antihypertensives, anticonvulsants, antidepressants, antispasmodics and antipsychotics.

Accordingly, it is to be noted that the present disclosure is further directed to methods of treatment involving the administration of the compound of the present disclosure, or a pharmaceutical composition comprising such a compound. Such methods may include, for example, a method for increasing gastrointestinal motility in a patient, the method comprising administering to the patient a substantially non-permeable or substantially non-bioavailable NHE-inhibiting compound, or a pharmaceutical composition comprising it. Additionally, or alternatively, the method may be for decreasing the activity of an intestinal NHE transporter in a patient, the method comprising administering to the patient a substantially non-permeable or substantially non-bioavailable NHE-inhibiting compound, or a pharmaceutical composition comprising it. Additionally, or alternatively, the method may be for treating a gastrointestinal tract disorder, a gastrointestinal motility disorder, irritable bowel syndrome, chronic calcium-induced constipation in osteoporotic patients, chronic constipation occurring in cystic fibrosis patients, chronic constipation occurring in chronic kidney disease patients, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, colonic pseudo-obstruction, Crohn's disease, ulcerative colitis, inflammatory bowel disease, the method comprising administering an antagonist of the intestinal NHE, and more specifically, a substantially non-permeable or substantially non-bioavailable NHE-inhibiting compound, or a pharmaceutical composition comprising it, either orally or by rectal suppository. Additionally, or alternatively, the method may be for treating or reducing pain, including visceral pain, pain associated with a gastrointestinal tract disorder or pain associated with some other disorder, the method comprising administering to a patient a substantially non-permeable or substantially non-bioavailable NHE-inhibiting compound, or a pharmaceutical composition comprising it. Additionally, or alternatively, the method may be for treating inflammation, including inflammation of the gastrointestinal tract, e.g., inflammation associated with a gastrointestinal tract disorder or infection or some other disorder, the method comprising administering to a patient a substantially non-permeable or substantially non-bioavailable NHE-inhibiting compound, or a pharmaceutical composition comprising it.

3. Metabolic Disorders

A pharmaceutical composition or preparation that may be used in accordance with the present disclosure for the treatment of various metabolic disorders including the treatment or reduction of type II diabetes mellitus (T2DM), metabolic syndrome, and/or symptoms associated with such disorders comprises, in general, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein).

Obesity is becoming a worldwide epidemic. In the United States, approximately ⅔rds of the population is either overweight (body mass index [BMI] 25 to 29.9) or obese (BMI≥30) (Ogden, C L et al, "Prevalence of overweight and obesity in the united states, 1999-2004" JAMA 2006, 295, 1549-1555). Obesity is a major risk factor for the development of diabetes and related complications, including cardiovascular disease and chronic kidney disease (CKD). The prevalence of T2DM has increased alarmingly in the United States. The American Diabes Associated (ADA) estimates that more than 23 million U.S. adults aged 20 years or older have diabetes, with T2DM accounting for approximately 95% of these cases. The World Health Organization (WHO) has put the number of persons with diabetes worldwide at approximately 170 million (Campbell, R. K. "Type 2 diabetes: where we are today: an overview of disease burden, current treatments, and treatment strategies" Journal of the American Pharmacists Association 2009, 49(5), S3-S9).

Obesity is also a major risk factor for the development of metabolic syndrome, and subsequently the development of CKD. Metabolic syndrome, previously known as Syndrome X, the plurimetabolic syndrome, the dysmetabolic syndrome, and other names, consists of a clustering of metabolic abnormalities including abdominal obesity, hypertriglyceridemia, low levels of high-density lipoprotein (HDL) cholesterol, elevated blood pressure (BP), and elevations in fasting glucose or diabetes (Townsend, R. R. et al "Metabolic Syndrome, Components, and Cardiovascular Disease Prevalence in Chronic Kidney Disease: Findings from the Chronic Renal Insufficiency Cohort (CRIC) Study" American Journal of Nephrology 2011, 33, 477-484). Metabolic syndrome is common in patients with CKD and an important risk factor for the development and progression of CKD.

Hemodynamic factors appear to play a significant role in obesity-induced renal dysfunction. Hypertension, which is closely linked to obesity, appears to be a major cause of renal dysfunction in obese patients (Wahba, I. M. et al "Obesity and obesity-initiated metabolic syndrome: mechanistic links to chronic kidney disease" Clinical Journal of the American Society of Nephrology 2007, 2, 550-562). Studies in animals and in humans have shown that obesity is associated with elevated glomerular filtration rate (GFR) and increased renal blood flow. This likely occurs because of afferent arteriolar dilation as a result of proximal salt reabsorption, coupled with efferent renal arteriolar vasoconstriction as a result of elevated angiotensin II levels. These effects may contribute to hyperfiltration, glomerulomegaly, and later focal glomerulosclerosis. Even though GFR is increased in obesity, urinary sodium excretion in response to a saline load is often delayed, and individuals exhibit an abnormal pressure natriuresis, indicating avid proximal tubular sodium reabsorption. In addition, increased fat distribution can cause increased intra-abdomial pressure, leading to renal vein compression, thus raising renal venous pressure and diminishing renal perfusion. In creased fat, through a variety of mechanisms, can cause elevated renal interstitial fluid hydrostatic fluid and may stimulate renal sodium retention the thereby contribute to hypertension (Wahba_2007).

In view of the above, there exists a need in the art for agents that can divert sodium and fluid from a subject via mechanisms that either avoid the kidney, or do not depend upon normal kidney function. A "subject" with metabolic disease, including T2DM, metabolic syndrome, and the like, is preferably a human, but can also be an animal in need of treatment with a compound of the disclosure, e.g., companion animals (e.g., dogs, cats, and the like), farm animals (e.g., cows, pigs, horses and the like) and laboratory animals (e.g., rats, mice, guinea pigs and the like).

Subjects "in need of treatment" with a compound of the present disclosure, or subjects "in need of NHE inhibition" include subjects with diseases and/or conditions that can be treated with substantially impermeable or substantially systemically non-bioavailable NHE-inhibiting compounds, with or without a fluid-absorbing polymer, to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject with a metabolic disorder causing or exacerbating chronic kidney disease would benefit from a treatment modality that could divert excess sodium and fluid from the body by a method that does not require normally functionaling kidneys. Such a treatment would include the method comprising administering to a patient a substantially non-permeable or substantially non-bioavailable NHE-inhibiting compound, or a pharmaceutical composition comprising it.

The compounds utilized in the treatment methods of the present disclosure, as well as the pharmaceutical compositions comprising them, may accordingly be administered alone, or as part of a combination therapy or regimen that includes the administration or use of other therapeutic compounds related to the treatment of metabolic disorders such as T2DM and metabolic syndrome. In some particular embodiments, the NHE-inhibiting compound, including any pharmaceutical composition comprising the compound, is administered with a fluid absorbing polymer.

B. Combination Therapies

1. Fluid Retention and/or Salt Overload Disorders

As previously noted, the compounds described herein can be used alone or in combination with other agents. For example, the compounds can be administered together with a diuretic (i.e., High Ceiling Loop Diuretics, Benzothiadiazide Diuretics, Potassium Sparing Diuretics, Osmotic Diuretics), cardiac glycoside, ACE inhibitor, angiotensin-2 receptor antagonist, calcium channel blocker, beta blocker, alpha blocker, central alpha agonist, aldosterone antagonist, aldosterone synthase inhibitor, renin inhibitor, vasodilator, blood thinner, anti-platelet agent, lipid-lowering agent, peroxisome proliferator-activated receptor (PPAR) gamma agonist agent or compound or with a fluid-absorbing polymer as more fully described below. The agent can be covalently attached to a compound described herein or it can be a separate agent that is administered together with or sequentially with a compound described herein in a combination therapy.

Combination therapy can be achieved by administering two or more agents, e.g., a substantially non-permeable or substantially systemically non-bioavailable NHE-inhibiting compound described herein and a diuretic, cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

The compounds described herein can be used in combination therapy with a diuretic. Among the useful diuretic agents are, for example: High Ceiling Loop Diuretics [Furosemide (Lasix), Ethacrynic Acid (Edecrin), Bumetanide (Bumex)], Benzothiadiazide Diuretics [Hydrochlorothiazide (Hydrodiuril), Chlorothiazide (Diuril), Clorthalidone (Hygroton), Benzthiazide (Aguapres), Bendroflumethiazide (Naturetin), Methyclothiazide (Aguatensen), Polythiazide (Renese), Indapamide (Lozol), Cyclothiazide (Anhydron), Hydroflumethiazide (Diucardin), Metolazone (Diulo), Quinethazone (Hydromox), Trichlormethiazide (Naqua)], Potassium Sparing Diuretics [Spironolactone (Aldactone), Triamterene (Dyrenium), Amiloride (Midamor)], and Osmotic Diuretics [Mannitol (Osmitrol)]. Diuretic agents in the various classes are known and described in the literature.

Cardiac glycosides (cardenolides) or other *digitalis* preparations can be administered with the compounds of the disclosure in co-therapy. Among the useful cardiac glycosides are, for example: Digitoxin (Cry stodigin), Digoxin (Lanoxin) or Deslanoside (Cedilanid-D). Cardiac glycosides in the various classes are described in the literature.

Angiotensin Converting Enzyme Inhibitors (ACE Inhibitors) can be administered with the compounds of the disclosure in co-therapy. Among the useful ACE inhibitors are, for example: Captopril (Capoten), Enalapril (Vasotec), Lisinopril (Prinivil). ACE inhibitors in the various classes are described in the literature.

Angiotensin-2 Receptor Antagonists (also referred to as $AT_1$-antagonists or angiotensin receptor blockers, or ARB's) can be administered with the compounds of the disclosure in co-therapy. Among the useful Angiotensin-2 Receptor Antagonists are, for example. Candesartan (Atacand), Eprosartan (Teveten), Irbesartan (Avapro), Losartan (Cozaar), Telmisartan (Micardis), Valsartan (Diovan). Angiotensin-2 Receptor Antagonists in the various classes are described in the literature.

Calcium channel blockers such as Amlodipine (Norvasc, Lotrel), Bepridil (Vascor), Diltiazem (Cardizem, Tiazac), Felodipine (Plendil), Nifedipine (Adalat, Procardia), Nimodipine (Nimotop), Nisoldipine (Sular), Verapamil (Calan, Isoptin, Verelan) and related compounds described in, for example, EP 625162B1, U.S. Pat. No. 5,364,842, U.S. Pat. No. 5,587,454, U.S. Pat. No. 5,824,645, U.S. Pat. No. 5,859,186, U.S. Pat. No. 5,994,305, U.S. Pat. No. 6,087,091, U.S. Pat. No. 6,136,786, WO 93/13128 A1, EP 1336409 A1, EP 835126 A1, EP 835126 B1, U.S. Pat. No. 5,795,864, U.S. Pat. No. 5,891,849, U.S. Pat. No. 6,054,429, WO 97/01351 A1, the entire contents of which are incorporated herein by reference for all relevant and consistent purposes, can be used with the compounds of the disclosure.

Beta blockers can be administered with the compounds of the disclosure in co-therapy. Among the useful beta blockers are, for example: Acebutolol (Sectral), Atenolol (Tenormin), Betaxolol (Kerlone), Bisoprolol/hydrochlorothiazide (Ziac), Bisoprolol (Zebeta), Carteolol (Cartrol), Metoprolol (Lopressor, Toprol XL), Nadolol (Corgard), Propranolol (Inderal), Sotalol (Betapace), Timolol (Blocadren). Beta blockers in the various classes are described in the literature.

PPAR gamma agonists such as thiazolidinediones (also called glitazones) can be administered with the compounds of the disclosure in co-therapy. Among the useful PPAR agonists are, for example; rosiglitazone (Avandia), pioglitazone (Actos) and rivoglitazone.

Aldosterone antagonists can be administered with the compounds of the disclosure in co-therapy. Among the useful Aldosterone antagonists are, for example: eplerenone, spironolactone, and canrenone.

Renin inhibitors can be administered with the compounds of the disclosure in co-therapy. Among the useful Renin inhibitors is, for example: aliskiren.

Alpha blockers can be administered with the compounds of the disclosure in co-therapy. Among the useful Alpha blockers are, for example: Doxazosin mesylate (Cardura), Prazosin hydrochloride (Minipress). Prazosin and polythiazide (Minizide), Terazosin hydrochloride (Hytrin). Alpha blockers in the various classes are described in the literature.

Central alpha agonists can be administered with the compounds of the disclosure in co-therapy. Among the useful Central alpha agonists are, for example: Clonidine hydrochloride (Catapres), Clonidine hydrochloride and chlorthalidone (Clorpres, Combipres), Guanabenz Acetate (Wytensin), Guanfacine hydrochloride (Tenex), Methyldopa (Aldomet), Methyldopa and chlorothiazide (Aldochlor), Methyldopa and hydrochlorothiazide (Aldoril). Central alpha agonists in the various classes are described in the literature.

Vasodilators can be administered with the compounds of the disclosure in co-therapy. Among the useful vasodilators are, for example: Isosorbide dinitrate (Isordil), Nesiritide (Natrecor), Hydralazine (Apresoline), Nitrates/nitroglycerin, Minoxidil (Loniten). Vasodilators in the various classes are described in the literature.

Blood thinners can be administered with the compounds of the disclosure in co-therapy. Among the useful blood thinners are, for example: Warfarin (Coumadin) and Heparin. Blood thinners in the various classes are described in the literature.

Anti-platelet agents can be administered with the compounds of the disclosure in co-therapy. Among the useful anti-platelet agents are, for example: Cyclooxygenase inhibitors (Aspirin), Adenosine diphosphate (ADP) receptor inhibitors [Clopidogrel (Plavix), Ticlopidine (Ticlid)], Phosphodiesterase inhibitors [Cilostazol (Pletal)], Glycoprotein IIB/IIIA inhibitors [Abciximab (ReoPro), Eptifibatide (Integrilin), Tirofiban (Aggrastat), Defibrotide], Adenosine reuptake inhibitors [Dipyridamole (Persantine)]. Anti-platelet agents in the various classes are described in the literature.

Lipid-lowering agents can be administered with the compounds of the disclosure in co-therapy. Among the useful lipid-lowering agents are, for example: Statins (HMG CoA reductase inhibitors), [Atorvastatin (Lipitor), Fluvastatin (Lescol), Lovastatin (Mevacor, Altoprev), Pravastatin (Pravachol), Rosuvastatin Calcium (Crestor), Simvastatin (Zocor)], Selective cholesterol absorption inhibitors [ezetimibe (Zetia)], Resins (bile acid sequestrant or bile acid-binding drugs) [Cholestyramine (Questran, Questran Light, Prevalite, Locholest, Locholest Light), Colestipol (Colestid), Colesevelam Hcl (WelChol)], Fibrates (Fibric acid derivatives) [Gemfibrozil (Lopid), Fenofibrate (Antara, Lofibra, Tricor, and Triglide), Clofibrate (Atromid-S)], Niacin (Nicotinic acid). Lipid-lowering agents in the various classes are described in the literature.

The compounds of the disclosure can be used in combination with peptides or peptide analogs that activate the Guanylate Cyclase-receptor in the intestine and results in elevation of the intracellular second messenger, or cyclic guanosine monophosphate (cGMP), with increased chloride and bicarbonate secretion into the intestinal lumen and concomitant fluid secretion. Example of such peptides are Linaclotide (MD-1100 Acetate), endogenous hormones guanylin and uroguanylin and enteric bacterial peptides of the heat stable enterotoxin family (ST peptides) and those described in U.S. Pat. No. 5,140,102, U.S. Pat. No. 5,489,670, U.S. Pat. No. 5,969,097, WO 2006/001931A2, WO 2008/002971A2, WO 2008/106429A2, US 2008/0227685A1 and U.S. Pat. No. 7,041,786, the entire contents of which are incorporated herein by reference for all relevant and consistent purposes.

The compounds of the disclosure can be used in combination with type-2 chloride channel agonists, such as Amitiza (Lubiprostone) and other related compounds described in U.S. Pat. No. 6,414,016, the entire contents of which are incorporated herein by reference for all relevant and consistent purposes.

The compounds described herein can be used in combination therapy with agents used for the treatment of obesity, T2DM, metabolic syndrome and the like. Among the useful agents include: insulin; insulin secretagogues, such as sulphonylureas; glucose-lowering effectors, such as metformin; activators of the peroxisome proliferator-activated receptor γ (PPARγ), such as the thiazolidinediones; incretin-based agents including dipeptidyl peptidase-4 inhibitors such as sitagliptin, and synthetic incretin mimetics such as liraglutide and exenatide; alpha-glucosidase inhibitors, such as acarbose; glinides, such as repaglinide and nateglinide, and the like.

The compounds of the disclosure can be used in combination with P2Y2 receptor agonists, such as those described in EP 1196396B1 and U.S. Pat. No. 6,624,150, the entire contents of which are incorporated herein by reference for all relevant and consistent purposes.

Other agents include natriuretic peptides such as nesiritide, a recombinant form of brain-natriuretic peptide (BNP)

and an atrial-natriuretic peptide (ANP). Vasopressin receptor antagonists such as tolvaptan and conivaptan may be co-administered as well as phosphate binders such as renagel, renleva, phoslo and fosrenol. Other agents include phosphate transport inhibitors (as described in U.S. Pat. Nos. 4,806,532; 6,355,823; 6,787,528; 7,119,120; 7,109,184; U.S. Pat. Pub. No. 2007/021509; 2006/0280719; 2006/0217426; International Pat. Pubs. WO 2001/005398, WO 2001/087294, WO 2001/082924, WO 2002/028353, WO 2003/048134, WO 2003/057225, WO2003/080630, WO 2004/085448, WO 2004/085382; European Pat. Nos. 1465638 and 1485391; and JP Patent No. 2007131532, or phosphate transport antagonists such as Nicotinamide.

2. Gastrointestinal Tract Disorders

As previously noted, the compounds described herein can be used alone or in combination with other agents. For example, the compounds can be administered together with an analgesic peptide or compound. The analgesic peptide or compound can be covalently attached to a compound described herein or it can be a separate agent that is administered together with or sequentially with a compound described herein in a combination therapy.

Combination therapy can be achieved by administering two or more agents, e.g., a substantially non-permeable or substantially non-bioavailable NHE-inhibiting compound described herein and an analgesic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

The compounds described herein can be used in combination therapy with an analgesic agent, e.g., an analgesic compound or an analgesic peptide. The analgesic agent can optionally be covalently attached to a compound described herein. Among the useful analgesic agents are, for example: Ca channel blockers, 5HT3 agonists (e.g., MCK-733), 5HT4 agonists (e.g., tegaserod, prucalopride), and 5HT1 receptor antagonists, opioid receptor agonists (loperamide, fedotozine, and fentanyl), NK1 receptor antagonists, CCK receptor agonists (e.g., loxiglumide), NK1 receptor antagonists, NK3 receptor antagonists, norepinephrine-serotonin reuptake inhibitors (NSR1), vanilloid and cannabanoid receptor agonists, and sialorphin. Analgesics agents in the various classes are described in the literature.

Opioid receptor antagonists and agonists can be administered with the compounds of the disclosure in co-therapy or linked to the compound of the disclosure, e.g., by a covalent bond. For example, opioid receptor antagonists such as naloxone, naltrexone, methyl nalozone, nalmefene, cypridime, beta funaltrexamine, naloxonazine, naltrindole, and nor-binaltorphimine are thought to be useful in the treatment of opioid-induced constipaption (OIC). It can be useful to formulate opioid antagonists of this type in a delayed or sustained release formulation, such that initial release of the antagonist is in the mid to distal small intestine and/or ascending colon. Such antagonists are described in U.S. Pat. No. 6,734,188 (WO 01/32180 A2), the entire contents of which are incorporated herein by reference for all relevant and consistent purposes. Enkephalin pentapeptide (HOE825; Tyr-D-Lys-Gly-Phe-L-homoserine) is an agonist of the µ- and γ-opioid receptors and is thought to be useful for increasing intestinal motility (Eur. J. Pharm., 219:445, 1992), and this peptide can be used in conjunction with the compounds of the disclosure. Also useful is trimebutine which is thought to bind to mu/delta/kappa opioid receptors and activate release of motilin and modulate the release of gastrin, vasoactive intestinal peptide, gastrin and glucagons. K-opioid receptor agonists such as fedotozine, ketocyclazocine, and compounds described in US 2005/0176746 (WO 03/097051 A2), the entire contents of which are incorporated herein by reference for all relevant and consistent purposes, can be used with or linked to the compounds of the disclosure. In addition, µ-opioid receptor agonists, such as morphine, diphenyloxylate, frakefamide (H-Tyr-D-Ala-Phe(F)-Phe-NH$_2$; disclosed in WO 01/019849 A1, the entire contents of which are incorporated herein by reference for all relevant and consistent purposes) and loperamide can be used.

Tyr-Arg (kyotorphin) is a dipeptide that acts by stimulating the release of met-enkephalins to elicit an analgesic effect (J. Biol. Chem. 262:8165, 1987). Kyotorphin can be used with or linked to the compounds of the disclosure. CCK receptor agonists such as caerulein from amphibians and other species are useful analgesic agents that can be used with or linked to the compounds of the disclosure.

Conotoxin peptides represent a large class of analgesic peptides that act at voltage gated Ca channels, NMDA receptors or nicotinic receptors. These peptides can be used with or linked to the compounds of the disclosure.

Peptide analogs of thymulin (U.S. Pat. No. 7,309,690 or FR 2830451, the entire contents of which are incorporated herein by reference for all relevant and consistent purposes) can have analgesic activity and can be used with or linked to the compounds of the disclosure.

CCK (CCKa or CCKb) receptor antagonists, including loxiglumide and dexloxiglumide (the R-isomer of loxiglumide) (U.S. Pat. No. 5,130,474 or WO 88/05774, the entire contents of which are incorporated herein by reference for all relevant and consistent purposes) can have analgesic activity and can be used with or linked to the compounds of the disclosure.

Other useful analgesic agents include 5-HT4 agonists such as tegaserod/zelnorm and lirexapride. Such agonists are described in: EP1321142 A1, WO 03/053432A1, EP 505322 A1, EP 505322 B1, EP 507672 A1, EP 507672 B1, U.S. Pat. No. 5,510,353 and U.S. Pat. No. 5,273,983, the entire contents of which are incorporated herein by reference for all relevant and consistent purposes.

Calcium channel blockers such as ziconotide and related compounds described in, for example, EP 625162B1, U.S. Pat. No. 5,364,842, U.S. Pat. No. 5,587,454, U.S. Pat. No. 5,824,645, U.S. Pat. No. 5,859,186, U.S. Pat. No. 5,994,305, U.S. Pat. No. 6,087,091, U.S. Pat. No. 6,136,786, WO 93/13128 A1, EP 1336409 A1, EP 835126 A1, EP 835126 B1, U.S. Pat. No. 5,795,864, U.S. Pat. No. 5,891,849, U.S. Pat. No. 6,054,429, WO 97/01351 A1, the entire contents of which are incorporated herein by reference for all relevant and consistent purposes, can be used with or linked to the compounds of the disclosure.

Various antagonists of the NK-1, NK-2, and NK-3 receptors (for a review see Giardina et al. 2003 Drugs 6:758) can be can be used with or linked to the compounds of the disclosure.

NK1 receptor antagonists such as: aprepitant (Merck & Co Inc), vofopitant, ezlopitant (Pfizer, Inc.), R-673 (Hoffmann-La Roche Ltd), SR-14033 and related compounds described in, for example, EP 873753 A1, U.S. 20010006972 A1, U.S. 20030109417 A1, WO 01/52844 A1, the entire contents of which are incorporated herein by reference for all relevant and consistent purposes, can be used with or linked to the compounds of the disclosure.

NK-2 receptor antagonists such as nepadutant (Menarini Ricerche SpA), saredutant (Sanofi-Synthelabo), SR-144190 (Sanofi-Synthelabo) and UK-290795 (Pfizer Inc) can be used with or linked to the compounds of the disclosure.

NK3 receptor antagonists such as osanetant (Sanofi-Synthelabo), talnetant and related compounds described in, for example, WO 02/094187 A2, EP 876347 A1, WO 97/21680 A1, U.S. Pat. No. 6,277,862, WO 98/11090, WO 95/28418, WO 97/19927, and Boden et al. (J Med. Chem. 39:1664-75, 1996), the entire contents of which are incorporated herein by reference for all relevant and consistent purposes, can be used with or linked to the compounds of the disclosure.

Norepinephrine-serotonin reuptake inhibitors such as milnacipran and related compounds described in WO 03/077897 A1, the entire contents of which are incorporated herein by reference for all relevant and consistent purposes, can be used with or linked to the compounds of the disclosure.

Vanilloid receptor antagonists such as arvanil and related compounds described in WO 01/64212 A1, the entire contents of which are incorporated herein by reference for all relevant and consistent purposes, can be used with or linked to the compounds of the disclosure.

The compounds can be used in combination therapy with a phosphodiesterase inhibitor (examples of such inhibitors can be found in U.S. Pat. No. 6,333,354, the entire contents of which are incorporated herein by reference for all relevant and consistent purposes).

The compounds can be used alone or in combination therapy to treat disorders associated with chloride or bicarbonate secretion that may lead to constipation, e.g., Cystic Fibrosis.

The compounds can also or alternatively be used alone or in combination therapy to treat calcium-induced constipation effects. Constipation is commonly found in the geriatric population, particularly patients with osteoporosis who have to take calcium supplements. Calcium supplements have shown to be beneficial in ostoporotic patients to restore bone density but compliance is poor because of constipation effects associated therewith.

The compounds of the current disclosure have can be used in combination with an opioid. Opioid use is mainly directed to pain relief, with a notable side-effect being GI disorder, e.g. constipation. These agents work by binding to opioid receptors, which are found principally in the central nervous system and the gastrointestinal tract. The receptors in these two organ systems mediate both the beneficial effects, and the undesirable side effects (e.g. decrease of gut motility and ensuing constipation). Opioids suitable for use typically belong to one of the following exemplary classes: natural opiates, alkaloids contained in the resin of the opium poppy including morphine, codeine and thebaine; semi-synthetic opiates, created from the natural opioids, such as hydromorphone, hydrocodone, oxycodone, oxymorphone, desomorphine, diacetylmorphine (Heroin), nicomorphine, dipropanoylmorphine, benzylmorphine and ethylmorphine; fully synthetic opioids, such as fentanyl, pethidine, methadone, tramadol and propoxyphene; endogenous opioid peptides, produced naturally in the body, such as endorphins, enkephalins, dynorphins, and endomorphins.

The compound of the disclosure can be used alone or in combination therapy to alleviate GI disorders encountered with patients with renal failure (stage 3-5). Constipation is the second u) most reported symptom in that category of patients (Murtagh et al., 2006; Murtagh et al., 2007a; Murtagh et al., 2007b). Without being held by theory, it is believed that kidney failure is accompanied by a stimulation of intestinal Na re-absorption (Hatch and Freel, 2008). A total or partial inhibition of such transport by administration of the compounds of the disclosure can have a therapeutic benefit to improve GI transit and relieve abdominal pain. In that context, the compounds of the disclosure can be used in combination with Angiotensin-modulating agents: Angiotensin Converting Enzyme (ACE) inhibitors (e.g. captopril, enalopril, lisinopril, ramipril) and Angiotensin II receptor antagonist therapy (also referred to as $AT_1$-antagonists or angiotensin receptor blockers, or ARB's); diuretics such as loop diuretics (e.g. furosemide, bumetanide), Thiazide diuretics (e.g. hydrochlorothiazide, chlorthalidone, chlorthiazide) and potassium-sparing diuretics: amiloride; beta blockers: bisoprolol, carvedilol, nebivolol and extended-release metoprolol; positive inotropes: Digoxin, dobutamine; phosphodiesterase inhibitors such as milrinone; alternative vasodilators: combination of isosorbide dinitrate/hydralazine; aldosterone receptor antagonists: spironolactone, eplerenone; natriuretic peptides: Nesiritide, a recombinant form of brain-natriuretic peptide (BNP), atrial-natriuretic peptide (ANP); vasopressin receptor antagonists: Tolvaptan and conivaptan; phosphate binder (Renagel, Renleva, Phoslo, Fosrenol); phosphate transport inhibitor such as those described in U.S. Pat. No. 4,806,532, U.S. Pat. No. 6,355,823, U.S. Pat. No. 6,787,528, WO 2001/005398, WO 2001/087294, WO 2001/082924, WO 2002/028353, WO 2003/048134, WO 2003/057225, U.S. Pat. No. 7,119,120, EP 1465638, US Appl. 2007/021509, WO 2003/080630, U.S. Pat. No. 7,109,184, US Appl. 2006/0280719, EP 1485391, WO 2004/085448, WO 2004/085382, US Appl. 2006/0217426, JP 2007/131532, the entire contents of which are incorporated herein by reference for all relevant and consistent purposes, or phosphate transport antagonist (Nicotinamide).

The compounds of the disclosure can be used in combination with peptides or peptide analogs that activate the Guanylate Cyclase-receptor in the intestine and results in elevation of the intracellular second messenger, or cyclic guanosine monophosphate (cGMP), with increased chloride and bicarbonate secretion into the intestinal lumen and concomitant fluid secretion. Example of such peptides are Linaclotide (MD-1100 Acetate), endogenous hormones guanylin and uroguanylin and enteric bacterial peptides of the heat stable enterotoxin family (ST peptides) and those described in U.S. Pat. No. 5,140,102, U.S. Pat. No. 5,489, 670, U.S. Pat. No. 5,969,097, WO 2006/001931A2, WO 2008/002971A2, WO 2008/106429A2, US 2008/

0227685A1 and U.S. Pat. No. 7,041,786, the entire contents of which are incorporated herein by reference for all relevant and consistent purposes.

The compounds of the disclosure can be used in combination with type-2 chloride channel agonists, such as Amitiza (Lubiprostone) and other related compounds described in U.S. Pat. No. 6,414,016, the entire contents of which are incorporated herein by reference for all relevant and consistent purposes.

The compounds of the disclosure can be used in combination with P2Y2 receptor agonists, such as those described in EP 1196396B1 and U.S. Pat. No. 6,624,150, the entire contents of which are incorporated herein by reference for all relevant and consistent purposes.

The compounds of the disclosure can be used in combination with laxative agents such as bulk-producing agents, e.g. psyllium husk (Metamucil), methylcellulose (Citrucel), polycarbophil, dietary fiber, apples, stool softeners/surfactant such as docusate (Colace, Diocto); hydrating agents (osmotics), such as dibasic sodium phosphate, magnesium citrate, magnesium hydroxide (Milk of magnesia), magnesium sulfate (which is Epsom salt), monobasic sodium phosphate, sodium biphosphate; hyperosmotic agents: glycerin suppositories, sorbitol, lactulose, and polyethylene glycol (PEG). The compounds of the disclosure can be also be used in combination with agents that stimulate gut peristalsis, such as Bisacodyl tablets (Dulcolax), Casanthranol, Senna and Aloin, from Aloe Vera.

In one embodiment, the compounds of the disclosure accelerate gastrointestinal transit, and more specifically in the colon, without substantially affecting the residence time in the stomach, i.e. with no significant effect on the gastric emptying time. Even more specifically the compounds of the invention restore colonic transit without the side-effects associated with delayed gastric emptying time, such as nausea. The GI and colonic transit are measured in patients using methods reported in, for example: Burton D D, Camilleri M, Mullan B P, et al., *J. Nucl. Med.*, 1997; 38:1807-1810; Cremonini F, Mullan B P, Camilleri M, et al., *Aliment. Pharmacol. Ther.*, 2002; 16:1781-1790; Camilleri M, Zinsmeister A R, *Gastroenterology*, 1992; 103:36-42; Bouras E P, Camilleri M, Burton D D, et al., *Gastroenterology*, 2001; 120:354-360; Coulie B, Szarka L A, Camilleri M, et al., *Gastroenterology*, 2000; 119:41-50; Prather C M, Camilleri M, Zinsmeister A R, et al., *Gastroenterology*, 2000; 118:463-468; and, Camilleri M, McKinzie S, Fox J, et al., *Clin. Gastroenterol. Hepatol.*, 2004; 2:895-904.

C. Polymer Combination Therapy

The NHE-inhibiting compounds described therein may be administered to patients in need thereof in combination with a fluid-absorbing polymer ("FAP"). The intestinal fluid-absorbing polymers useful for administration in accordance with embodiments of the present disclosure may be administered orally in combination with non-absorbable NHE-inhibiting compounds (e.g., a NHE-3 inhibitor) to absorb the intestinal fluid resulting from the action of the sodium transport inhibitors. Such polymers swell in the colon and bind fluid to impart a consistency to stools that is acceptable for patients. The fluid-absorbing polymers described herein may be selected from polymers with laxative properties, also referred to as bulking agents (i.e., polymers that retain some of the intestinal fluid in the stools and impart a higher degree of hydration in the stools and facilitate transit). The fluid-absorbing polymers may also be optionally selected from pharmaceutical polymers with anti-diarrhea function, i.e., agents that maintain some consistency to the stools to avoid watery stools and potential incontinence.

The ability of the polymer to maintain a certain consistency in stools with a high content of fluid can be characterized by its "water holding power." Wenzl et al. (in *Determinants of decreased fecal consistency in patients with diarrhea*; Gastroenterology, v. 108, no. 6, p. 1729-1738 (1995)) studied the determinants that control the consistency of stools of patients with diarrhea and found that they were narrowly correlated with the water holding power of the feces. The water holding power is determined as the water content of given stools to achieve a certain level of consistency (corresponding to "formed stool" consistency) after the reconstituted fecal matter has been centrifuged at a certain g number. Without being held to any particular theory, has been found that the water holding power of the feces is increased by ingestion of certain polymers with a given fluid absorbing profile. More specifically, it has been found that the water-holding power of said polymers is correlated with their fluid absorbancy under load (AUL); even more specifically the AUL of said polymers is greater than 15 g of isotonic fluid/g of polymer under a static pressure of 5 kPa, even more preferably under a static pressure of 10 kPa.

The FAP utilized in the treatment method of the present disclosure preferably has a AUL of at least about 10 g, about 15 g, about 20 g, about 25 g or more of isotonic fluid/g of polymer under a static pressure of about 5 kPa, and preferably about 10 kPA, and may have a fluid absorbancy of about 20 g, about 25 g or more, as determined using means generally known in the art. Additionally or alternatively, the FAP may impart a minimum consistency to fecal matter and, in some embodiments, a consistency graded as "soft" in the scale described in the test method below, when fecal non water-soluble solid fraction is from 10% to 20%, and the polymer concentration is from 1% to 5% of the weight of stool. The determination of the fecal non water-soluble solid fraction of stools is described in Wenz et al. The polymer may be uncharged or may have a low charge density (e.g., 1-2 meq/gr). Alternatively or in addition, the polymer may be delivered directly to the colon using known delivery methods to avoid premature swelling in the esophagus.

In one embodiment of the present disclosure, the FAP is a "superabsorbent" polymer (i.e., a lightly crosslinked, partially neutralized polyelectrolyte hydrogel similar to those used in baby diapers, feminine hygiene products, agriculture additives, etc.). Superabsorbent polymers may be made of a lightly crosslinked polyacrylate hydrogel. The swelling of the polymer is driven essentially by two effects: (i) the hydration of the polymer backbone and entropy of mixing and (ii) the osmotic pressure arising from the counter-ions (e.g., Na ions) within the gel. The gel swelling ratio at equilibrium is controlled by the elastic resistance inherent to the polymer network and by the chemical potential of the bathing fluid, i.e., the gel will de-swell at higher salt concentration because the background electrolyte will reduce the apparent charge density on the polymer and will reduce the difference of free ion concentrations inside and outside the gel that drives osmotic pressure. The swelling ratio SR (g of fluid per g of dry polymer and synonymously "fluid absorbency") may vary from 1000 in pure water down to 30 in 0.9% NaCl solution representative of physiological saline (i.e., isotonic). SR may increase with the degree of neutralization and may decrease with the crosslinking density. SR generally decreases with an applied load with the extent of reduction dependent on the strength of the gel, i.e., the crosslinking density. The salt concentration within the gel, as compared with the external solution, may be lower as a result of the Donnan effect due to the internal electrical potential.

The fluid-absorbing polymer may include crosslinked polyacrylates which are fluid absorbent such as those prepared from $\alpha,\beta$-ethylenically unsaturated monomers, such as monocarboxylic acids, polycarboxylic acids, acrylamide and their derivatives. These polymers may have repeating units of acrylic acid, methacrylic acid, metal salts of acrylic acid, acrylamide, and acrylamide derivatives (such as 2-acrylamido-2-methylpropanesulfonic acid) along with various combinations of such repeating units as copolymers. Such derivatives include acrylic polymers which include hydrophilic grafts of polymers such as polyvinyl alcohol. Examples of suitable polymers and processes, including gel polymerization processes, for preparing such polymers are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; 4,190,562; 4,286,082; 4,857,610; 4,985,518; 5,145,906; 5,629,377 and 6,908,609 which are incorporated herein by reference for all relevant and consistent purposes (in addition, see Buchholz, F. L. and Graham, A. T., "Modern Superabsorbent Polymer Technology," John Wiley & Sons (1998), which is also incorporated herein by reference for all relevant and consistent purposes). A class of preferred polymers for treatment in combination with NHE-inhibitors is polyelectrolytes.

The degree of crosslinking can vary greatly depending upon the specific polymer material; however, in most applications the subject superabsorbent polymers are only lightly crosslinked, that is, the degree of crosslinking is such that the polymer can still absorb over 10 times its weight in physiological saline (i.e., 0.9% saline). For example, such polymers typically include less than about 0.2 mole % crosslinking agent.

In some embodiments, the FAP's utilized for treatment are Calcium Carbophil (Registry Number: 9003-97-8, also referred as Carbopol EX-83), and Carpopol 934P.

In some embodiments, the fluid-absorbing polymer is prepared by high internal phase emulsion ("HIPE") processes. The HIPE process leads to polymeric foam slabs with a very large porous fraction of interconnected large voids (about 100 microns) (i.e., open-cell structures). This technique produces flexible and collapsible foam materials with exceptional suction pressure and fluid absorbency (see U.S. Pat. Nos. 5,650,222; 5,763,499 and 6,107,356, which are incorporated herein for all relevant and consistent purposes). The polymer is hydrophobic and, therefore, the surface should be modified so as to be wetted by the aqueous fluid. This is accomplished by post-treating the foam material by a surfactant in order to reduce the interfacial tension. These materials are claimed to be less compliant to loads, i.e., less prone to de-swelling under static pressure.

In some embodiments, fluid-absorbing gels are prepared by aqueous free radical polymerization of acrylamide or a derivative thereof, a crosslinker (e.g., methylene-bis-acrylamide) and a free radical initiator redox system in water. The material is obtained as a slab. Typically the swelling ratio of crosslinked polyacrylamide at low crosslinking density (e.g., 2%-4% expressed as weight % of methylene-bis-acrylamide) is between 25 and 40 (F. Horkay, Macromolecules, 22, pp. 2007-09 (1989)). The swelling properties of these polymers have been extensively studied and are essentially the same of those of crosslinked polyacrylic acids at high salt concentration. Under those conditions, the osmotic pressure is null due to the presence of counter-ions and the swelling controlled by the free energy of mixing and the network elastic energy. Stated differently, a crosslinked polyacrylamide gel of same crosslink density as a neutralized polyacrylic acid will exhibit the same swelling ratio (i.e., fluid absorbing properties) and it is believed the same degree of deswelling under pressure, as the crosslinked polyelectrolyte at high salt content (e.g., 1 M). The properties (e.g., swelling) of neutral hydrogels will not be sensitive to the salt environment as long as the polymer remains in good solvent conditions. Without being held to any particular theory, it is believed that the fluid contained within the gel has the same salt composition than the surrounding fluid (i.e., there is no salt partitioning due to Donnan effect).

Another subclass of fluid-absorbing polymers that may be utilized is hydrogel materials that include N-alkyl acrylamide polymers (e.g., N-isopropylacrylamide (NIPAM)). The corresponding aqueous polyNIPAM hydrogel shows a temperature transition at about 35° C. Above this temperature the hydrogel may collapse. The mechanism is generally reversible and the gel re-swells to its original swelling ratio when the temperature reverts to room temperature. This allows production of nanoparticles by emulsion polymerization (R. Pelton, *Advances in Colloid and Interface Science*, 85, pp. 1-33, (2000)). The swelling characteristics of poly-NIPAM nanoparticles below the transition temperature have been reported and are similar to those reported for bulk gel of polyNIPAM and equivalent to those found for polyacrylamide (i.e. 30-50 g/g) (W. McPhee, *Journal of Colloid and Interface Science*, 156, pp. 24-30 (1993); and, K. Oh, *Journal of Applied Polymer Science*, 69, pp. 109-114 (1997)).

In some embodiments, the FAP utilized for treatment in combination with a NHE-inhibitor is a superporous gel that may delay the emptying of the stomach for the treatment of obesity (J. Chen, *Journal of Controlled Release*, 65, pp. 73-82 (2000), or to deliver proteins. Polyacrylate-based SAP's with a macroporous structure may also be used. Macroporous SAP and superporous gels differ in that the porous structure remains almost intact in the dry state for superporous gels, but disappears upon drying for macroporous SAP's. The method of preparation is different although both methods use a foaming agent (e.g., carbonate salt that generates CO2 bubbles during polymerization). Typical swelling ratios, SR, of superporous materials are around 10. Superporous gels keep a large internal pore volume in the dry state.

Macroporous hydrogels may also be formed using a method whereby polymer phase separation in induced by a non-solvent. The polymer may be poly-NIPAM and the non-solvent utilized may be glucose (see, e.g., Z. Zhang, *J. Org. Chem.*, 69, 23 (2004)) or NaCl (see, e.g., Cheng et al., *Journal of Biomedical Materials Research—Part A*, Vol. 67, Issue 1, 1 Oct. 2003, Pages 96-103). The phase separation induced by the presence of NaCl leads to an increase in swelling ratio. These materials are preferred if the swelling ratio of the material, SR, is maintained in salt isotonic solution and if the gels do not collapse under load. The temperature of "service" should be shifted beyond body temperature, e.g. by diluting NIPAM in the polymer with monomer devoid of transition temperature phenomenon.

In some embodiments, the fluid-absorbing polymer may be selected from certain naturally-occurring polymers such as those containing carbohydrate moieties. In a preferred embodiment, such carbohydrate-containing hydrogels are non-digestible, have a low fraction of soluble material and a high fraction of gel-forming materials. In some embodiments, the fluid-absorbing polymer is selected from xanthan, guar, wellan, hemicelluloses, alkyl-cellulose, hydro-alkylcellulose, carboxy-alkyl-cellulose, carrageenan, dextran, hyaluronic acid and agarose. In a preferred embodiment, the gel forming polymer is *psyllium*. *Psyllium* (or "ispaghula") is the common name used for several members of the plant genus *Plantago* whose seeds are used commercially for the production of mucilage. Most preferably, the fluid-absorbing polymer is in the gel-forming fraction of *psyllium*, i.e., a neutral saccharide copolymer of arabinose (25%) and xylose (75%) as characterized in (J. Marlett, *Proceedings of the Nutrition* Society, 62, pp. 2-7-209 (2003); and, M. Fischer, *Carbohydrate* Research, 339, 2009-2012 (2004)), and further described in U.S. Pat. Nos. 6,287,609; 7,026,303; 5,126,150; 5,445,831; 7,014,862; 4,766,004; 4,999,200, each of which is incorporated herein for all relevant and consistent purposes, and over-the-counter psillium-containing agents such as those marketed under the name Metamucil (The Procter and Gamble company). Preferably the a psyllium-containing dosage form is suitable for chewing, where the chewing action disintegrates the tablet into smaller, discrete particles prior to swallowing but which undergoes minimal gelling in the mouth, and has acceptable mouthfeel and good aesthetics as perceived by the patient.

The psyllium-containing dosage form includes physically discrete unit suitable as a unitary dosage for human subjects and other mammals, each containing a predetermined quantity of active material (e.g. the gel-forming polysaccharide) calculated to produce the desired therapeutic effect. Solid oral dosage forms that are suitable for the present compositions include tablets, pills, capsules, lozenges, chewable tablets, troches, cachets, pellets, wafer and the like.

In some embodiments, the FAP is a polysaccharide particle wherein the polysaccharide component includes xylose and arabinose. The ratio of the xylose to the arabinose may be at least about 3:1 by weight, as described in U.S. Pat. Nos. 6,287,609; 7,026,303 and 7,014,862, each of which is incorporated herein for all relevant and consistent purposes.

The fluid-absorbing polymers described herein may be used in combination with the NHE-inhibiting compound or a pharmaceutical composition containing it. The NHE-inhibiting compound and the FAP may also be administered with other agents including those described under the heading "Combination Therapies" without departing from the scope of the present disclosure. As described above, the NHE-inhibiting compound may be administered alone without use of a fluid-absorbing polymer to resolve symptoms without eliciting significant diarrhea or fecal fluid secretion that would require the co-administration of a fluid-absorbing polymer.

The fluid-absorbing polymers described herein may be selected so as to not induce any substantial interaction with the NHE-inhibiting compound or a pharmaceutical composition containing it. As used herein, "no substantial interaction" generally means that the co-administration of the FAP polymer would not substantially alter (i.e., neither substantially decrease nor substantially increase) the pharmacological property of the NHE-inhibiting compounds administered alone. For example, FAPs containing negatively charged functionality, such as carboxylates, sulfonates, and the like, may potentially interact ionically with positively charged NHE-inhibiting compounds, preventing the inhibitor from reaching its pharmacological target. In addition, it may be possible that the shape and arrangement of functionality in a FAP could act as a molecular recognition element, and sequester NHE-inhibiting compounds via "host-guest" interactions via the recognition of specific hydrogen bonds and/or hydrophobic regions of a given inhibitor. Accordingly, in various embodiments of the present disclosure, the FAP polymer may be selected, for co-administration or use with a compound of the present disclosure, to ensure that (i) it does not ionically interact with or bind with the compound of the present disclosure (by means of, for example, a moiety present therein possessing a charge opposite that of a moiety in the compound itself), and/or (ii) it does not possess a charge and/or structural conformation (or shape or arrangement) that enables it to establish a "host-guest" interaction with the compound of the present disclosure (by means of, for example, a moiety present therein that may act as a molecular recognition element and sequester the NHE inhibitor or inhibiting moiety of the compound).

D. Dosage

It is to be noted that, as used herein, an "effective amount" (or "pharmaceutically effective amount") of a compound disclosed herein, is a quantity that results in a beneficial clinical outcome of the condition being treated with the compound compared with the absence of treatment. The amount of the compound or compounds administered will depend on the degree, severity, and type of the disease or condition, the amount of therapy desired, and the release characteristics of the pharmaceutical formulation. It will also depend on the subject's health, size, weight, age, sex and tolerance to drugs. Typically, the compound is administered for a sufficient period of time to achieve the desired therapeutic effect.

In embodiments wherein both an NHE-inhibitor compound and a fluid-absorbing polymer are used in the treatment protocol, the NHE-inhibiting compound and FAP may be administered together or in a "dual-regimen" wherein the two therapeutics are dosed and administered separately. When the NHE-inhibiting compound and the fluid-absorbing polymer are dosed separately, the typical dosage administered to the subject in need of the NHE-inhibiting compound typically from about 5 mg per day and about 5000 mg per day and, in other embodiments, from about 50 mg per day and about 1000 mg per day. Such dosages may induce fecal excretion of sodium (and its accompanying anions), from about 10 mmol up to about 250 mmol per day, from about 20 mmol to about 70 mmol per day or even from about 30 mmol to about 60 mmol per day.

The typical dose of the fluid-absorbing polymer is a function of the extent of fecal secretion induced by the non-absorbable NHE-inhibiting compound. Typically the dose is adjusted according to the frequency of bowel movements and consistency of the stools. More specifically the dose is adjusted so as to avoid liquid stools and maintain stool consistency as "soft" or semi-formed, or formed. To achieve the desired stool consistency and provide abdominal relief to patients, typical dosage ranges of the fluid-absorbing polymer to be administered in combination with the NHE-inhibiting compound, are from about 2 g to about 50 g per day, from about 5 g to about 25 g per day or even from about 10 g to about 20 g per day. When the NHE-inhibiting compound and the FAP are administered as a single dosage regimen, the daily uptake may be from about 2 g to about 50 g per day, from about 5 g to about 25 g per day, or from about 10 g to about 20 g per day, with a weight ratio of NHE-inhibiting compound to fluid-absorbing polymer being from about 1:1000 to 1:10 or even from about 1:500 to 1:5 or about 1:100 to 1:5.

A typical dosage of the substantially impermeable or substantially systemically non-bioavailable, NHE-inhibiting compound when used alone without a FAP may be between about 0.2 mg per day and about 2 g per day, or between about 1 mg and about 1 g per day, or between about 5 mg and about 500 mg, or between about 10 mg and about 250 mg per day, which is administered to a subject in need of treatment.

The frequency of administration of therapeutics described herein may vary from once-a-day (QD) to twice-a-day (BID) or thrice-a-day (TID), etc., the precise frequency of administration varying with, for example, the patient's condition, the dosage, etc. For example, in the case of a dual-regimen, the NHE-inhibiting compound could be taken once-a-day while the fluid-absorbing polymer could be taken at each meal (TID). Furthermore, as disclosed in U.S. Application No. 61/584,753 filed Jan. 9, 2012, the NHE-inhibiting compound is administered twice-a-day (BID), or thrice-a-day (TID), and in a more specific embodiment, the NHE-inhibiting compound is administered in an amount ranging from 2-200 mg per dose BID, or 2-100 mg per dose TID. In more specific embodiments, the NHE-inhibiting compound is administered in an amount of about 15 mg per dose, about 30 mg per dose, or about 45 mg per dose, and in a more specific embodiment, in an amount of 15 mg per dose, 30 mg per dose, or 45 mg per dose.

E. Modes of Administration

The substantially impermeable or substantially systemically non-bioavailable NHE-inhibiting compounds of the present disclosure with or without the fluid-absorbing polymers described herein may be administered by any suitable route. The compound is preferably administrated orally (e.g., dietary) in capsules, suspensions, tablets, pills, dragees, liquids, gels, syrups, slurries, and the like. Methods for encapsulating compositions (such as in a coating of hard gelatin or cyclodextran) are known in the art (Baker, et al., "Controlled Release of Biological Active Agents", John Wiley and Sons, 1986). The compounds can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers are biocompatible, i.e., non-toxic, non-inflammatory, non-immunogenic and devoid of other undesired reactions at the administration site. Examples of pharmaceutically acceptable carriers include, for example, saline, commercially available inert gels, or liquids supplemented with albumin, methyl cellulose or a collagen matrix. Standard pharmaceutical formulation techniques can be employed, such as those described in Remington's Pharmaceutical Sciences, Mack Publishing Company, Easton, Pa.

Pharmaceutical preparations for oral use can be obtained by combining a compound of the present disclosure with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of a suitable material, such as gelatin, as well as soft, sealed capsules made of a suitable material, for example, gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

It will be understood that, certain compounds of the disclosure may be obtained as different stereoisomers (e.g., diastereomers and enantiomers) or as isotopes and that the disclosure includes all isomeric forms, racemic mixtures and isotopes of the disclosed compounds and a method of treating a subject with both pure isomers and mixtures thereof, including racemic mixtures, as well as isotopes. Stereoisomers can be separated and isolated using any suitable method, such as chromatography.

F. Delayed Release

NHE proteins show considerable diversity in their patterns of tissue expression, membrane localization and functional roles. (See, e.g., *The sodium-hydrogen exchanger— From molecule To Its Role In Disease*, Karmazyn, M., Avkiran, M., and Fliegel, L., eds., Kluwer Academics (2003).)

In mammals, nine distinct NHE genes (NHE-1 through -9) have been described. Of these nine, five (NHE-1 through -5) are principally active at the plasma membrane, whereas NHE-6, -7 and -9 reside predominantly within intracellular compartments.

NHE-1 is ubiquitously expressed and is chiefly responsible for restoration of steady state intracellular pH following cytosolic acidification and for maintenance of cell volume. Recent findings show that NHE-1 is crucial for organ function and survival (e.g., NHE-1-null mice exhibit locomotor abnormalities, epileptic-like seizures and considerable mortality before weaning).

In contrast with NHE-1 expressed at the basolateral side of the nephrons and gut epithelial cells, NHE-2 through -4 are predominantly expressed on the apical side of epithelia of the kidney and the gastrointestinal tract. Several lines of evidence show that NHE-3 is the major contributor of renal bulk Na+ and fluid re-absorption by the proximal tubule. The associated secretion of H+ by NHE-3 into the lumen of renal tubules is also essential for about ⅔ of renal $HCO_3^-$ re-absorption. Complete disruption of NHE-3 function in mice causes a sharp reduction in $HCO_3^-$, Na+ and fluid re-absorption in the kidney, which is consistently associated with hypovolemia and acidosis.

In one embodiment, the compounds of the disclosure are intended to target the apical NHE antiporters (e.g. NHE-3, NHE-2 and NHE-8) without substantial permeability across the layer of gut epithelial cells, and/or without substantial activity towards NHEs that do not reside predominantly in the GI tract. This invention provides a method to selectively inhibit GI apical NHE antiporters and provide the desired effect of salt and fluid absorption inhibition to correct abnormal fluid homeostasis leading to constipations states. Because of their absence of systemic exposure, said compounds do not interfere with other key physiological roles of NHEs highlighted above. For instance, the compounds of the disclosure are expected to treat constipation in patients in need thereof, without eliciting undesired systemic effects, such as for example salt wasting or bicarbonate loss leading to hyponatriemia and acidosis among other disorders.

In another embodiment, the compounds of the disclosure are delivered to the small bowel with little or no interaction with the upper GI such as the gastric compartment and the duodenum. The applicant found that an early release of the compounds in the stomach or the duodenum can have an untoward effect on gastric secretion or bicarbonate secretion (also referred to as "bicarbonate dump"). In this embodiment the compounds are designed so as to be released in an active form past the duodenum. This can be accomplished by either a prodrug approach or by specific drug delivery systems.

As used herein, "prodrug" is to be understood to refer to a modified form of the compounds detailed herein that is inactive (or significantly less active) in the upper GI, but once administered is metabolised in vivo into an active metabolite after getting past, for example, the duodenum. Thus, in a prodrug approach, the activity of the NHE-inhibiting compound can be masked with a transient protecting group that is liberated after compound passage through the desired gastric compartment. For example, acylation or alkylation of the essential guanidinyl functionality of the NHE-inhibiting compound would render it biochemically inactive; however, cleavage of these functional groups by intestinal amidases, esterases, phosphatases, and the like, as well enzymes present in the colonic flora, would liberate the active parent compound. Prodrugs can be designed to exploit the relative expression and localization of such phase I metabolic enzymes by carefully optimizing the structure of the prodrug for recognition by specific enzymes. As an example, the anti-inflammatory agent sulfasalazine is converted to 5-aminosalicylate in the colon by reduction of the diazo bond by intestinal bacteria.

In a drug delivery approach the NHE-inhibiting compounds of the disclosure are formulated in certain pharmaceutical compositions for oral administration that release the active in the targeted areas of the GI, i.e., jejunum, ileum or colon, or preferably the distal ileum and colon, or even more preferably the colon.

Methods known from the skilled-in-the-art are applicable. (See, e.g., Kumar, P. and Mishra, B., Colon Targeted Drug Delivery Systems—An Overview, *Curr. Drug Deliv.*, 2008, 5 (3), 186-198; Jain, S. K. and Jain, A., Target-specific Drug Release to the Colon., *Expert Opin. Drug Deliv.*, 2008, 5 (5), 483-498; Yang, L., Biorelevant Dissolution Testing of Colon-Specific Delivery Systems Activated by Colonic Microflora, *J. Control Release*, 2008, 125 (2), 77-86; Siepmann, F; Siepmann, J.; Walther, M.; MacRae, R. J.; and Bodmeier, R., Polymer Blends for Controlled Release Coatings, *J. Control Release* 2008, 125 (1), 1-15; Patel, M.; Shah, T.; and Amin, A, Therapeutic Opportunities in Colon-Specific Drug-Delivery Systems, *Crit. Rev. Ther. Drug Carrier Syst.*, 2007, 24 (2), 147-202; Jain, A.; Gupta, Y.; Jain, S. K., Perspectives of Biodegradable Natural Polysaccharides for Site-specific Drug Delivery to the Colon., *J. Pharm. Sci.*, 2007, 10 (1), 86-128; Van den, M. G., Colon Drug Delivery, *Expert Opin. Drug Deliv.*, 2006, 3 (1), 111-125; Basit, A. W., Advances in Colonic Drug Delivery, *Drugs* 2005, 65 (14), 1991-2007; Chourasia, M. K.; Jain, S. K., Polysaccharides for Colon-Targeted Drug Delivery, *Drug Deliv.* 2004, 11 (2), 129-148; Shareef, M. A.; Khar, R. K.; Ahuja, A.; Ahmad, F. J.; and Raghava, S., Colonic Drug Delivery: An Updated Review, *AAPS Pharm. Sci.* 2003, 5 (2), E17; Chourasia, M. K.; Jain, S. K., Pharmaceutical Approaches to Colon Targeted Drug Delivery Systems, *J. Pharm. Sci.* 2003, 6 (1), 33-66; and, Sinha, V. R.; Kumria, R., Colonic Drug Delivery: Prodrug Approach, *Pharm. Res.* 2001, 18 (5), 557-564. Typically the active pharmaceutical ingredient (API) is contained in a tablet/capsule designed to release said API as a function of the environment (e.g., pH, enzymatic activity, temperature, etc.), or as a function of time. One example of this approach is Eudracol™ (Pharma Polymers Business Line of Degussa's Specialty Acrylics Business Unit), where the API-containing core tablet is layered with various polymeric coatings with specific dissolution profiles. The first layer ensures that the tablet passes through the stomach intact so it can continue through the small intestine. The change from an acidic environment in the stomach to an alkaline environment in the small intestine initiates the release of the protective outer layer. As it travels through the colon, the next layer is made permeable by the alkalinity and intestinal fluid. This allows fluid to penetrate to the interior layer and release the active ingredient, which diffuses from the core to the outside, where it can be absorbed by the intestinal wall. Other methods are contemplated without departing, from the scope of the present disclosure.

In another example, the pharmaceutical compositions of the invention can be used with drug carriers including pectin and galactomannan, polysaccharides that are both degradable by colonic bacterial enzymes. (See, e.g., U.S. Pat. No. 6,413,494, the entire contents of which are incorporated herein by reference for all relevant and consistent purposes.) While pectin or galactomannan, if used alone as a drug carrier, are easily dissolved in simulated gastric fluid and simulated intestinal fluid, a mixture of these two polysaccharides prepared at a pH of about 7 or above produces a strong, elastic, and insoluble gel that is not dissolved or disintegrated in the simulated gastric and intestinal fluids, thus protecting drugs coated with the mixture from being released in the upper GI tract. When the mixture of pectin and galactomannan arrives in the colon, it is rapidly degraded by the synergic action of colonic bacterial enzymes. In yet another aspect, the compositions of the invention may be used with the pharmaceutical matrix of a complex of gelatin and an anionic polysaccharide (e.g., pectinate, pectate, alginate, chondroitin sulfate, poly galacturonic acid, tragacanth gum, arabic gum, and a mixture thereof), which is degradable by colonic enzymes (U.S. Pat. No. 6,319,518).

In yet other embodiments, fluid-absorbing polymers that are administered in accordance with treatment methods of the present disclosure are formulated to provide acceptable/pleasant organoleptic properties such as mouthfeel, taste, and/or to avoid premature swelling/gelation in the mouth and in the esophagus and provoke choking or obstruction. The formulation may be designed in such a way so as to ensure the full hydration and swelling of the FAP in the GI tract and avoid the formation of lumps. The oral dosages for the FAP may take various forms including, for example, powder, granulates, tablets, wafer, cookie and the like, and are most preferably delivered to the small bowel with little or no interaction with the upper GI such as the gastric compartment and the duodenum.

The above-described approaches or methods are only some of the many methods reported to selectively deliver an active in the lower part of the intestine, and therefore should not be viewed to restrain or limit the scope of the disclosure.

The following non-limiting examples are provided to further illustrate the present disclosure.

EXAMPLES

Exemplary Compound Synthesis

Intermediate A (S)—N-(2-(2-(aminomethoxy)ethoxy)ethyl)-3-(6,8-dichloro-2-methyl-1,2,3,4-tetrahydroisoquinolin-4-yl)benzenesulfonamide

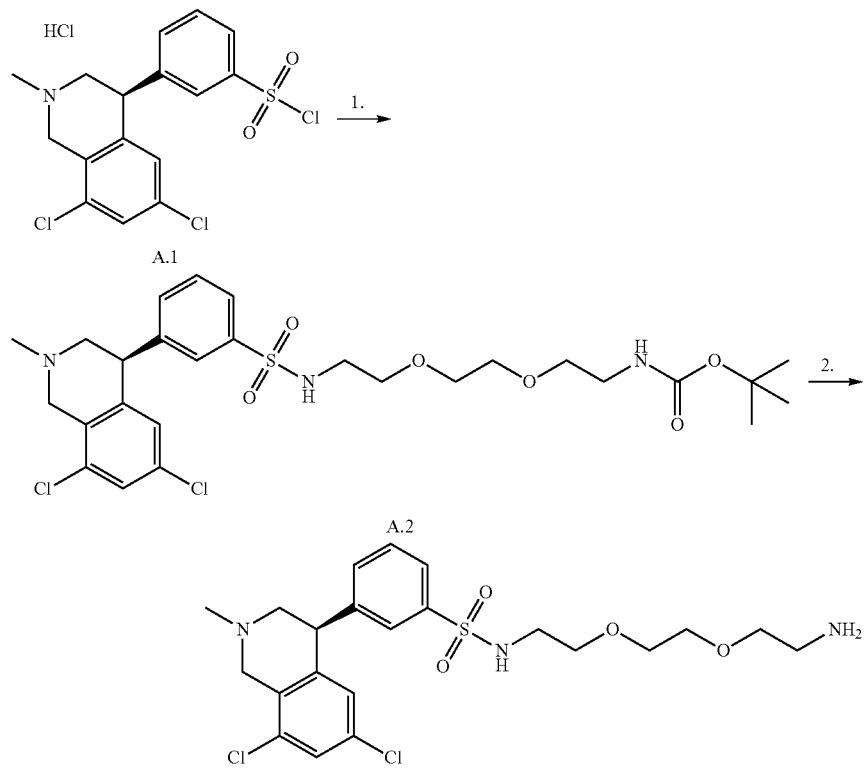

1. tert-butyl 2-(2-(2-aminoethoxy)ethoxy)ethylcarbamate, $K_3PO_4$, water, THF;
2. Aqueous 25% $H_2SO_4$, 2-propanol.

Intermediate A.2: (S)-tert-Butyl (2-(2-(2-(3-(6,8-dichloro-2-methyl-1,2,3,4-tetrahydroisoquinolin-4-yl)phenylsulfonamido)ethoxy)ethoxy)ethyl)carbamate. tert-Butyl (2-(2-(2-aminoethoxy)ethoxy)ethyl)carbamate (8.72 g, 35.1 mmol) was dissolved in THF (90 mL). To this solution was added a solution of $K_3PO_4$ (37.3 g, 175 mmol) in water (90 mL). To this rapidly stirring mixture was added solid sulfonyl chloride A.1 (see International PCT Publication No. WO 2010/078449) (15.0 g, 35.1 mmol) in ~1 g portions over 15 min. After 1h, the mixture was diluted with EtOAc (90 mL), and the organic layer separated. The aqueous layer was washed with EtOAc (10 mL), and the organic extracts combined. The solution was concentrated, and purified by flash chromatography on silica gel eluting with a gradient of 0% to 10% methanol in DCM to give intermediate A.2 (18.7 g) as a viscous oil. $^1$H NMR (400 MHz, $CDCl_3$) δ 7.75 (d, J=7.5 Hz, 1H), 7.68 (s, 1H), 7.44 (t, J=7.7 Hz, 1H), 7.36 (d, J=7.4 Hz, 1H), 7.26-7.21 (m, 1H), 6.73 (s, 1H), 5.28 (s, 1H), 5.08 (s, 1H), 4.25 (t, J=6.1 Hz, 1H), 3.79-3.44 (m, 10H), 3.30 (d, J=4.5 Hz, 2H), 3.12 (t, J=4.6 Hz, 2H), 2.93 (dd, J=11.5, 5.2 Hz, 1H), 2.58 (dd, J=11.6, 7.2 Hz, 1H), 2.44 (s, 3H), 1.42 (s, 9H). Mass (ESI+) 602.10 (M+H$^+$).

Intermediate A: (S)—N-(2-(2-(aminomethoxy)ethoxy)ethyl)-3-(6,8-dichloro-2-methyl-1,2,3,4-tetrahydroisoquinolin-4-yl)benzenesulfonamide Intermediate A.2 (15.2 g, 25.2 mmol) was dissolved in warm (45° C.) 2-propanol (80 mL). This solution was added to aqueous 25% $H_2SO_4$ at 45° C., over 1h. The solution was stirred for an additional hour, then concentrated under reduced pressure to remove the 2-propanol. DCM (150 mL) was added, and the pH of the mixture was adjusted with $K_3PO_4$ to pH 7-8 using pH paper. The DCM layer was separated, and the aqueous layer was extracted three more times with DCM (150 mL). The organic layer was dried, and concentrated under reduced pressure to give intermediate A (12 g) as a foam. $^1$H NMR (400 MHz, $CDCl_3$) δ 7.83 (d, J=7.9 Hz, 1H), 7.77 (s, 1H), 7.41 (t, J=7.4 Hz, 1H), 7.31 (d, J=7.4 Hz, 1H), 7.22 (s, 1H), 6.72 (s, 1H), 4.26 (t, J=5.3 Hz, 1H), 3.79-3.47 (m, 12H), 3.13 (d, J=32.2 Hz, 4H), 2.93 (dd, J=11.8, 5.1 Hz, 1H), 2.59 (dd, J=10.7, 7.4 Hz, 1H), 2.43 (s, 3H). Mass (ESI+) 502.11 (M+H$^+$).

Intermediate B bis(perfluorophenyl) 4-nitro-4-(3-oxo-3-(perfluorophenoxy)propyl)heptanedioate Scheme B: perfluorophenyl 2,2,2-trifluoroacetate, TEA, DCM.

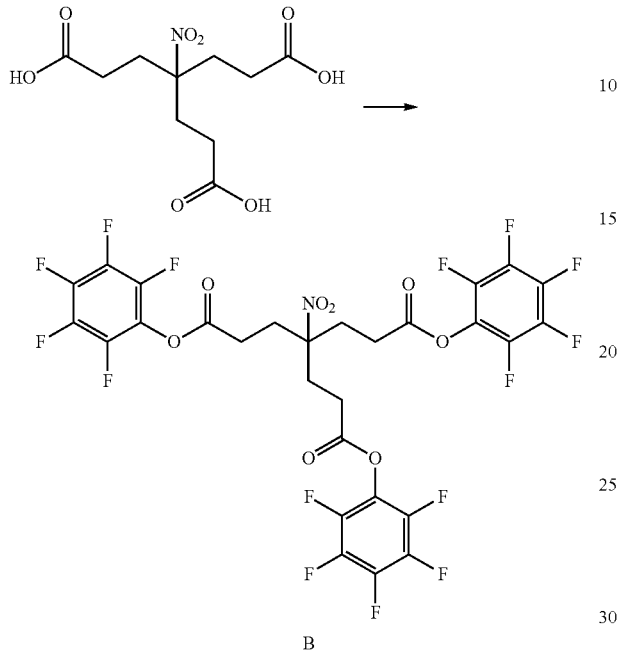

Intermediate B: A solution of 4-(2-carboxyethyl)-4-nitroheptanedioic acid (3.00 g, 10 8 mmol) in DCM (54 mL) was charged in an additional funnel and added dropwise to a solution of perfluorophenyl 2,2,2-trifluoroacetate (6.15 mL, 35.7 mmol) and TEA (9.0 mL, 65 mmol) in DCM (54 mL). Upon completion of addition, the solution was stirred an additional 20 min at room temperature, during which time a white precipitate formed. The precipitate was filtered and washed with 3:7 DCM:hexanes and then washed with hexanes to give the title compound (6.87 g, 82%) as a white solid. $^1$H-NMR (400 MHz, CDCl$_3$) δ 2.88-2.71 (m, 6H), 2.59-2.41 (m, 6H). $^{19}$F-NMR (376 MHz, CDCl$_3$) δ −152.71 (d, J=17.1 Hz), −157.08 (t, J=21.7 Hz), −161.86 (dt, J=21.4, 10.7 Hz).

Intermediate C tris(perfluorophenyl) 2,2',2''-nitrilotriacetate

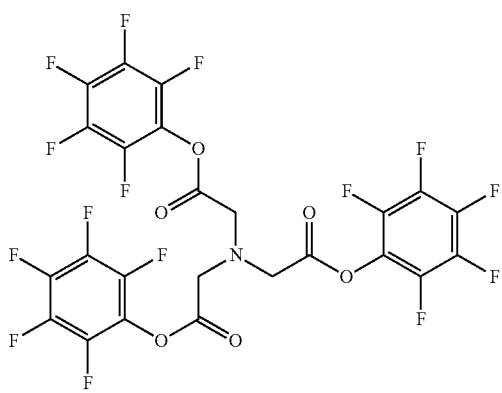 [SMILES: O=C(CN(CC(=O)Oc1c(F)c(F)c(F)c(F)c1F)CC(=O)Oc1c(F)c(F)c(F)c(F)c1F)Oc1c(F)c(F)c(F)c(F)c1F]

Intermediate C: The title compound was synthesized in a manner similar to bis(perfluorophenyl) 4-nitro-4-(3-oxo-3-(perfluorophenoxy)propyl)heptanedioate, using 2,2',2''-nitrilotriacetic acid in place of 4-(2-carboxyethyl)-4-nitroheptanedioic acid.

Intermediate D

(9H-fluoren-9-yl)methyl 1,25-bis(3-((S)-6,8-dichloro-2-methyl-1,2,3,4-tetrahydroisoquinolin-4-yl)phenylsulfonamido)-13-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-10,16-dioxo-3,6,20,23-tetraoxa-9,17-diazapentacosan-13-ylcarbamate Scheme D.

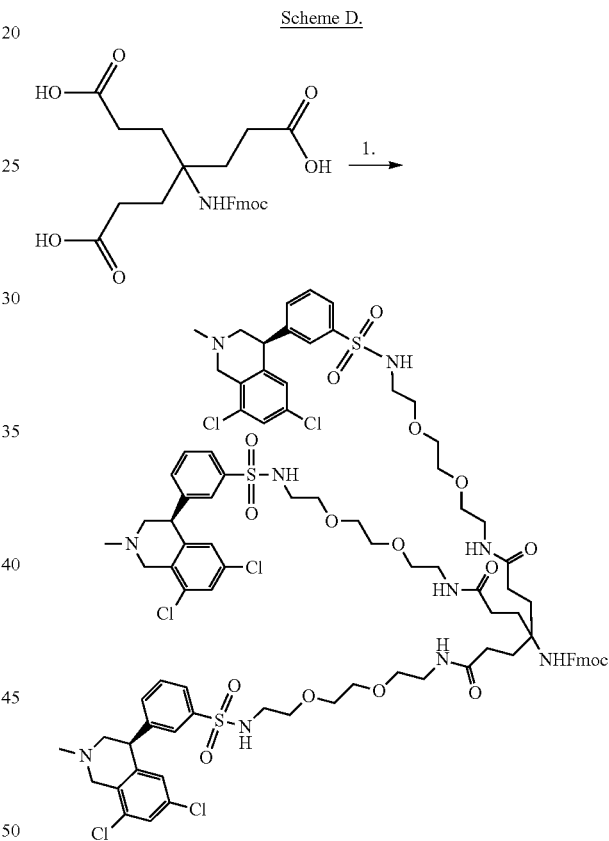

1. Carbonyldiimidazole, THF, then A, DMF.

Intermediate D: 4-(((9H-fluoren-9-yl)methoxy)carbonylamino)-4-(2-carboxyethyl)heptanedioic acid (2.07 g, 4.40 mmol) was dissolved in THF (80 mL), then carbonyldiimidazole (2.21 g, 13.6 mmol) was added and the resulting mixture stirred for 2 h at room temperature. Additional carbonyldiimidazole (357 mg, 2.20 mmol) was the added in three portions over a period of 1.5 h, until a sample of the reaction mixture quenched with N$^1$,N$^1$-dimethylpropane-1,3-diamine showed all of the starting material was consumed. To the mixture was then added a solution of A (7.30 g, 14.5 mmol) in DMF and the resulting solution stirred for 2 h at room temperature. The solution was then poured into H$_2$O (800 mL) and the resulting white precipitate filtered. The precipitate was then dissolved in DCM and washed with 1 M aqueous HCl and saturated aqueous NaHCO₃, then the solvent removed under reduced pressure to give D (8.36 g, 99%) as a light yellow foam. ¹H-NMR (400 MHz, CDCl₃) δ 7.76-7.67 (m, 7H), 7.57 (t, J=8.1 Hz, 3H), 7.39 (t, J=7.7 Hz, 3H), 7.37-7.27 (m, 6H), 7.26-7.18 (m, 2H), 6.73-6.63 (m, 5H), 4.30-4.19 (m, 6H), 4.05 (t, J=6.7 Hz, 1H), 3.61 (dd, J=36.9, 16.2 Hz, 6H), 3.54-3.42 (m, 21H), 3.37 (dd, J=10.1, 4.9 Hz, 6H), 3.11-3.01 (m, 6H), 2.95-2.84 (m, 5H), 2.55 (dd, J=11.5, 7.2 Hz, 3H), 2.41 (s, 9H), 2.28-2.17 (m, 6H), 2.04-1.93 (m, 6H). MS (ES, m/z): 1919.3 [M+H]⁺.

Intermediate E (S)—N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide a viscous oil. ¹H NMR (400 MHz, CDCl₃) 7.73 (d, J=7.9 Hz, 1H), 7.67 (s, 1H), 7.43 (t, J=7.9 Hz, 1H), 7.35 (d, J=7.6 Hz, 1H), 6.72 (s, 1H), 5.23 (dd, J=6.1, 5.7 Hz, 1H), 4.23-4.25 (m, 1H), 3.67-3.47 (comp, 14H), 3.37 (t, J=4.9 Hz, 2H), 3.11 (q, J=10.4, 5.5 Hz, 2H), 2.93 (dd, J=5.2, 11.6 Hz, 2H), 2.58 (dd, J=11.7, 7.4 Hz, 1H), 2.43 (s, 3H). Mass (ESI+) 572.12 (M+H⁺)

Intermediate E: (S)—N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide. To a solution of Intermediate E.1 (13.0 g, 22.7 mmol) in THF (75 mL) at 10° C., was added trimethylphosphine (3.46 g, 45 4 mmol) keeping the internal temperature under 15° C. The solution was stirred for 1h at 10° C., then warmed to 20° C. for 1 hr. An aqueous solution of ice cold NaOH (1M, 10 mmol, 10 mL) was added, then after 15 min, the mixture was concen-

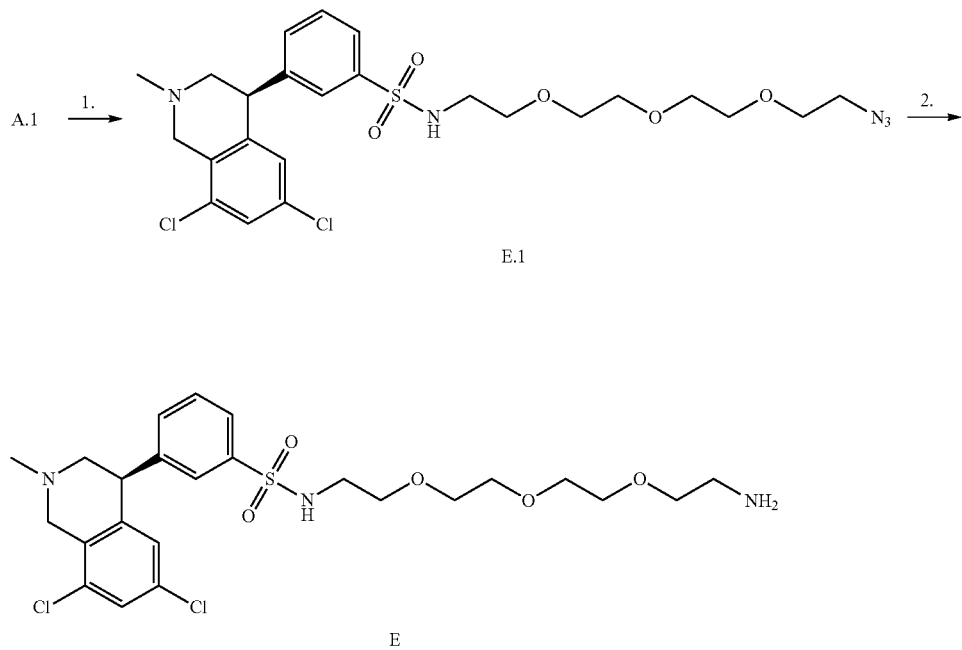

1. 2-(2-(2-(2-azidoethoxy)ethoxy)ethoxy)ethanamine, K₃PO₄, water, THF;
2. Me₃P, THF, water, NaOH.

Intermediate E.1: (S)—N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide 2-(2-(2-(2-azidoethoxy)ethoxy)ethoxy)ethanamine (6.49, 29.7 mmol) was dissolved in THF (90 mL). To this solution was added a solution of K₃PO₄ (27.5 g, 130 mmol) in water (90 mL). To this rapidly stirring mixture was added solid sulfonyl chloride A.1 (12.1 g, 28.3 mmol) in ~1 g portions over 15 min. After 1h, the mixture was diluted with EtOAc (90 mL), and the organic layer separated. The aqueous layer was washed with EtOAc (10 mL), and the organic extracts combined. The solution was concentrated, and purified by flash chromatography on silica eluting with a gradient of 0% to 10% methanol in DCM to give intermediate E.1 (16 g) as trated under reduced pressure to remove the bulk of the THF. The stirring aqueous mixture was diluted with DCM (1.5 L), and water (100 mL) was added, followed by aqueous 25% NaCl solution (25 mL). Aggitation was stopped, and the mixture separated (~1h). The aqueous layer was extracted twice with DCM (200 mL), and the combined extracts were dried (MgSO₄), and concentrated under reduced pressure to give intermediate E (13.5 g) as a tacky foam. 1H NMR (400 MHz, CDCl₃) δ 7.78-7.71 (m, 1H), 7.67 (t, J=1.7 Hz, 1H), 7.42 (t, J=7.7 Hz, 1H), 7.33 (d, J=7.8 Hz, 1H), 7.26-7.21 (m, 1H), 6.73 (s, 1H), 4.25 (t, J=6.3 Hz, 1H), 3.76-3.46 (m, 8H), 3.14-3.08 (m, 2H), 2.93 (dd, J=11.7, 5.6 Hz, 1H), 2.84 (t, 2H), 2.58 (dd, J=11.7, 7.4 Hz, 1H), 2.44 (s, 3H). Mass (ESI+) 546.12 (M+H⁺).

Intermediate F

Tris(perfluorophenyl) 3,3',3''-nitrilotripropanoate

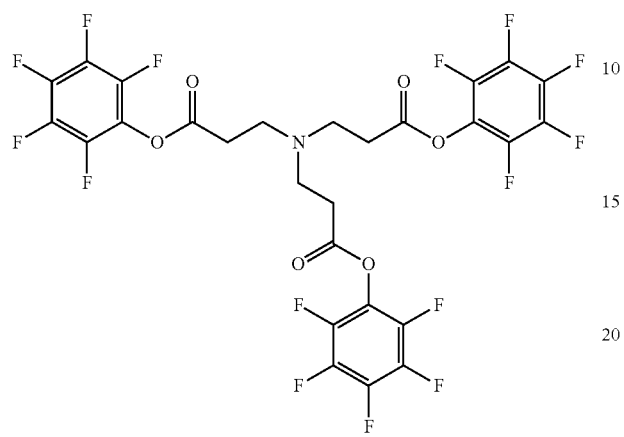

Intermediate F: The title compound was synthesized in a manner similar to bis(perfluorophenyl) 4-nitro-4-(3-oxo-3-(perfluorophenoxy)propyl)heptanedioate, using 3,3',3''-nitrilotripropanoic acid in place of 4-(2-carboxyethyl)-4-nitroheptanedioic acid.

Intermediate G

N$^1$,N$^7$-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-4-isocyanatoheptanediamide Scheme G:

2 →

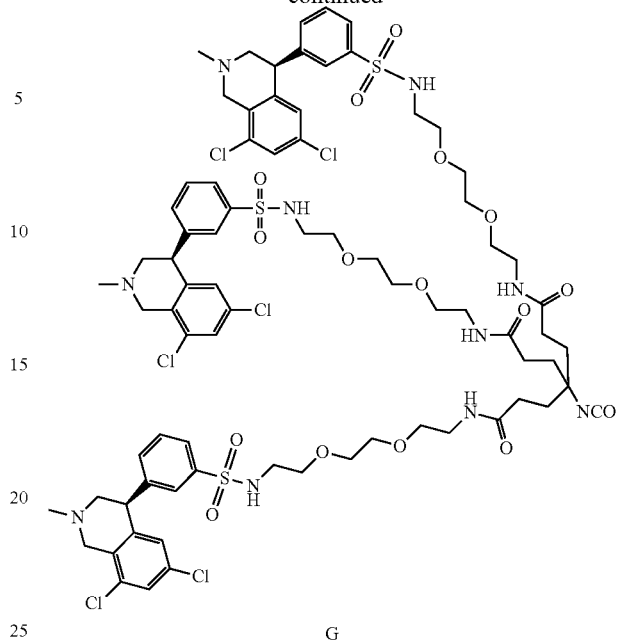

1. triphosgene, triethylamine, DCM, THF.

Intermediate G: To a solution of example 2 (120 mg, 0.0706 mmol) and triethylamine (49 µL, 0.35 mmol) in DCM (2 mL) and THF (2 mL) cooled to 0° C. was added triphosgene (10.5 mg, 0.353 mmol). The solution was then allowed to warm to room temperature and stirred for 30 min, then stirred an additional 1 h at 40° C. The mixture was then diluted with DCM and washed with saturated aqueous NaHCO$_3$. The organic layer dried over Na$_2$SO4 and then the solvent removed under reduces pressure to give the product as a yellow oil, which was used directly without further purification. MS (ES, m/z): 1722.8 [M+H]$^+$.

Intermediate H

(S)-3-(6,8-dichloro-2-methyl-1,2,3,4-tetrahydroisoquinolin-4-yl)-N-(2-(2-(2-(methylamino)ethoxy)ethoxy)ethyl)benzenesulfonamide Scheme H.

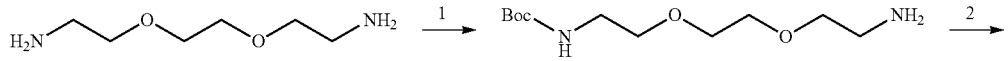

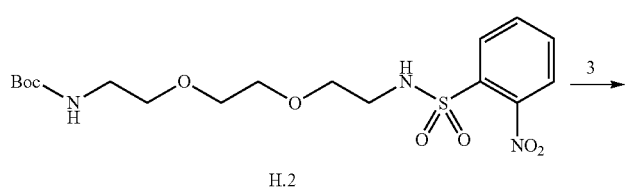

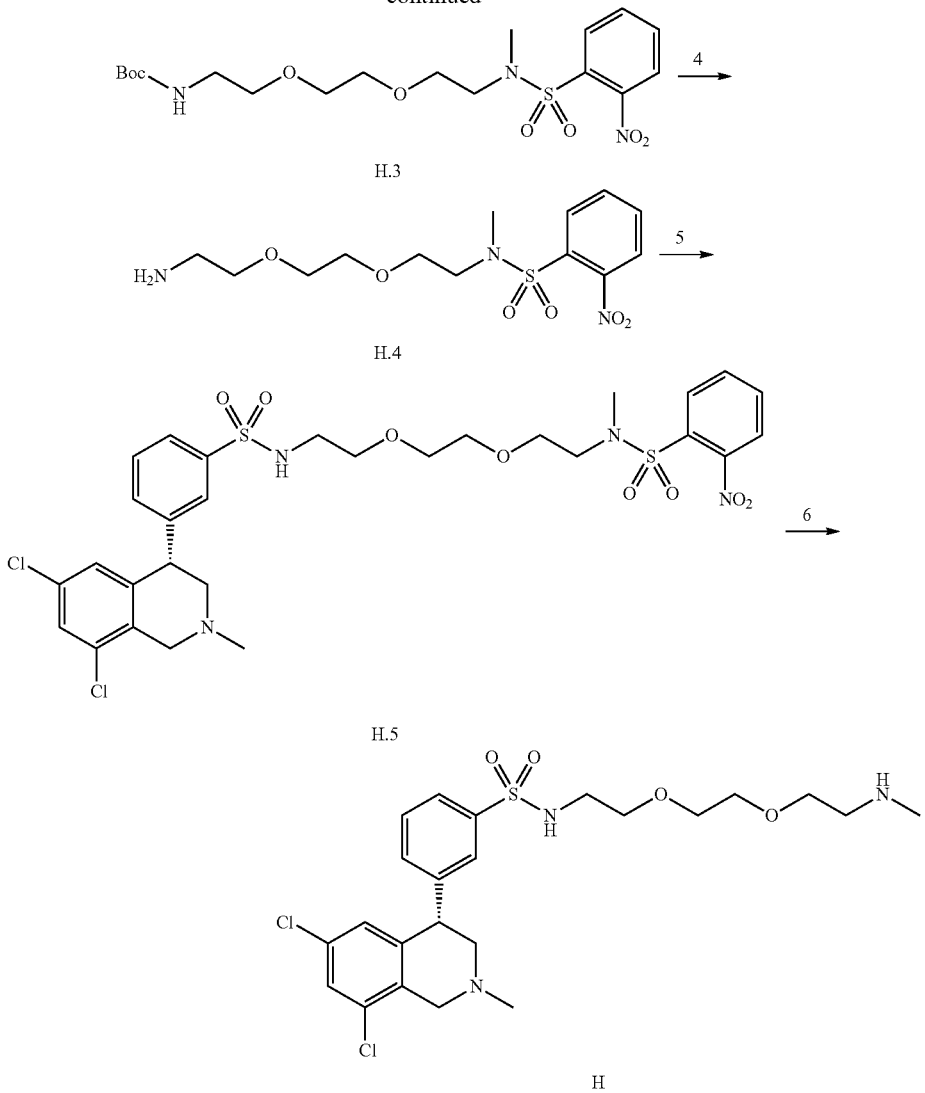

1. DCM;
2. 2-nitrobenzenesulfonyl chloride, TEA, DCM;
3. MeI, K₂CO₃, DMF;
4. HCl, dioxane, DCM;
5. Intermediate A.1;
6. thiophenol, K₂CO₃, DMF.

Intermediate H.1: tert-butyl (2-(2-(2-aminoethoxy)ethoxy)ethyl)carbamate. To a mixture of 2,2'-(ethylenedioxy)bis(ethylamine) (153 g, 1.032 mol, 4.5 equiv) in DCM (250 mL) at 0° C. was added a solution of di-tert-butyl dicarbonate (50 g, 0.229 mol, 1 equiv) in DCM (100 mL) over 3.5 h. The mixture was slowly warmed to rt, stirred at rt overnight and washed with 25% aqueous NaCl solution (3×100 mL) and water (100 mL). The organic layer was extracted with 20% aqueous citric acid (250 mL). The aqueous layer was washed with DCM (150 mL), basified to pH 13-14 by aqueous NaOH solution (2 M), extracted with DCM (3×). The combined organic layers were dried and concentrated to give 47 g (83%) of intermediate H.1 as clear oil.

Intermediate H.2: tert-butyl (2-(2-(2-(2-nitrophenylsulfonamido)ethoxy)ethoxy)ethyl)carbamate, To a mixture of tert-butyl (2-(2-(2-aminoethoxy)ethoxy)ethyl)carbamate (4.0 g, 16.15 mmol, 1.0 equiv) and triethylamine (3.38 mL, 24.22 mmol, 1.5 equiv) in DCM (30 mL) at 0° C. was added a solution of 2-nitrobenzenesulfonyl chloride (3.76 g, 16.95 mmol, 1.05 equiv) in DCM (20 mL) dropwise. The mixture was stirred at rt overnight, diluted with ethyl acetate and washed with 10% citric acid (1×), H₂O (1×), sat. aqueous NaHCO₃ (1×), brine (1×). The organic layer was dried and concentrated to give 7.34 g of intermediate H.2 as yellow syrup.

Intermediate H.3: tert-butyl (2-(2-(2-(N-methyl-2-nitrophenylsulfonamido)ethoxy)ethoxy)ethyl)carbamate. To a mixture of tert-butyl (2-(2-(2-(2-nitrophenylsulfonamido)ethoxy)ethoxy)ethyl)carbamate (7.34 g, 16.96 mmol, 1.0 equiv) in DMF (50 mL) were added K₂CO₃ (3.51 g, 25.44 mmol, 1.5 equiv) and iodomethane (1.48 mL, 23.74 mmol, 1.4 equiv). The mixture was stirred at rt for 1.5 h, diluted with ethyl acetate, washed with H$_2$O (2×) and brine (1×), dried, and concentrated to give 7.58 g of intermediate H.3 as yellow syrup.

Intermediate H.4: N-(2-(2-(2-aminoethoxy)ethoxy)ethyl)-N-methyl-2-nitrobenzenesulfonamide. To a mixture of tert-butyl (2-(2-(2-(N-methyl-2-nitrophenylsulfonamido)ethoxy)ethoxy)ethyl)carbamate (7.58 g) in DCM (2 mL) was added a solution of HCl in dioxane (4 M, 40 mL). The mixture was stirred at rt for 40 minutes and concentrated to give 7.3 g of intermediate H.4 HCl salt as yellow syrup.

Intermediate H.5: (S)—N-(2-(2-(2-(3-(6,8-dichloro-2-methyl-1,2,3,4-tetrahydroisoquinolin-4-yl)-phenylsulfonamido)ethoxy)ethoxy)ethyl)-N-methyl-2-nitrobenzenesulfonamide. To a mixture of N-(2-(2-(2-aminoethoxy)ethoxy)ethyl)-N-methyl-2-nitrobenzenesulfonamide (7.3 g crude, about 16.15 mmol, 1 equiv) and TEA (11.25 mL, 80.73 mmol, 5 equiv) in DCM (80 mL) at 0° C. was added (S)-3-(6,8-dichloro-2-methyl-1,2,3,4-tetrahydroisoquinolin-4-yl)benzene-1-sulfonyl chloride A.1 (7.24 g, 16.95 mmol, 1.05 equiv). The mixture was stirred at rt for 1h, diluted with ethyl acetate, washed with water (1×) and brine (1×), dried, concentrated, and purified by column to give 9.84 g (87%, 4 steps) of intermediate H.5 as a yellow solid.

Intermediate H: (S)-3-(6,8-dichloro-2-methyl-1,2,3,4-tetrahydroisoquinolin-4-yl)-N-(2-(2-(2-(methylamino)ethoxy)ethoxy)ethyl)benzenesulfonamide. To a mixture of (S)—N-(2-(2-(2-(3-(6,8-dichloro-2-methyl-1,2,3,4-tetrahydroisoquinolin-4-yl)-phenylsulfonamido)ethoxy)ethoxy)ethyl)-N-methyl-2-nitrobenzenesulfonamide (5.1 g, 7.28 mmol, 1 equiv) and K$_2$CO$_3$ (3.01 g, 21.83 mmol, 3 equiv) in DMF (30 mL) at rt was added thiophenol (1.12 mL, 10.91 mmol, 1.5 equiv). The mixture was stirred at rt for 1h, diluted with ether and extracted with 1N aqueous HCl. The aqueous layer was washed with ether (2×), basified with NaHCO$_3$ to pH 9, and extracted with DCM (3×). The combined organic layers were dried, concentrated and purified by C-18 column to give 4.03 g (75%) of the title compound TFA salt as a white solid. MS (ES, m/z): 516 [M+H]$^+$. $^1$H NMR (400 MHz, CD$_3$OD) δ 7.77 (dt, J=7.6, 1.5 Hz, 1H), 7.70-7.65 (m, 1H), 7.58-7.47 (m, 2H), 7.35 (d, J=1.5 Hz, 1H), 6.80 (d, J=1.2 Hz, 1H), 4.40 (t, J=6.5 Hz, 1H), 3.78 (d, J=16.2 Hz, 1H), 3.70-3.62 (m, 3H), 3.62-3.58 (m, 2H), 3.57-3.53 (m, 2H), 3.51-3.46 (m, 2H), 3.05-2.99 (m, 3H), 2.98-2.91 (m, 2H), 2.67 (dd, J=11.7, 7.8 Hz, 1H), 2.55 (s, 3H), 2.48 (s, 3H).

Intermediate I (S)—N-(2-(2-(2-aminoethoxy)ethoxy)ethyl)-3-(6,8-dichloro-2-methyl-1,2,3,4-tetrahydroisoquinolin-4-yl)-N-methylbenzenesulfonamide Scheme I.

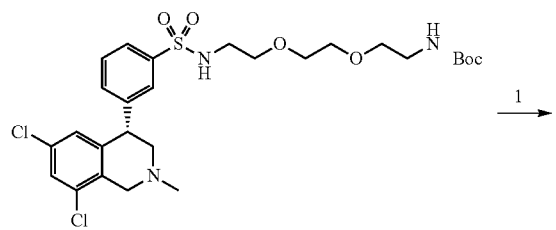

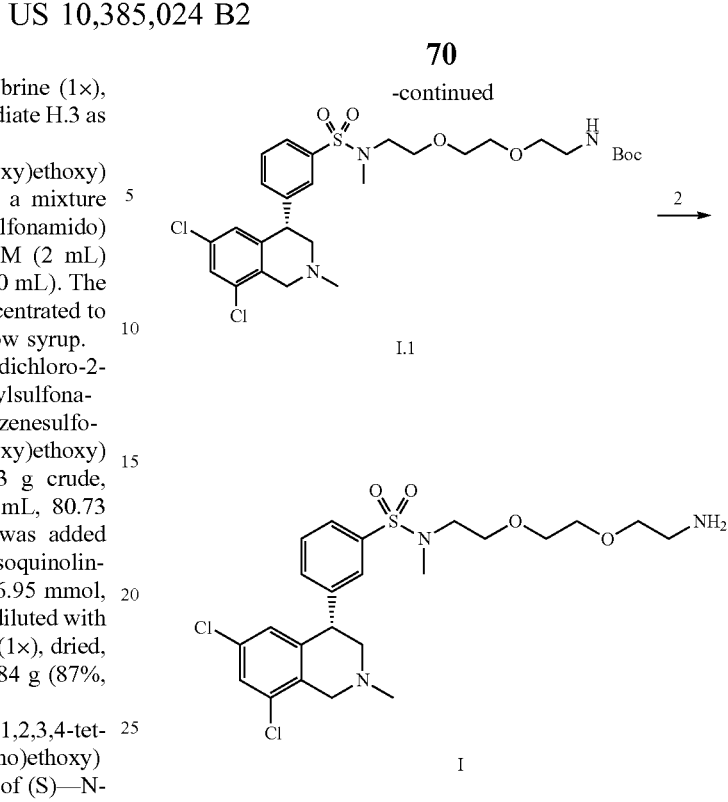

1. DEAD, PPh$_3$, methanol, THF;
2. HCl, dioxane, DCM.

Intermediate I.1: (S)-t-butyl (2-(2-(2-(3-(6,8-dichloro-2-methyl-1,2,3,4-tetrahydroisoquinolin-4-yl)-N-methylphenylsulfonamido)ethoxy)ethoxy)ethyl)carbamate. To a mixture of (S)-t-butyl (2-(2-(2-(3-(6,8-dichloro-2-methyl-1,2,3,4-tetrahydroisoquinolin-4-yl)phenylsulfonamido)ethoxy)ethoxy)ethyl)carbamate (352 mg, 0.586 mmol, 1 equiv), methanol (47.4 µL, 1.17 mmol, 2 equiv) and PPh$_3$ (307 mg, 1.17 mmol, 2 equiv) in THF (2 mL) at 0° C. was added dropwise a solution of diethyl azodicarboxylate (40% in toluene, 0.534 mL, 1.17 mmol, 2 equiv). The mixture was stirred at rt overnight, concentrated and purified by column to give 0.9 g (crude) of intermediate I.1 as yellow syrup.

Intermediate I: (S)—N-(2-(2-(2-aminoethoxy)ethoxy)ethyl)-3-(6,8-dichloro-2-methyl-1,2,3,4-tetrahydroisoquinolin-4-yl)-Nmethylbenzenesulfonamide. To a mixture of (S)-t-butyl (2-(2-(2-3-(6,8-dichloro-2-methyl-1,2,3,4-tetrahydroisoquinolin-4-yl)-N-methylphenylsulfonamido)ethoxy)ethoxy)ethyl)carbamate (0.7 g) in DCM (0.5 mL) was added a solution of HCl in dioxane 4 M, 3 mL). The mixture was stirred at rt for 0.5 h, concentrated and purified by prep HPLC to give 200 mg (59%, 2 steps) of intermediate I as a white solid. MS (ES, m/z): 516 [M+H]$^+$. $^1$H NMR (400 MHz, CD$_3$OD) δ 7.87-7.80 (m, 1H), 7.73-7.64 (m, 2H), 7.60 (d, J=7.8 Hz, 1H), 7.55 (d, J=2.0 Hz, 1H), 6.83 (s, 1H), 4.84-4.73 (m, 2H), 4.50 (d, J=16.0 Hz, 1H), 3.90 (ddd, J=12.2, 5.9, 1.3 Hz, 1H), 3.75-3.70 (m, 2H), 3.69-3.62 (m, 6H), 3.59 (d, J=12.0 Hz, 1H), 3.21 (dd, J=9.3, 5.2 Hz, 2H), 3.17-3.08 (m, 5H), 2.80 (s, 3H).

Intermediate J

N$^1$-methyl-N$^3$,N$^3$-bis(3-(methylamino)propyl)propan-1,3-diamine

Scheme J.

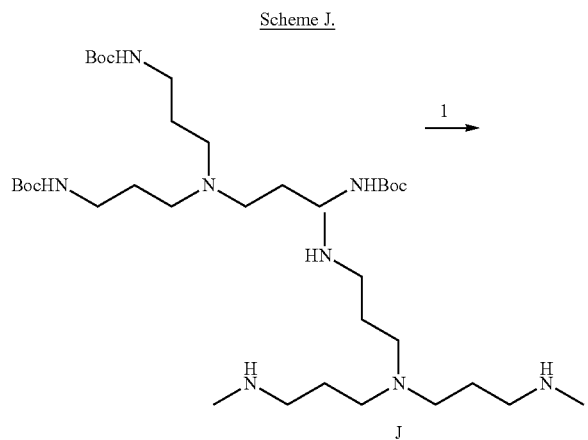

1. LAH, THF.

Intermediate J: N$^1$-methyl-N$^3$,N$^3$-bis(3-(methylamino)propyl)propan-1,3-diamine. To a mixture of tri-t-butyl(nitrilotris(propane-3,1-diyl))tricarbamate (689 mg, 1.41 mmol, 1 equiv) in THF (8 mL) 0° C. was added lithium aluminium hydride (2M in THF, 4.24 mL, 8.48 mmol, 6 equiv). The mixture was slowly warmed to 70° C. and stirred at 70° C. for 3 h. The reaction was carefully quenched with Na$_2$SO$_4$.10H$_2$O and filtered. The filtrate was concentrated to give 281 mg (87%) of intermediate J as clear syrup. MS (ES, m/z): 231 [M+H]$^+$. $^1$H NMR (400 MHz, CD$_3$OD) δ 2.57 (t, J=6.8 Hz, 6H), 2.47-2.34 (m, 15H), 1.62 (dt, J=14.0, 7.0 Hz, 6H).

Intermediate K (S)—N-(2-(2-(2-aminoethoxy)ethoxy)ethyl)-3-(6,8-dichloro-2-methyl-1,2,3,4-tetrahydroisoquinolin-4-yl)-N-(2-hydroxyethyl)benzenesulfonamide

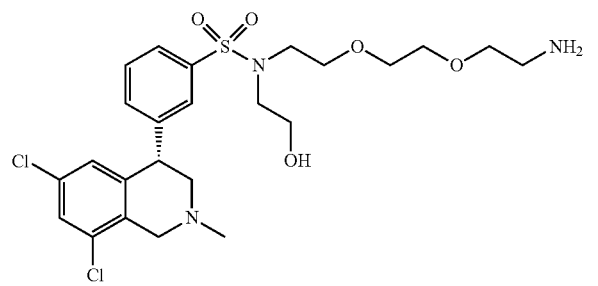 [SMILES: CN1Cc2c(Cl)cc(Cl)cc2[C@H](c2cccc(S(=O)(=O)N(CCO)CCOCCOCCN)c2)C1]

Intermediate K: (S)—N-(2-(2-(2-aminoethoxy)ethoxy)ethyl)-3-(6,8-dichloro-2-methyl-1,2,3,4-tetrahydroisoquinolin-4-yl)-N-(2-hydroxyethyl)benzenesulfonamide. Intermediate K was synthesized in an analogous fashion to intermediate I, using 2-(tert-butoxy)ethanol in place of methanol. MS (ES, m/z): 546 [M+H]$^+$.

Intermediate L (S)—N-(2-(2-(2-aminoethoxy)ethoxy)ethyl)-3-(6,8-dichloro-2-methyl-1,2,3,4-tetrahydroisoquinolin-4-yl)-N-ethylbenzenesulfonamide

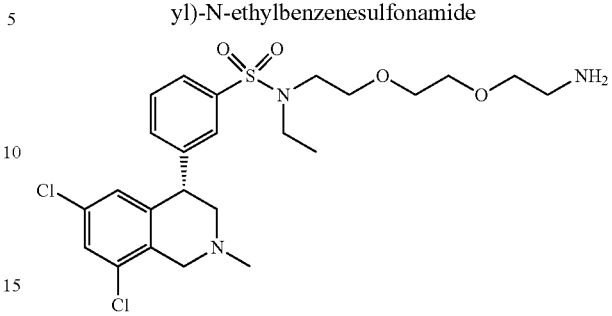

Intermediate L: (S)—N-(2-(2-(2-aminoethoxy)ethoxy)ethyl)-3-(6,8-dichloro-2-methyl-1,2,3,4-tetrahydroisoquinolin-4-yl)-N-ethylbenzenesulfonamide. Intermediate L was synthesized in an analogous fashion to intermediate I, using ethanol in place of methanol. MS (ES, m/z): 530 [M+H]$^+$.

Intermediate M 3-amino-N,N-bis(3-aminopropyl)-N-methylpropan-1-aminium

Scheme M.

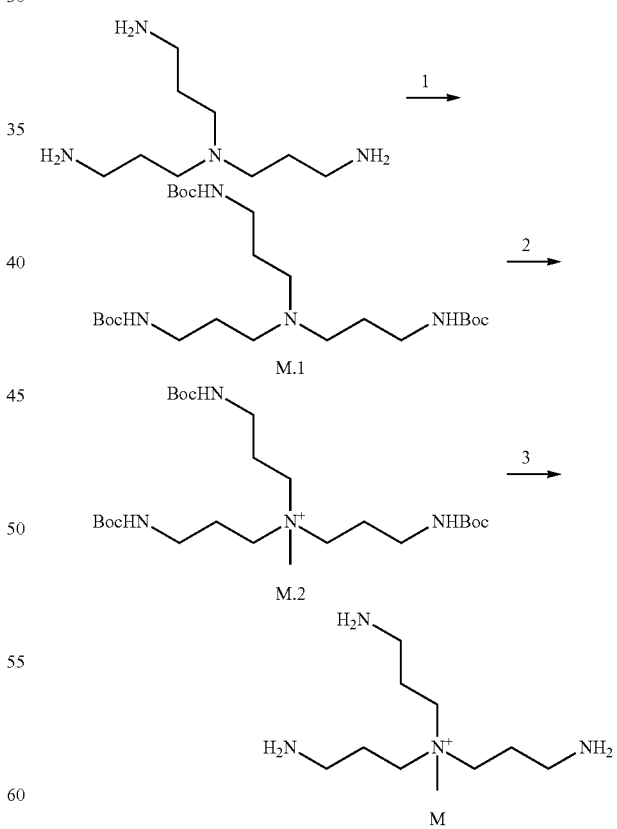

1. (Boc)$_2$O, TEA, DCM;
2. MeI, CH$_3$CN;
3. HCl, dioxane, DCM.

Intermediate M.1: tri-t-butyl(nitrilotris(propane-3,1-diyl))tricarbamate. To a mixture of N$^1$,N$^1$-bis(3-aminopropyl)

propane-1,3-diamine (499 mg, 2.65 mmol, 1 equiv) in DCM (10 mL) at 0° C. were added di-tert-butyl dicarbonate (2.08 g, 9.54 mol, 3.6 equiv) and TEA (1.66 mL, 11.92 mmol, 4.5 equiv). The mixture was slowly warmed to rt, stirred at rt overnight, diluted with ethyl acetate, washed with water (1×) and brine (1×), dried and concentrated to give 1.4 g (crude) of intermediate M.1.

Intermediate M.2: 3-((t-butoxycarbonyl)amino)-N,N-bis (3-((t-butoxycarbonyl)amino)propyl)-N-methylpropan-1-aminium. To a mixture of tri-t-butyl(nitrilotris(propane-3,1-diyl))tricarbamate (258.2 mg, 0.529 mmol, 1 equiv) in acetonitrile (5 mL) at rt was added iodomethane (39.6 µL, 0.635 mol, 1.2 equiv). The mixture was stirred at rt overnight and concentrated to give 286 mg (86%) of intermediate M.2 as clear syrup.

Intermediate M: 3-amino-N,N-bis(3-aminopropyl)-N-methylpropan-1-aminium. To a mixture of 3-((t-butoxycarbonyl)amino)-N,N-bis(3-((t-butoxycarbonyl)amino)propyl)-N-methylpropan-1-aminium (286 mg) in DCM (0.5 mL) was added a solution of HCl in dioxane (4 M, 3 mL). The mixture was stirred at rt for 1 h and concentrated to give 190 mg (crude) of intermediate M as a yellow solid. MS (ES, m/z): 203 [M]$^+$. $^1$H NMR (400 MHz, CD$_3$OD) δ 3.62-3.54 (m, 6H), 3.22 (s, 3H), 3.11 (t, J=7.4 Hz, 6H), 2.30-2.19 (m, 6H).

Intermediate N 4-acetyl-4-(2-carboxyethyl)heptanedioic acid

Scheme N.

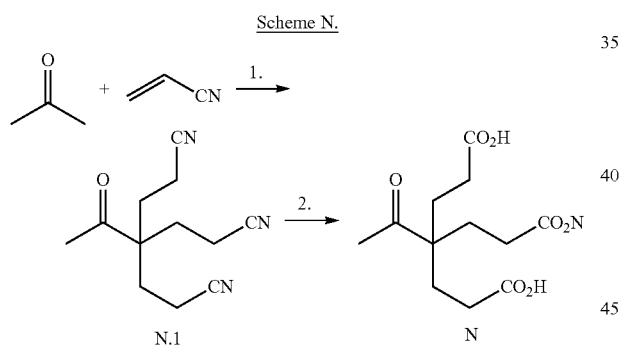

1. KOH, t-BuOH;
2. KOH, H$_2$O (ref. Bruson, H.A.; Riener, T.W. J. Am. Chem. Soc. 1942, 64, 2850-2858.)

Intermediate N.1 To a well-stirred solution of acetone (300 mg, 5.15 mmol) and 30% ethanolic KOH (25 µL) in t-BuOH (0.30 mL) at 0° C. was added a solution of acrylonitrile (0.82 g, 15.5 mmol) in t-BuOH (0.40 mL) over 1 hour. The reaction mixture was then stored at 4° C. overnight. The solids were collected on a Büchner funnel, and washed with water (2×5 mL). The product was dissolved in acetonitrile (10 mL) and DCM (50 mL), dried (Na$_2$SO$_4$) and concentrated to give N.1 (667 mg) as an off-white solid.

Intermediate N: A mixture of 4-acetyl-4-(2-cyanoethyl) heptanedinitrile (667 mg, 3.1 mmol) and KOH, 840 g, 15 mmol) in water (4.8 mL) was heated at reflux for 5 hours. The reaction mixture was cooled to 50° C. and decanted from insoluble gum. The supernatant was acidified to pH-2-3 with Conc. HCl and concentrated to dryness under vacuum. The semisolid residue was heated at 50° C. with acetone (20 mL) and the mixture was filtered hot, and concentrated to give intermediate N as an oil (690 mg) which crystallized on seeding with crystals generated from a small aliquot in DCM.

Example 1

N1,N7-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-4-nitroheptanediamide Scheme 1. bis(perfluorophenyl) 4-nitro-4-(3-oxo-3-perfluorophenoxy)propyl)heptanedioate, DIEA, DCM

A ⟶

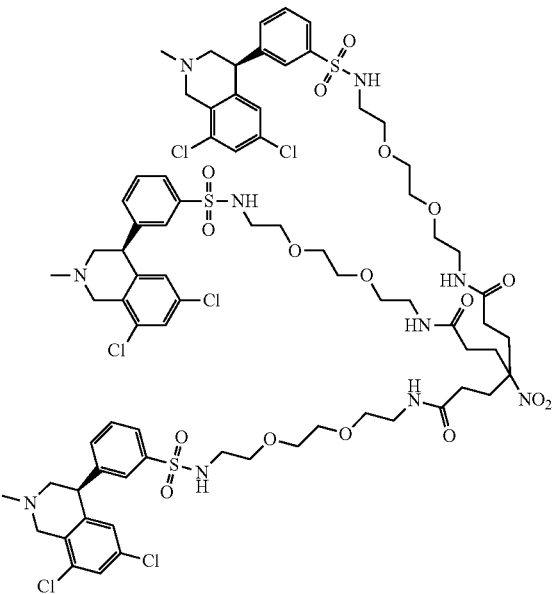

1

Example 1: To a solution of A (972 mg, 1.93 mmol) and DIEA (657 µL, 3.87 mmol) in DCM (20 mL) was added bis(perfluorophenyl) 4-nitro-4-(3-oxo-3-(perfluorophenoxy) propyl)heptanedioate (intermediate B, 500 mg, 0.645 mmol) and the resulting solution stirred at room temperature for 20 h. The solvent was removed under reduced pressure and the resulting residue purified by automated flash column silica gel chromatography using a gradient of DCM:MeOH (99:1 to 9:1) to give the title compound as a yellow solid (516 mg, 46%) after the solvent was removed. $^1$H-NMR (400 MHz, CD$_3$OD) δ 7.79-7.75 (m, 3H), 7.70 (t, J=1.5 Hz, 3H), 7.53 (t, J=7.6 Hz, 3H), 7.50-7.45 (m, 3H), 7.34 (d, J=2.1 Hz, 3H), 6.80 (s, 3H), 4.44-4.36 (m, 3H), 3.77 (d, J=16.1 Hz, 3H), 3.64 (d, J=15.6 Hz, 3H), 3.57-3.48 (m, 18H), 3.45 (t, J=5.5 Hz, 6H), 3.34 (t, J=5.2 Hz, 6H), 3.07-2.99 (m, 9H), 2.67 (dd, J=11.7, 7.8 Hz, 3H), 2.47 (s, 9H), 2.28-2.16 (m, 12H). MS (ES, m/z): 1727.1 [M+H]$^+$.

Example 2

4-amino-$N^1,N^7$-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)heptanediamide Scheme 2a. $N^1$, $N^1$-Bis(2-aminoethyl)ethane-1,2-diamine, DMF.

D ⟶

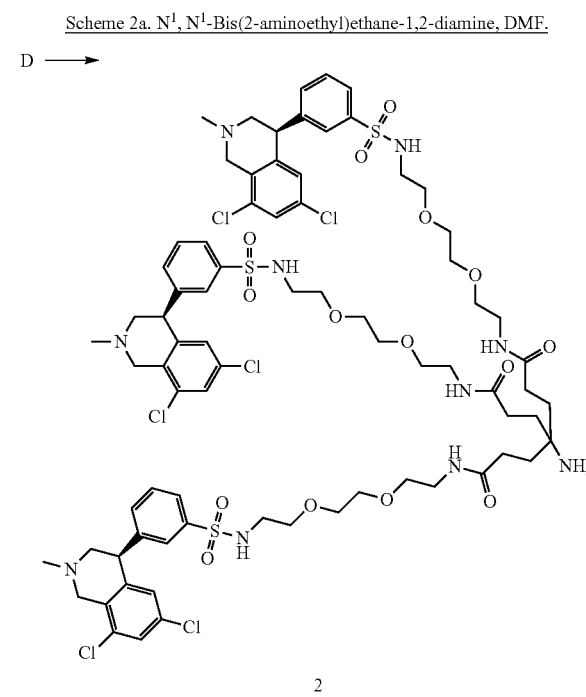

2

Scheme 2b. $H_2$, Raney nickel, MeOH.

1 ⟶

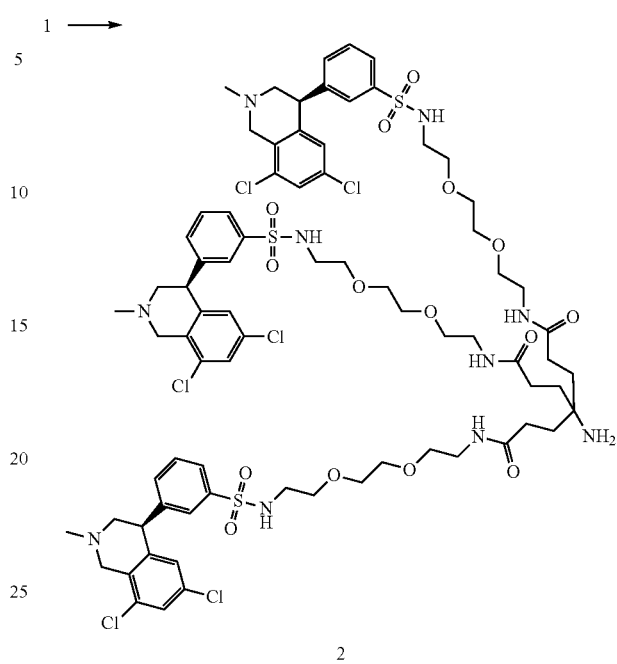

2

Example 2, method A: To a solution of $N^1,N^1$-bis(2-aminoethyl)ethane-1,2-diamine (1.21 mL, 8.06 mmol) in DMF (2 mL) was slowly added a solution of intermediate D (7.75 g, 4.03 mmol) in DMF (10 mL) and the resulting mixture stirred for 30 min at room temperature. The solution was cooled 0° C. and 1 M aqueous TFA was added (20 mL), until the solution reached pH=1. The solution was then diluted with 1:1 MeCN:H$_2$O to give a final volume of 60 mL. The solution was purified by automated flash column reverse phase chromatography using a gradient of H$_2$O 0.05% TFA: CH$_3$CN 0.05% TFA (80:20 to 60:40) and detection by UV at 254 nm in three batches. The fractions containing pure material were concentrated and then neutralized to pH=7 with NaHCO$_3$, resulting in the formation of a white precipitate. The suspension was extracted twice with a 95:5 DCM:MeOH solution. The combined organic layers were dried over Na$_2$SO$_4$ and the solvent removed to give the title compound (3.52 g, 51% yield) as a white foam. $^1$H-NMR (400 MHz, CD$_3$OD) δ 7.89 (d, J=7.9 Hz, 3H), 7.77 (t, J=1.6 Hz, 3H), 7.65 (t, J=7.8 Hz, 3H), 7.58-7.52 (m, 6H), 6.83 (s, 3H), 4.81-4.71 (m, 6H), 4.47 (d, J=15.9 Hz, 3H), 3.87 (dd, J=12.4, 6.0 Hz, 3H), 3.64-3.51 (m, 21H), 3.48 (t, J=5.4 Hz, 6H), 3.36 (t, J=5.5 Hz, 6H), 3.13 (s, 9H), 3.05 (t, J=5.4 Hz, 6H), 2.44-2.34 (m, 6H), 1.97 (m, 6H). MS (ES, m/z): 1697.2 [M+H]$^+$.

Example 2, method B: To a Parr hydrogenation bottle was added example 1 (926 mg, 0.535 mmol) in MeOH (40 mL) and Raney® nickel (1.0 g), which had been washed five times with H$_2$O, until the aqueous layer pH=7. The bottle was shaken for 16 h at room temperature under 50 psi of H$_2$. Additional washed Raney® nickel (1.0 g) was then added and the suspension shaken for 16 h under 50 psi of H$_2$. A final addition of washed Raney® nickel (2.0 g) was then added and shaken for 16 h under 50 psi of H$_2$, at which time analysis by LCMS showed all starting material has been consumed. The suspension was filtered through a pad of Celite® and the pad washed twice with EtOH. To combined organic layers were concentrated under reduced pressure and was purified by automated flash column reverse phase chromatography using a gradient of H$_2$O 0.05% TFA: CH$_3$CN 0.05% TFA (80:20 to 50:50) and detection by UV at 254 nm. The solvent was removed under reduced pressure and the resulting residue dissolved in DCM and washed with saturated aqueous NaHCO$_3$. The organic phase was dried over Na$_2$SO$_4$ and the solvent removed under reduced pressure to give the title compound (280 mg, 31%).

Example 3

1-(3-((S)-6,8-dichloro-2-methyl-1,2,3,4-tetrahydroisoquinolin-4-yl)phenylsulfonamido)-13,13-bis(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-10-oxo-3,6-dioxa-9,14-diazahexadecane-16-sulfonic acid Scheme 3. Taurine, DIEA, N,N'-disuccinimidyl carbonate, H$_2$O, DMF.

2 ⟶

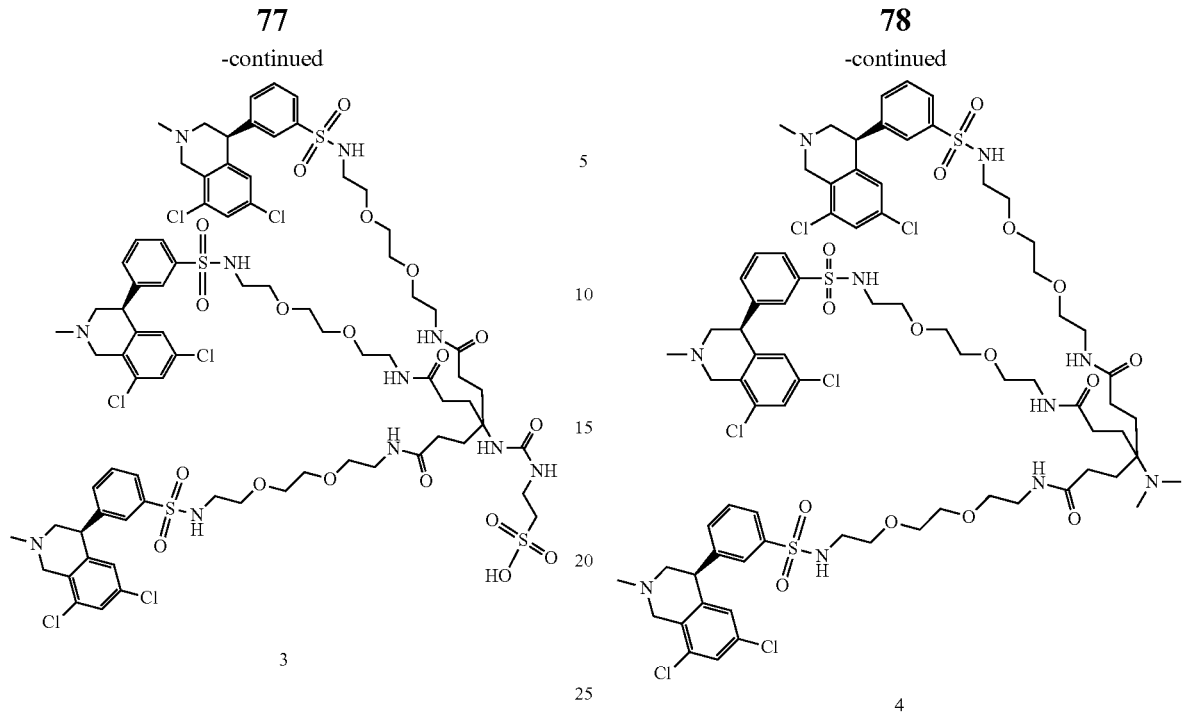

Example 3: Taurine (9.2 mg, 0.074 mmol) was dissolved in H₂O (200 μL), to which was added DIEA (26 μL, 0.15 mmol), followed by DMF (800 μL). To the resulting solution was added N,N'-disuccinimidyl carbonate (19 mg, 0.074 mmol) and the solution stirred at 50° C. for 1. Example 2 (25 mg, 0.015 mmol) was then added and the solution stirred for 18 h at 50° C. The solution was then diluted with H₂O and acidified with TFA, then purified by preparative HPLC with a C₁₈ silica gel stationary phase using a gradient of H₂O 0.05% TFA:CH₃CN 0.05% TFA (80:20 to 40:60) and detection by UV at 254 nm to give the title compound tri-TFA salt (10 mg, 30% yield) as a white solid. ¹H-NMR (400 MHz, CD₃OD) δ 7.91-7.86 (m, 3H), 7.86-7.82 (m, 3H), 7.64 (t, J=7.8 Hz, 3H), 7.58-7.51 (m, 6H), 6.84 (s, 3H), 4.83-4.74 (m, 6H), 4.54 (d, J=15.4 Hz, 3H), 3.93 (dd, J=12.0, 6.2 Hz, 3H), 3.66 (t, J=11.9 Hz, 3H), 3.58-3.49 (m, 18H), 3.47 (t, J=5.4 Hz, 6H), 3.44-3.37 (m, 2H), 3.35-3.32 (m, 6H), 3.17 (d, J=9.0 Hz, 9H), 3.06 (t, J=5.3 Hz, 6H), 2.90 (t, J=6.2 Hz, 2H), 2.24-2.13 (m, 6H), 1.92-1.81 (m, 6H). MS (ES, m/z): 1847.9 [M+H]⁺.

Example 4

N¹,N⁷-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-4-(dimethylamino)heptanediamide Scheme 4. Formaldehyde, sodium triacetoxyborohydride, acetic acid, MeCN, H₂O.

Example 4:

Example 2 (200 mg, 0.118 mmol) and 33 weight % aqueous formaldehyde (30 μL) were combined in a mixture of MeCN (2 mL) and H₂O (2 mL). Five drops of acetic acid were then added, followed by sodium triacetoxyborohydride (15 mg, 0.24 mmol) and the mixture stirred for 30 min at room temperature. The mixture was then purified by preparative HPLC with a C18 silica gel stationary phase using a gradient of H₂O 0.05% TFA:CH₃CN 0.05% TFA (80:20 to 40:60) and detection by UV at 254 nm to give the title compound tetra-TFA salt (146 mg, 57% yield) as a white solid. ¹H-NMR (400 MHz, CD₃OD) δ 7.89 (d, J=7.9 Hz, 3H), 7.77 (s, 3H), 7.66 (t, J=7.8 Hz, 3H), 7.59-7.51 (m, 6H), 6.83 (s, 3H), 4.82-4.74 (m, 6H), 4.50 (d, J=15.9 Hz, 3H), 3.90 (dd, J=11.8, 6.3 Hz, 3H), 3.67-3.51 (m, 21H), 3.48 (t, J=5.4 Hz, 6H), 3.37 (t, J=5.4 Hz, 6H), 3.16 (s, 9H), 3.05 (t, J=5.4 Hz, 6H), 2.91 (s, 6H), 2.50-2.37 (m, 6H), 2.16-2.06 (m, 6H). MS (ES, m/z): 1725.0 [M+H]⁺.

Example 5

N¹,N⁷-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-4-(methylsulfonamido)heptanediamide Scheme 5. Methanesulfonic anhydride, DIEA, MeCN.

5

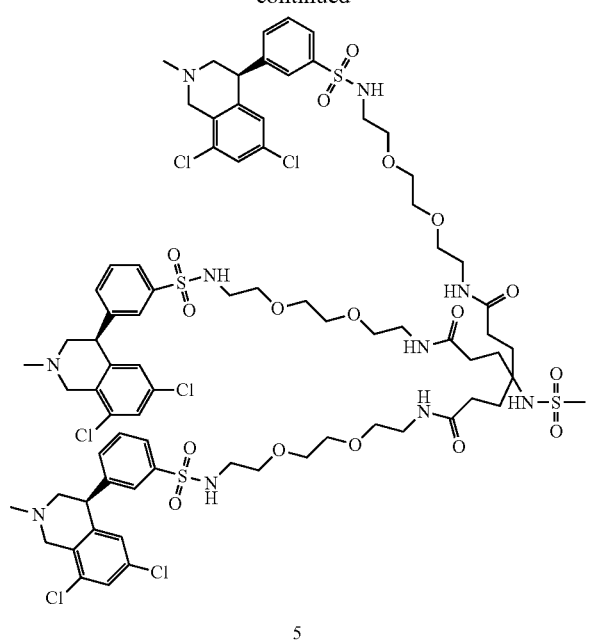

6

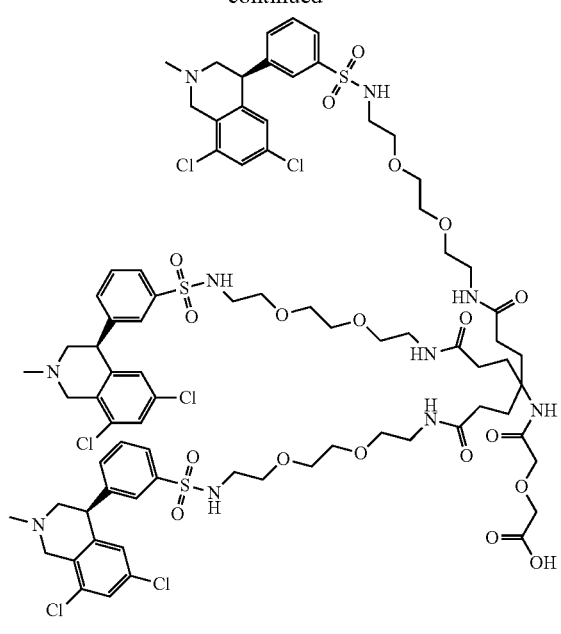

Example 5: Example 2 (47 mg, 0.028 mmol) and DIEA (14 µL, 0.83 mmol) were dissolved in MeCN (1 mL). Methanesulfonic anhydride (6.0 mg, 0.35 mmol) was then added and the solution stirred for 1 h at room temperature and then stirred for an additional 1 h at 50° C. The solution was then diluted with $H_2O$ and acidified with TFA, then purified by preparative HPLC with a $C_{18}$ silica gel stationary phase using a gradient of $H_2O$ 0.05% TFA: $CH_3CN$ 0.05% TFA (80:20 to 20:80) and detection by UV at 254 nm to give the title compound tri-TFA salt (6.7 mg, 11% yield) as a white solid. $^1$H-NMR (400 MHz, $CD_3OD$) δ 7.89 (d, J=8.1 Hz, 3H), 7.78 (s, 3H), 7.65 (t, J=7.8 Hz, 3H), 7.58-7.52 (m, 6H), 6.84 (s, 3H), 4.81-4.72 (m, 6H), 4.51 (d, J=15.6 Hz, 3H), 3.91 (dd, J=12.0, 6.0 Hz, 3H), 3.63 (t, J=12.1 Hz, 3H), 3.58-3.50 (m, 18H), 3.48 (t, J=5.4 Hz, 6H), 3.34 (t, J=5.5 Hz, 6H), 3.17 (s, 9H), 3.09-3.02 (m, 9H), 2.34-2.24 (m, 6H), 1.96-1.86 (m, 6H). MS (ES, m/z): 1775.1 [M+H]$^+$.

Example 6

1-(3-((S)-6,8-dichloro-2-methyl-1,2,3,4-tetrahydroisoquinolin-4-yl)phenylsulfonamido)-13,13-bis(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-10,15-dioxo-3,6,17-trioxa-9,14-diazanonadecan-19-oic Acid Scheme 6. 1,4-Dioxane-2,6-dione, DIEA, DMF.

2 →

Example 6: Example 2 (50 mg, 0.029 mmol) and DIEA (15 µL, 0.088 mmol) were dissolved in DMF (1 mL). 1,4-Dioxane-2,6-dione (6.0 mg, 0.038 mmol) was then added and the solution stirred at 40° C. for 1 h, then diluted with $H_2O$ and acidified with TFA. The mixture was then purified by preparative HPLC with a C18 silica gel stationary phase using a gradient of $H_2O$ 0.05% TFA: $CH_3CN$ 0.05% TFA (80:20 to 20:80) and detection by UV at 254 nm to give the title compound tri-TFA salt (40 mg, 63% yield) as a white solid. $^1$H-NMR (400 MHz, $CD_3OD$) δ 7.91-7.86 (m, 3H), 7.79 (t, J=1.6 Hz, 3H), 7.64 (t, J=7.8 Hz, 3H), 7.58-7.52 (m, 6H), 6.84 (s, 3H), 4.84-4.75 (m, 6H), 4.52 (d, J=15.9 Hz, 3H), 4.17 (s, 2H), 3.99 (s, 2H), 3.92 (dd, J=11.1, 6.0 Hz, 3H), 3.64 (t, J=12.0 Hz, 3H), 3.58-3.49 (m, 18H), 3.47 (t, J=5.4 Hz, 6H), 3.37-3.32 (m, 6H), 3.17 (s, 9H), 3.06 (t, J=5.5 Hz, 6H), 2.26-2.16 (m, 6H), 2.05-1.96 (m, 6H). MS (ES, m/z): 1813.1 [M+H]$^+$.

Example 7

18-(3-((S)-6,8-dichloro-2-methyl-1,2,3,4-tetrahydroisoquinolin-4-yl)phenylsulfonamido)-6,6-bis(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-4,9-dioxo-13,16-dioxa-3,5,10-triazaoctadecan-1-oic acid Scheme 7. ethyl 2-isocyanatoacetate, DIEA, THF; then LiOH•$H_2O$, $H_2O$.

2 →

81

-continued

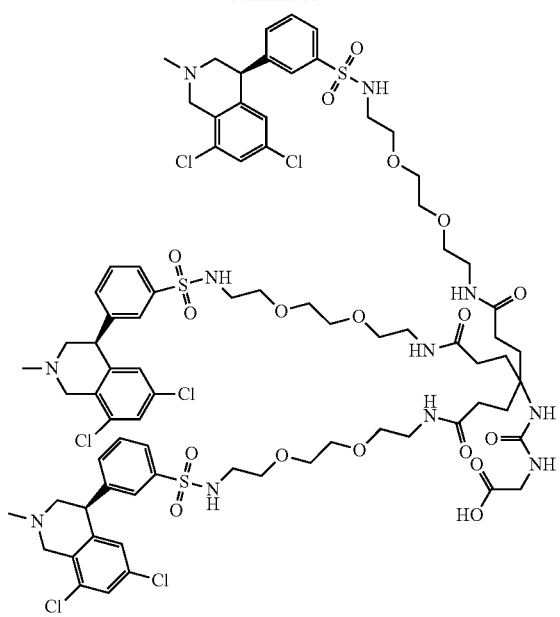

7

Example 7: To a solution of example 2 (150 mg, 0.0882 mmol) and DIEA (30 μL, 0.18 mmol) in THF (3 mL) was added ethyl 2-isocyanatoacetate (20 μL, 0.18 mmol) and the resulting solution stirred for 1.5 h at room temperature. H$_2$O (2 mL) and LiOH.H$_2$O (18.5 mg, 0.441 mmol) was then added and the resulting mixture stirred for 2 h at room temperature. The mixture was diluted with DCM and washed with H$_2$O, then the organic layer dried over Na$_2$SO$_4$ and the solvent remove under reduced pressure. The resulting residue was then purified by preparative HPLC with a C18 silica gel stationary phase using a gradient of H$_2$O 0.05% TFA:CH$_3$CN 0.05% TFA (70:30 to 40:60) and detection by UV at 254 nm to give the title compound tri-TFA salt (94 mg, 25% yield) as a white solid. $^1$H-NMR (400 MHz, CD$_3$OD) δ 7.92-7.86 (m, 3H), 7.79 (t, J=1.6 Hz, 3H), 7.65 (t, J=7.8 Hz, 3H), 7.58-7.52 (m, 6H), 6.84 (s, 3H), 4.80 (dd, J=16.8, 5.4 Hz, 6H), 4.51 (d, J=16.1 Hz, 3H), 3.91 (dd, J=12.6, 6.4 Hz, 3H), 3.77 (s, 2H), 3.63 (t, J=12.0 Hz, 3H), 3.58-3.50 (m, 18H), 3.47 (t, J=5.4 Hz, 6H), 3.36-3.32 (m, 6H), 3.17 (s, 9H), 3.06 (t, J=5.5 Hz, 6H), 2.25-2.15 (m, 6H), 1.96-1.85 (m, 6H). MS (ES, m/z): 1798.1 [M+H]$^+$.

Example 8

N1,N7-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-4-ureidoheptanediamide Scheme 8. isocyanatotrimethylsilane, TEA, DCM.

2 ⟶

82

-continued

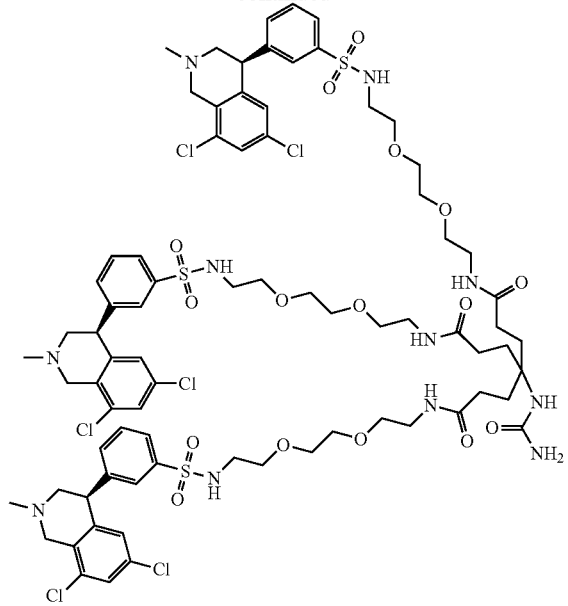

8

Example 8: To a solution of example 2 (50 mg, 0.029 mmol) and TEA (12 μL, 0.088 mmol) in DCM (1 mL) was added isocyanatotrimethylsilane (5.9 μL, 0.044 mmol). The resulting solution was stirred for 1 h at room temperature, then stirred for an additional 16 h at 40° C. The solvent was then removed under reduced pressure and the crude residue purified by preparative HPLC with a C18 silica gel stationary phase using a gradient of H$_2$O 0.05% TFA: CH$_3$CN 0.05% TFA (80:20 to 20:80) and detection by UV at 254 nm to give the title compound tri-TFA salt (26 mg, 42% yield) as a white solid. $^1$H-NMR (400 MHz, CD$_3$OD) δ 7.89 (d, J=7.9 Hz, 3H), 7.79 (t, J=5.7 Hz, 3H), 7.65 (t, J=7.8 Hz, 3H), 7.58-7.50 (m, 6H), 6.84 (s, 3H), 4.80 (d, J=12.2 Hz, 6H), 4.51 (d, J=15.6 Hz, 3H), 3.92 (dd, J=12.2, 5.7 Hz, 3H), 3.64 (t, J=12.0 Hz, 3H), 3.58-3.49 (m, 18H), 3.47 (t, J=5.4 Hz, 6H), 3.36-3.32 (m, 6H), 3.17 (d, J=5.5 Hz, 9H), 3.06 (t, J=5.4 Hz, 6H), 2.25-2.15 (m, 5H), 2.03-1.86 (m, 6H). MS (ES, m/z): 1740.1 [M+H]$^+$.

Example 9

4-amino-4-(1-(3-((S)-6,8-dichloro-2-methyl-1,2,3,4-tetrahydroisoquinolin-4-yl)phenylsulfonamido)-13-oxo-3,6,9-trioxa-12-azapentadecan-15-yl)-N$^1$,N$^7$-bis(2-(2-(2-(2-(3-((S)-6,8-dichloro-2-methyl-1,2,3,4-tetrahydroisoquinolin-4-yl)phenylsulfonamido)ethoxy)ethoxy)ethoxy)ethyl)heptanediamide

9

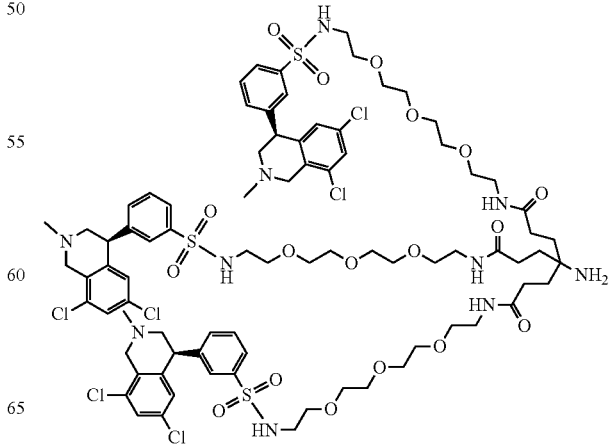

Example 9: The title compound was synthesized in a manner similar to example 2 (method B), using intermediate E in place of intermediate A. MS (ES, m/z): 1829.2 [M+H]$^+$.

Example 10

4-(1-(3-((S)-6,8-dichloro-2-methyl-1,2,3,4-tetrahydroisoquinolin-4-yl)phenylsulfonamido)-13-oxo-3,6,9-trioxa-12-azapentadecan-15-yl)-N1,N7-bis(2-(2-(2-(2-(3-((S)-6,8-dichloro-2-methyl-1,2,3,4-tetrahydroisoquinolin-4-yl)phenylsulfonamido)ethoxy)ethoxy)ethoxy)ethyl)-4-propionamidoheptanediamide

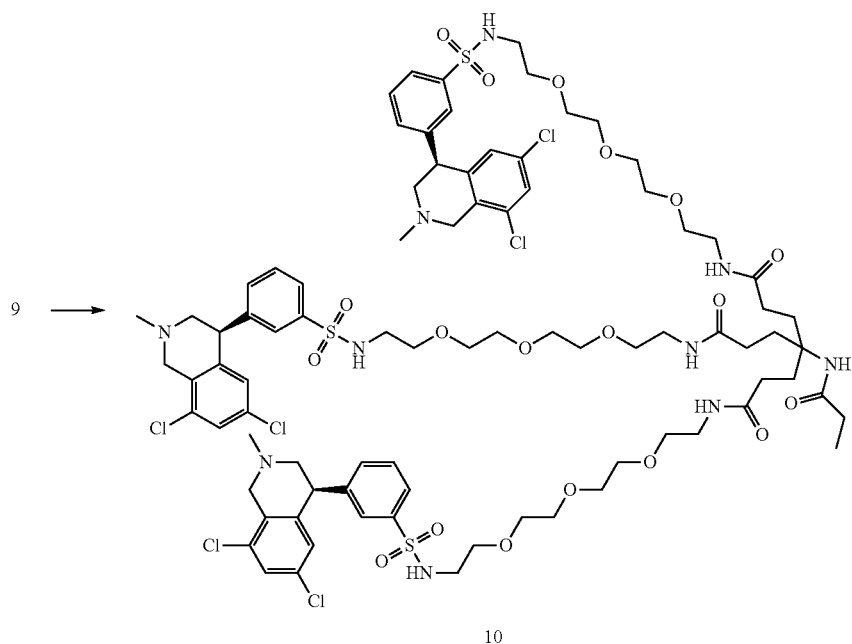

Scheme 10. Propionyl chloride, DIEA, MeCN.

9 → 10

Example 10: Example 9 (75 mg, 0.041 mmol) and DIEA (21 µL, 0.12 mmol) were dissolved in MeCN (1 mL) and cooled to 0° C. To the stirring solution was added propionyl chloride (4.3 µL, 0.049 mmol), then the resulting mixture allowed to warm to room temperature and stirred for 30 min. The mixture was diluted with H$_2$O and acidified with TFA, then purified by preparative HPLC with a C18 silica gel stationary phase using a gradient of H$_2$O 0.05% TFA: CH$_3$CN 0.05% TFA (80:20 to 20:80) and detection by UV at 254 nm to give the title compound tri-TFA salt (18 mg, 23% yield) as a white solid. $^1$H-NMR (400 MHz, CD$_3$OD) δ 7.90 (d, J=7.9 Hz, 3H), 7.80-7.75 (m, 3H), 7.66 (t, J=7.8 Hz, 3H), 7.59-7.52 (m, 6H), 6.85 (s, 3H), 4.82-4.73 (m, 6H), 4.51 (d, J=16.4 Hz, 3H), 3.95-3.87 (m, 3H), 3.69-3.50 (m, 23H), 3.46 (t, J=5.4 Hz, 6H), 3.38-3.32 (m, 6H), 3.17 (s, 9H), 3.06 (t, J=5.4 Hz, 6H), 2.20-2.12 (m, 6H), 2.00-1.90 (m, 6H), 1.08 (t, J=7.6 Hz, 3H). MS (ES, m/z): 1885.1 [M+H]$^+$.

Example 11

N$^1$,N$^7$-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-4-(3-(1,3-dihydroxy-2-(hydroxymethyl)propan-2-yl)ureido)heptanediamide Scheme 11.
2-Amino-2-(hydroxymethyl)-1,3-propanediol•HCl, DIEA, DMF.

G →

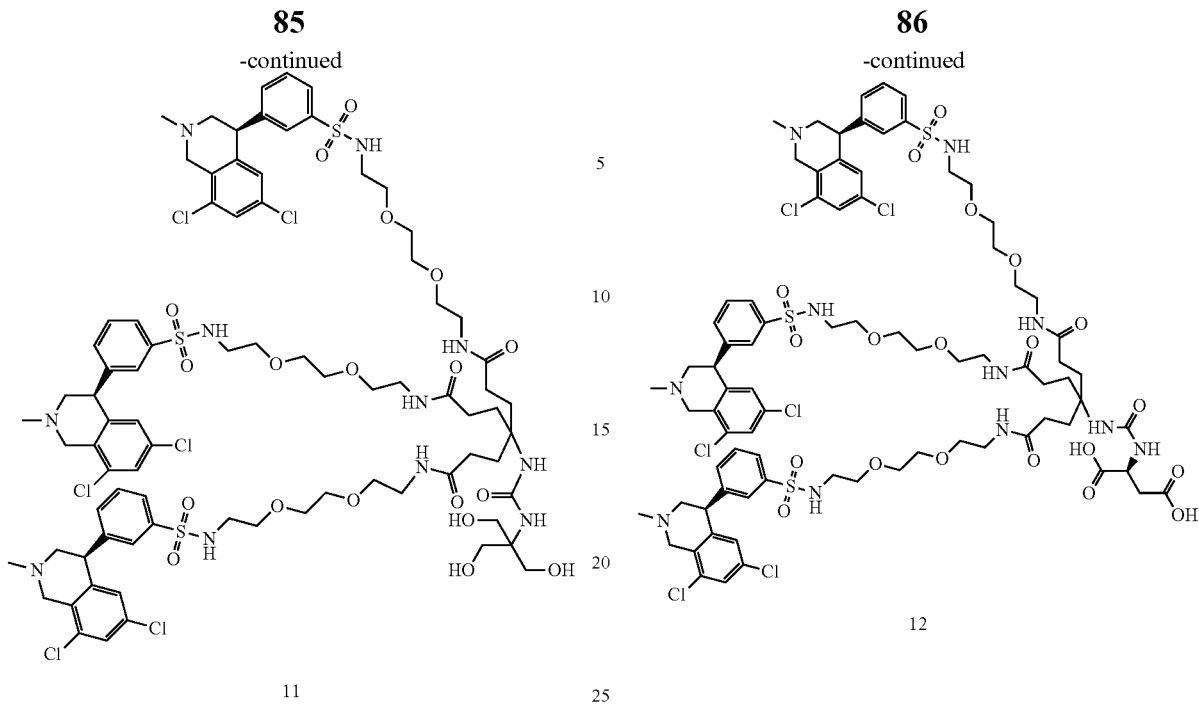

Example 11: To a solution of intermediate G (51 mg, 0.29 mmol) and DIEA (25 μL, 0.15 mmol) dissolved in DMF (1 mL) was added 2-Amino-2-(hydroxymethyl)-1,3-propanediol.HCl (9.2 mg, 0.059 mmol). The resulting solution was stirred at room temperature for 2 h, then diluted with $H_2O$, and acidified with TFA. The mixture was then purified by preparative HPLC with a C18 silica gel stationary phase using a gradient of $H_2O$ 0.05% TFA:$CH_3CN$ 0.05% TFA (80:20 to 40:60) and detection by UV at 254 nm to give the title compound tri-TFA salt (17 mg, 26% yield) as a white solid. $^1$H-NMR (400 MHz, $CD_3OD$) δ 7.92-7.86 (m, 3H), 7.80-7.76 (m, 3H), 7.65 (t, J=7.8 Hz, 3H), 7.58-7.53 (m, 6H), 6.84 (s, 3H), 4.83-4.74 (m, 6H), 4.52 (d, J=16.1 Hz, 3H), 3.91 (dd, J=11.5, 6.1 Hz, 3H), 3.70-3.61 (m, 9H), 3.61-3.50 (m, 18H), 3.47 (t, J=5.4 Hz, 6H), 3.34 (t, J=5.5 Hz, 6H), 3.17 (s, 9H), 3.06 (t, J=5.4 Hz, 6H), 2.20 (dd, J=9.8, 6.4 Hz, 6H), 1.91 (dd, J=9.8, 6.5 Hz, 6H). MS (ES, m/z): 1844.0 $[M+H]^+$.

Example 12

(S)-2-(3-(1,25-bis(3-((S)-6,8-dichloro-2-methyl-1,2,3,4-tetrahydroisoquinolin-4-yl)phenylsulfonamido)-13-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-10,16-dioxo-3,6,20,23-tetraoxa-9,17-diazapentacosan-13-yl)ureido)succinic acid Scheme 12. (S)-di-tert-butyl 2-aminosuccinate, DIEA, MeCN.

G  ⟶

Example 12: To a solution of intermediate G (50 mg, 0.029 mmol) and DIEA (10 μL, 0.059 mmol) in MeCN (1 mL) was added (S)-di-tert-butyl 2-aminosuccinate (11 mg, 0.044 mmol). The resulting solution was stirred for 18 h at 40° C., then diluted with $H_2O$, acidified with TFA, and then purified by preparative HPLC with a C18 silica gel stationary phase using a gradient of $H_2O$ 0.05% TFA: $CH_3CN$ 0.05% TFA (80:20 to 20:80) and detection by UV at 254 nm. The fractions with pure material were combined and the lyophilized. The resulting solid was dissolved in TFA and left at room temperature for 30 min, then solvent removed under a stream of $N_2$. The resulting residue was dissolved in 1:1 MeCN:$H_2O$ and lyophilized to give the title compound tri-TFA salt (13.5 mg, 21% yield) as a white solid. $^1$H-NMR (400 MHz, $CD_3OD$) δ 7.92-7.87 (m, 3H), 7.80 (t, J=1.6 Hz, 3H), 7.65 (t, J=7.8 Hz, 3H), 7.59-7.51 (m, 6H), 6.84 (s, 3H), 4.80 (d, J=11.4 Hz, 6H), 4.57-4.44 (m, 4H), 3.92 (dd, J=12.5, 6.1 Hz, 3H), 3.65 (d, J=12.1 Hz, 3H), 3.58-3.49 (m, 18H), 3.47 (t, J=5.4 Hz, 6H), 3.36-3.33 (m, 6H), 3.18 (s, 9H), 3.06 (t, J=5.6 Hz, 6H), 2.79 (ddd, J=21.5, 16.7, 5.5 Hz, 2H), 2.24-2.13 (m, 6H), 1.93-1.83 (m, 6H). MS (ES, m/z): 1856.1 $[M+H]^+$.

Example 13

4-(1-(3-((S)-6,8-dichloro-2-methyl-1,2,3,4-tetrahydroisoquinolin-4-yl)phenylsulfonamido)-13-oxo-3,6,9-trioxa-12-azapentadecan-15-yl)-N$^1$,N$^7$-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-phenylureido)heptanediamide

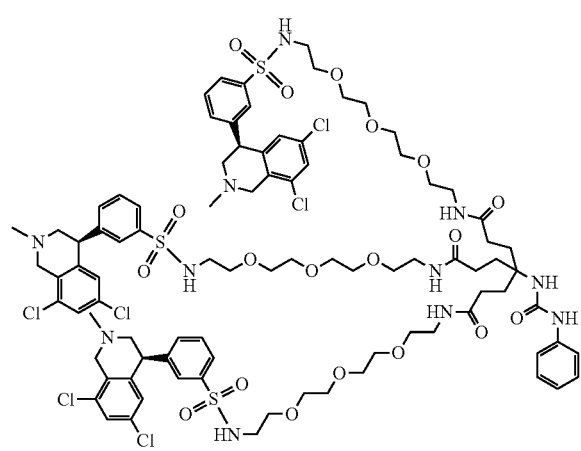

13

Example 13: The title compound was synthesized in a manner similar to example 11, using example 9 in place of example 2 and phenylisocyanate in place of isocyanatotrimethylsilane. MS (ES, m/z): 1948.2 [M+H]$^+$.

Example 14

N$_1$,N$_7$-bis(2-(2-(2-(3-((S)-6,8-dichloro-2-methyl-1,2,3,4-tetrahydroisoquinolin-4-yl)phenylsulfonamido)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-4-(2-(dimethylamino)acetamido)heptanediamide Scheme 14. N,N-dimethylglycine, HATU, DIEA, DMF.

2 ⟶

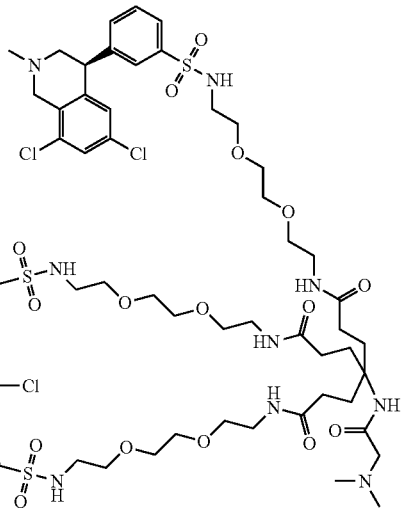

14

Example 14: To a solution of example 2 (100 mg, 0.0588 mmol), N,N-dimethylglycine (9.0 mg, 0.088 mmol), and DIEA (50 μL, 0.29 mmol) in DMF (2 mL) was added HATU (27 mg, 0.071 mmol). The resulting mixture was stirred for 2 h at room temperature, then diluted with H$_2$O and acidified with TFA, then purified by preparative HPLC with a C18 silica gel stationary phase using a gradient of H$_2$O 0.05% TFA: CH$_3$CN 0.05% TFA (80:20 to 40:60) and detection by UV at 254 nm to give the title compound tri-TFA salt (70 mg, 53% yield) as a white solid. $^1$H-NMR (400 MHz, CD$_3$OD) δ 7.89 (d, J=7.9 Hz, 3H), 7.78 (d, J=1.6 Hz, 3H), 7.65 (t, J=7.8 Hz, 3H), 7.58-7.52 (m, 6H), 6.83 (s, 3H), 4.83-4.73 (m, 6H), 4.51 (d, J=15.7 Hz, 3H), 3.95-3.87 (m, 5H), 3.63 (t, J=12.1 Hz, 3H), 3.59-3.50 (m, 18H), 3.47 (t, J=5.4 Hz, 6H), 3.35 (t, J=5.5 Hz, 6H), 3.17 (s, 9H), 3.05 (t, J=5.4 Hz, 6H), 2.94 (s, 6H), 2.30-2.15 (m, 6H), 2.07-1.94 (m, 6H). MS (ES, m/z): 1782.2 [M+H]$^+$.

Example 15

4-(1-(3-((S)-6,8-dichloro-2-methyl-1,2,3,4-tetrahydroisoquinolin-4-yl)phenylsulfonamido)-13-oxo-3,6,9-trioxa-12-azapentadecan-15-yl)-N¹,N⁷-bis(2-(2-(2-(2-(3-((S)-6,8-dichloro-2-methyl-1,2,3,4-tetrahydroisoquinolin-4-yl)phenylsulfonamido)ethoxy)ethoxy)ethoxy)ethyl)-4-undecanamidoheptanediamide

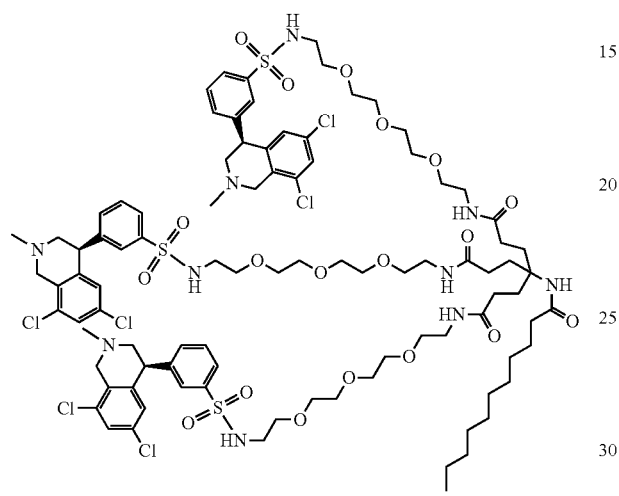

Example 15: The title compound was synthesized in a manner similar to example 14, using example 9 in place of example 2 and undecanoic acid in place N,N-dimethylglycine. MS (ES, m/z): 1997.2 [M+H]⁺.

Example 16

4-(4'-chlorobiphenyl-4-ylcarboxamido)-4-(1-(3-((S)-6,8-dichloro-2-methyl-1,2,3,4-tetrahydroisoquinolin-4-yl)phenylsulfonamido)-13-oxo-3,6,9-trioxa-12-azapentadecan-15-yl)-N¹,N⁷-bis(2-(2-(2-(2-(3-((S)-6,8-dichloro-2-methyl-1,2,3,4-tetrahydroisoquinolin-4-yl)phenylsulfonamido)ethoxy)ethoxy)ethoxy)ethyl)heptanediamide

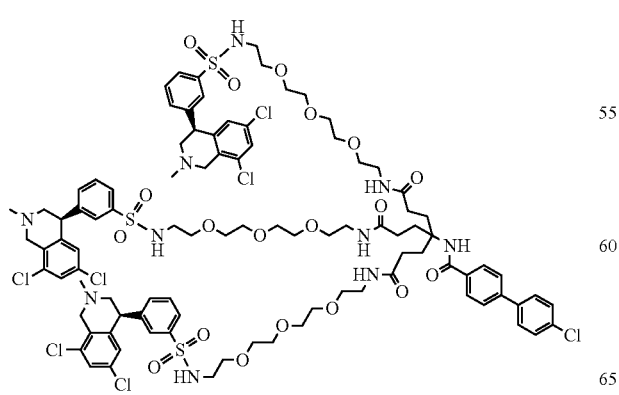

Example 16: The title compound was synthesized in a manner similar to Example 14, using example 9 in place of example 2 and 4'-chlorobiphenyl-4-carboxylic acid in place of N,N-dimethylglycine. MS (ES, m/z): 1022.4 [M+2H]²⁺.

Example 17

N¹,N⁷-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-4-(3-(2-morpholinoethyl)ureido)heptanediamide Scheme 17.

-continued

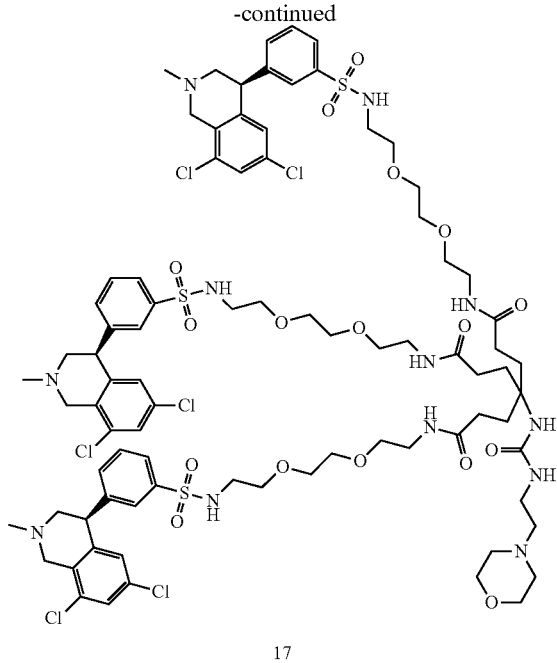

17

1. 2-morpholinoethanamine, THF, then formic acid;
2. intermediate A, HATU, DIEA, DMF.

Intermediate 17a: To a stirring solution of di-tert-butyl 4-(3-tert-butoxy-3-oxopropyl)-4-isocyanatoheptanedioate (150 mg, 0.340 mmol) in THF (2 mL) was added 2-morpholinoethanamine (47 µL, 0.36 mmol). The solution was stirred at room temperature for 2 h and then the solvent removed under reduced pressure. The resulting residue was dissolved in formic acid and stirred at room temperature for 16 h and the solvent was then removed under reduced pressure to give 4-(2-carboxyethyl)-4-(3-(2-morpholinoethyl)ureido)heptanedioic acid as a white solid, which was used directly without further purification.

Example 17: To a stirring solution of 17a (24 mg, 0.060 mmol), intermediate A (100 mg, 0.199 mmol), and DIEA (102 µL) in DMF (1 mL) was added HATU (82 mg, 0.22 mmol). The resulting mixture was stirred for 2 h at room temperature, then diluted with H$_2$O and acidified with TFA and purified by preparative HPLC with a C18 silica gel stationary phase using a gradient of H$_2$O 0.05% TFA: CH$_3$CN 0.05% TFA (80:20 to 40:60) and detection by UV at 254 nm to give the title compound tri-TFA salt (63 mg, 45% yield) as a white solid. $^1$H-NMR (400 MHz, CD$_3$OD) δ 7.89 (m, 3H), 7.78 (t, J=1.5 Hz, 3H), 7.65 (t, J=7.8 Hz, 3H), 7.60-7.51 (m, 6H), 6.83 (s, 3H), 4.82-4.71 (m, 6H), 4.49 (d, J=15.9 Hz, 3H), 4.03 (s, 2H), 3.89 (dd, J=11.6, 6.3 Hz, 3H), 3.85-3.75 (m, 2H), 3.69-3.51 (m, 21H), 3.48 (t, J=5.4 Hz, 6H), 3.36 (t, J=5.4 Hz, 6H), 3.25 (d, J=4.6 Hz, 2H), 3.15 (s, 9H), 3.05 (t, J=5.4 Hz, 6H), 2.46-2.35 (m, 2H), 2.29-2.13 (m, 6H), 2.05-1.92 (m, 6H). MS (ES, m/z): 1853.1 [M+H]$^+$.

Example 18

(S,S)—N,N',N''-(2,2',2''-(2,2',2''-(2,2',2''-(4,4',4''-nitrilotris(methylene)tris(1H-1,2,3-triazole-4,1-diyl))tris(ethane-2,1-diyl))tris(oxy)tris(ethane-2,1-diyl))tris(oxy)tris(ethane-2,1-diyl))tris(oxy)tris(ethane-2,1-diyl))tris(3-((S)-6,8-dichloro-2-methyl-1,2,3,4-tetrahydroisoquinolin-4-yl)benzenesulfonamide)

Scheme 18. triprop-2-ynylamine, CuI, DMF.

E.1 →

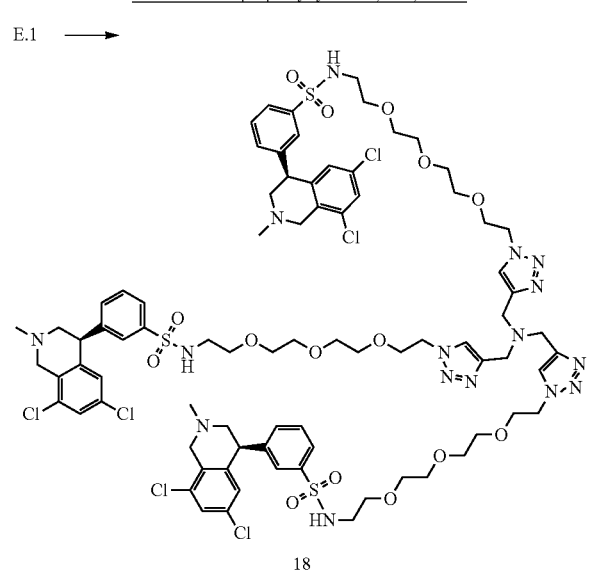

18

Example 18: To a solution of intermediate E.1 (70 mg, 0.158 mmol) and triprop-2-ynylamine (6.3 mg, 0.0478 mmol) in DMF (1 mL) was added CuI (1.4 mg, 0.0072 mmol) and the resulting mixture stirred for 16 h at room temperature. The mixture was then diluted with H$_2$O and acidified with TFA, then purified by preparative HPLC with a C18 silica gel stationary phase using a gradient of H$_2$O 0.05% TFA: CH$_3$CN 0.05% TFA (80:20 to 20:80) and detection by UV at 254 nm to give the title compound tri-TFA salt (40 mg, 36% yield) as a white solid. $^1$H-NMR (400 MHz, CD$_3$OD) δ 8.37 (s, 3H), 7.86 (d, J=8.3 Hz, 3H), 7.77 (s, 3H), 7.63 (t, J=7.8 Hz, 3H), 7.57-7.50 (m, 6H), 6.82 (s, 3H), 4.84-4.74 (m, 6H), 4.66 (t, J=4.9 Hz, 6H), 4.55-4.44 (m, 8H), 3.97-3.83 (m, 8H), 3.71-3.38 (m, 35H), 3.16 (s, 9H), 3.01 (t, J=5.4 Hz, 6H). MS (ES, m/z): 1845.2 [M+H]$^+$.

Example 19

4-((4'-chlorobiphenyl-4-yl)methylamino)-4-(1-(3-((S)-6,8-dichloro-2-methyl-1,2,3,4-tetrahydroisoquinolin-4-yl)phenylsulfonamido)-13-oxo-3,6,9-trioxa-12-azapentadecan-15-yl)-N$^1$,N$^7$-bis(2-(2-(2-(2-(3-((S)-6,8-dichloro-2-methyl-1,2,3,4-tetrahydroisoquinolin-4-yl)phenylsulfonamido)ethoxy)ethoxy)ethoxy)ethyl)heptanediamide Scheme 19. 4'-chlorobiphenyl-4-carbaldehyde, NaBH$_4$, MeOH.

9 →

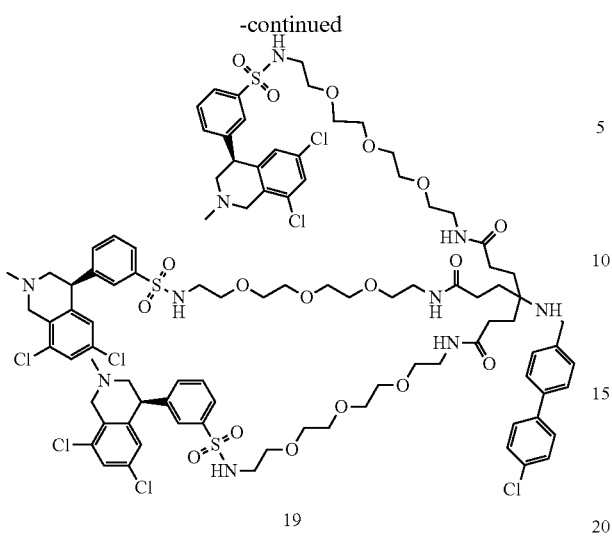

19

Example 19: A solution of example 9 (75 mg, 0.041 mmol) and 4'-chlorobiphenyl-4-carbaldehyde (8.9 mg, 0.041 mmol) in MeOH (1 mL) was stirred at room temperature for 4 h. NaBH$_4$ (2.5 mg, 0.065 mmol) was then added and the resulting mixture stirred at room temperature for 30 min. The solvent was then removed under reduced pressure and the resulting residue dissolved in DCM and washed with 1 M aqueous HCl, saturated aqueous NaHCO$_3$, and brine. The organic layer was then dried over Na$_2$SO$_4$ and the solvent removed under reduced pressure. The residue was then purified by preparative HPLC with a C18 silica gel stationary phase using a gradient of H$_2$O 0.05% TFA:CH$_3$CN 0.05% TFA (80:20 to 20:80) and detection by UV at 254 nm to give the title compound tri-TFA salt (26 mg, 25% yield) as a white solid. $^1$H-NMR (400 MHz, CD$_3$OD) δ 7.88 (d, J=7.9 Hz, 3H), 7.77 (s, 3H), 7.72-7.59 (m, 9H), 7.59-7.51 (m, 6H), 7.45 (m, 2H), 6.81 (s, 3H), 4.82-4.73 (m, 6H), 4.49 (d, J=16.2 Hz, 4H), 4.25 (s, 2H), 3.89 (dd, J=12.2, 6.0 Hz, 3H), 3.68-3.48 (m, 33H), 3.45 (t, J=5.4 Hz, 6H), 3.40 (t, J=5.4 Hz, 6H), 3.15 (s, 9H), 3.05 (t, J=5.4 Hz, 6H), 2.50 (t, J=7.2 Hz, 6H), 2.13 (t, J=7.2 Hz, 6H). MS (ES, m/z): 1015.3 [M+2H]$^{2+}$.

Example 20

4-(1-(3-((S)-6,8-dichloro-2-methyl-1,2,3,4-tetrahydroisoquinolin-4-yl)phenylsulfonamido)-13-oxo-3,6,9-trioxa-12-azapentadecan-15-yl)-N$^1$,N$^7$-bis(2-(2-(2-(2-(3-((S)-6,8-dichloro-2-methyl-1,2,3,4-tetrahydroisoquinolin-4-yl)phenylsulfonamido)ethoxy)ethoxy)ethoxy)ethyl)-4-(4-(octyloxy)benzylamino)heptanediamide

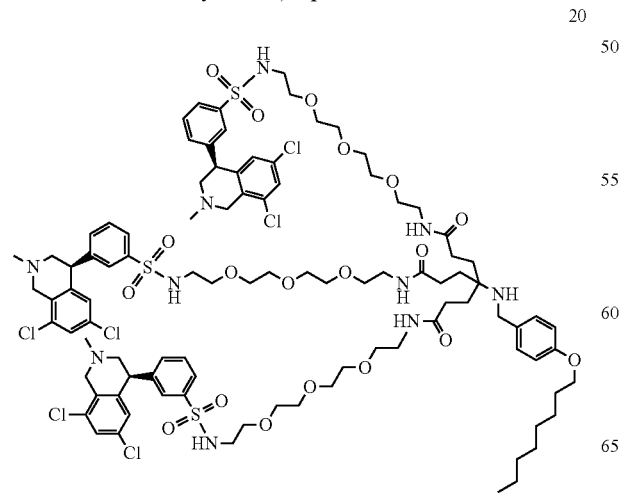

Example 20: The title compound was synthesized in a manner similar to example 19, 4-(octyloxy)benzaldehyde in place of 4'-chlorobiphenyl-4-carbaldehyde. MS (ES, m/z): 1024.5 [M+2H]$^{2+}$.

Examples 22-41

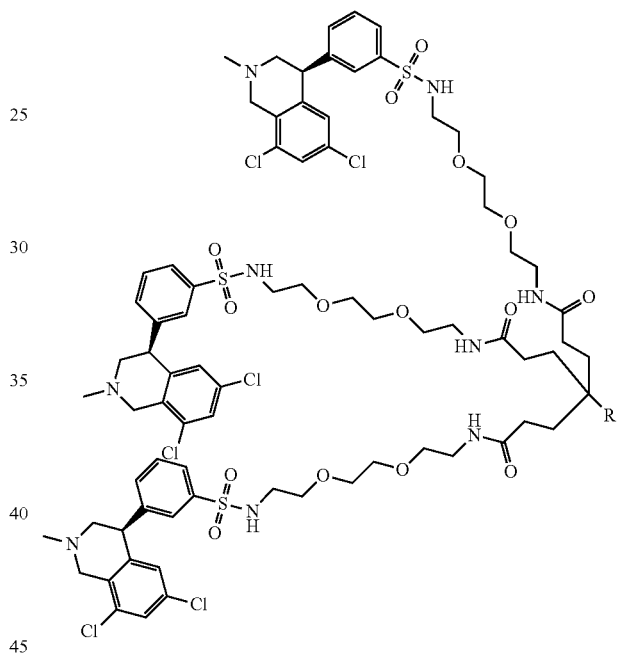

The following examples were synthesized using methods similar to the prior example given in Table 2 below:

TABLE 2

| Example # | R | Method | Exact Mass | Observed Mass |
|---|---|---|---|---|
| 22 | *decanoyl amide group* | Example 14 | 1864.6 | 1865.3 [M + H]+ |
| 23 | *4-(heptyloxy)benzylamine group* | Example 19 | 1914.6 | 1915.2 [M + H]+ |
| 24 | *(4'-chlorobiphenyl-4-yl)methylamine group* | Example 19 | 1896.5 | 1897.0 [M + H]+ |
| 25 | *N,N-dimethylurea group* | Example 11 | 1767.5 | 1768.2 [M + H]+ |
| 26 | *N-methylurea group* | Example 11 | 1753.5 | 1754.1 [M + H]+ |
| 27 | *N-methyliminodiacetyl group* | Example 6 | 1825.5 | 1826.1 [M + H]+ |
| 28 | ± *trans-cyclohexane-1,2-dicarboxamide group* | Example 6 | 1850.5 | 1851.5 [M + H]+ |
| 29 | *N-methyl-glucamine urea group* | Example 11 | 1917.5 | 1918.2 [M + H]+ |
| 30 | *imidazol-1-yl-acetamide group* | Example 14 | 1804.5 | 1805.4 [M + H]+ |
| 31 | *threoninamide urea group* | Example 11 | 1840.5 | 1841.0 [M + H]+ |

TABLE 2-continued

| Example # | R | Method | Exact Mass | Observed Mass |
|---|---|---|---|---|
| 32 | | Example 11 | 1833.4 | 1834.0 [M + H]+ |
| 33 | | Example 11 | 1896.6 | 1897.2 [M + H]+ |
| 34 | | Example 11 | 1813.5 | 1814.2 [M + H]+ |
| 35 | | Example 14 | 1910.5 | 1911.0 [M + H]+ |
| 36 | | Example 6 | 1810.5 | 1811.2 [M + H]+ |
| 37 | | Example 11 | 1903.5 | 1903.9 [M + H]+ |
| 38 | | Example 14 | 1806.5 | 1807.0 [M + H]+ |
| 39 | | Example 11 | 1827.5 | 914.9 [M + 2H]2+ |
| 40 | | Example 6 | 1796.5 | 1797.1 [M + H]+ |
| 41 | | Example 17 | 1822.5 | 1823.2 [M + H]+ |

Example 42

3,12-bis(14-(3-((S)-6,8-dichloro-2-methyl-1,2,3,4-tetrahydroisoquinolin-4-yl)phenylsulfonamido)-2-oxo-6,9,12-trioxa-3-azatetradecyl)-$N^1$,$N^{14}$-bis(2-(2-(2-(2-(3-((S)-6,8-dichloro-2-methyl-1,2,3,4-tetrahydroisoquinolin-4-yl)phenylsulfonamido)ethoxy)ethoxy)ethoxy)ethyl)-6,9-dioxa-3,12-diazatetradecane-1,14-diamide

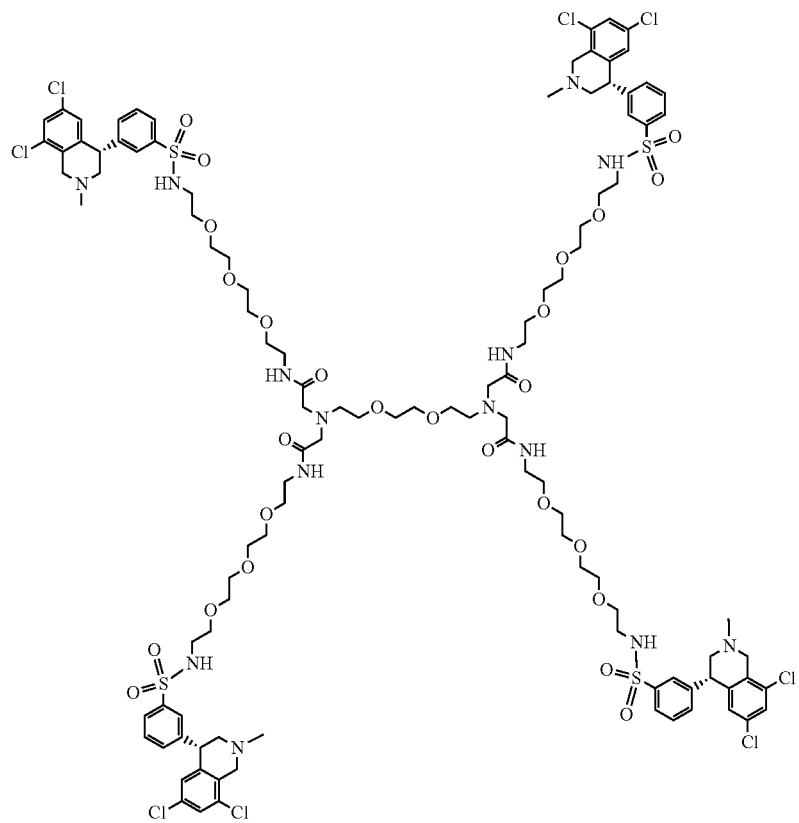

Example 42: 3,12-bis(14-(3-((S)-6,8-dichloro-2-methyl-1,2,3,4-tetrahydroisoquinolin-4-yl)phenylsulfonamido)-2-oxo-6,9,12-trioxa-3-azatetradecyl)-N1,N14-bis(2-(2-(2-(2-(3-((S)-6,8-dichloro-2-methyl-1,2,3,4-tetrahydroisoquinolin-4-yl)phenylsulfonamido)ethoxy)ethoxy)ethoxy)ethyl)-6,9-dioxa-3,12-diazatetradecane-1,14-diamide. To a mixture of ethylene glycol-bis(2-aminoethylether)-N,N,N',N'-tetraacetic acid (40 mL, 0.105 mmol, 1 equiv) in DMF (1.5 mL) at rt were added DIEA (147 µL, 0.84 mmol, 8 equiv) and HBTU (160 mg, 0.42 mmol, 4 equiv). The mixture was stirred at rt for 0.5 h to give an activated tetraacid mixture. To a mixture of intermediate E (104.9 mg, 0.193 mol, 1.83 equiv) in DMF (0.2 mL) at rt was added the activated tetracid mixture (626 µL) in portions over 20 minutes. The mixture was stirred at rt for 1 h and purified by prep HPLC to give 44.2 mg (29%) of the title compound TFA salt as a pale yellow solid. MS (ES, m/z): 831 [M+3H]$^{3+}$. $^1$H NMR (400 MHz, CD$_3$OD) δ 7.89 (d, J=7.8 Hz, 4H), 7.77 (s, 4H), 7.66 (t, J=7.8 Hz, 4H), 7.59-7.53 (m, 8H), 6.83 (s, 4H), 4.82-4.73 (m, 8H), 4.49 (d, J=15.9 Hz, 4H), 3.96-3.85 (m, 12H), 3.82-3.75 (m, 4H), 3.68-3.50 (m, 52H), 3.45 (dt, J=14.2, 5.5 Hz, 16H), 3.15 (s, 12H), 3.05 (t, J=5.3 Hz, 8H).

Example 43

(S)—N,N'-(15-(1-(3-((S)-6,8-dichloro-2-methyl-1,2,3,4-tetrahydroisoquinolin-4-yl)phenylsulfonamido)-10-oxo-3,6-dioxa-9,11-diazatetradecan-14-yl)-10,20-dioxo-3,6,24,27-tetraoxa-9,11,15,19,21-pentaazanonacosane-1,29-diyl)bis(3-((S)-6,8-dichloro-2-methyl-1,2,3,4-tetrahydroisoquinolin-4-yl)benzenesulfonamide)

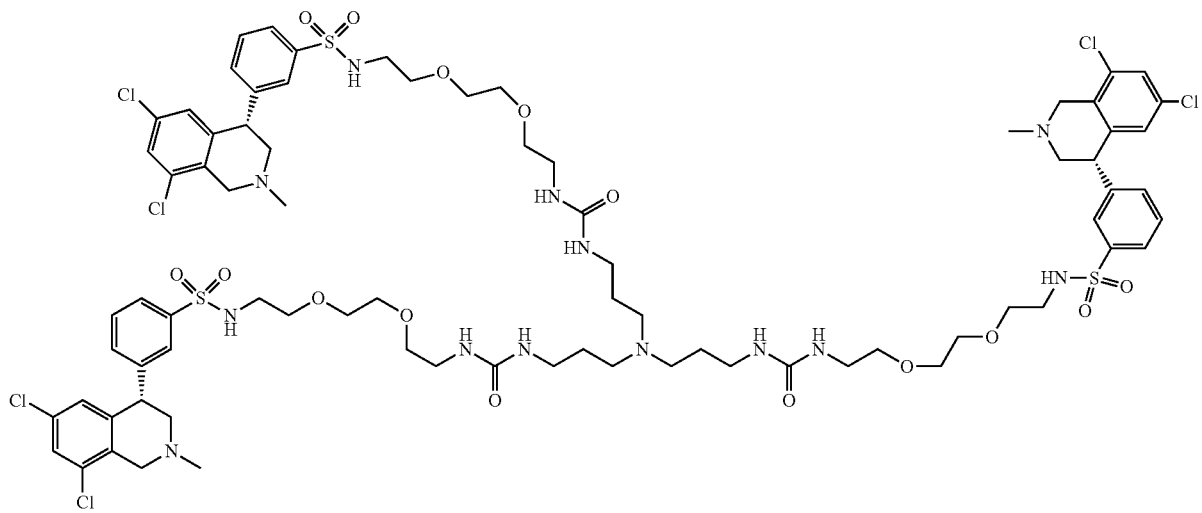

43

Example 43: (S)—N,N'-(15-(1-(3-((S)-6,8-dichloro-2-methyl-1,2,3,4-tetrahydroisoquinolin-4-yl)phenylsulfonamido)-10-oxo-3,6-dioxa-9,11-diazatetradecan-14-yl)-10,20-dioxo-3,6,24,27-tetraoxa-9,11,15,19,21-pentaazanonacosane-1,29-diyl)bis(3-((S)-6,8-dichloro-2-methyl-1,2,3,4-tetrahydroisoquinolin-4-yl)benzenesulfonamide). To a mixture of N,N'-carbonyldiimidazole (56.6 mg, 0.349 mmol, 3 equiv) in DMF (0.6 mL) was added dropwise a solution of tris(3-aminopropyl)amine (21.9 mg, 0.116 mmol, 1 equiv) in DMF (0.4 mL). The mixture was stirred at rt for 3 h and used in next step without purification. To a mixture of intermediate A (83.6 mg, 0.167 mol, 1.44 equiv) in DMF (0.2 mL) at 50° C. was added the above tris(3-aminopropyl)amine reaction mixture (560 µL) in portions over 30 minutes. The mixture was stirred at 50° C. for 2 h and purified by prep. HPLC to give 50.5 mg (41%) of the title compound TFA salt as a white solid. MS (ES, m/z): 1770 [M+H]$^+$. $^1$H NMR (400 MHz, CD$_3$OD) δ 7.89 (d, J=7.8 Hz, 3H), 7.78 (s, 3H), 7.65 (t, J=7.8 Hz, 3H), 7.59-7.50 (m, 6H), 6.83 (s, 3H), 4.85-4.74 (m, 6H), 4.50 (d, J=16.0 Hz, 3H), 3.90 (dd, J=12.0, 6.3 Hz, 3H), 3.62 (t, J=12.0 Hz, 3H), 3.59-3.55 (m, 6H), 3.55-3.53 (m, 6H), 3.49 (dt, J=12.5, 5.4 Hz, 12H), 3.30-3.27 (m, 6H), 3.23 (t, J=6.3 Hz, 6H), 3.20-3.12 (m, 15H), 3.05 (t, J=5.4 Hz, 6H), 2.00-1.76 (m, 6H).

Example 44

N$^1$,N$^1$,N$^{12}$,N$^{12}$-tetrakis(13-(3-((S)-6,8-dichloro-2-methyl-1,2,3,4-tetrahydroisoquinolin-4-yl)phenylsulfonamido)-4-oxo-8,11-dioxa-3,5-diazatridecyl)dodecanediamide

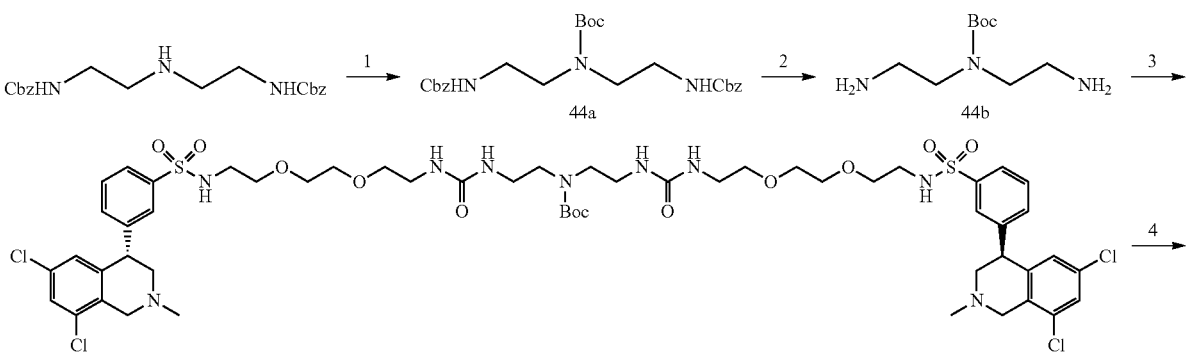

-continued

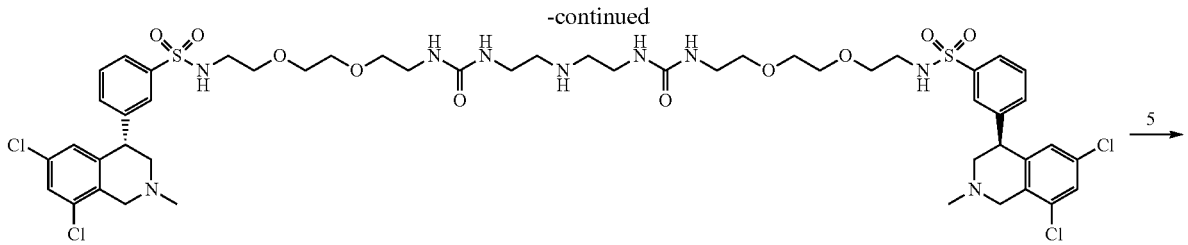

44d

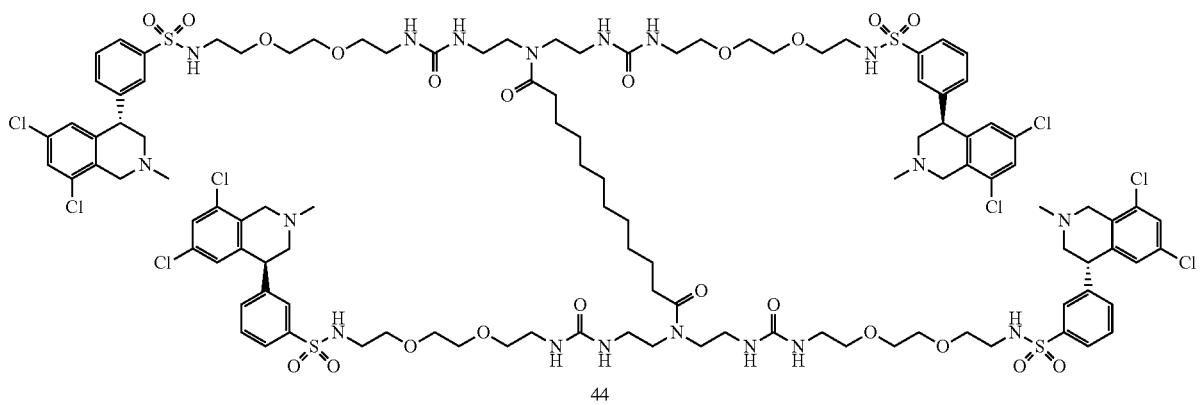

44

1. (Boc)₂O, TEA, DCM;
2. Pd/C, H₂, MeOH;
3. Intermediate A, CDI, DMF;
4. HCl, dioxane, DCM;
5. Dodecanedioic acid, HATU, DIEA.

Intermediate 44a: dibenzyl (((tert-butoxycarbonyl)azanediyl)bis(ethane-2,1-diyl))dicarbamate. To a mixture of N,N'-di-2-diethylenetriamine (740 mg, 1.99 mmol, 1 equiv) in DCM (3 mL) at 0° C. was added di-tert-butyl dicarbonate (522 mg, 2.39 mol, 1.2 equiv) and TEA (0.416 mL, 2.99 mmol, 1.5 equiv). The mixture was stirred at rt overnight, diluted with ethyl acetate, washed with H₂O (1×) and brine (1×), dried, concentrated and purified by column to give 0.918 mg (98%) of intermediate 44a as clear syrup.

Intermediate 44b: tert-butyl bis(2-aminoethyl)carbamate. To a mixture of dibenzyl (((tert-butoxycarbonyl)azanediyl)bis(ethane-2,1-diyl))dicarbamate (918 mg, 1.95 mmol, 1.0 equiv) in MeOH (20 mL) was added 10% Pd/C (150 mg). The mixture was stirred at rt under H₂ for 1.5 h, filtered and concentrated to give 400 mg (crude) of intermediate 44b as a white solid.

Intermediate 44c: tert-butyl bis(13-(3-((S)-6,8-dichloro-2-methyl-1,2,3,4-tetrahydroisoquinolin-4-yl)phenylsulfonamido)-4-oxo-8,11-dioxa-3,5-diazatridecyl)carbamate. To a mixture of N,N'-carbonyldiimidazole (88.8 mg, 0.548 mmol, 2 equiv) in DMF (1.4 mL) was added dropwise a mixture of tert-butyl bis(2-aminoethyl)carbamate (55.6 mg, 0.274 mmol, 1 equiv). The mixture was stirred at rt for 3 h and used in next step without purification. To a mixture of intermediate A (191.5 mg, 0.382 mol, 1.39 equiv) in DMF (0.4 mL) at 50° C. was added portion is the above tert-butyl bis(2-aminoethyl)carbamate reaction mixture and stirred at 50° C. for 1 h. The mixture was diluted with ethyl acetate, washed with H₂O (2×) and brine (1×), dried, concentrated and purified by column to give 172 mg (71%) of intermediate 44c as clear syrup.

Intermediate 44d: (S)—N,N'-(10,18-dioxo-3,6,22,25-tetraoxa-9,11,14,17,19-pentaazaheptacosane-1,27-diyl)bis(3-((S)-6,8-dichloro-2-methyl-1,2,3,4-tetrahydroisoquinolin-4-yl)benzenesulfonamide). To a mixture of tert-butylbis(13-(3-((S)-6,8-dichloro-2-methyl-1,2,3,4-tetrahydroisoquinolin-4-yl)phenylsulfonamido)-4-oxo-8,11-dioxa-3,5-diazatridecyl)carbamate (172 mg) in DCM (0.5 mL) was added a solution of HCl in dioxane (4 M, 2 mL). The mixture was stirred at rt for 30 minutes and concentrated to give 200 mg of intermediate 44d HCl salt as a white solid.

Example 44: $N^1,N^1,N^{12},N^{12}$-tetrakis(13-(3-((S)-6,8-dichloro-2-methyl-1,2,3,4-tetrahydroisoquinolin-4-yl)phenylsulfonamido)-4-oxo-8,11-dioxa-3,5-diazatridecyl)dodecanediamide. To a mixture of (S)—N,N'-(10,18-dioxo-3,6,22,25-tetraoxa-9,11,14,17,19-pentaazaheptacosane-1,27-diyl)bis(3-((S)-6,8-dichloro-2-methyl-1,2,3,4-tetrahydroisoquinolin-4-yl)benzenesulfonamide) (44.3 mg, 0.0349 mmol, 1 equiv) and dodecanedioic acid (3.66 mg, 0.0159 mmol, 0.46 equiv) in DMF (0.4 mL) at rt were added DIEA (30.4 µL, 0.175 mmol, 5 equiv) and HATU (14.6 mg, 0.0384 mmol, 1.1 equiv). The mixture was stirred at rt for 0.5h and purified by prep HPLC to give 28 mg (59%) of the title compound TFA salt as a white solid. MS (ES, m/z): 1255 $[M+2H]^{2+}$. $^1$H NMR (400 MHz, CD₃OD) δ 7.89 (d, J=7.9 Hz, 4H), 7.79 (d, J=1.4 Hz, 4H), 7.65 (t, J=7.8 Hz, 4H), 7.59-7.51 (m, 8H), 6.83 (s, 4H), 4.83-4.73 (m, 8H), 4.52 (d, J=16.2 Hz, 4H), 3.92 (dd, J=12.2, 6.0 Hz, 4H), 3.64 (t, J=11.8 Hz, 4H), 3.58-3.49 (m, 16H), 3.49-3.36 (m, 24H), 3.26 (dd, J=13.0, 5.5 Hz, 16H), 3.17 (s, 12H), 3.05 (t, J=5.4 Hz, 8H), 2.37 (t, J=8.0 Hz, 4H), 1.61-1.48 (m, 4H), 1.36-1.21 (m, 12H).

Example 45

(S)—N,N'-(14-((1-(3-((S)-6,8-dichloro-2-methyl-1,2,3,4-tetrahydroisoquinolin-4-yl)phenylsulfonamido)-14-(13-(3-((S)-6,8-dichloro-2-methyl-1,2,3,4-tetrahydroisoquinolin-4-yl)phenylsulfonamido)-4-oxo-8,11-dioxa-3,5-diazatridecyl)-10,15-dioxo-3,6-dioxa-9,11,14,16-tetraazaoctacosan-28-yl)carbamoyl)-10,18-dioxo-3,6,22,25-tetraoxa-9,11,14,17,19-pentaazaheptacosane-1,27-diyl)bis(3-((S)-6,8-dichloro-2-methyl-1,2,3,4-tetrahydroisoquinolin-4-yl)benzenesulfonamide)

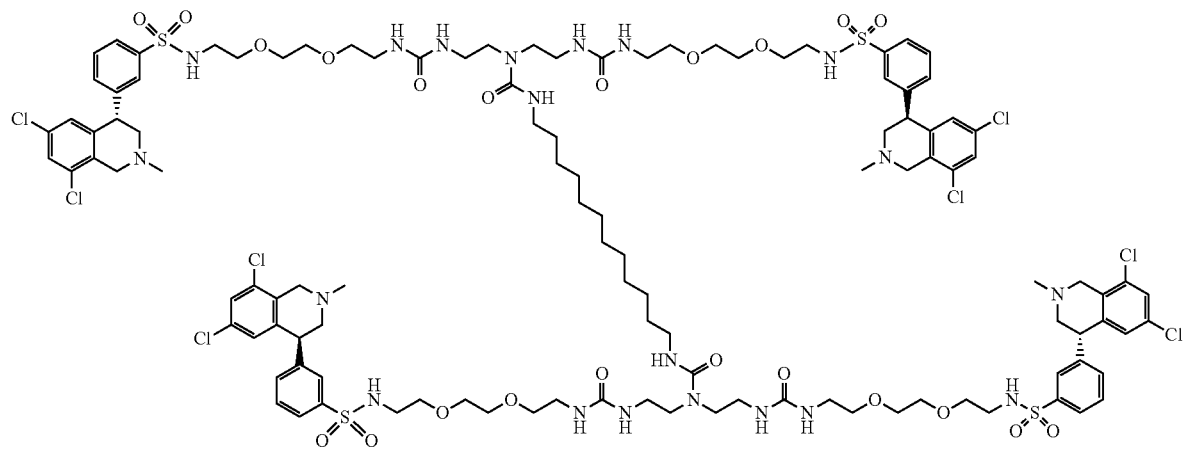

45

Example 45: (S)—N,N'-(14-((1-(3-((S)-6,8-dichloro-2-methyl-1,2,3,4-tetrahydroisoquinolin-4-yl)phenylsulfonamido)-14-(13-(3-((S)-6,8-dichloro-2-methyl-1,2,3,4-tetrahydroisoquinolin-4-yl)phenylsulfonamido)-4-oxo-8,11-dioxa-3,5-diazatridecyl)-10,15-dioxo-3,6-dioxa-9,11,14,16-tetraazaoctacosan-28-yl)carbamoyl)-10,18-dioxo-3,6,22,25-tetraoxa-9,11,14,17,19-pentaazaheptacosane-1,27-diyl)bis(3-((S)-6,8-dichloro-2-methyl-1,2,3,4-tetrahydroisoquinolin-4-yl)benzenesulfonamide). To a mixture of intermediate 44d (42.3 mg, 0.0365 mmol, 2.1 equiv) in DCM (0.25 mL) was added portionwise a solution of 1,2-diisocyanatododecane (4.7 μL, 0.0174 mmol, 1 equiv) and TEA (4.8 μL, 0.0347 mmol, 2 equiv) in DCM (0.1 mL). The mixture was stirred at rt for 20 minutes, concentrated, and purified by prep HPLC to give 31.6 mg (60%) of example 45 TFA salt as a white solid. MS (ES, m/z): 1284.6 [M+2H]$^{2+}$. $^1$H NMR (400 MHz, CD$_3$OD) δ 7.92-7.84 (m, 4H), 7.79 (s, 4H), 7.64 (t, J=7.8 Hz, 4H), 7.58-7.48 (m, 8H), 6.83 (s, 4H), 4.84-4.75 (m, 8H), 4.51 (d, J=15.9 Hz, 4H), 3.92 (dd, J=11.8, 6.5 Hz, 4H), 3.63 (t, J=12.1 Hz, 4H), 3.58-3.53 (m, 8H), 3.53-3.51 (m, 8H), 3.51-3.43 (m, 16H), 3.30-3.25 (m, 16H), 3.21 (t, J=6.8 Hz, 8H), 3.17 (s, 12H), 3.15-3.09 (m, 4H), 3.05 (t, J=5.4 Hz, 8H), 1.56-1.44 (m, 4H), 1.35-1.22 (m, 16H).

Example 46

(S)—N,N'-(14-amino-14-(13-(3-((S)-6,8-dichloro-2-methyl-1,2,3,4-tetrahydroisoquinolin-4-yl)phenylsulfonamido)-4-oxo-8,11-dioxa-3,5-diazatridecyl)-10,18-dioxo-3,6,22,25-tetraoxa-9,11,17,19-tetraazaheptacosane-1,27-diyl)bis(3-((S)-6,8-dichloro-2-methyl-1,2,3,4-tetrahydroisoquinolin-4-yl)benzenesulfonamide)

Scheme 46.

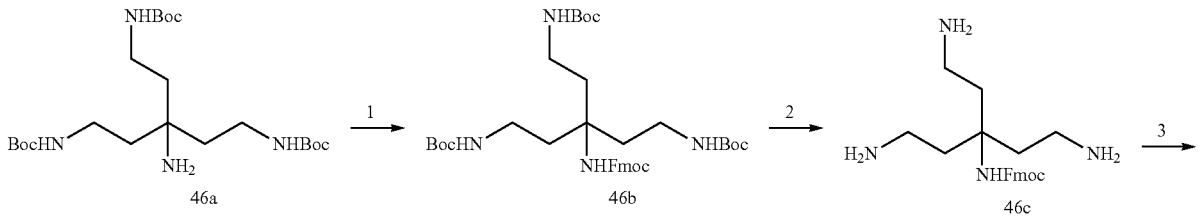

-continued

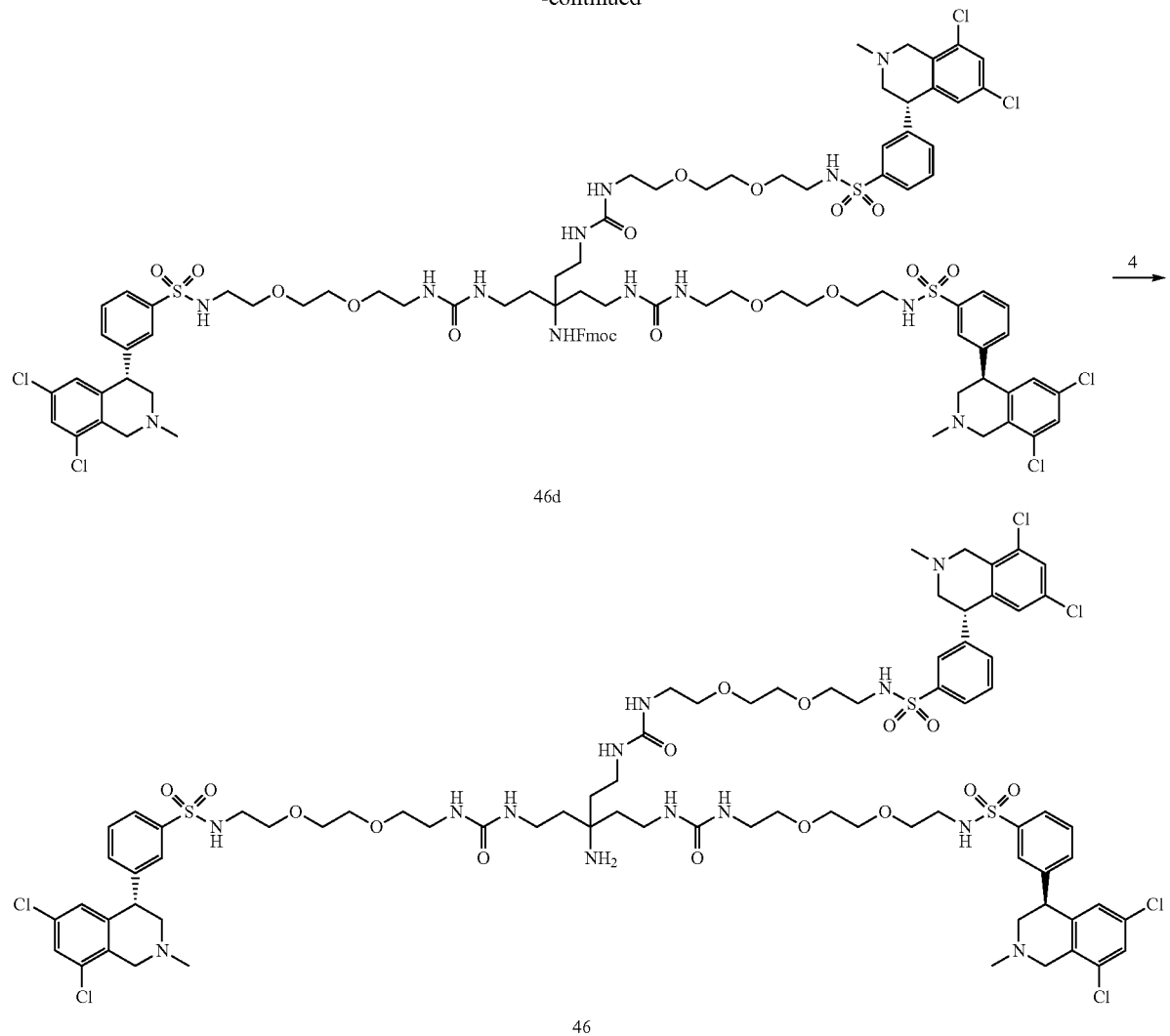

46

1. Fmoc-OSu, DIEA, DCM;
2. HCl, dioxane;
3. Intermediate A, phosgene, TEA, DCM, DIEA, DMF;
4. tris(2-aminoethyl)amine.

Intermediate 46b: To a mixture of intermediate 46a (Ref 1, 411 mg, 0.893 mmol, 1 equiv) and DIEA (238.6 µL, 1.34 mmol, 1.5 equiv) in DCM (3.3 mL) at 0° C. was added Fmoc-OSu (362 mg, 1.07 mmol, 1.2 equiv). The mixture was stirred at rt for 4 h, concentrated and purified by column to give 0.59 g (97%) of intermediate 46b as a white solid.

Intermediate 46c: (9H-fluoren-9-yl)methyl (1,5-diamino-3-(2-aminoethyl)pentan-3-yl)carbamate. To intermediate 46b was added a solution of HCl in dioxane (3 mL). The mixture was stirred at rt for 0.5 h, concentrated and triturated with ethyl acetate to give 0.216 g of intermediate 46c as a white solid.

Intermediate 46d: (9H-fluoren-9-yl)methyl (1,27-bis(3-((S)-6,8-dichloro-2-methyl-1,2,3,4-tetrahydroisoquinolin-4-yl)phenylsulfonamido)-14-(13-(3-((S)-6,8-dichloro-2-methyl-1,2,3,4-tetrahydroisoquinolin-4-yl)phenylsulfonamido)-4-oxo-8,11-dioxa-3,5-diazatridecyl)-10,18-dioxo-3,6,22,25-tetraoxa-9,11,17,19-tetraazaheptacosan-14-yl)carbamate. To a mixture of phosgene (15% in toluene, 577 µL, 0.808 mmol, 2 equiv) in DCM (1 mL) at 0° C. was added dropwise a mixture of intermediate A (202.4 mg, 0.404 mmol, 1 equiv) and TEA (113 µL, 0.808 mmol, 2 equiv) in DCM (3 mL). The mixture was stirred at rt for 0.5 h and concentrated. The residue was diluted with THF and filtered. The filtrate was concentrated to give a yellow solid. To a mixture of this yellow solid in DMF (2.5 mL) was added intermediate 46c (52.2 mg, 0.106 mmol, 0.263 equiv) and DIEA (141 µL, 0.808 mmol, 2 equiv). The mixture was stirred at rt for 1 h and diluted with water. The yellow precipitate was collected via filtration and purified by column to give 122 mg (58%) of intermediate 46d as a slightly yellow solid.

Example 46: (S)—N,N'-(14-amino-14-(13-(3-((S)-6,8-dichloro-2-methyl-1,2,3,4-tetrahydroisoquinolin-4-yl)phenylsulfonamido)-4-oxo-8,11-dioxa-3,5-diazatridecyl)-10,18-dioxo-3,6,22,25-tetraoxa-9,11,17,19-tetraazaheptacosane-1,27-diyl)bis(3-((S)-6,8-dichloro-2-methyl-1,2,3,4-tetrahydroisoquinolin-4-yl)benzenesulfonamide) To a mixture of intermediate 46d (122 mg, 0.062 mmol, 1 equiv) in DMF (2 mL) was added tris(2-aminoethyl)amine. The mixture was stirred at rt for 0.5 h and purified by prep HPLC to give 81.5 mg (60%) of the title compound TFA salt as a white solid. MS (ES, m/z): 1742.8 [M+H]$^+$. $^1$H NMR (400 MHz, CD$_3$OD) δ 7.92-7.86 (m, 3H), 7.78 (t, J=1.6 Hz, 3H), 7.65 (t, J=7.8 Hz, 3H), 7.59-7.51 (m, 6H), 6.83 (s, 3H), 4.83-4.74 (m, 6H), 4.50 (d, J=16.0 Hz, 3H), 3.95-3.85 (m, 3H), 3.62 (t, J=12.1 Hz, 3H), 3.58-3.54 (m, 6H), 3.53 (dd, J=3.7, 1.7 Hz, 6H), 3.49 (dt, J=10.7, 5.5 Hz, 12H), 3.30-3.22 (m, 12H), 3.16 (s, 9H), 3.05 (t, J=5.4 Hz, 6H), 1.87 (t, J=8.0 Hz, 6H).

Example 47

(S)—N,N'-(15-(1-(3-((S)-6,8-dichloro-2-methyl-1,2,3,4-tetrahydroisoquinolin-4-yl)phenylsulfonamido)-11-methyl-10-oxo-3,6-dioxa-9,11-diazatetradecan-14-yl)-11,19-dimethyl-10,20-dioxo-3,6,24,27-tetraoxa-9,11,15,19,21-pentaazanonacosane-1,29-diyl)bis(3-((S)-6,8-dichloro-2-methyl-1,2,3,4-tetrahydroisoquinolin-4-yl)benzenesulfonamide)

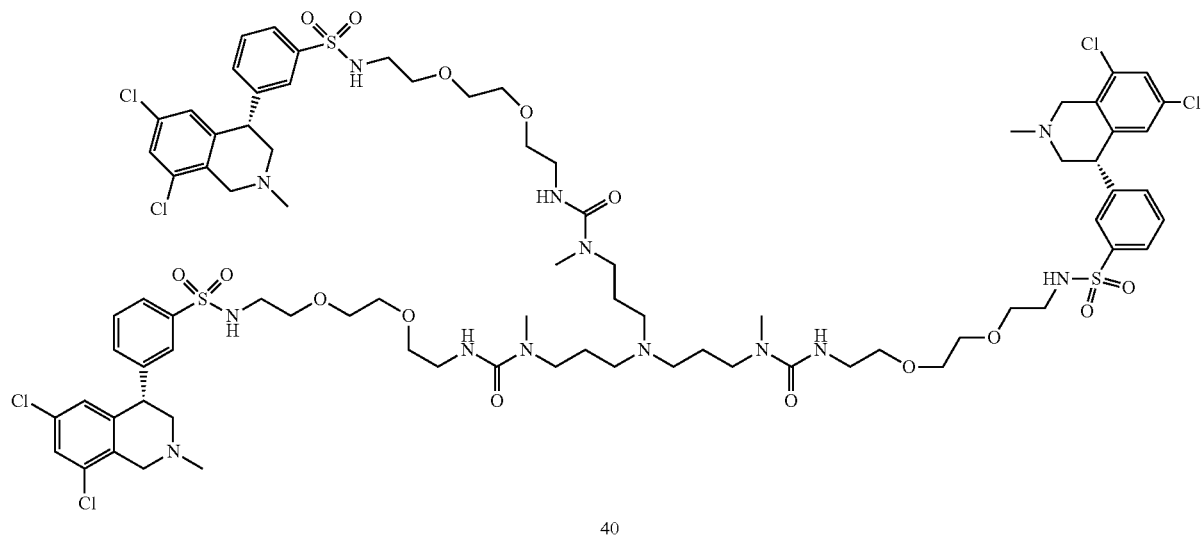

Example 47: (S)—N,N'-(15-(1-(3-((S)-6,8-dichloro-2-methyl-1,2,3,4-tetrahydroisoquinolin-4-yl)phenylsulfonamido)-11-methyl-10-oxo-3,6-dioxa-9,11-diazatetradecan-14-yl)-11,19-dimethyl-10,20-dioxo-3,6,24,27-tetraoxa-9,11,15,19,21-pentaazanonacosane-1,29-diyl)bis(3-((S)-6,8-dichloro-2-methyl-1,2,3,4-tetrahydroisoquinolin-4-yl) benzenesulfonamide). To a mixture of phosgene (15% in toluene, 127 µL, 0.178 mmol, 1.5 equiv) in DCM (0.2 mL) at 0° C. was added dropwise a mixture of intermediate A (59.3 mg, 0.118 mmol, 1 equiv) and TEA (25 uL, 0.178 mmol, 1.5 equiv) in DCM (1 mL). The mixture was stirred at rt for 0.5 h and concentrated. To a mixture of the above isocyanate residue in DCM (0.3 mL) was added a mixture of N'-methyl-$N^3$,$N^3$-bis(3-(methylamino)propyl)propan-1,3-diamine (intermediate J, 9 mg, 0.039 mmol, 0.33 equiv) and TEA (16.4 µL, 0.118 mmol, 1 equiv) in DCM (0.44 mL) portionwise. The mixture was stirred at rt for 0.5 h, concentrated and purified by prep HPLC to give 51.3 mg (57%) of the title compound TFA salt as a white solid. MS (ES, m/z): 1812.1 [M+H]$^+$. $^1$H NMR (400 MHz, CD$_3$OD) δ 7.92-7.86 (m, 3H), 7.78 (t, J=1.6 Hz, 3H), 7.65 (t, J=7.8 Hz, 3H), 7.59-7.51 (m, 6H), 6.82 (s, 3H), 4.84-4.73 (m, 6H), 4.50 (d, J=16.0 Hz, 3H), 3.96-3.85 (m, 3H), 3.63 (t, J=12.1 Hz, 3H), 3.59-3.55 (m, 6H), 3.55-3.50 (m, 12H), 3.47 (t, J=5.4 Hz, 6H), 3.40 (t, J=6.6 Hz, 6H), 3.35 (t, J=5.8 Hz, 6H), 3.16 (s, 9H), 3.15-3.10 (m, 6H), 3.05 (t, J=5.4 Hz, 6H), 2.92 (s, 9H), 2.05-1.86 (m, 6H).

Examples 48-71
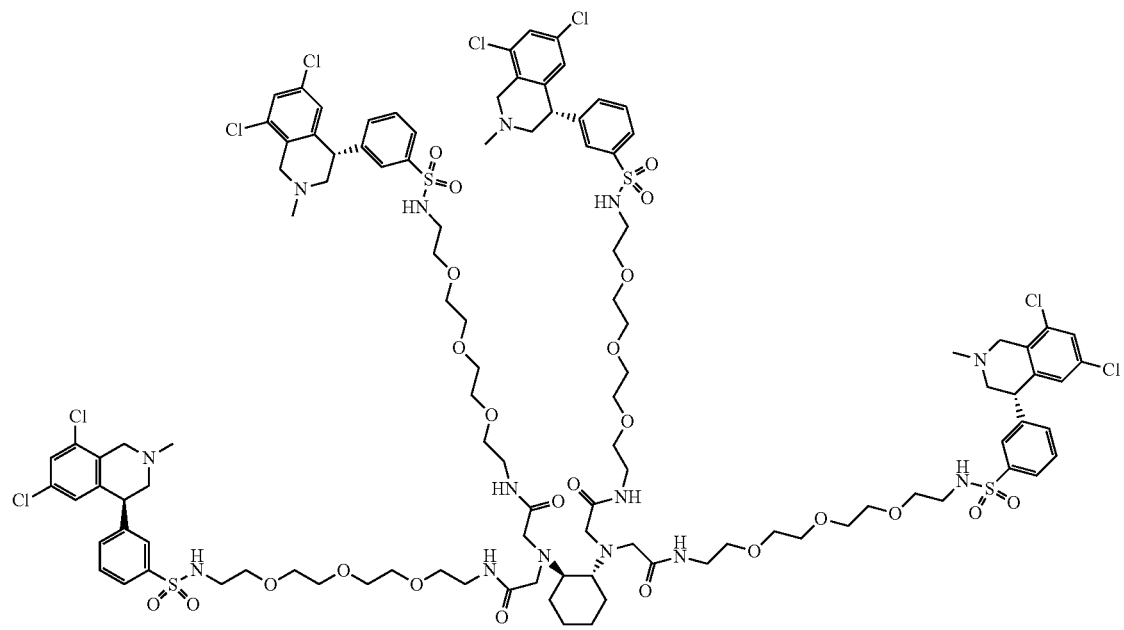
48
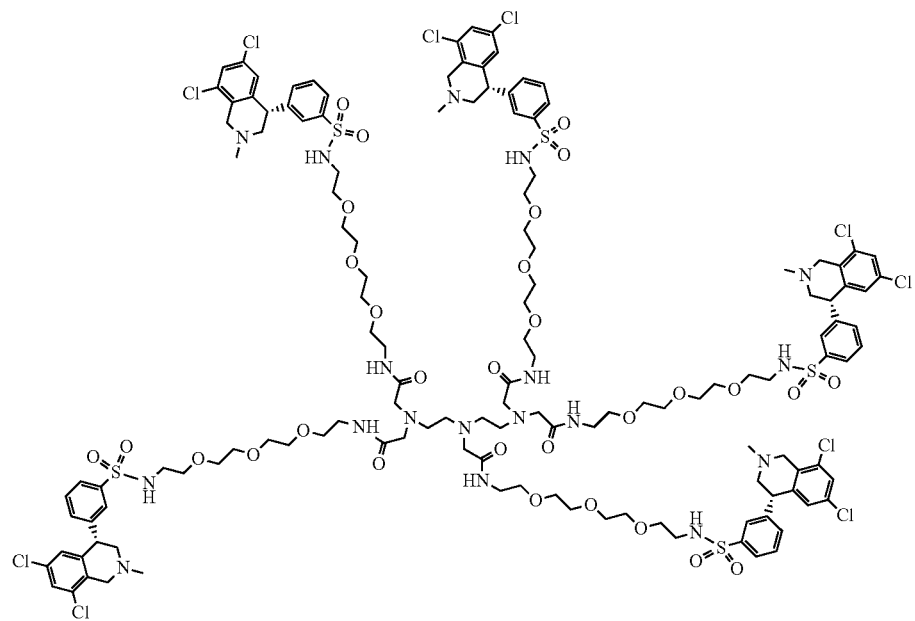
49

50
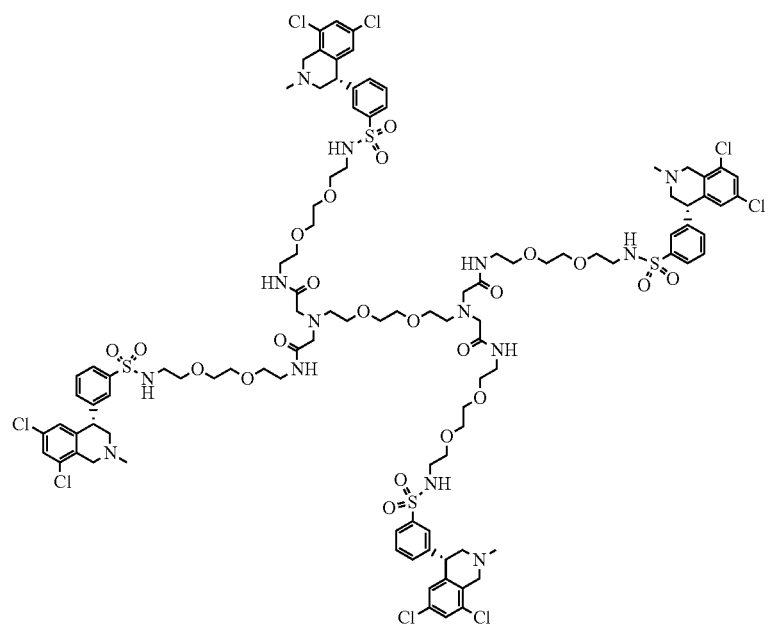
51
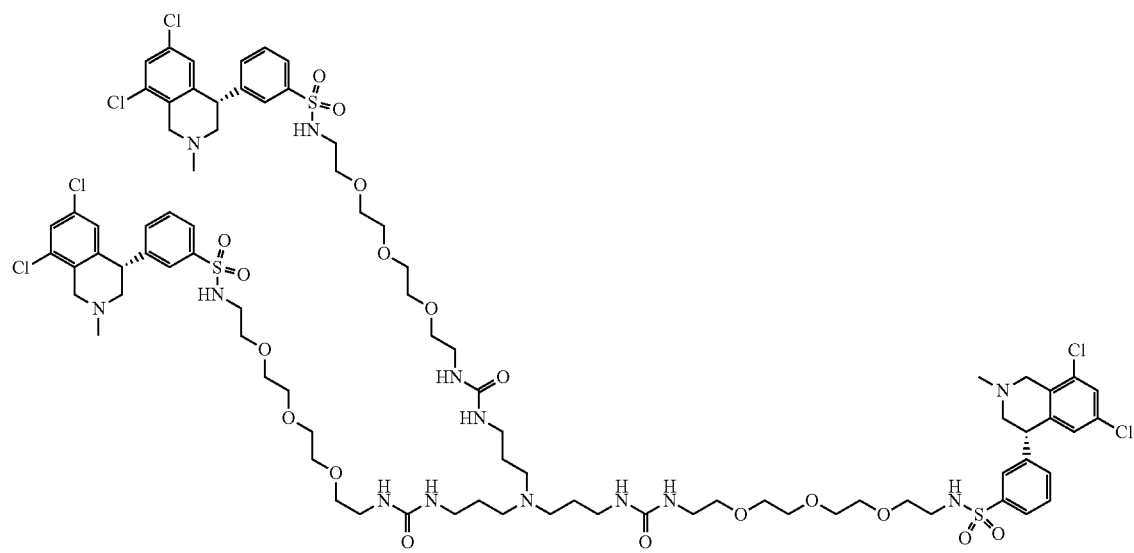

52
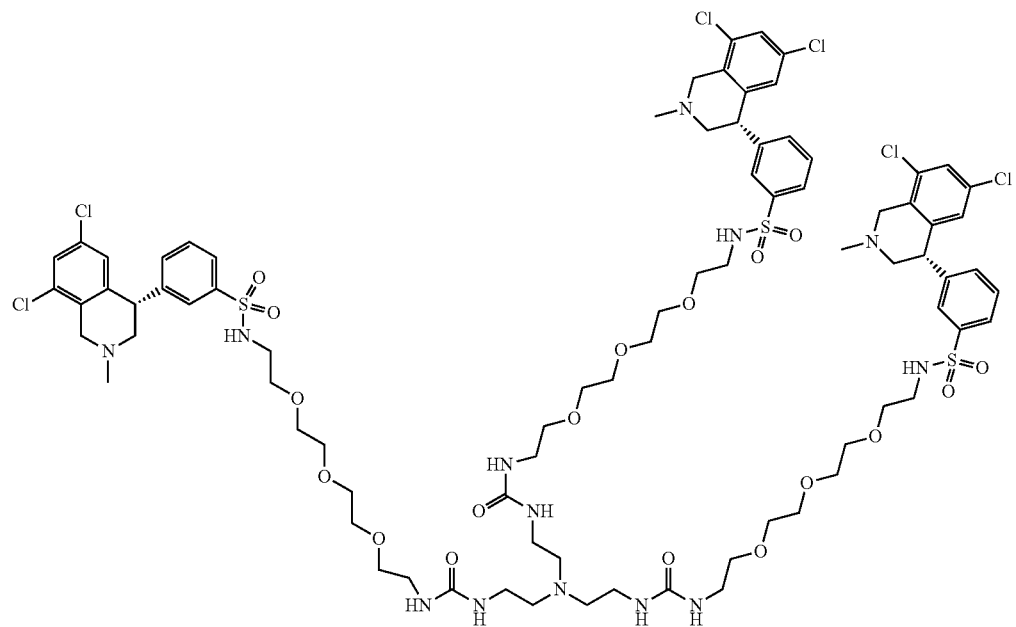
53
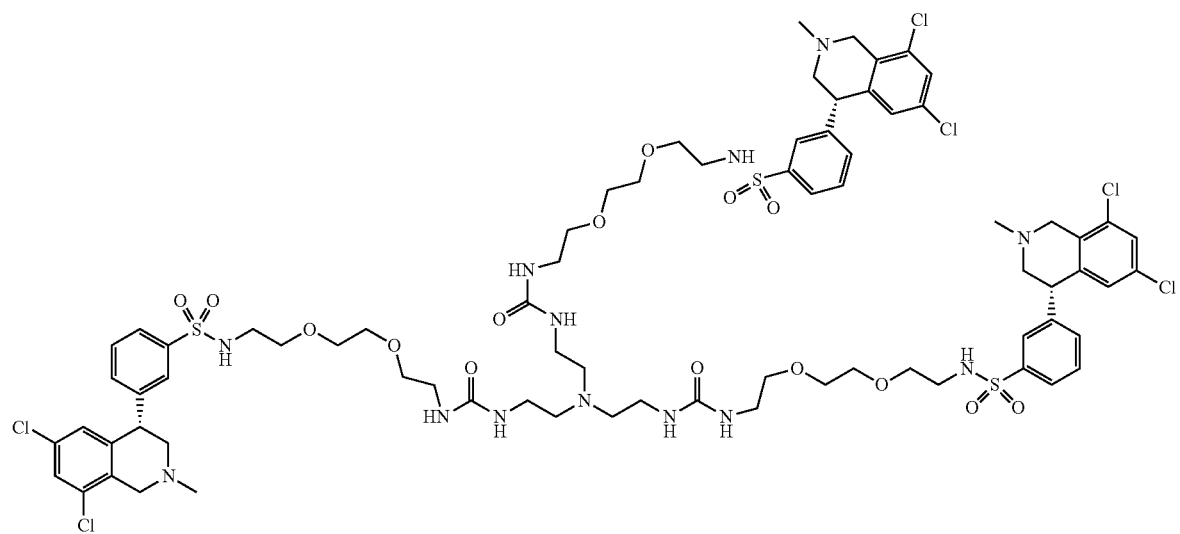

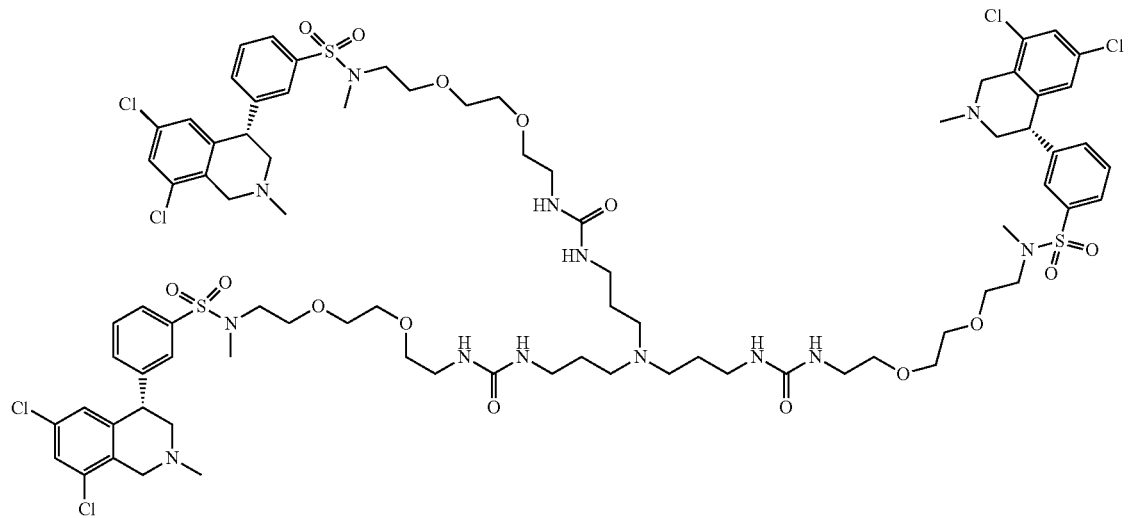
54
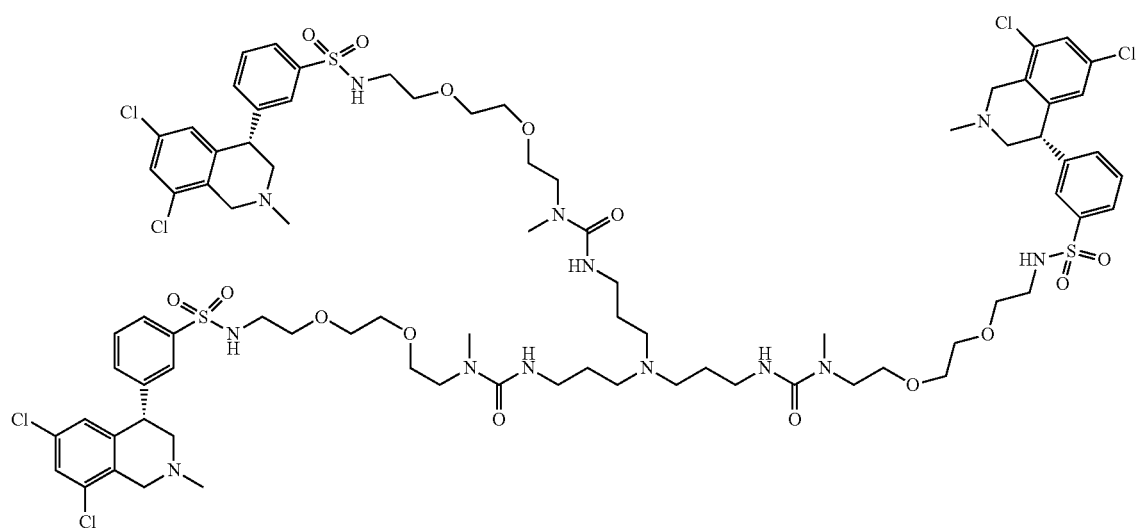
55
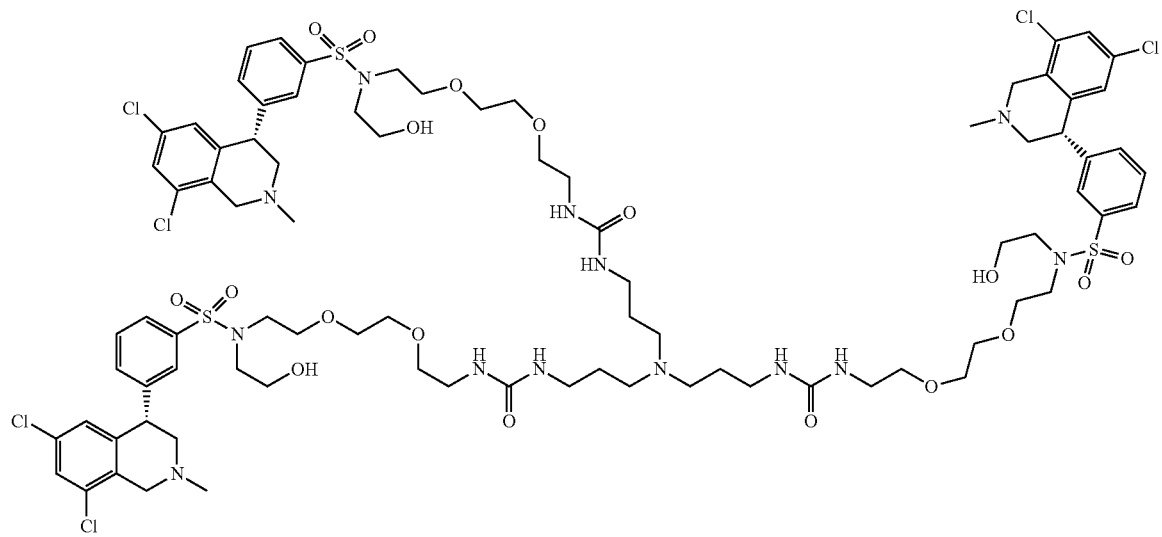
56

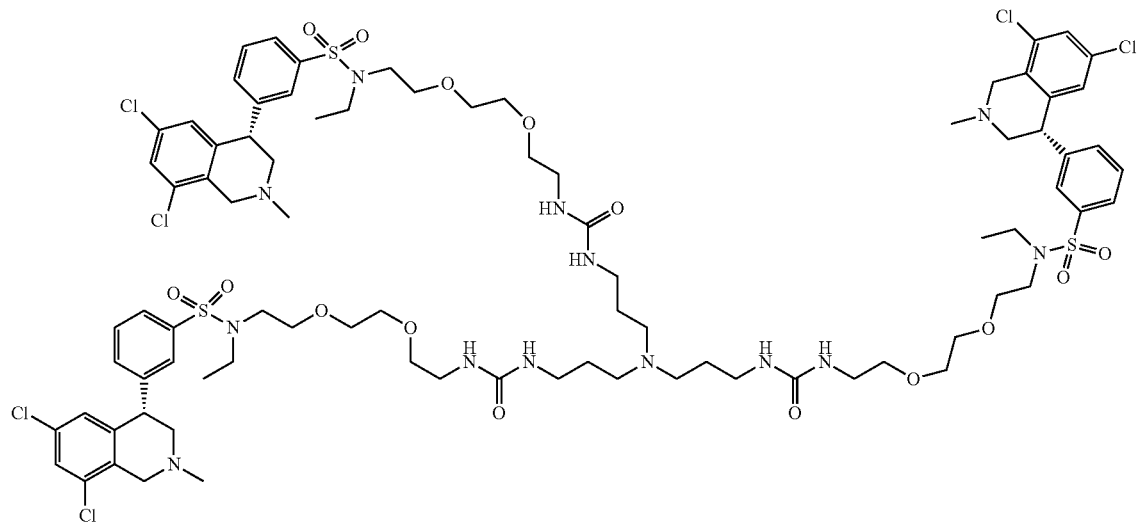
57
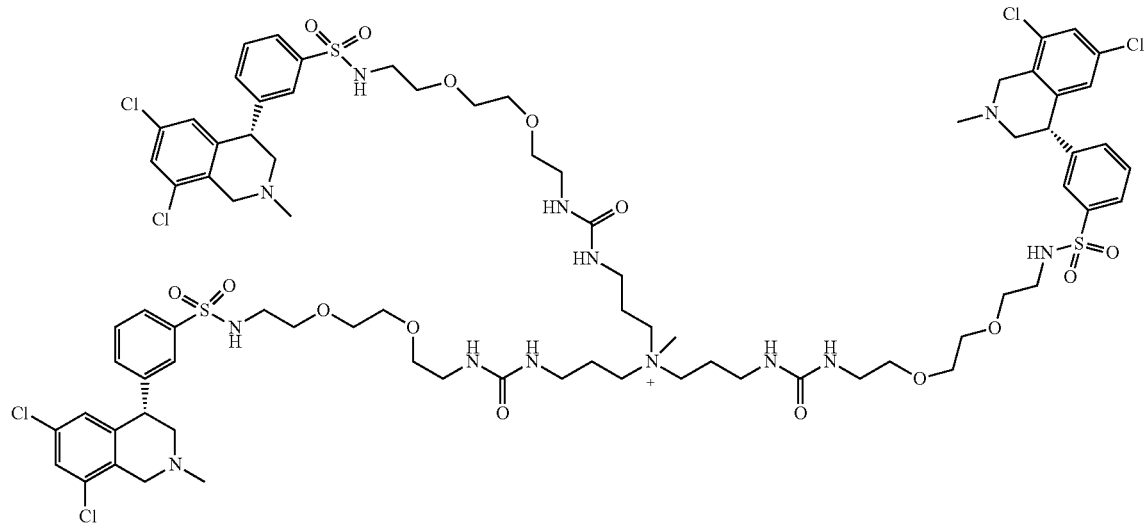
58
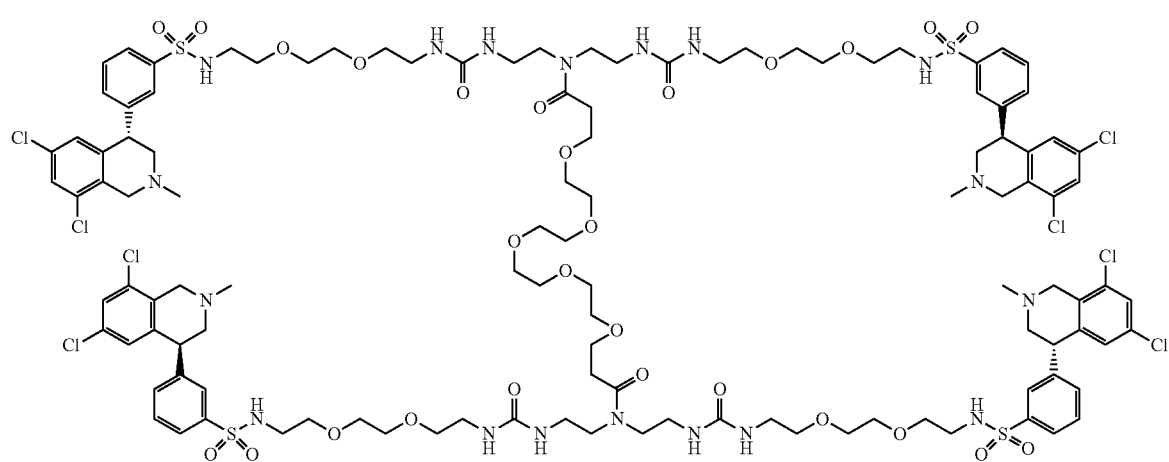
59

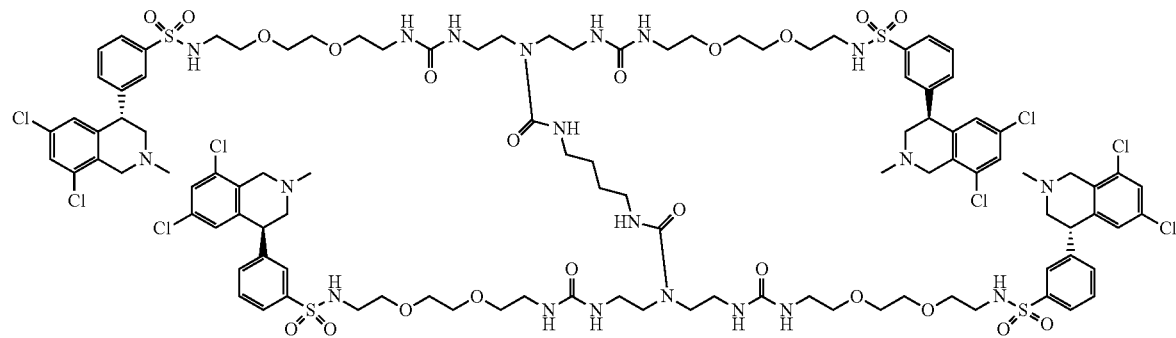
60
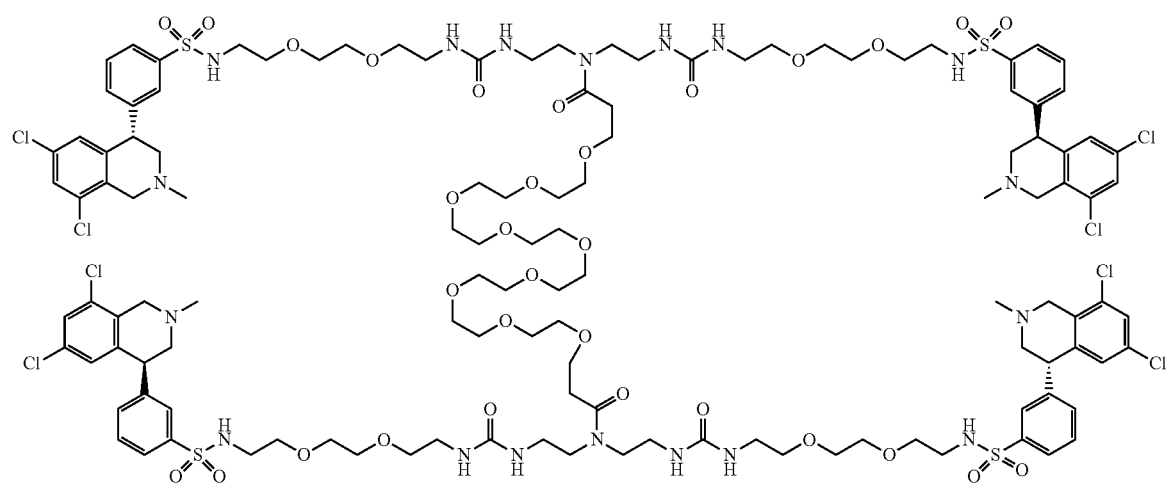
61
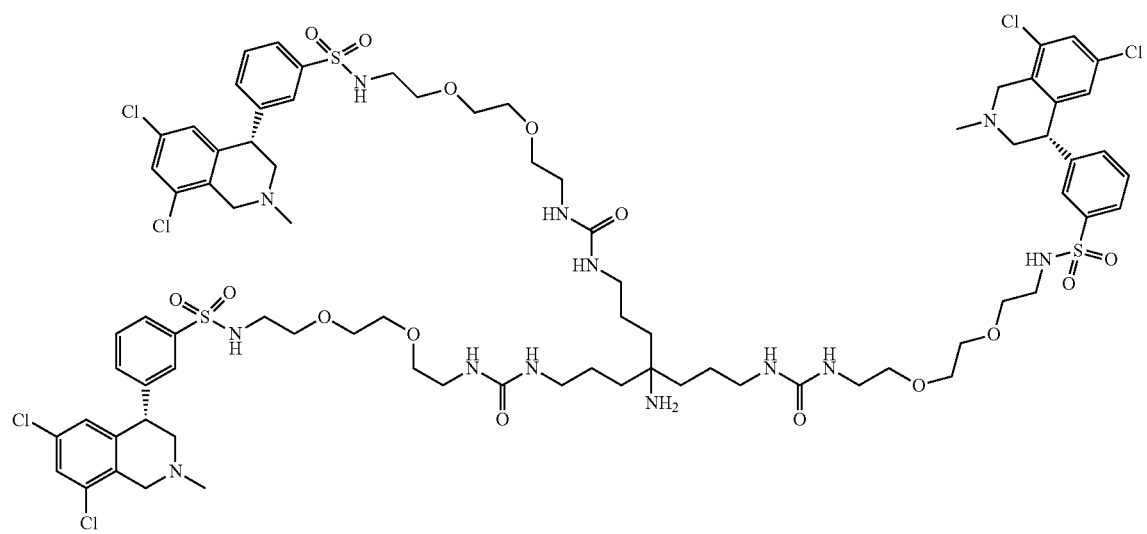
62

-continued
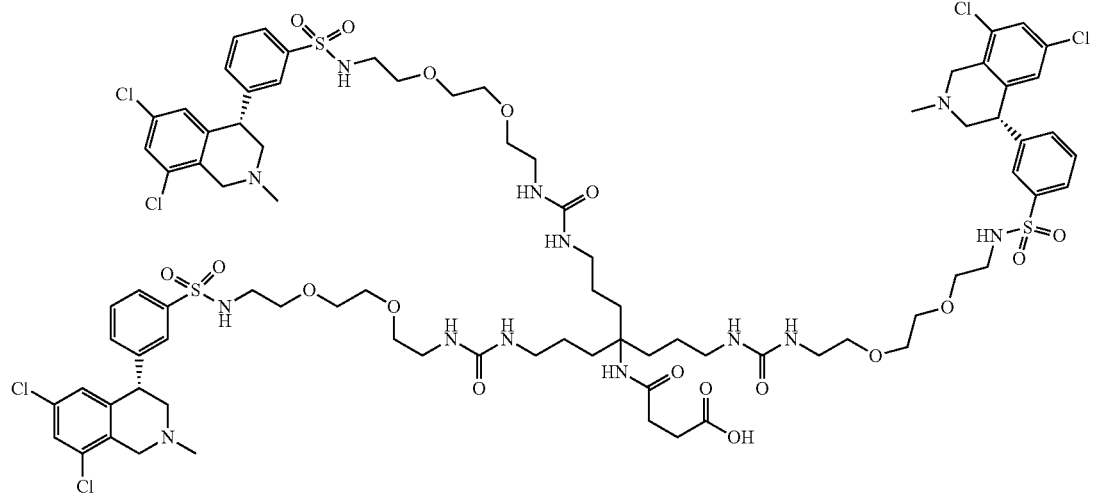
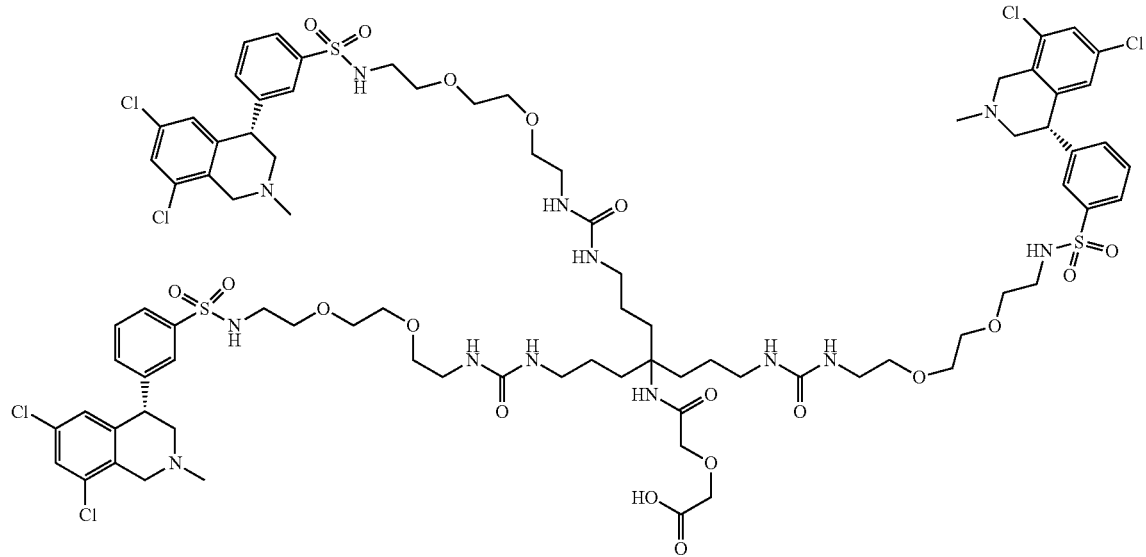

65
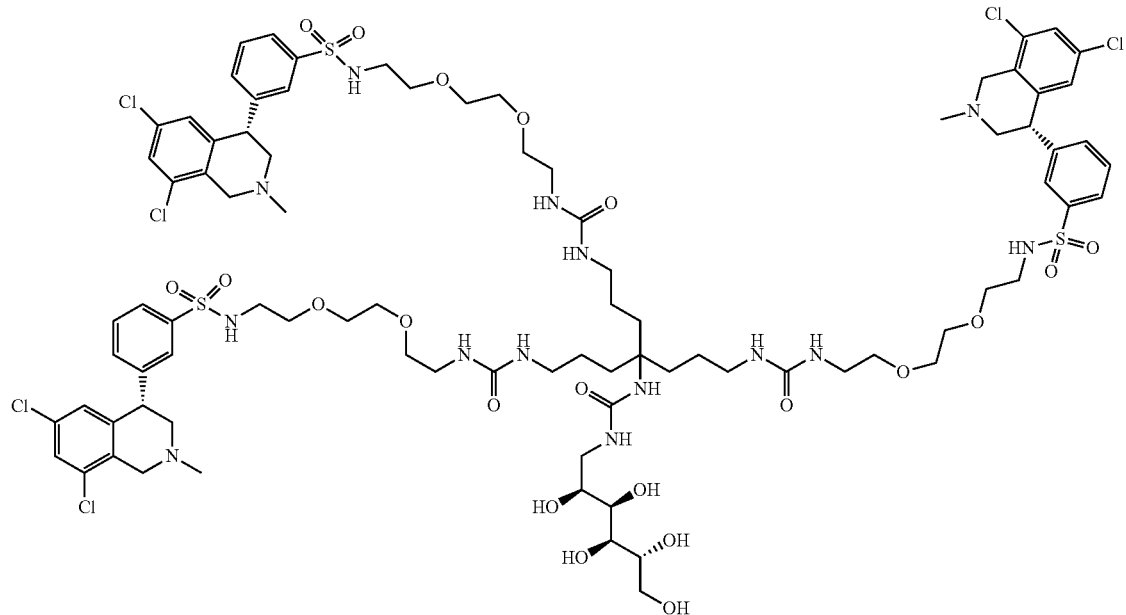
66
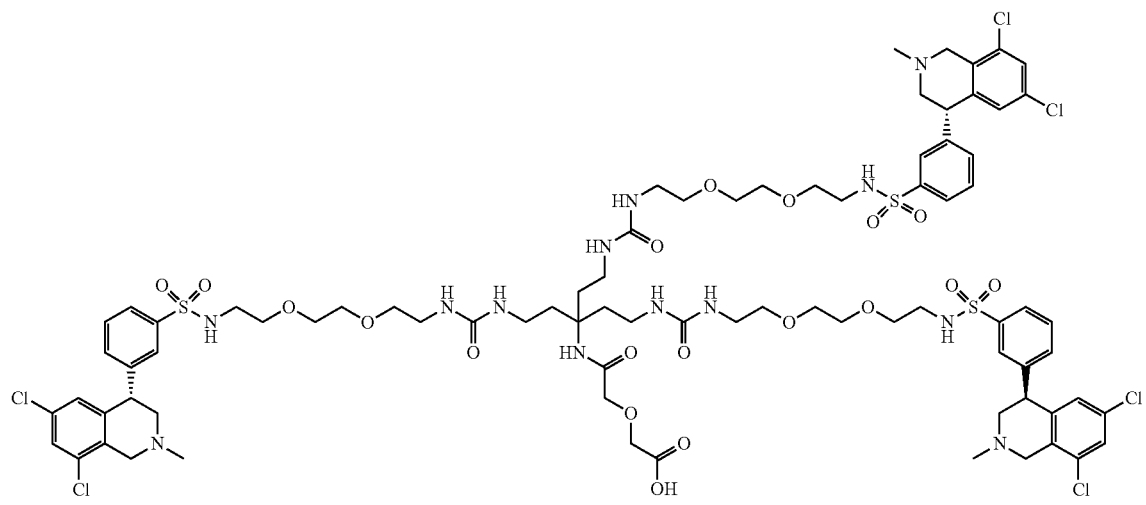

127
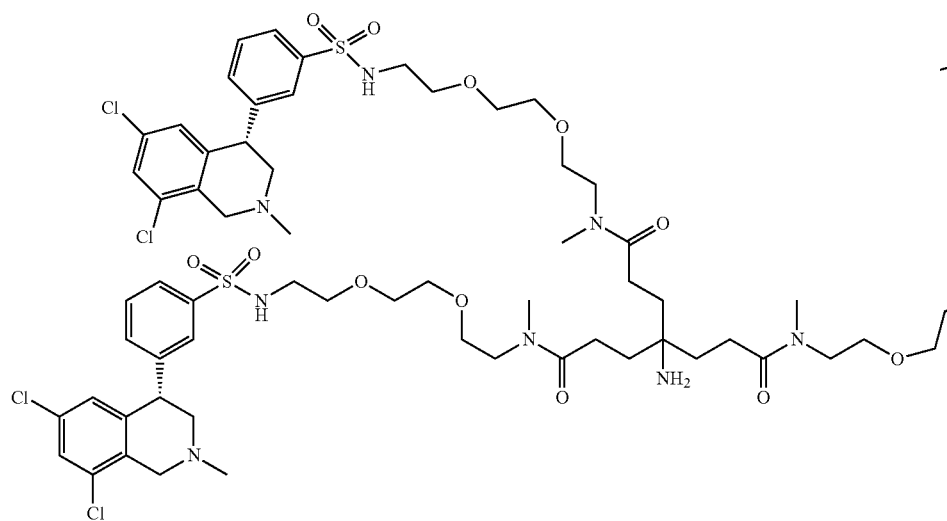
128
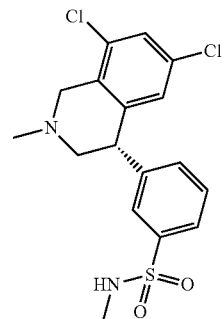
67
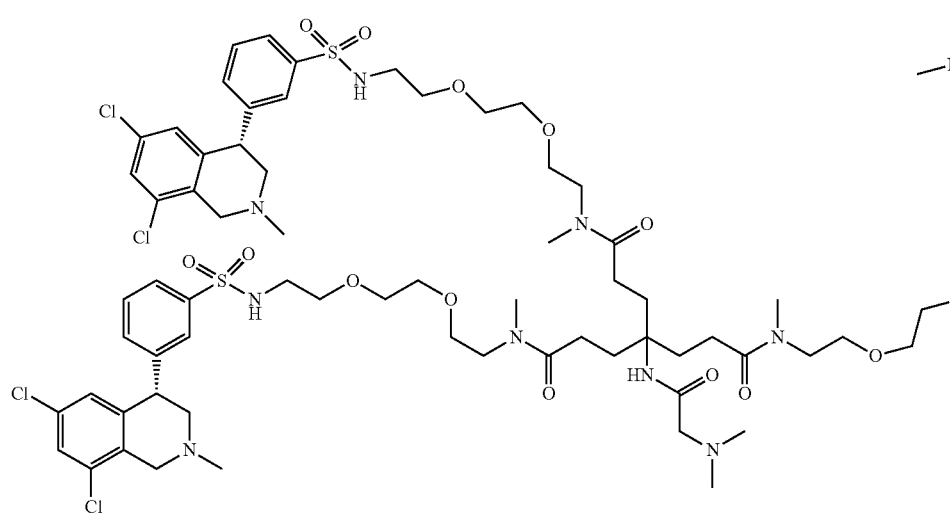
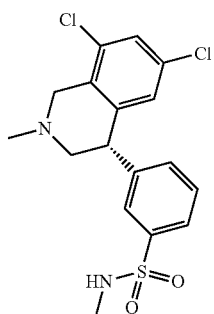
68

129 130
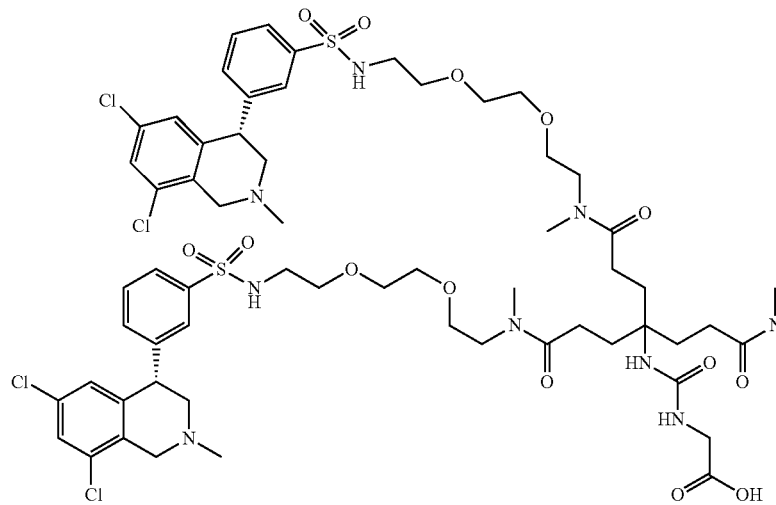
69
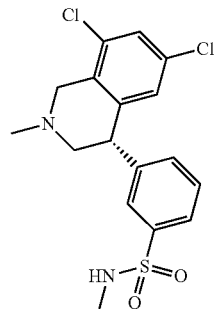
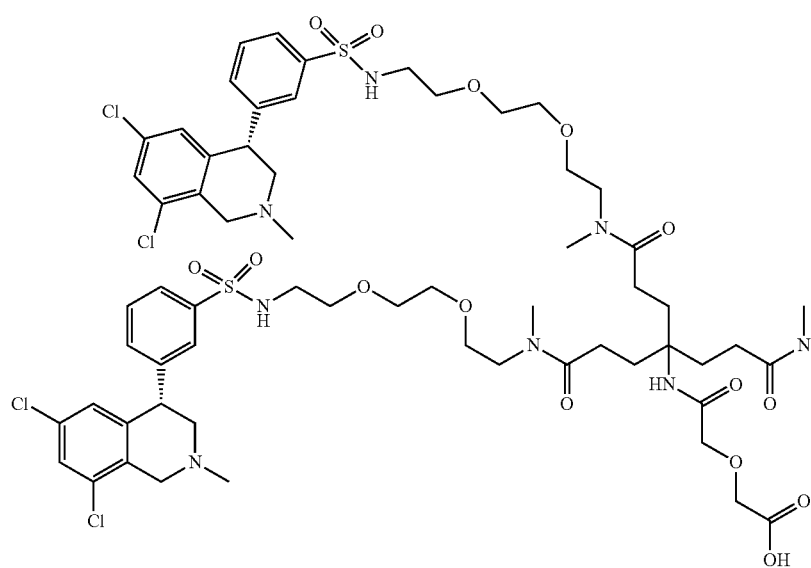
70
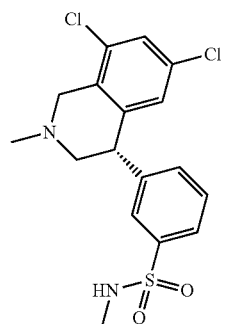

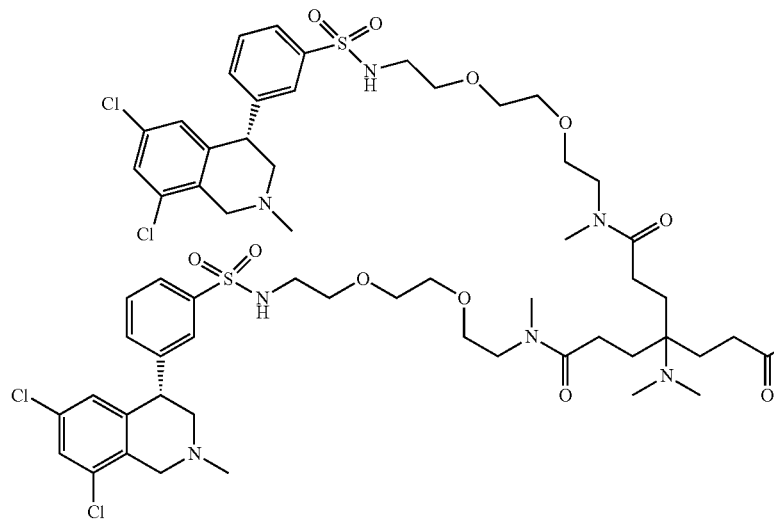
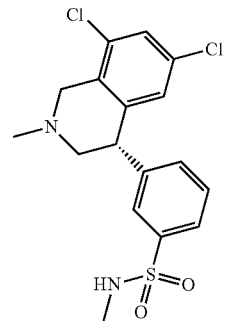

| Example | Method used | Calc. MS | Observed MS |
|---|---|---|---|
| Example 48 | Example 42 | 2454.7 | 1228.6 [M + 2H]$^{2+}$ |
| Example 49 | Example 42 | 3028.8 | 1011 [M + 3H)]$^{3+}$ |
| Example 50 | Example 42 | 2312.6 | 1157 [M + 2H]$^{2+}$ |
| Example 51 | Example 43 | 1901.6 | 1903 [M + H]$^+$ |
| Example 52 | Example 43 | 1859.6 | 1860.4 [M + H]$^+$ |
| Example 53 | Example 43 | 1727.5 | 1728 [M + H]$^+$ |
| Example 54 | Example 43 | 1811.6 | 1812.2 [M + H]$^+$ |
| Example 55 | Example 43 | 1811.6 | 1812.2 [M + H]$^+$ |
| Example 56 | Example 43 | 1901.6 | 1902.2 [M + H]$^+$ |
| Example 57 | Example 47 | 1853.6 | 1854.2 [M + H]$^+$ |
| Example 58 | Example 47 | 1784.5 | 1785.5 [M + H]$^+$ |
| Example 59 | Example 44 | 2616.8 | 1309.5 [M + 2H]$^{2+}$ |
| Example 60 | Example 45 | 2454.7 | 1228.5 [M + 2H]$^{2+}$ |
| Example 61 | Example 44 | 2792.9 | 1397.5 [M + 2H]$^{2+}$ |
| Example 62 | Example 46 | 1783.5 | 1784.1 [M + H]$^+$ |
| Example 63 | Example 6 | 1883.6 | 1884.2 [M + H]$^+$ |
| Example 64 | Example 2 | 1899.5 | 1900.2 [M + H]$^+$ |
| Example 65 | Example 11 | 1990.6 | 1992.1 [M + H]$^+$ |
| Example 66 | Example 6 | 1857.5 | 1858.2 [M + H]$^+$ |
| Example 67 | Example 2 | 1738.5 | 1739.6 [M + H]$^+$ |
| Example 68 | Example 14 | 1823.4 | 1824.4 [M + H]$^+$ |
| Example 69 | Example 7 | 1839.5 | 1840.3 [M + H]$^+$ |
| Example 70 | Example 6 | 1854.5 | 1855.4 [M + H]$^+$ |
| Example 71 | Example 4 | 1766.5 | 1767.2 [M + H]$^+$ |

Example 72

4-acetyl-N1,N7-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)heptanediamide Scheme 72.

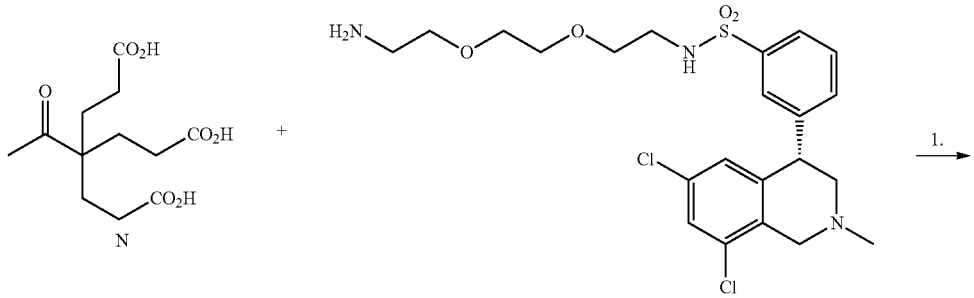

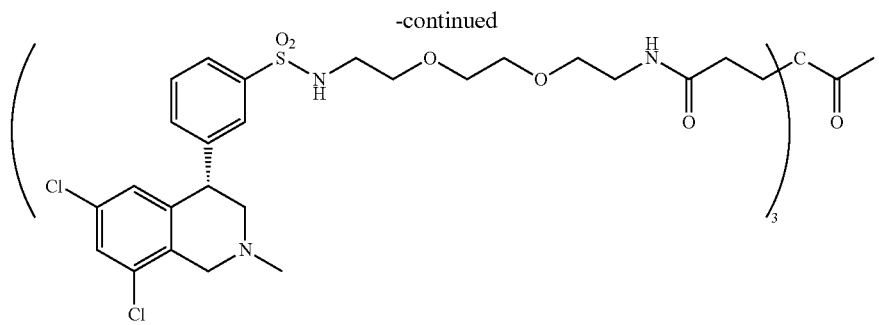

72

1. HATU, DIEA, DMF

Example 72. HATU (42 mg, 0.11 mmol) was added to a solution of 4-acetyl-4-(2-carboxyethyl)heptanedioic acid (intermediate N, 8.2 mg, 0.03 mmol), (S)—N-(2-(2-(2-aminoethoxy)ethoxy)ethyl)-3-(6,8-dichloro-2-methyl-1,2,3,4-tetrahydroisoquinolin-4-yl)benzenesulfonamide (intermediate A, 50 mg, 0.10 mmol) and DIEA (28 mg, 0.022 mmol) in DMF (0.50 mL). After 30 minutes, the solvent was removed under vacuum and the residue was purified by reverse phase HPLC (ACN/water/0.1% TFA) to give a TFA salt of the title compound (13 mg). $^1$H-NMR (400 MHz, CD$_3$OD): δ 7.87 (ddd, $J_{1,2}$=7.8 Hz, $J_{1,3}$=1.8 Hz, $J_{1,4}$=1.2 Hz, 3H), 7.75 (t, J=1.8 Hz, 3H), 7.63 (t, J=7.7 Hz), 7.53 (m, 6H), 6.82 (s, 3H), 4.84-4.74 (m, 6H), 4.49 (d, J=16.2 Hz, 3H), 3.89, (dd, $J_{1,2}$=6.1 Hz, $J_{1,3}$=12.3 Hz, 3H), 3.61 (t, J=12.1 Hz, 3H), 3.55-3.48 (m, 18H), 3.45 (t, J=5.5 Hz, 6H), 3.30 (m, 6H), 3.15 (s, 9H), 3.03 (t, J=5.5 Hz, 6H), 2.14 (s, 3H), 2.05-2.01 (m, 6H), 1.85-1.81 (m, 6H). MS (m/z): 1724.3 (M+H).

Example 73

N1,N7-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)-4-(1-hydroxyethyl)heptanediamide Scheme 73.

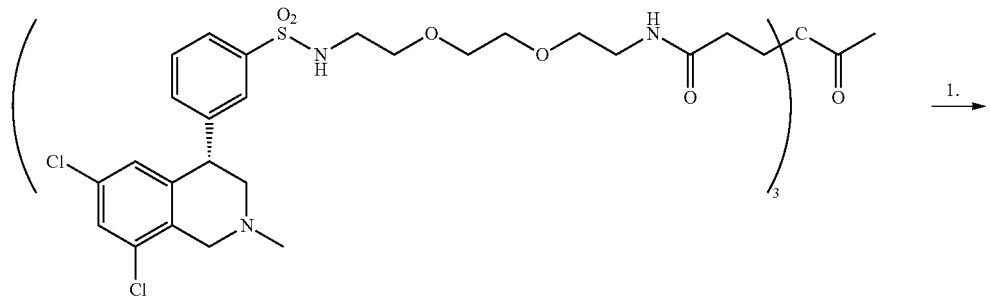

72

1.

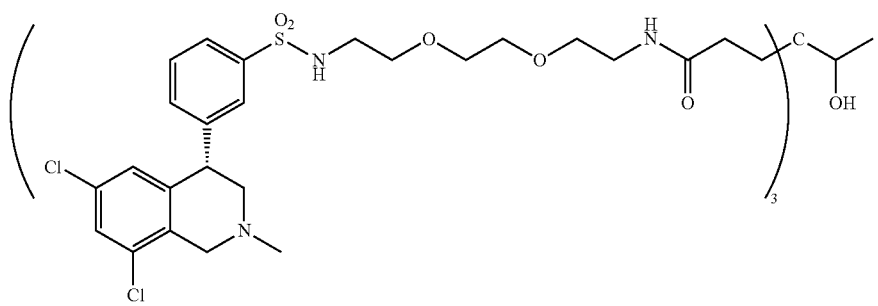

73

1. NaBH$_4$, MeOH

Example 73: Sodium borohydride (1 mg, 0.03 mmol) was added to a solution of a TFA salt of 4-acetyl-N1,N7-bis(2-(2-(2-(3-((S)-6,8-dichloro-2-methyl-1,2,3,4-tetrahydroisoquinolin-4-yl)phenylsulfonamido)ethoxy)ethoxy)ethyl)-4-(3-(2-(2-(2-(3-((S)-6,8-dichloro-2-methyl-1,2,3,4-tetrahydroisoquinolin-4-yl)phenylsulfonamido)ethoxy)ethoxy)ethylamino)-3-oxopropyl)heptanediamide (example 72, 15 mg, 0.007 mmol) in MeOH 200 µL and DCM (50 µL). After 2 hours, the reaction was concentrated at reduce pressure and purified by reverse phase HPLC (ACN/water/ 0.1% TFA) to give a TFA salt of the title compound (6.2 mg). $^1$H-NMR (400 MHz, CD$_3$OD) δ 7.87 (ddd, $J_{1,2}$=7.8 Hz, $J_{1,3}$=1.8 Hz, $J_{1,4}$=1.2 Hz, 3H), 7.75 (t, J=1.8 Hz, 3H), 7.63 (t, J=7.8 Hz, 3H), 7.53 m, 6H), 6.82 (s, 3H), 4.79-4.74 (m, 6H), 4.49 (d, J=16.2 Hz, 3H), 3.88 (dd, $J_{1,2}$=11.6 Hz, $J_{1,3}$=6.1 Hz, 3H), 3.64-3.58 (m, 4H), 3.55-3.47 (m, 18H), 3.45 (t, J=5.4 Hz), 3.31 (m, 6H), 3.14 (s, 9H), 3.03 (t, J=5.5 Hz, 6H), 2.27-2.17 (m, 6H), 1.63-1.53 (m, 6H), 1.14 (d, J=5.7 Hz, 3H). MS (m/z): 1726.1 (M+H).

Pharmacological Data

Example 74

Cell-Based Assay of NHE-3 Activity

Rat or human NHE-3-mediated Na$^+$-dependent H$^+$ antiport was measured using a modification of the pH sensitive dye method originally reported by Paradiso (*Proc. Natl. Acad. Sci. USA*. (1984) 81(23): 7436-7440). Opossum kidney (OK) cells were obtained from the ATCC and propagated per their instructions. The rat NHE-3 gene (GenBank M85300) or the human NHE-3 gene (GenBank NM_004174.1) was introduced into OK cells via electroporation, and cells were seeded into 96 well plates and grown overnight. Medium was aspirated from the wells, cells were washed twice with NaCl-HEPES buffer (100 mM NaCl, 50 mM HEPES, 10 mM glucose, 5 mM KCl, 2 mM CaCl$_2$, 1 mM MgCl$_2$, pH 7.4), then incubated for 30 min at room temperature with NH$_4$Cl-HEPES buffer (20 mM NH$_4$Cl, 80 mM NaCl, 50 mM HEPES, 5 mM KCl, 2 mM CaCl$_2$, 1 mM MgCl$_2$, pH 7.4) containing 5 µM bis(acetoxymethyl) 3,3'-(3',6'-bis(acetoxymethoxy)-5-((acetoxymethoxy)carbonyl)-3-oxo-3H-spiro[isobenzofuran-1,9'-xanthene]-2',7'-diyl) dipropanoate (BCECF-AM). Cells were washed twice with Ammonium free, Na$^+$-free HEPES (100 mM choline, 50 mM HEPES, 10 mM glucose, 5 mM KCl, 2 mM CaCl$_2$, 1 mM MgCl$_2$, pH 7.4) and incubated in the same buffer for 10 minutes at room temperature to lower intracellular pH. NHE-3-mediated recovery of neutral intracellular pH was initiated by addition of Na-HEPES buffer containing 0.4 µM ethyl isopropyl amiloride (EIPA, a selective antagonist of NHE-1 activity that does not inhibit NHE-3) and 0-30 µM test compound, and monitoring the pH sensitive changes in BCECF fluorescence ($\lambda_{ex}$ 505 nm, $\lambda_{em}$ 538 nm) normalized to the pH insensitive BCECF fluorescence ($\lambda_{ex}$ 439 nm, $\lambda_{em}$ 4538 nm). Initial rates were plotted as the average 2 or more replicates, and pIC$_{50}$ values were estimated using GraphPad Prism.

TABLE 4

Data for examples in human NHE3 inhibition assay

| Example # | Human NHE3 pIC$_{50}$ |
| --- | --- |
| 1 | B |
| 2 | C |
| 3 | C |
| 4 | C |
| 5 | B |
| 6 | C |
| 7 | C |
| 8 | C |
| 9 | C |
| 10 | C |
| 11 | B |
| 12 | C |
| 13 | B |
| 14 | C |
| 15 | B |
| 16 | A |
| 17 | C |
| 18 | B |
| 19 | A |
| 20 | C |
| 21 | B |
| 22 | B |
| 23 | C |
| 24 | A |
| 25 | B |
| 26 | C |
| 27 | C |
| 28 | C |
| 29 | C |
| 30 | B |
| 31 | C |
| 32 | B |
| 33 | C |
| 34 | C |
| 35 | B |
| 36 | C |
| 37 | C |
| 38 | C |
| 39 | C |
| 40 | C |
| 41 | C |
| 42 | C |
| 43 | C |
| 44 | A |
| 45 | B |
| 46 | C |
| 47 | C |
| 48 | C |
| 49 | B |
| 50 | B |
| 51 | C |
| 52 | C |
| 53 | B |
| 54 | C |
| 55 | C |
| 56 | C |
| 57 | C |
| 58 | C |
| 59 | C |
| 60 | C |
| 61 | C |
| 62 | C |
| 63 | C |
| 64 | C |
| 65 | C |
| 66 | C |
| 67 | C |
| 68 | C |
| 69 | C |
| 70 | C |
| 71 | C |
| 72 | B |
| 73 | C |

A NHE3 pIC$_{50}$ < 5
B NHE3 pIC$_{50}$ 5-7
C NHE3 pIC$_{50}$ > 7

Example 75

Inhibition of Intestinal Sodium Absorption

Urinary sodium concentration and fecal form were measured to assess the ability of selected example compounds to inhibit the absorption of sodium from the intestinal lumen. Eight-week old Sprague-Dawley rats were purchased from Charles River Laboratories (Hollister, Calif.), were housed 2 per cage, and acclimated for at least 3 days before study initiation. Animals were fed Harlan Teklad Global 2018 rodent chow (Indianapolis, Ind.) and water ad libitum throughout the study and maintained in a standard light/dark cycle of 6 AM to 6 PM. On the day of the study, between 4 PM and 5 PM, a group of rats (n=6) were dosed via oral gavage with test compound at the dosage indicated or vehicle (water) at a volume of 10 mL/kg. After dose administration animals were placed in individual metabolic cages where they were also fed the same chow in meal form and watered ad libitum. At 16 h post-dose, the urine samples were collected and fecal form was assessed by two independent observations. Fecal forms were scored according to a common scale associated with increasing fecal water to the wettest observation in the cage's collection funnel (1, normal pellet; 2, pellet adhering to sides of collection funnel due to moisture; 3, loss of normal pellet shape; 4, complete loss of shape with a blotting pattern; 5, liquid fecal streams evident). A rat's fecal form score (FFS) was determined by averaging both observational scores for all rats within a group (n=6). In every study the vehicle group average was 1. These averages are reported in Table 5. For urine samples, the volumes were determined gravimetrically and centrifuged at 3,600×g. The supernatants were diluted 100-fold in deionized Milli-Q water then filtered through a 0.2 μm GHP Pall AcroPrep filter plate (Pall Life Sciences, Ann Arbor, Mich.) prior to analysis by ion chromatography. Ten microliters of each filtered extract was injected onto a Dionex ICS-3000 ion chromatograph system (Dionex, Sunnyvale, Calif.). Cations were separated by an isocratic method using 25 mM methanesulfonic acid as the eluent on an IonPac CS12A 2 mm i.d.×250 mm, 8 μm particle size cation exchange column (Dionex). Sodium was quantified using standards prepared from a cation standard mix containing $Li^+$, $Na^+$, $NH_4^+$, $K^+$, $Mg^{2+}$, and $Ca^{2+}$ (Dionex). The mean mass of sodium urinated for every group in the 16 h period was determined with the vehicle group usually urinating approximately 21 mg sodium. The urine Na (uNa) for rats in the test groups were expressed as a percentage of the vehicle mean and the means were compared to that of the vehicle group by utilizing a one-way analysis of variance coupled with a Dunnett's post hoc test. Means that were significantly lower than the vehicle group as determined by statistical analysis were denoted: *, $P<0.05$; , $P<0.01$; *, $P<0.001$.

TABLE 5

Rat urinary sodium and fecal form 16 h post-dose of test compound at 3 mg/kg

| Example # | uNa (% of vehicle) | FFS |
|---|---|---|
| 2 | A*** | 3 |
| 3 | A*** | 3 |
| 4 | A*** | 2 |
| 5 | B*** | 2 |
| 6 | A*** | 3 |
| 7 | A*** | 3 |
| 8 | A*** | 2 |
| 9 | A** | 1 |
| 10 | B | 2 |
| 11 | B | 2 |
| 12 | B* | 3 |
| 14 | A*** | 2 |
| 17 | A*** | 2 |
| 21 | B | 1 |
| 25 | A*** | 2 |
| 26 | A*** | 2 |
| 27 | B** | 2 |
| 28 | B | 2 |
| 29 | B | 2 |
| 30 | C | 1 |
| 31 | A | 2 |
| 32 | B | 2 |
| 33 | A** | 2 |
| 34 | A*** | 3 |
| 36 | A*** | 3 |
| 37 | A*** | 3 |
| 38 | A** | 3 |
| 39 | A** | 2 |
| 40 | A*** | 3 |
| 41 | A** | 3 |
| 43 | B*** | 2 |
| 47 | B* | 1 |
| 53 | B* | 2 |
| 54 | C | 2 |
| 55 | B** | 2 |
| 56 | B | 2 |
| 57 | B | 1 |
| 58 | B | 2 |
| 62 | B*** | 2 |
| 63 | B | 2 |
| 64 | B | 2 |
| 65 | B* | 2 |
| 66 | A* | 2 |
| 67 | C | 1 |
| 68 | B | 1 |
| 70 | B** | 2 |
| 72 | B** | 2 |
| 73 | B | 2 |

In Table 5, A indicates that urine sodium was <35% of the percentage of the vehicle mean; B indicates that urine sodium was 35-75% of the percentage of the vehicle mean; C indicates that urine sodium was >75% of the percentage of the vehicle mean.

Example 76

Plasma PK

Sprague-Dawley rats (n=3) were dosed with test compounds by oral gavage. Blood was collected at 0.5, 1, 2 and 4 h via retro-orbital bleeds and processed to plasma using $K_2EDTA$ as an anticoagulant. Plasma samples were treated with acetonitrile containing an internal standard and precipitated proteins were removed by centrifugation. Supernatants were analyzed by LC-MS/MS and compound concentrations were determined by interpolation from a calibration curve prepared in plasma. Accurate recovery of quality control samples were confirmed to accept each analytical run. Table 6 illustrates data from the pharmacokinetic profiling of selected example compounds. From studies in which one or more rats had samples with test compound levels below the quantitative limit, $C_{max}$ and AUC (reported as the mean of n=3) may be reported as "<X" to indicate an upper bound.

TABLE 6

Plasma pharmacokinetics for example compounds

| Example | Nominal Dose (mg/kg) | LLOQ (ng/mL) | Cmax (ng/mL) | AUC (ng × hr/mL) |
|---|---|---|---|---|
| 2 | 30 | 2 | <4.0 | <12.0 |
| 4 | 30 | 2 | <5.0 | <13.0 |
| 7 | 30 | 2 | <2.0 | <8.0 |
| 52 | 30 | 5 | <5.0 | <19.0 |

Example 77

Fecal Recovery

Three male Sprague Dawley rats were administered 1 mg/kg test compound by oral gavage. Feces were collected from study animals from 0-48 or 0-72 hours after dosing, dried by lyophilization, and homogenized. Replicate aliquots of 40-60 mg each were subjected to extraction/protein precipitation with 7:1 acetonitrile:water and centrifuged. Supernatants were diluted 1:10 in 50:50 acetonitrile:water prior to analysis by LC-MS/MS. Compound concentrations, determined by interpolation from a standard calibration curve prepared in blank feces matrix, were converted to the percentage of dosed material recovered by taking into account the total collected fecal matter. The percent recovery for each rat was reported as the mean of the calculations from replicate samples. The overall percent recovery (Fecal Recovery [%]) was reported as the mean percent recovery from three rats. Accurate quality control sample recoveries were confirmed in each run, and extraction efficiency was periodically verified. Table 7 illustrates fecal recovery data for selected example compounds.

TABLE 7

Fecal recovery example compounds

| Example # | Nominal Dose (mg/kg) | Collection Time (h) | Fecal Recovery (%) |
|---|---|---|---|
| 2 | 1 | 48 | 87 |
| 3 | 1 | 72 | 110.2 |
| 6 | 1 | 48 | 51.5 |
| 7 | 1 | 48 | 83.2 |
| 11 | 1 | 48 | 64.1 |
| 14 | 1 | 72 | 75.3 |
| 17 | 1 | 72 | 96.9 |
| 36 | 1 | 48 | 68 |
| 37 | 1 | 48 | 90.5 |
| 40 | 1 | 48 | 99.1 |
| 43 | 1 | 48 | 53.8 |
| 46 | 1 | 48 | 75.8 |
| 55 | 1 | 48 | 64.6 |
| 62 | 1 | 48 | 81.5 |
| 65 | 1 | 48 | 112.2 |

Example 78

Cell-Based Assay of NHE-3 Activity (Persistent Inhibition)

The ability of compounds to inhibit Rat NHE-3-mediated $Na^+$-dependent $H^+$ antiport after application and washout was measured using a modification of the pH sensitive dye method described above in Example 74. Opossum kidney (OK) cells were obtained from the ATCC and propagated per their instructions. The rat NHE-3 gene was introduced into OK cells via electroporation, and cells were seeded into 96 well plates and grown overnight. Medium was aspirated from the wells, cells were washed twice with NaCl-HEPES buffer (100 mM NaCl, 50 mM HEPES, 10 mM glucose, 5 mM KCl, 2 mM $CaCl_2$, 1 mM $MgCl_2$, pH 7.4), then overlayed with NaCl-HEPES buffer containing 0-30 µM test compound. After a 60 min incubation, the test drug containing buffer was aspirated from the cells, cells were washed twice with NaCl-HEPES buffer without drug, then incubated for 30 min at room temperature with $NH_4Cl$-HEPES buffer (20 mM $NH_4Cl$, 80 mM NaCl, 50 mM HEPES, 5 mM KCl, 2 mM $CaCl_2$, 1 mM $MgCl_2$, pH 7.4) containing 5 µM BCECF-AM. Cells were washed twice with ammonium free, $Na^+$-free HEPES (100 mM choline, 50 mM HEPES, 10 mM glucose, 5 mM KCl, 2 mM $CaCl_2$, 1 mM $MgCl_2$, pH 7.4) and incubated in the same buffer for 10 minutes at room temperature to lower intracellular pH. NHE-3-mediated recovery of neutral intracellular pH was initiated (40 min after compound washout) by addition of Na-HEPES buffer containing 0.4 µM ethyl isopropyl amiloride (EIPA, a selective antagonist of NHE-1 activity that does not inhibit NHE-3), and monitoring the pH sensitive changes in BCECF fluorescence 505 nm, 538 nm) normalized to the pH insensitive BCECF fluorescence ($\lambda_{ex}$ 439 nm, $\lambda_{em}$ 538 nm). Initial rates were plotted as the average 2 or more replicates, and $pIC_{50}$ values were estimated using GraphPad Prism.

TABLE 8

Data for examples in rat NHE-3 prompt and persistent inhibition assays

| Example # | Rat NHE3 $pIC_{50}$ (prompt) | Rat NHE3 $pIC_{50}$ (persistent) |
|---|---|---|
| 1 | B | C |
| 2 | C | C |
| 3 | C | C |
| 4 | C | C |
| 5 | B | C |
| 6 | C | C |
| 7 | C | C |
| 8 | B | C |
| 9 | C | C |
| 10 | C | C |
| 11 | A | C |
| 12 | C | C |
| 13 | B | C |
| 14 | C | C |
| 15 | A | B |
| 16 | B | B |
| 17 | C | C |
| 18 | B | A |
| 19 | A | C |
| 20 | B | C |
| 21 | B | C |
| 22 | A | B |
| 23 | B | B |
| 24 | A | B |
| 25 | B | C |
| 26 | B | C |
| 27 | C | C |
| 28 | B | C |
| 29 | C | C |
| 30 | B | C |
| 31 | C | C |
| 32 | C | C |
| 33 | C | C |
| 34 | C | C |
| 36 | C | C |
| 37 | C | C |
| 38 | B | C |
| 39 | C | C |
| 40 | C | C |
| 41 | B | C |
| 42 | C | C |
| 43 | B | C |
| 44 | A | B |
| 45 | B | A |
| 46 | C | C |
| 47 | B | C |

TABLE 8-continued

Data for examples in rat NHE-3 prompt and persistent inhibition assays

| Example # | Rat NHE3 pIC$_{50}$ (prompt) | Rat NHE3 pIC$_{50}$ (persistent) |
|---|---|---|
| 48 | B | C |
| 49 | B | B |
| 51 | C | C |
| 52 | B | C |
| 53 | B | C |
| 54 | B | C |
| 55 | B | C |
| 56 | C | C |
| 57 | B | C |
| 58 | C | C |
| 59 | B | C |
| 61 | B | B |
| 62 | B | C |
| 63 | C | C |
| 64 | C | C |
| 65 | B | C |
| 66 | C | C |
| 67 | C | C |
| 68 | C | C |
| 69 | C | C |
| 70 | C | C |
| 72 | B | C |
| 73 | C | C |

A NHE3 pIC$_{50}$ < 5
B NHE3 pIC$_{50}$ 5-7
C NHE3 pIC$_{50}$ > 7

Example 79

Pharmacokinetic Evaluation in Bile

Bile duct cannulated (BDC) Sprague-Dawley rats were dosed with test compounds by oral gavage and a single aliquot of bile was collected via cannula over the 24 h following dosing. Bile samples were treated with acetonitrile and precipitated proteins were removed by centrifugation. Some compounds required liquid-liquid extraction using MTBE. After centrifugation, samples were diluted as appropriate in mobile phase and analyzed by LC-MS/MS. The concentrations of compounds in bile were determined by interpolation from a standard calibration curve prepared in rat bile from untreated BDC rats. Accurate recovery of quality control samples was confirmed to accept each analytical run. Table 9 illustrates data from the bile exposure of selected example compounds. Concentration in bile is reported in nM and represents the mean result from n=3 rats.

TABLE 9

Bile concentration for example compounds

| Example | Nominal Dose (mg/kg) | Concentration in Bile (nM) |
|---|---|---|
| 2 | 30 | 4 |
| 3 | 30 | 10 |
| 4 | 30 | 45 |
| 6 | 30 | 21 |
| 7 | 30 | 19 |
| 14 | 30 | 28 |
| 36 | 30 | 17 |
| 40 | 30 | 23 |
| 43 | 30 | 6 |
| 46 | 30 | 3 |
| 62 | 30 | 7 |

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound selected from the group consisting of:

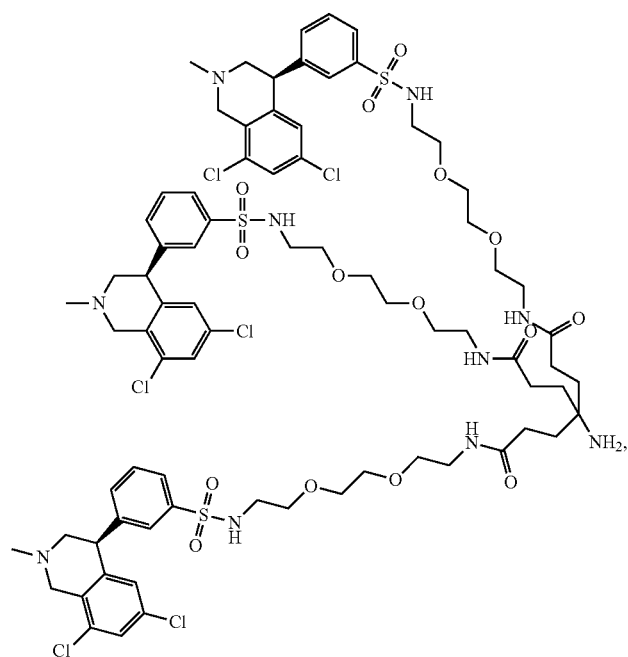

-continued
3
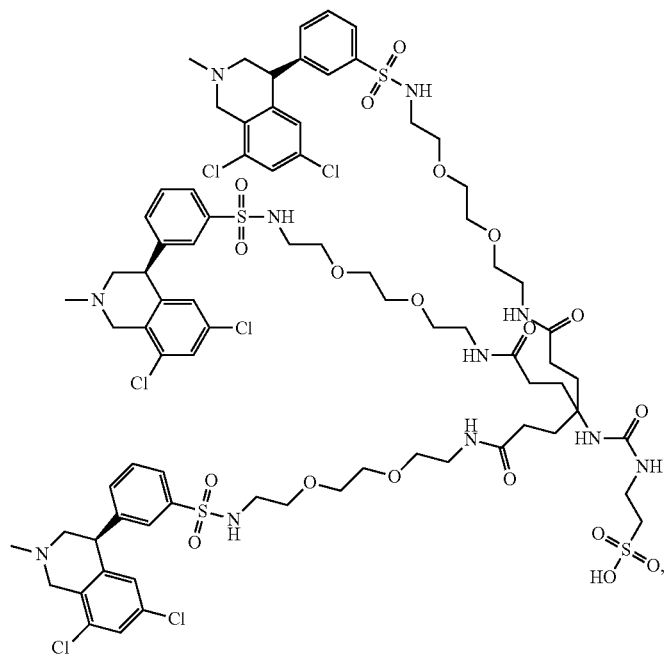
4
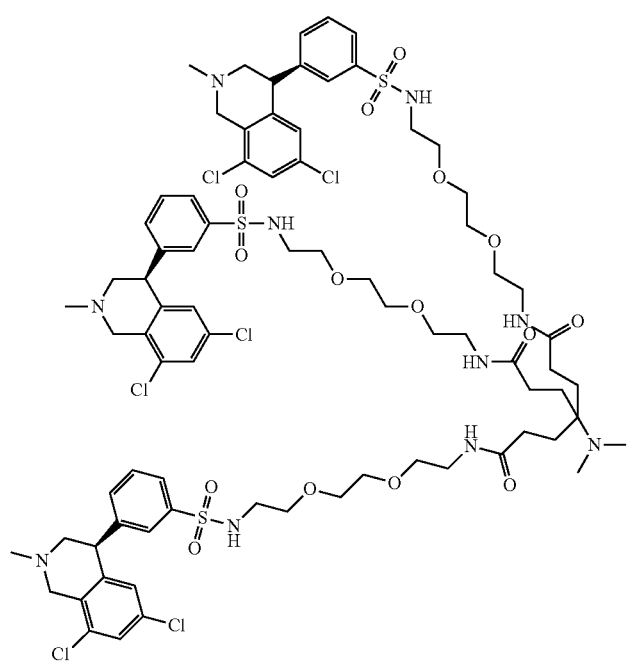

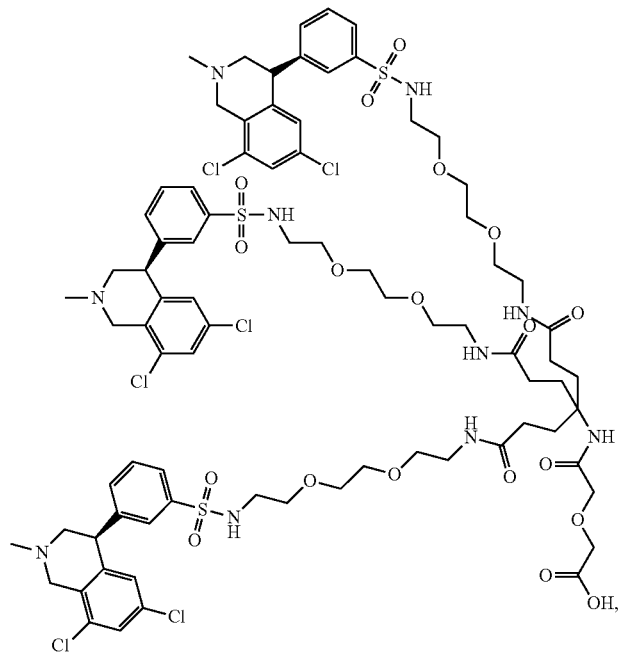
6
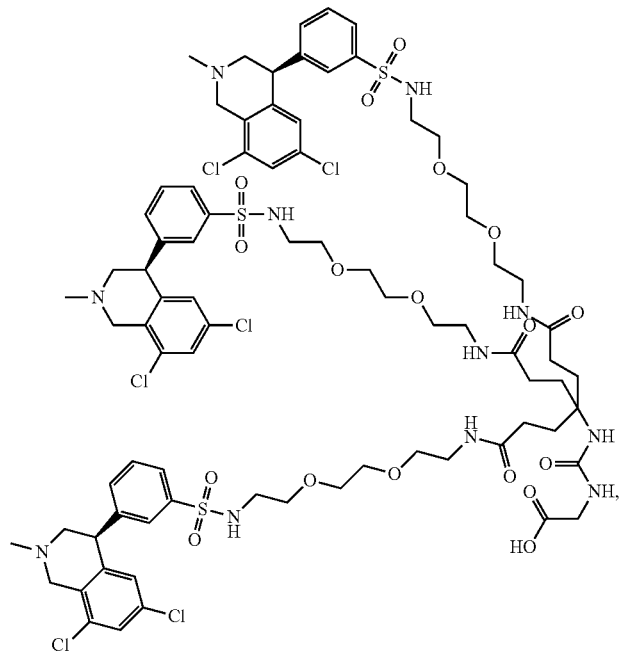
7

-continued
8
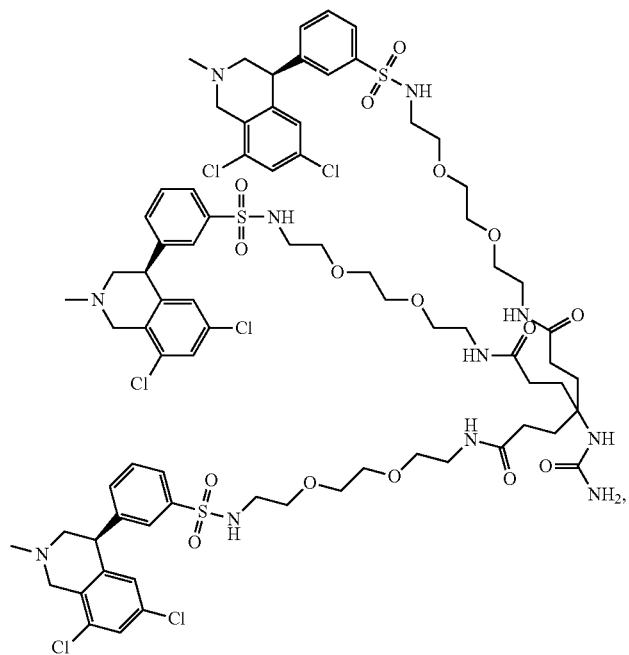
9
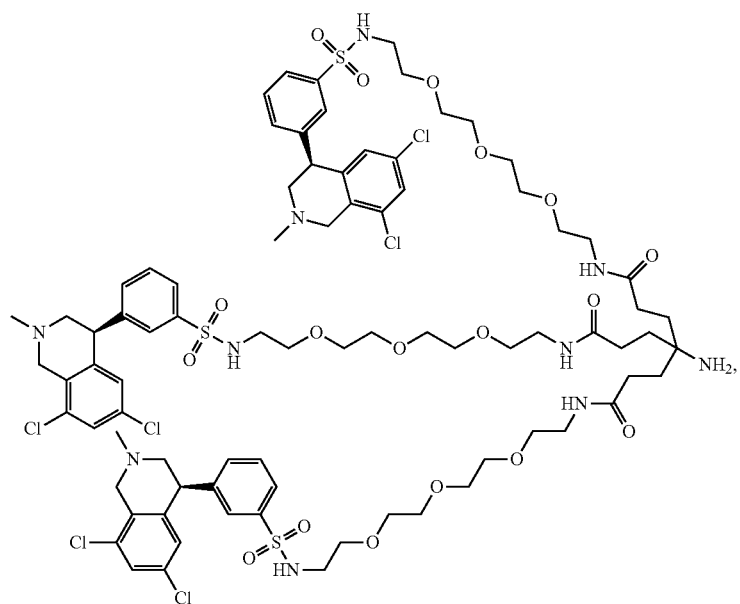

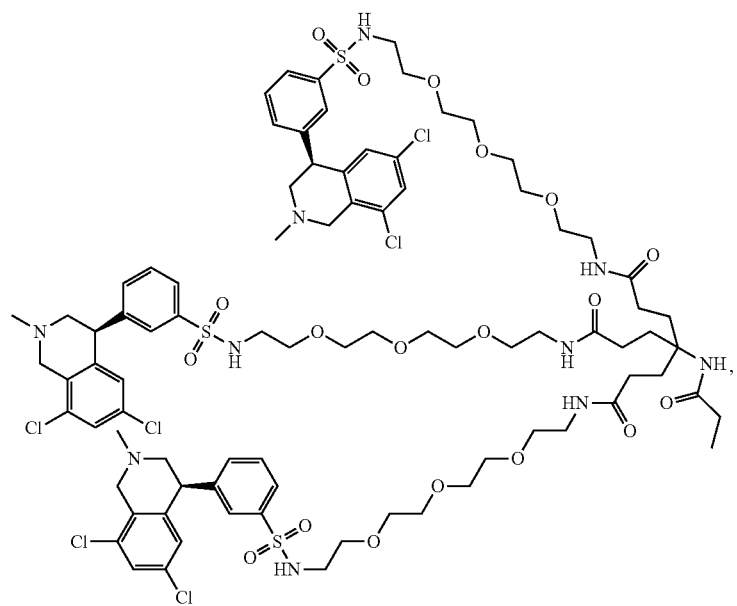
10
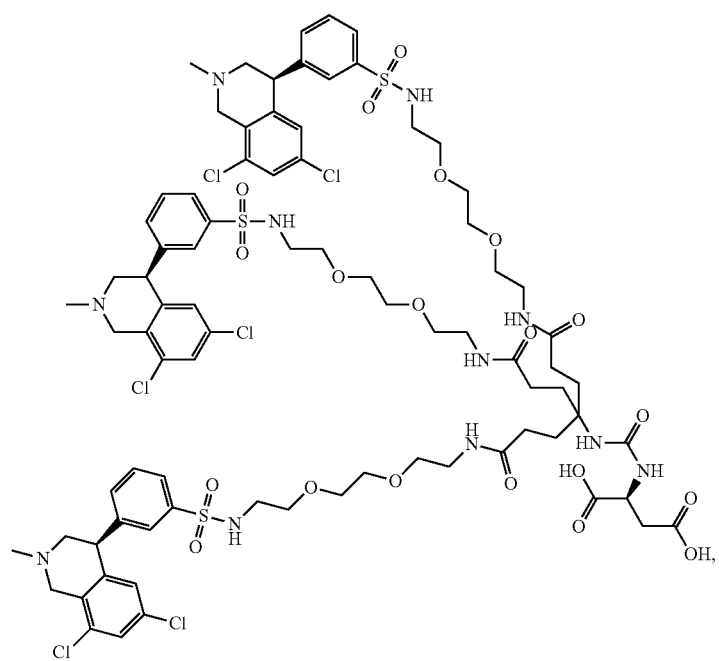
12

14
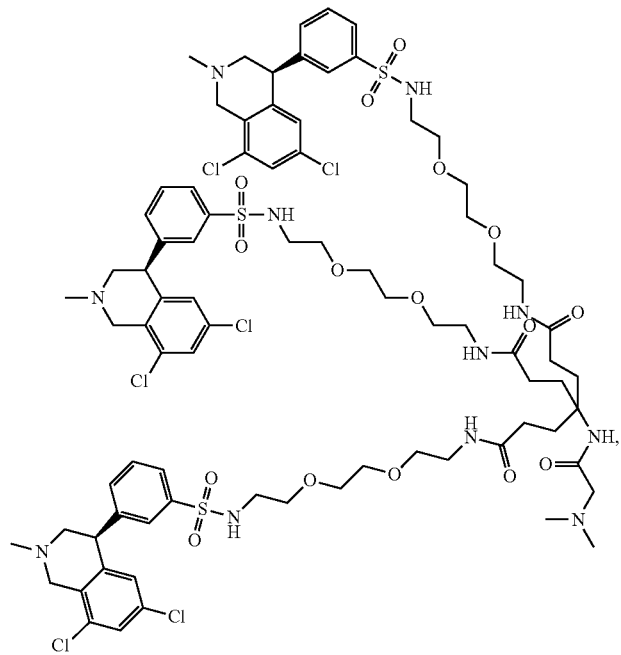
17
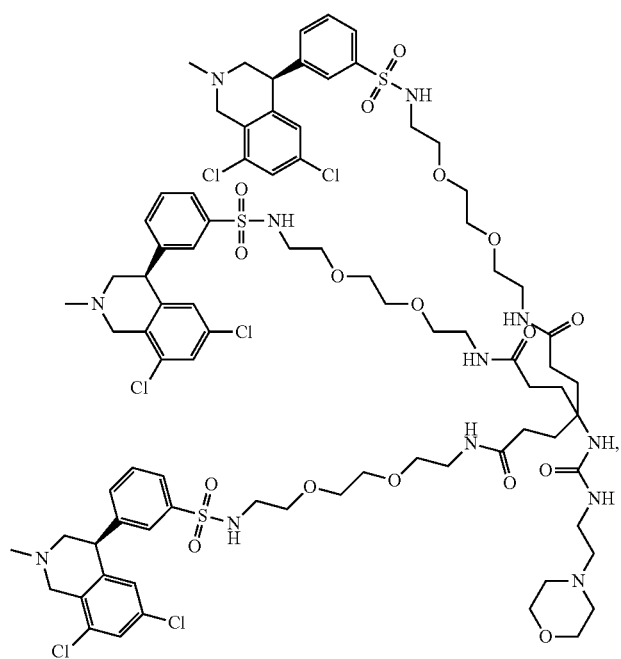

20
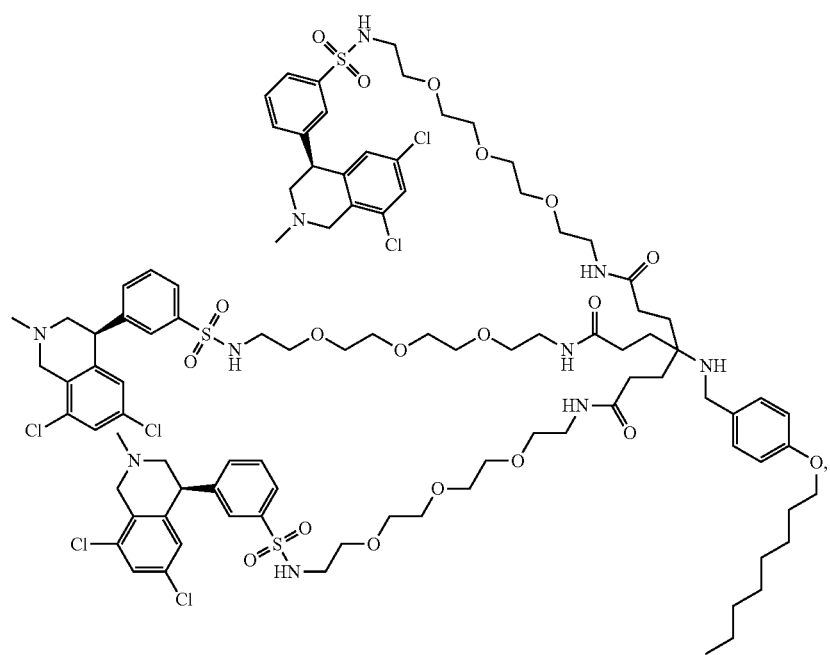
43
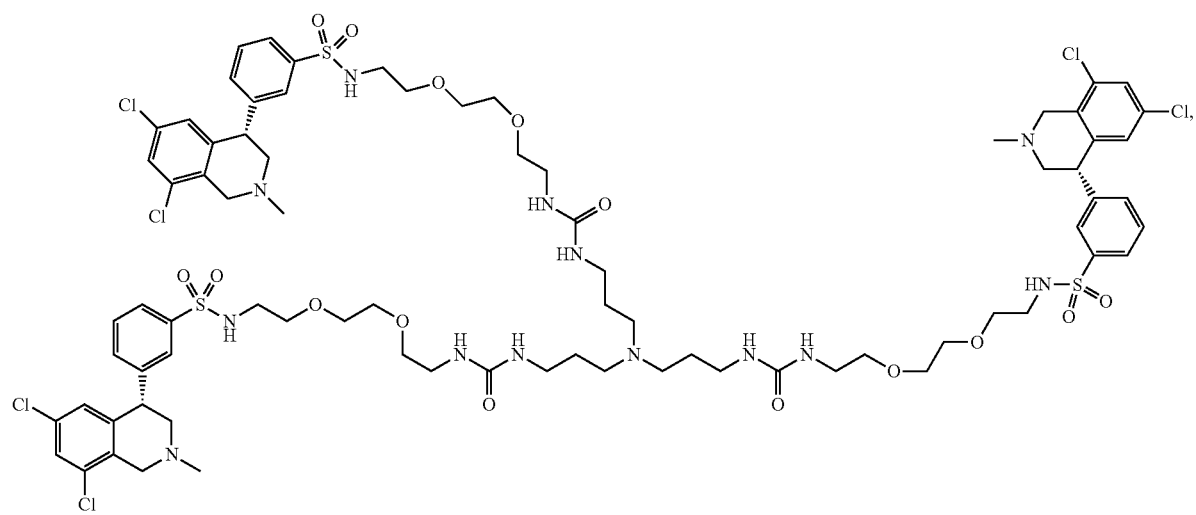

46
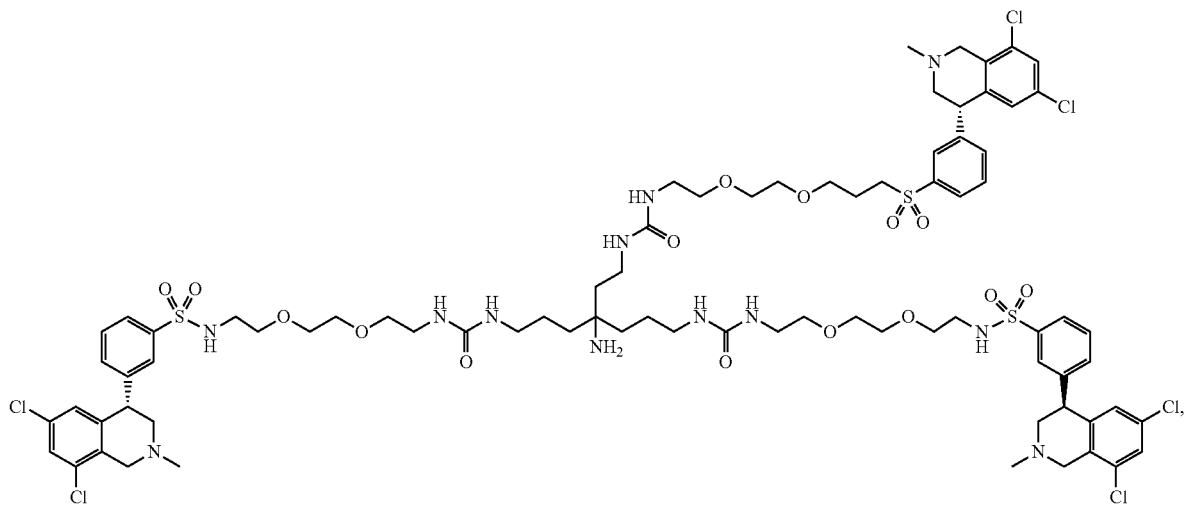
47
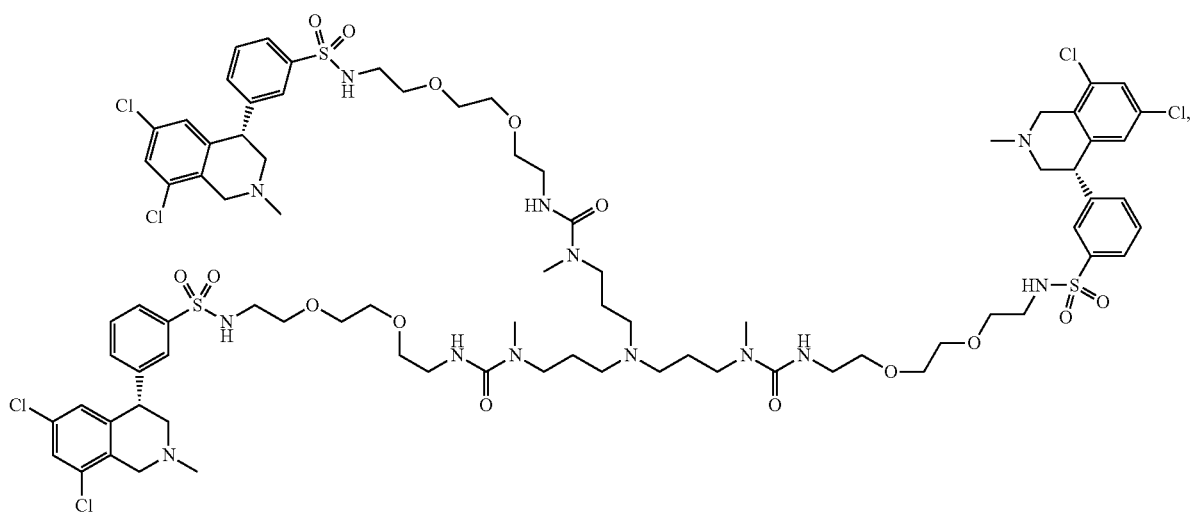
51
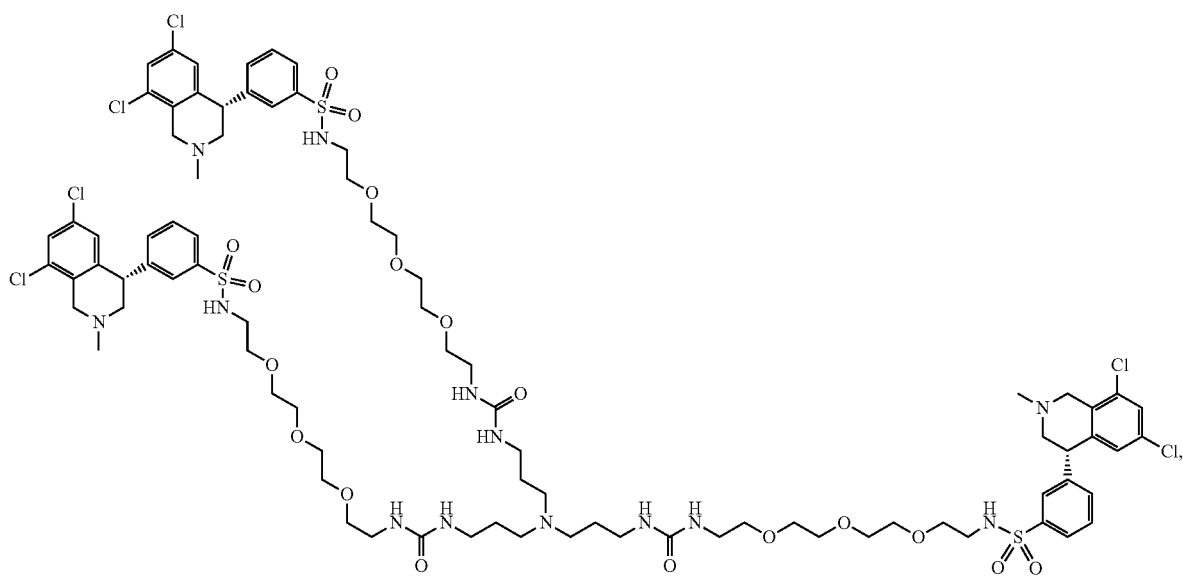

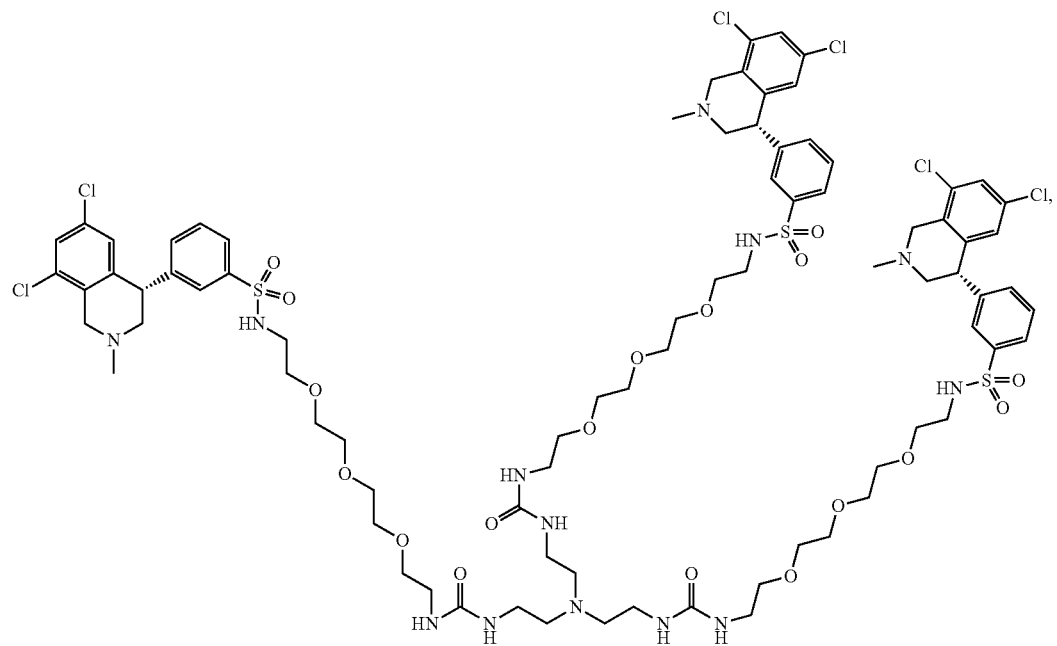
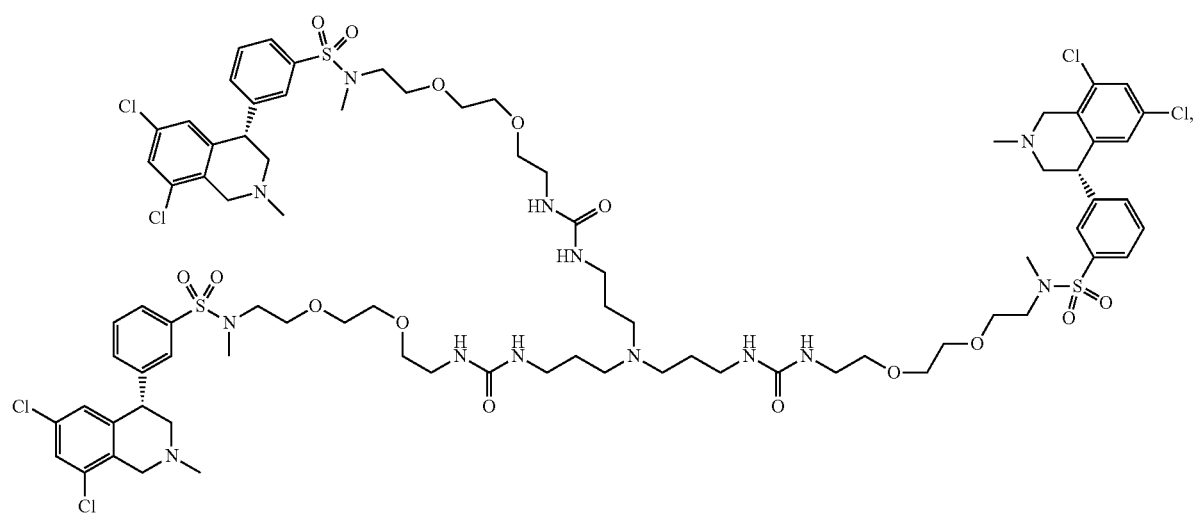

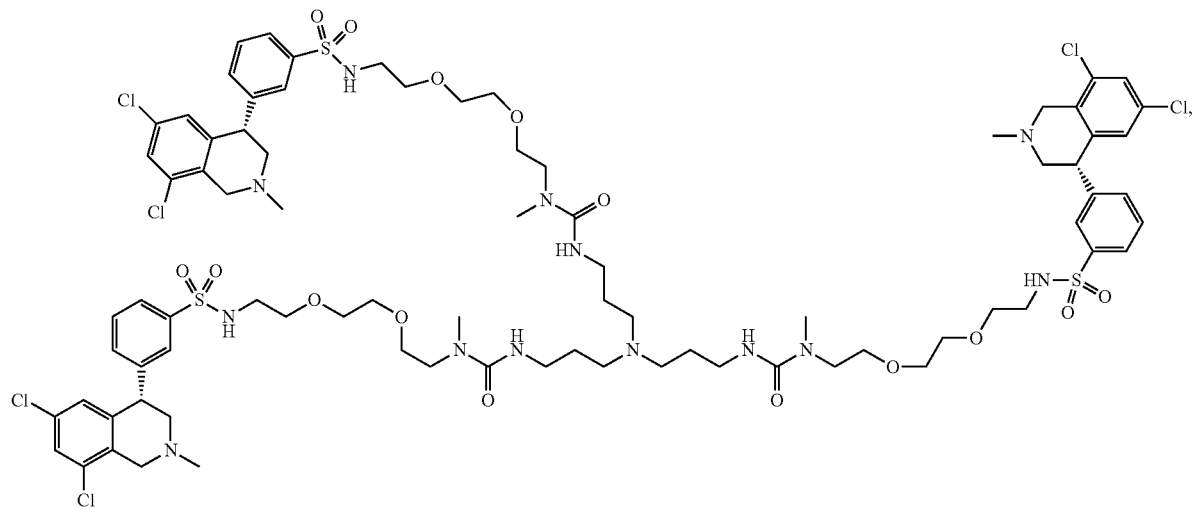
55
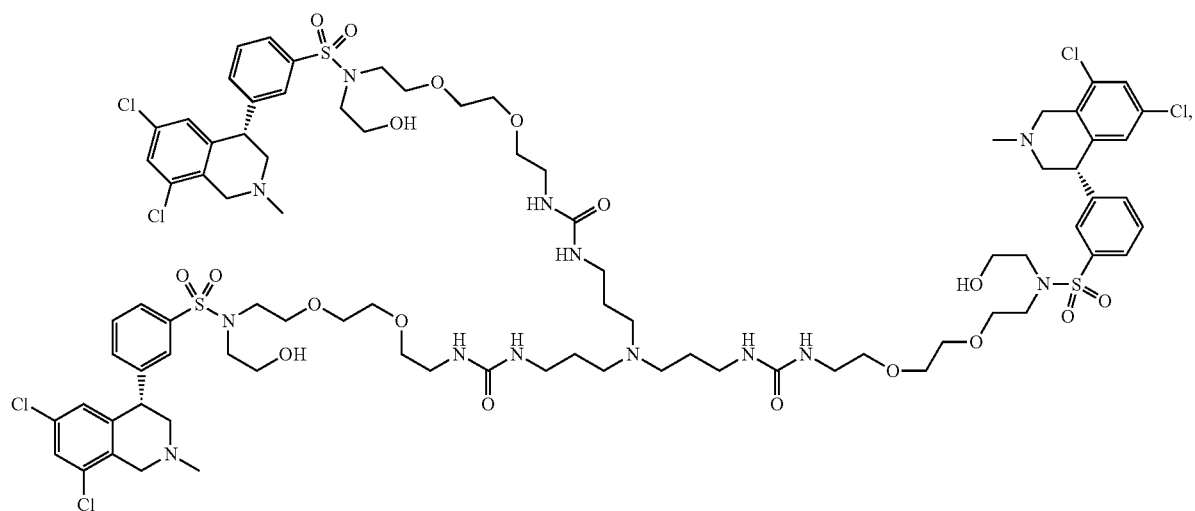
56
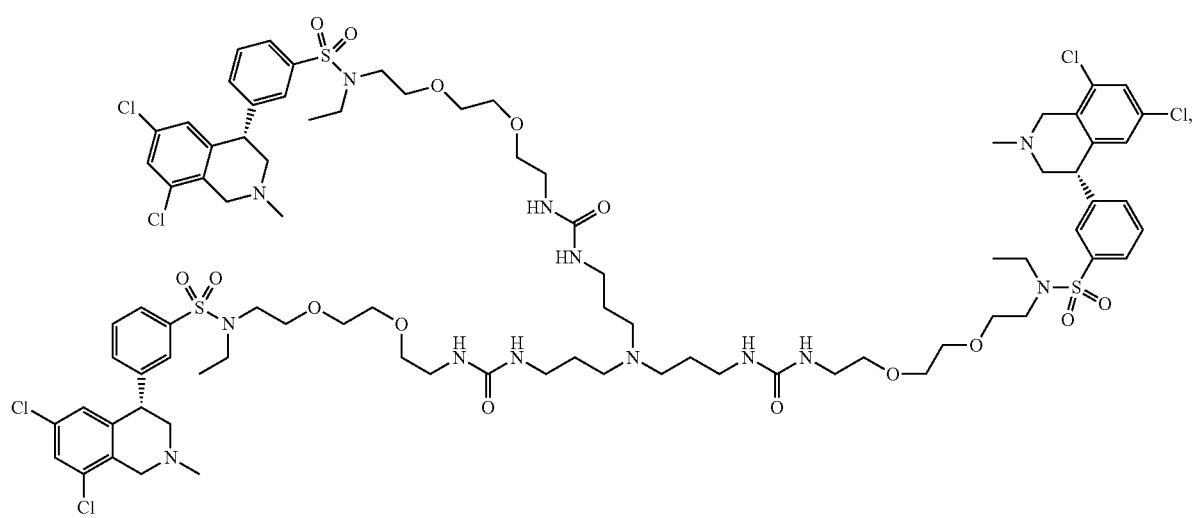
57

-continued
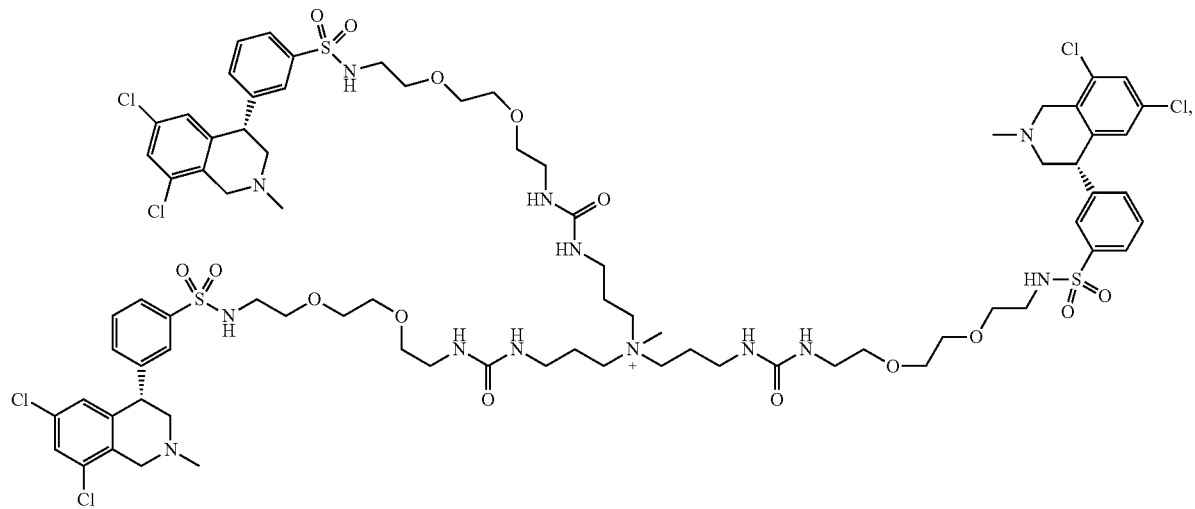
58
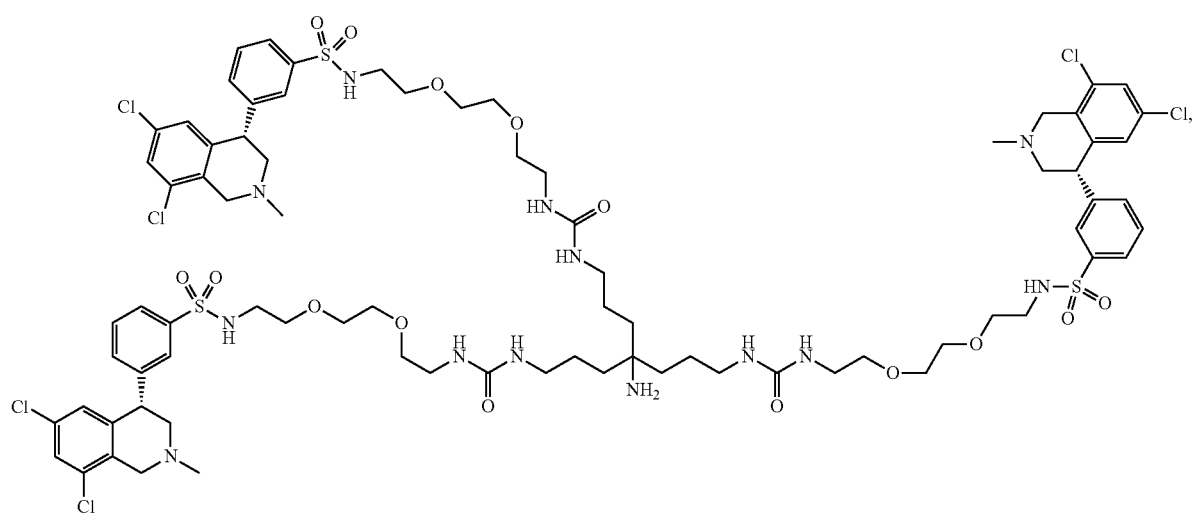
62
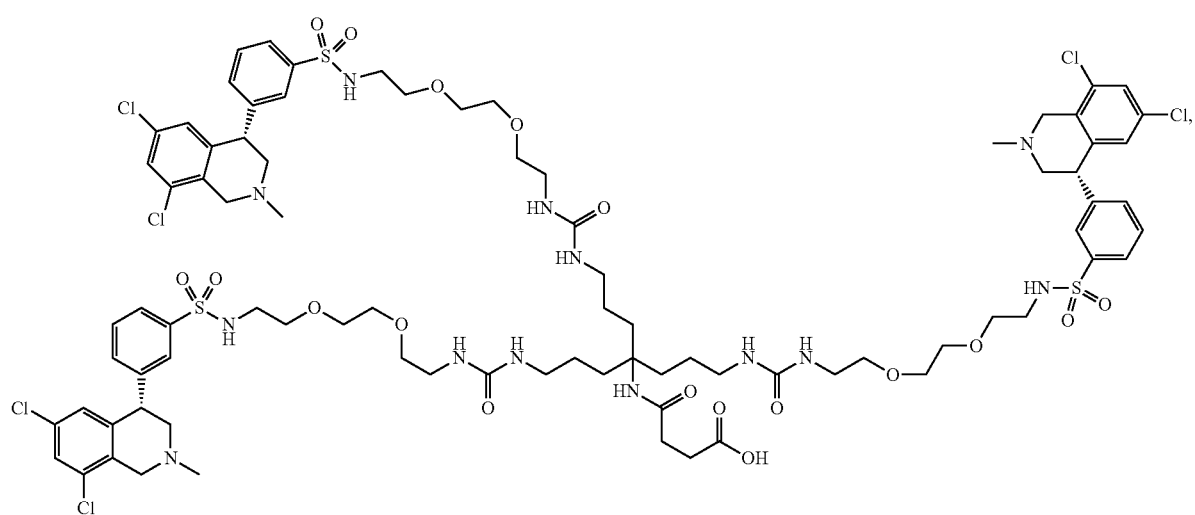
63

64
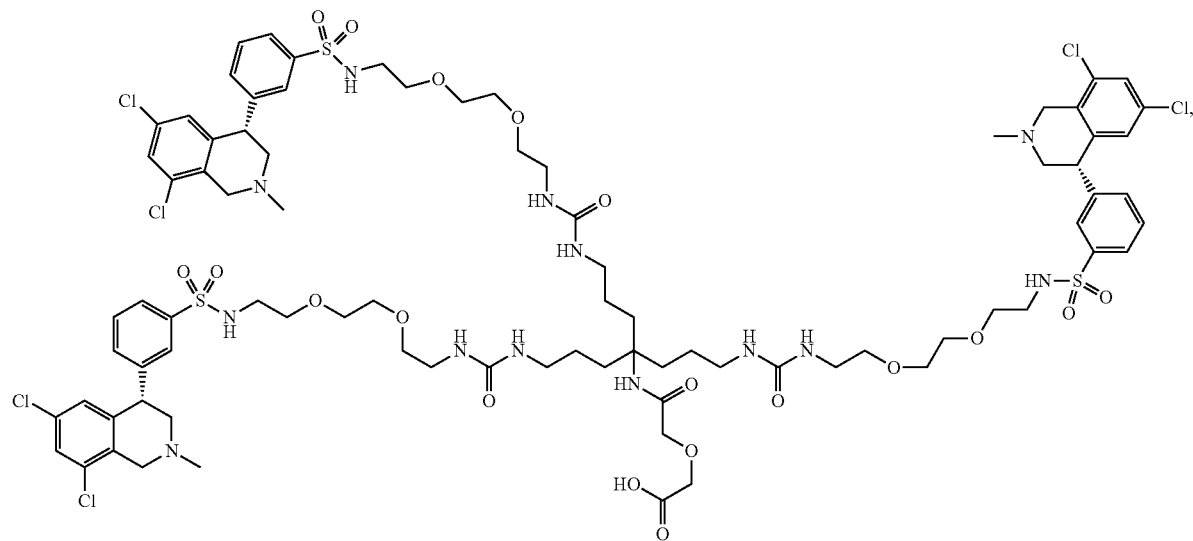
65
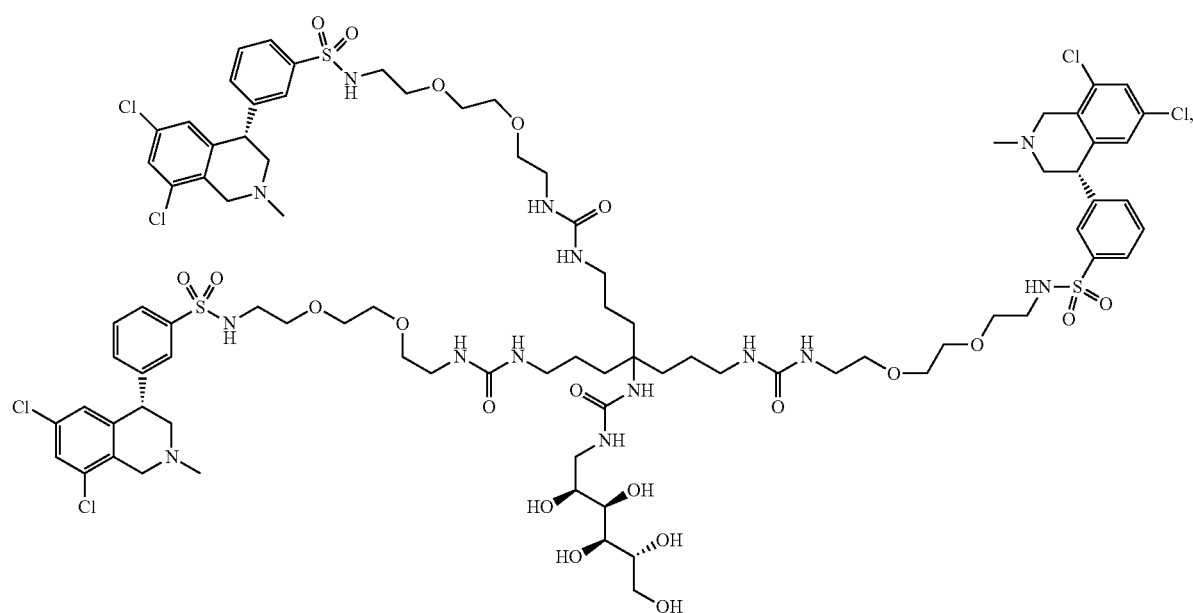

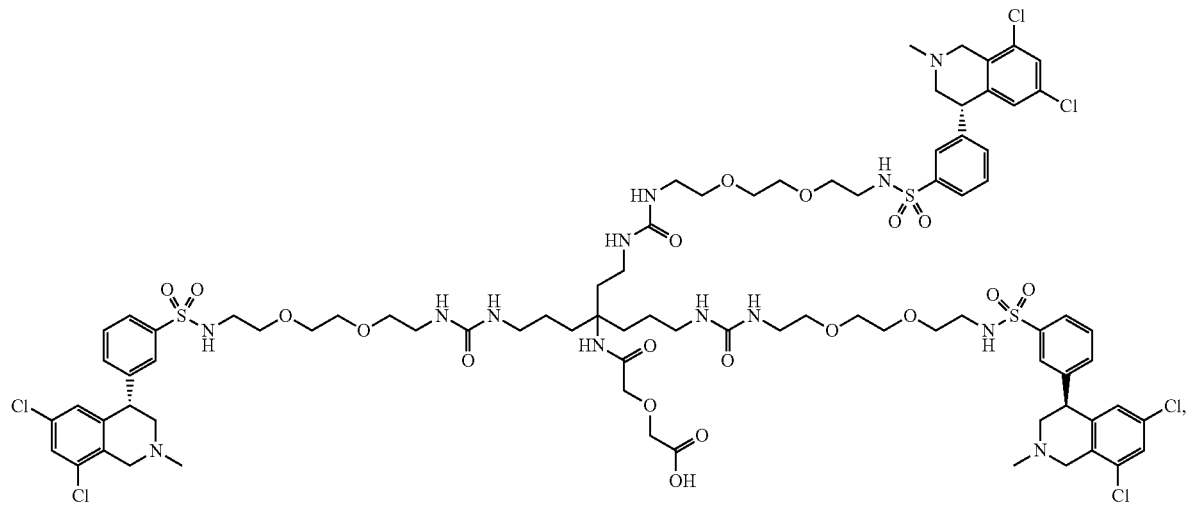
66
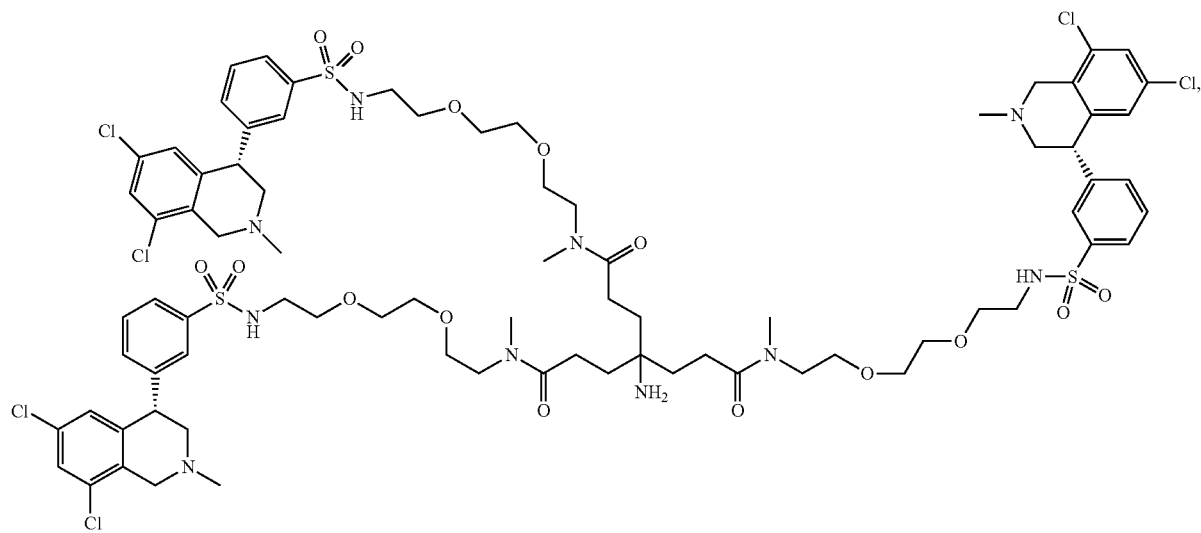
67
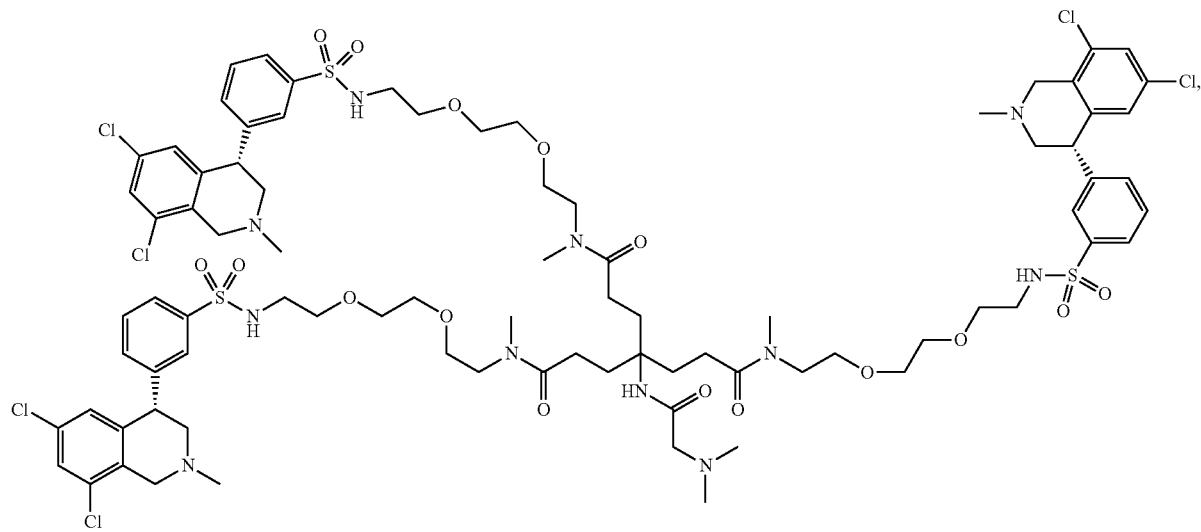
68

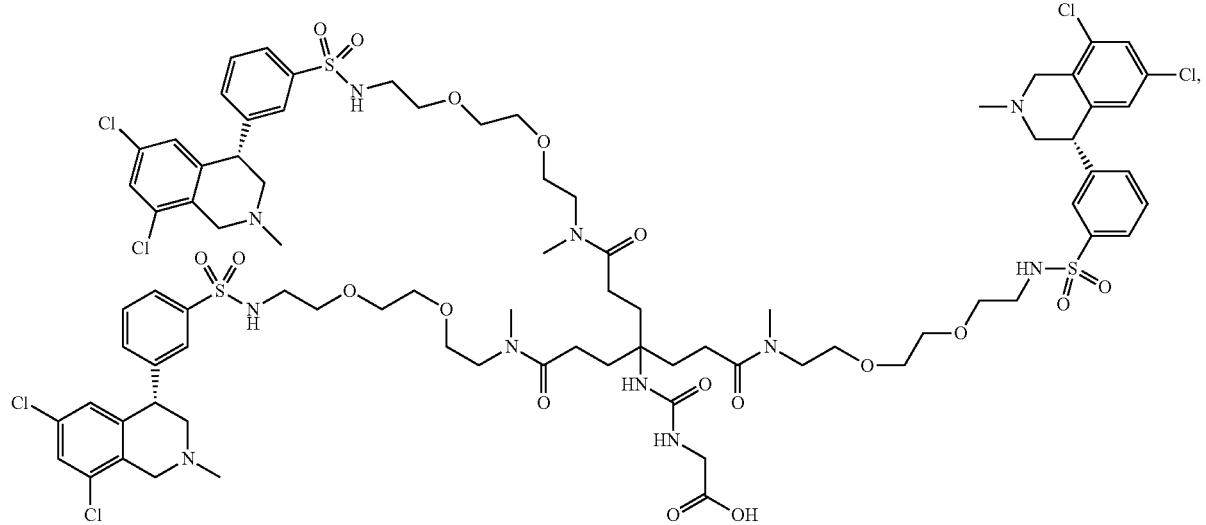
69
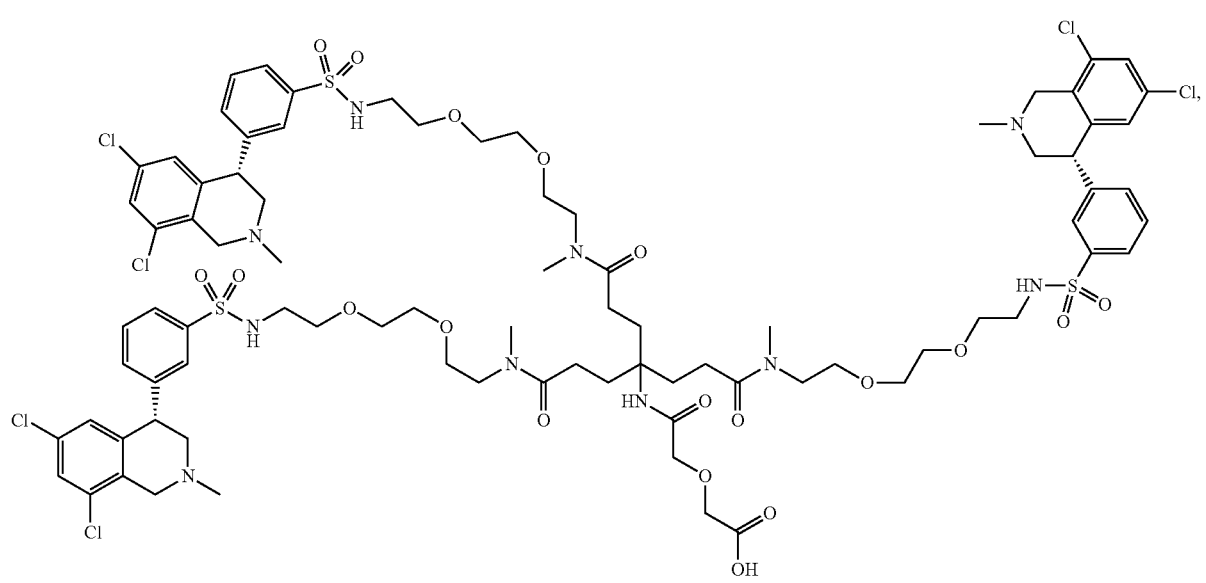
70

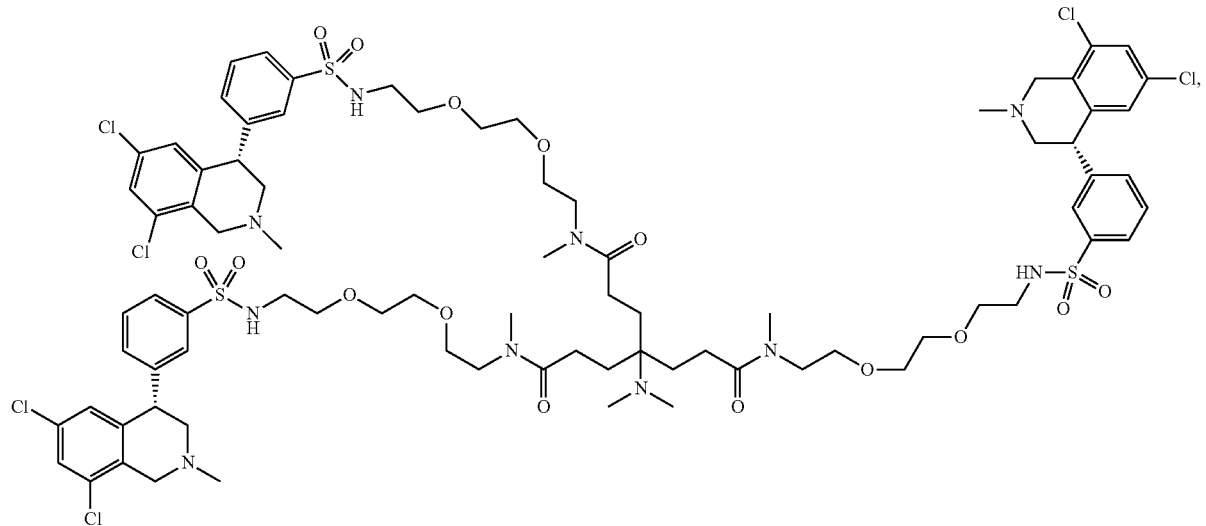
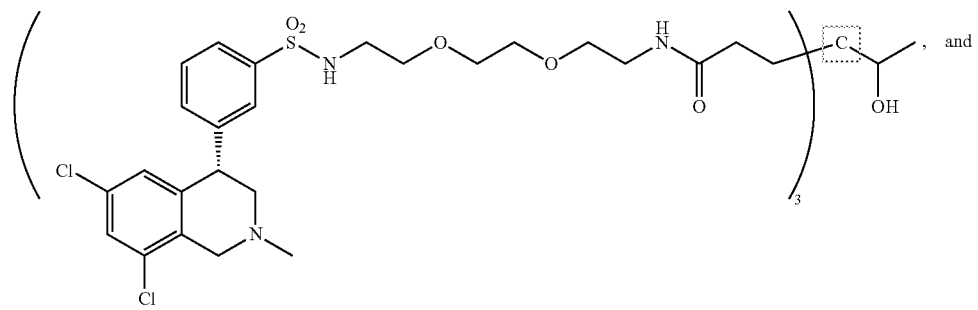

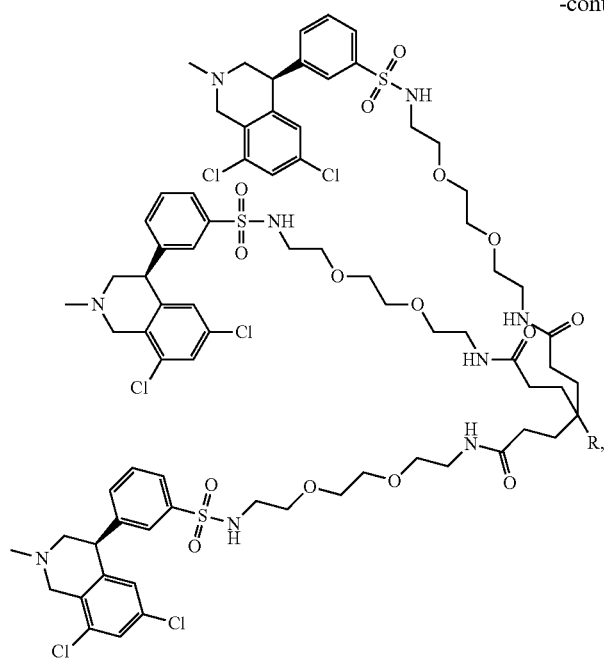
wherein R is selected from the group consisting of:
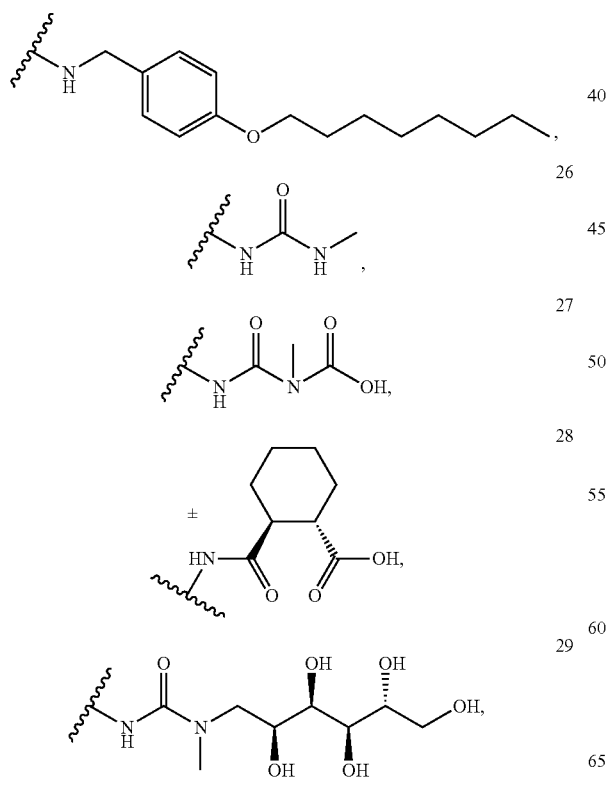
-continued
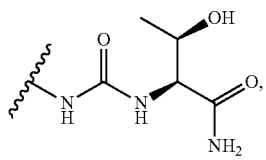
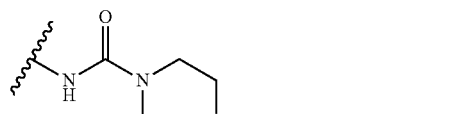
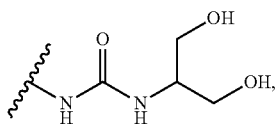
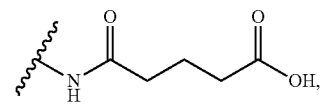
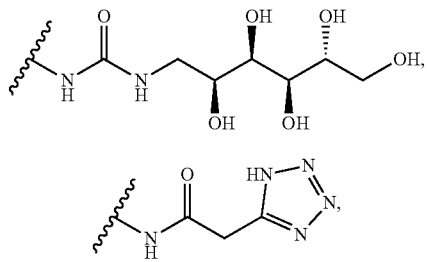

173
-continued

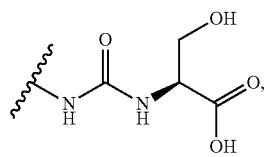

39

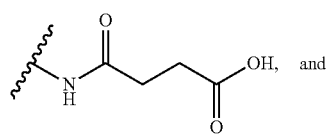

40 and

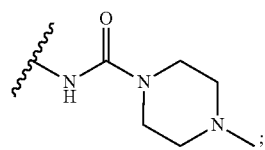

41 or a stereoisomer or pharmaceutically acceptable salt thereof.

2. A pharmaceutical composition comprising the compound of claim 1, or a stereoisomer, or pharmaceutically acceptable salt thereof, and a pharmaceutically acceptable carrier, diluent or excipient.

3. The pharmaceutical composition of claim 2, further comprising a fluid-absorbing polymer.

4. The pharmaceutical composition of claim 3, wherein the fluid-absorbing polymer is delivered directly to the colon.

5. The pharmaceutical composition of claim 3, wherein the fluid-absorbing polymer has a fluid absorbency of at least about 15 g of isotonic fluid per g of polymer under a static pressure of about 5 kPa.

6. The pharmaceutical composition of claim 3, wherein the fluid-absorbing polymer has a fluid absorbency of at least about 15 g of isotonic fluid per g of polymer under a static pressure of about 10 kPa.

7. The pharmaceutical composition of claim 3, wherein the fluid-absorbing polymer is characterized by a fluid absorbency of at least about 10 g/g.

8. The pharmaceutical composition of claim 3, wherein the fluid-absorbing polymer is characterized by a fluid absorbency of at least about 15 g/g.

9. The pharmaceutical composition of claim 3, wherein the fluid-absorbing polymer is superabsorbent.

10. The pharmaceutical composition of claim 3, wherein the fluid-absorbing polymer is a crosslinked, partially neutralized polyelectrolyte hydrogel.

11. The pharmaceutical composition of claim 3, wherein the fluid-absorbing polymer is a crosslinked polyacrylate.

12. The pharmaceutical composition of claim 3, wherein the fluid-absorbing polymer is a polyelectrolyte.

13. The pharmaceutical composition of claim 3, wherein the fluid-absorbing polymer is calcium Carbophil.

174

14. The pharmaceutical composition of claim 3, wherein the fluid-absorbing polymer is prepared by a high internal phase emulsion process.

15. The pharmaceutical composition of claim 3, wherein the fluid-absorbing polymer is a foam.

16. The pharmaceutical composition of claim 3, wherein the fluid-absorbing polymer is prepared by a aqueous free radical polymerization of acrylamide or a derivative thereof, a crosslinker and a free radical initiator redox system in water.

17. The pharmaceutical composition of claim 3, wherein the fluid-absorbing polymer is a hydrogel.

18. The pharmaceutical composition of claim 3, wherein the fluid-absorbing polymer is an N-alkyl acrylamide.

19. The pharmaceutical composition of claim 3, wherein the fluid-absorbing polymer is a superporous gel.

20. The pharmaceutical composition of claim 3, wherein the fluid-absorbing polymer is naturally occurring.

21. The pharmaceutical composition of claim 3, wherein the fluid-absorbing polymer is selected from the group consisting of xanthan, guar, wellan, hemicelluloses, alkyl-cellulose hydro-alkyl-cellulose, carboxy-alkyl-cellulose, carrageenan, dextran, hyaluronic acid and agarose.

22. The pharmaceutical composition of claim 3, wherein the fluid-absorbing polymer is psyllium.

23. The pharmaceutical composition of claim 3, wherein the fluid-absorbing polymer is a polysaccharide that includes xylose and arabinose.

24. The pharmaceutical composition of claim 3, wherein the fluid-absorbing polymer is a polysaccharide that includes xylose and arabinose, wherein the ratio of xylose to arabinose is at least about 3:1, by weight.

25. The pharmaceutical composition of claim 3, further comprising another pharmaceutically active agent or compound.

26. The pharmaceutical composition of claim 25, wherein the composition further comprises another pharmaceutically active agent or compound selected from the group consisting of a diuretic, cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent, lipid-lowering agent, and peroxisome proliferator-activated receptor (PPAR) gamma agonist agent.

27. The pharmaceutical composition of claim 26, wherein the diuretic is selected from the group consisting of a high ceiling loop diuretic, a benzothiadiazide diuretic, a potassium sparing diuretic, and a osmotic diuretic.

28. The pharmaceutical composition of claim 25, wherein the composition further comprises another pharmaceutically active agent or compound selected from the group consisting of an analgesic peptide or agent.

29. The pharmaceutical composition of claim 28, wherein the composition further comprises another pharmaceutically active agent or compound selected from the group consisting of a laxative agent selected from a bulk-producing agent, methylcellulose, polycarbophil, dietary fiber, apples, stool softeners/surfactant, a hydrating or osmotic agent, and a hyperosmotic agent.

30. A compound selected from the group consisting of:
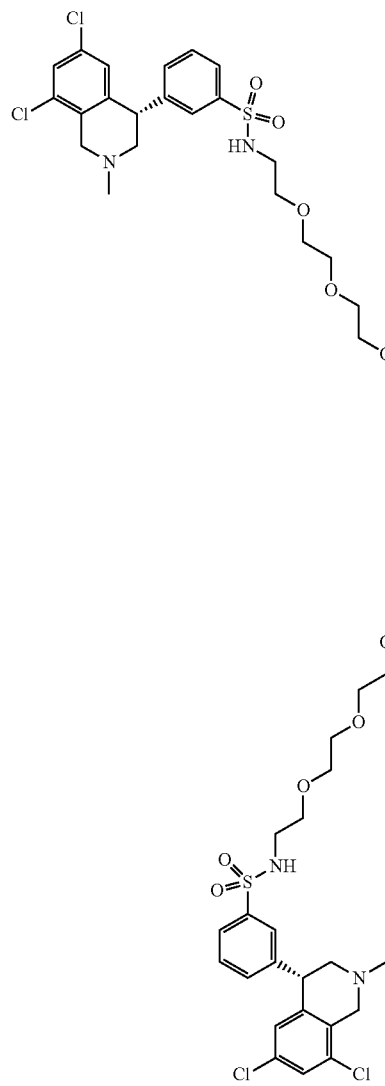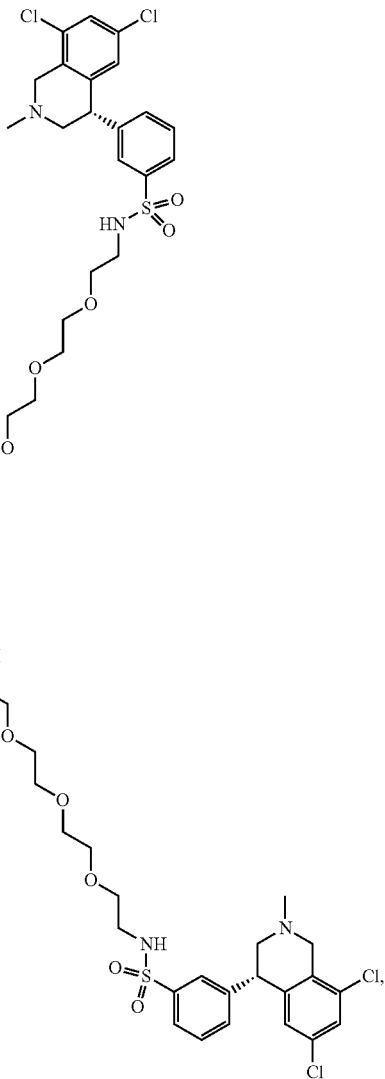

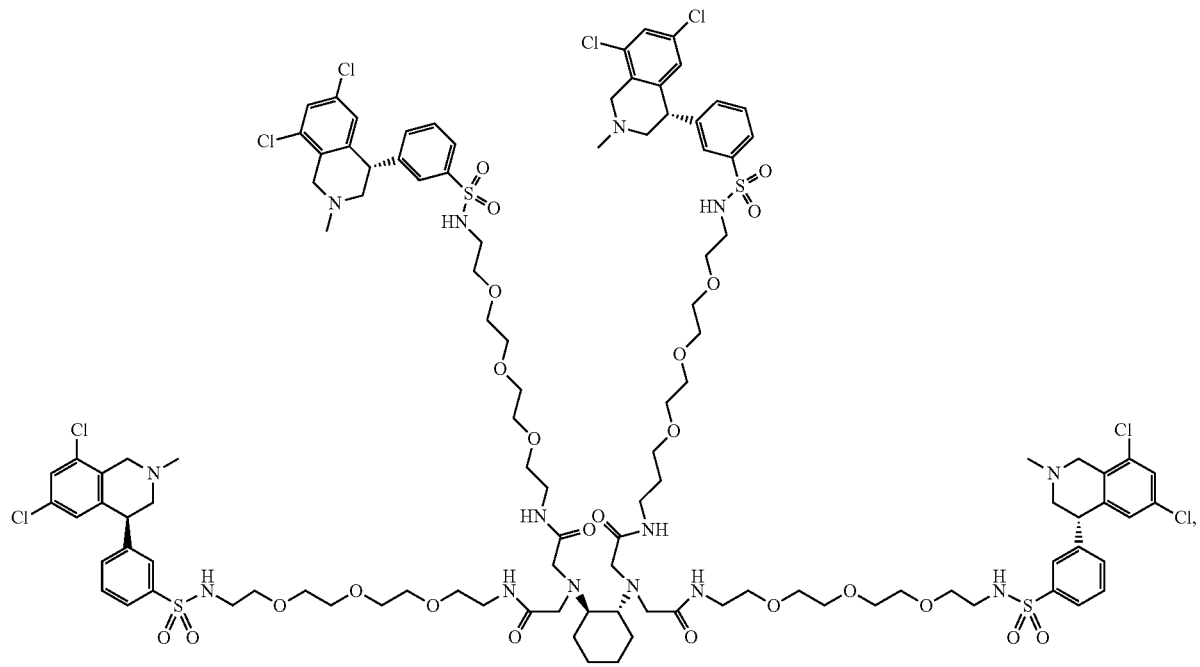
48
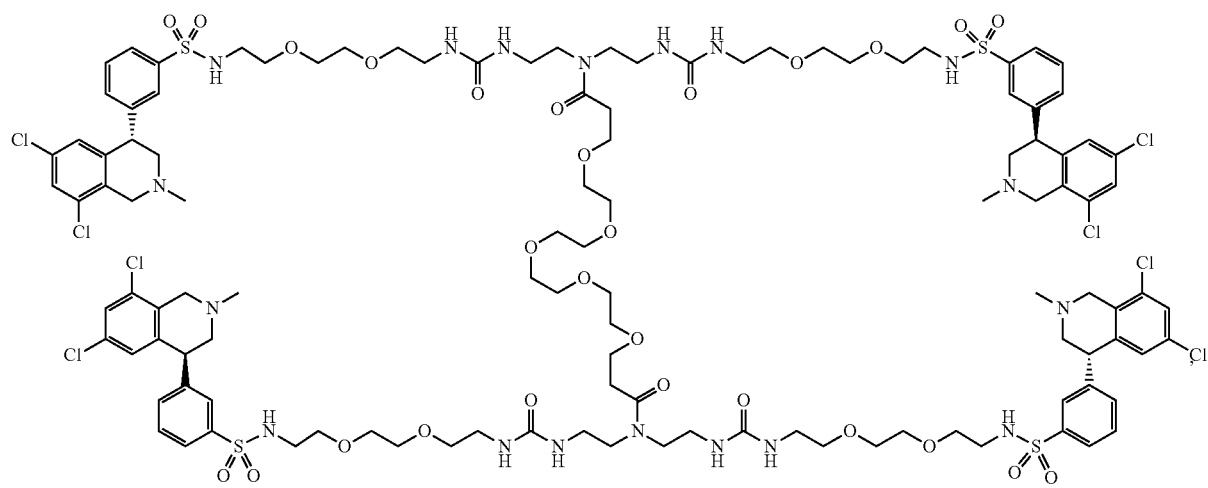
59
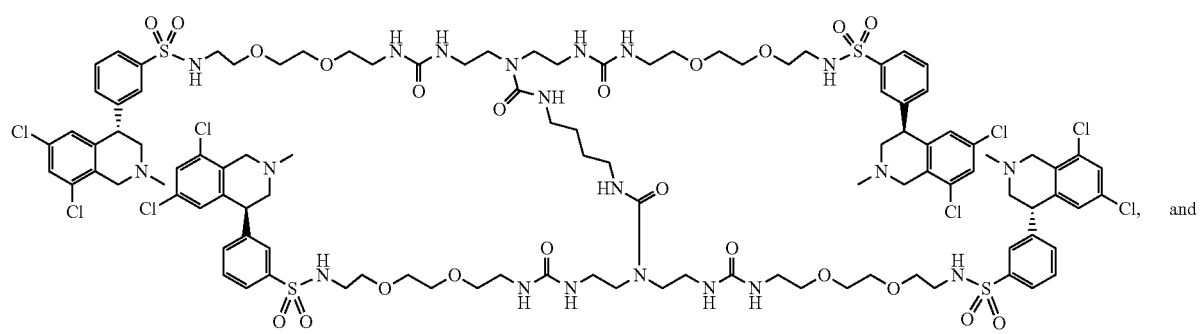
60
and

-continued

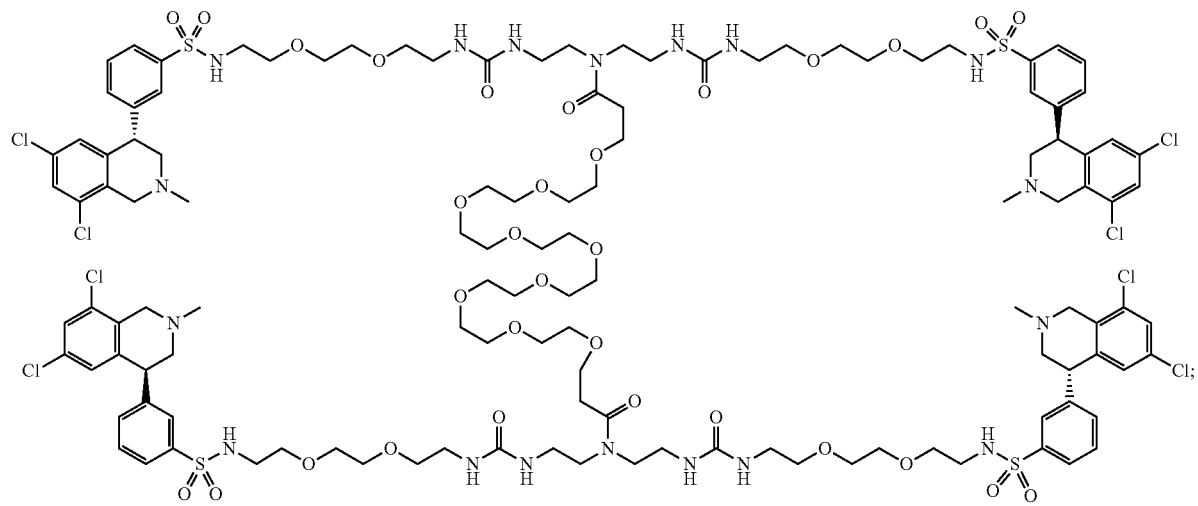

or a stereoisomer or pharmaceutically acceptable salt thereof.

31. A pharmaceutical composition comprising the compound of claim 30, or a stereoisomer, or pharmaceutically acceptable salt thereof, and a pharmaceutically acceptable carrier, diluent or excipient.

32. The pharmaceutical composition of claim 31, further comprising a fluid-absorbing polymer.

33. The pharmaceutical composition of claim 32, further comprising another pharmaceutically active agent or compound.

34. The pharmaceutical composition of claim 33, wherein the composition further comprises another pharmaceutically active agent or compound selected from the group consisting of a diuretic, cardiac glycoside, ACE inhibitor, angiotensin-2 receptor antagonist, aldosterone antagonist, aldosterone synthase inhibitor, renin inhibitor, calcium channel blocker, beta blocker, alpha blocker, central alpha agonist, vasodilator, blood thinner, anti-platelet agent, lipid-lowering agent, and peroxisome proliferator-activated receptor (PPAR) gamma agonist agent.

35. The pharmaceutical composition of claim 34, wherein the composition further comprises another pharmaceutically active agent or compound selected from the group consisting of an analgesic peptide or agent.

36. The pharmaceutical composition of claim 35, wherein the composition further comprises another pharmaceutically active agent or compound selected from the group consisting of a laxative agent selected from a bulk-producing agent, methylcellulose, polycarbophil, dietary fiber, apples, stool softeners/surfactant, a hydrating or osmotic agent, and a hyperosmotic agent.

\* \* \* \* \*

UNITED STATES PATENT AND TRADEMARK OFFICE
CERTIFICATE OF CORRECTION

PATENT NO. : 10,385,024 B2  
APPLICATION NO. : 16/007622  
DATED : August 20, 2019  
INVENTOR(S) : Noah Bell et al.

Page 1 of 6

It is certified that error appears in the above-identified patent and that said Letters Patent is hereby corrected as shown below:

In the Claims

Column 143, Structure 3, Claim 1, please delete the following compound:

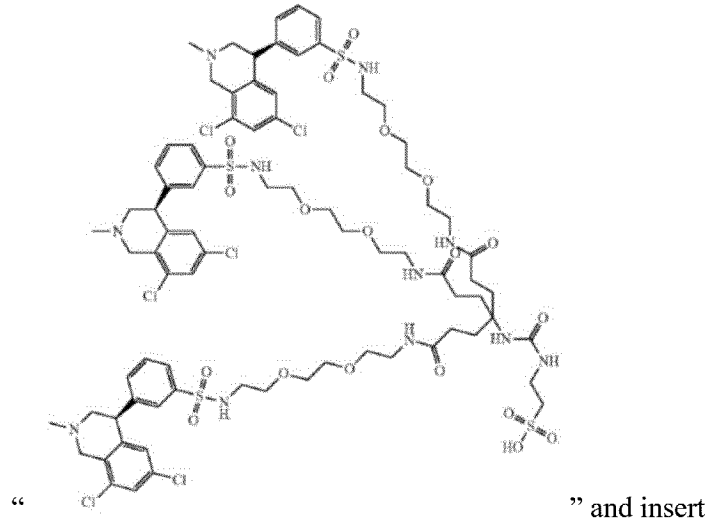

" and insert

Signed and Sealed this  
Third Day of December, 2019

Andrei Iancu  
*Director of the United States Patent and Trademark Office*

CERTIFICATE OF CORRECTION (continued)
U.S. Pat. No. 10,385,024 B2

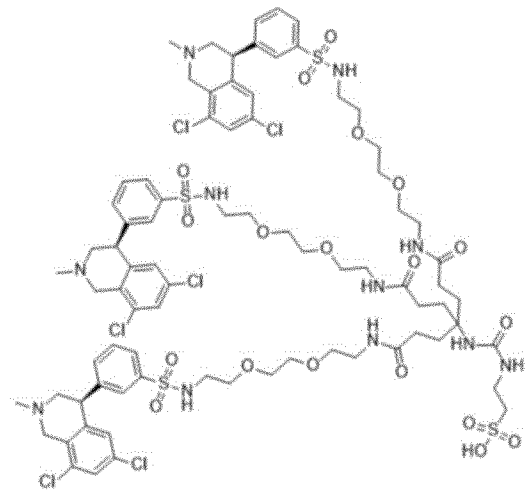

--             --;

Column 143, Structure 4, Claim 1, please delete the following compound:

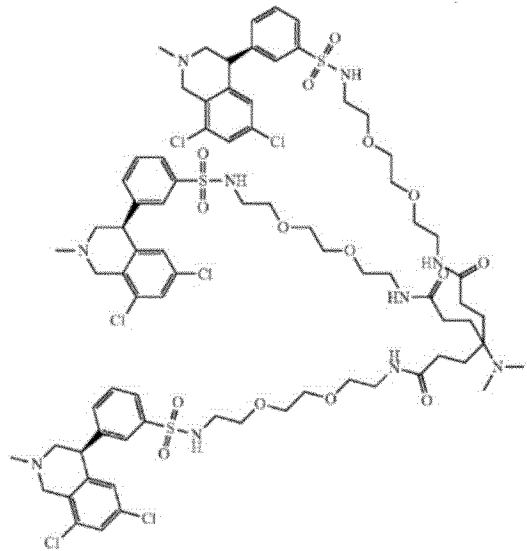

"             " and insert

CERTIFICATE OF CORRECTION (continued)
U.S. Pat. No. 10,385,024 B2

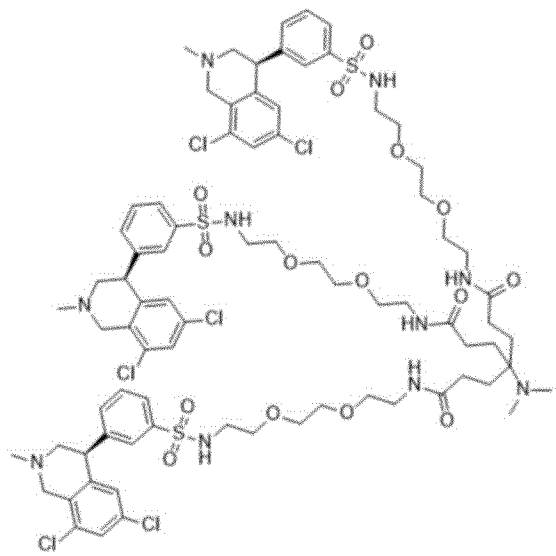

-- --;

Column 145, Structure 6, Claim 1, please delete the following compound:

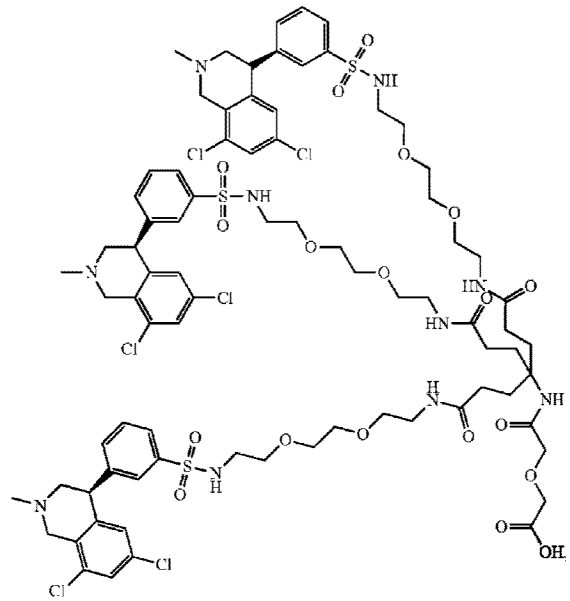

" " and insert

CERTIFICATE OF CORRECTION (continued)
U.S. Pat. No. 10,385,024 B2

Page 4 of 6

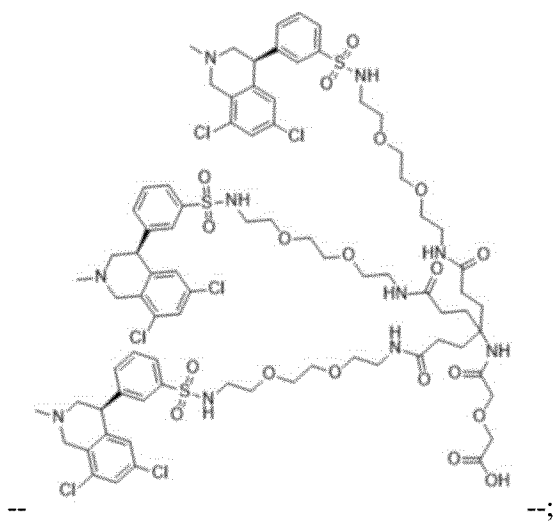

--                                    --;

Columns 155-156, Top Structure 46, Claim 1, please delete the following compound:

"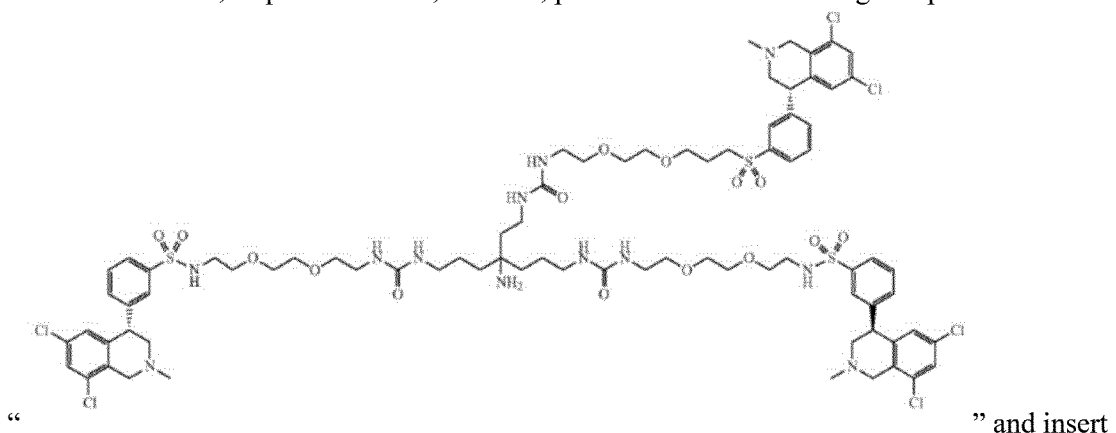" and insert

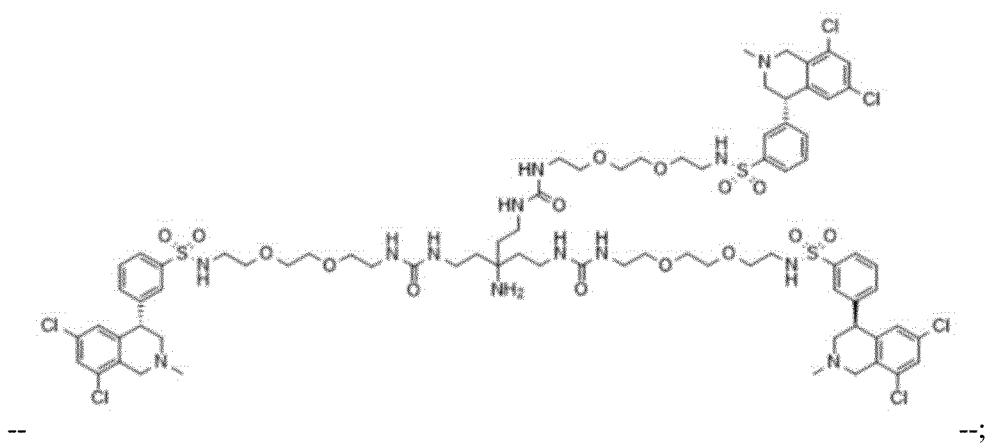

--                                    --;

Columns 165-166, Structure 66, Claim 1, please delete the following compound:
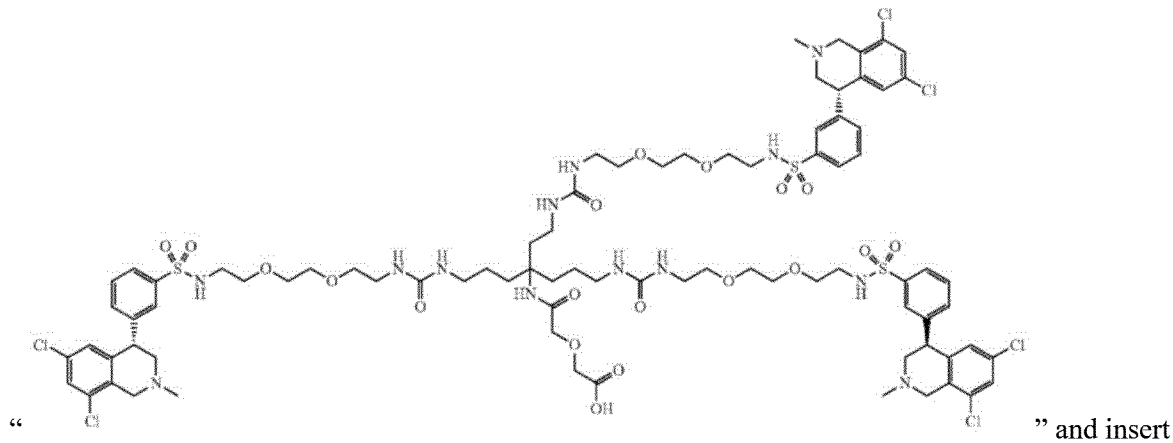
" and insert
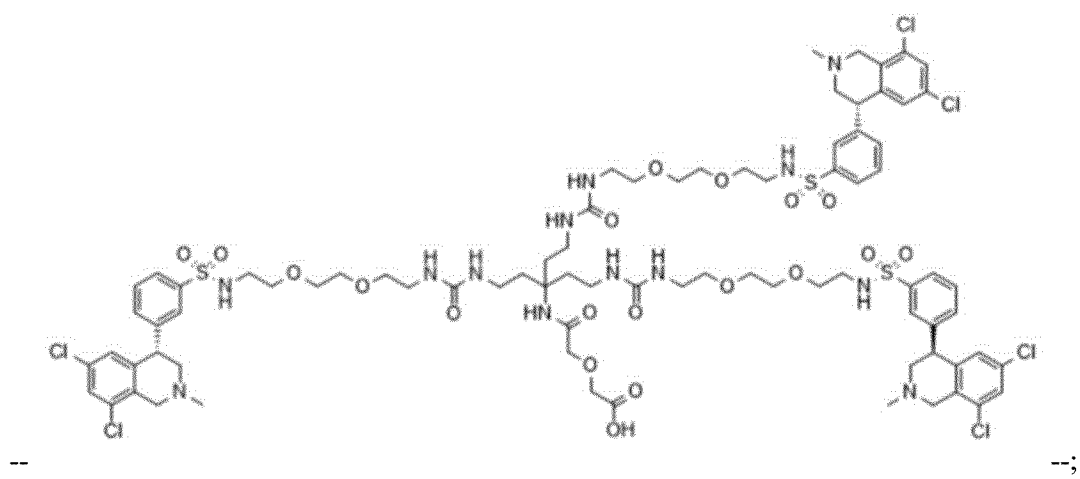
--;
Columns 169-170, Structure 73, Claim 1, please add the following after the bottom the structure:
-- 73 --;
Column 171, Lines 47-52, Claim 1, please delete the following compound:
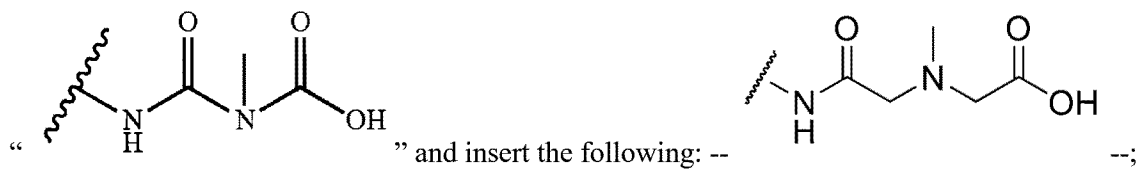
" and insert the following: -- --;

CERTIFICATE OF CORRECTION (continued)
U.S. Pat. No. 10,385,024 B2

Columns 177-178, Structure 48, Claim 30, please delete the following compound:

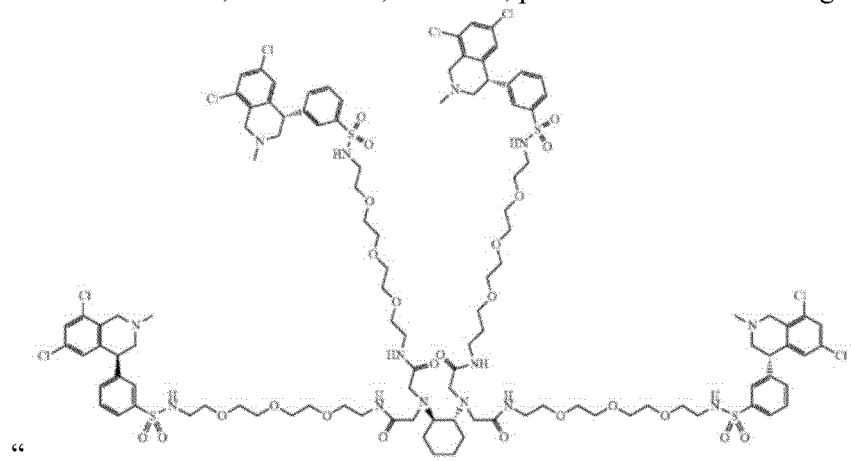

" and insert

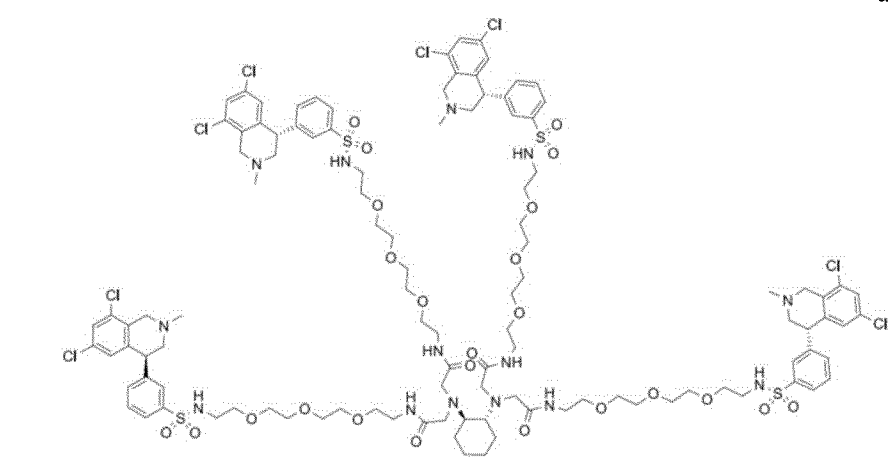

-- therefor.